(12) United States Patent
Fancelli et al.

(10) Patent No.: US 7,531,531 B2
(45) Date of Patent: May 12, 2009

(54) METHOD OF TREATING DISEASES ASSOCIATED WITH ALTERED KINASE ACTIVITY WITH BICYCLO-PYRAZOLES

(75) Inventors: Daniele Fancelli, Milan (IT); Valeria Pittalà, Catania (IT); Mario Varasi, Milan (IT)

(73) Assignee: Pfizer Italia S.r.l., Rome (IT)

( * ) Notice: Subject to any disclaimer, the term of this patent is extended or adjusted under 35 U.S.C. 154(b) by 0 days.

(21) Appl. No.: 11/784,980

(22) Filed: Apr. 10, 2007

(65) Prior Publication Data

US 2007/0191386 A1 Aug. 16, 2007

Related U.S. Application Data

(60) Division of application No. 10/344,480, filed as application No. PCT/EP01/08639 on Jul. 25, 2001, which is a continuation-in-part of application No. 09/635,914, filed on Aug. 10, 2000, now abandoned.

(51) Int. Cl.
*A61K 31/55* (2006.01)
*A61K 31/501* (2006.01)
*A61K 31/437* (2006.01)
*A61K 31/426* (2006.01)

(52) U.S. Cl. ............... 514/215; 514/252.06; 514/303; 514/365

(58) Field of Classification Search ............ 514/252.06, 514/215, 234.2, 254.06, 255.05, 303, 314, 514/321, 338, 406, 407, 365, 422
See application file for complete search history.

(56) References Cited

U.S. PATENT DOCUMENTS 3,947,467 A 3/1976 Verge et al.
5,593,997 A * 1/1997 Dow et al. ............... 514/262.1
5,922,741 A * 7/1999 Davis et al. .............. 514/341

FOREIGN PATENT DOCUMENTS

JP 48003639 B4 * 2/1973
WO WO 97/40019 10/1997
WO WO 99/32455 7/1999

OTHER PUBLICATIONS

Cohen, Philip, The development and therapeutic potential of protein kinase inhibitors, 1999, Current Opinion in Chemical Biology, vol. 3, 460.*
Antonio R. Damasio, Cecil Textbook of Medicine, 1996, W.B. Saunders Company, 20th Edition, Volumune 2, pp. 1992-1996.*
Robert B. Layzer, Cecil Textbook of Medicine, 1996, W.B. Saunders Company, 20th Edition, Volumune 2, pp. 2050-2057.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/index.html.*
Joel R. Huff, HIV Protease: A Novel Chemotherapeutic Target for AIDS, 1991, Journal of Medicinal Chemistry, vol. 34, No. 8, pp. 2305-2314.*
Golub et al., Molecular Classification of Cancer: Class Discovery and Class Prediction by Gene Expression Monitoring, 1999, Science, vol. 286, pp. 531-537.*
Lala et al., Role of nitric oxide in tumor progression: Lessons from experimental tumors, 1998, Cancer and Metastasis Reviews, 17(1), pp. 91-106.*
Philip Cohen, The development and therapeutic potential of protein kinase inhibitors, 1999, Current Opinion in Chemical Biology, 3, p. 459.*
Nakanishi M. et al., "4,5,6,7-Tetrahydro-1(or2)H-Pyrazolo-4,3-Cpyridine Derivatives", Online Database, p. 1 (1973).

* cited by examiner

*Primary Examiner*—Kamal A Saeed
*Assistant Examiner*—Kristin Bianchi
(74) *Attorney, Agent, or Firm*—Scully, Scott, Murphy & Presser, P.C.

(57) ABSTRACT

Bicyclo-pyrazole compounds of formula (I), as herein defined, are useful for treating diseases linked to disregulated protein kinases.

1 Claim, No Drawings

METHOD OF TREATING DISEASES ASSOCIATED WITH ALTERED KINASE ACTIVITY WITH BICYCLO-PYRAZOLES

CROSS-REFERENCE TO RELATED APPLICATIONS

The present application is a divisional of U.S. application Ser. No. 10/344,480, filed on Feb. 10, 2003 as a national stage application under 35 U.S.C. §371 of PCT/EP01/08639, filed Jul. 25, 2001, which claims priority to U.S. application Ser. No. 09/635,914, filed Aug. 10, 2000, now abandoned, which are incorporated herein by reference in their entirety.

STATEMENTS REGARDING FEDERALLY SPONSORED RESEARCH OR DEVELOPMENT

N/A

REFERENCE TO A SEQUENCE LISTING

N/A

DETAILED DESCRIPTION

The present invention relates to pyrazole derivatives active as kinase inhibitors and, more in particular, it relates to bicyclo-pyrazole derivatives, to a process for their preparation, to pharmaceutical compositions comprising them and to their use as therapeutic agents, particularly in the treatment of diseases linked to disregulated protein kinases.

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

Embodiments of the invention provide compounds which are useful in therapy as agents against a host of diseases caused by a disregulated protein kinase activity.

Embodiments may also provide compounds which are endowed with multiple protein kinase inhibiting activity.

The present inventors have now discovered that bicyclo-pyrazoles are endowed with multiple protein kinase inhibiting activity and are thus useful in therapy in the treatment of diseases associated with disregulated protein kinases.

More specifically, the bicyclo-pyrazole embodiments of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratocanthomas, thyroid follicular cancer and Kaposi's sarcoma.

Due to the key role of PKs in the regulation of cellular proliferation, these bicyclo-pyrazoles are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

Embodiments of the invention can be useful in the treatment of Alzheimer's disease, as suggested by the fact that cdk5 is involved in the phosphorylation of tau protein (J. Biochem., 117, 741-749, 1995).

Embodiments of this invention, as modulators of apoptosis, may also be useful in the treatment of cancer, viral infections, prevention of AIDS development in HIV-infected individuals, autoimmune diseases and neurodegenerative disorders.

Embodiments of this invention may be useful in inhibiting tumor angiogenesis and metastasis.

Embodiments of the invention are useful as cyclin dependent kinase (cdk) inhibitors and also as inhibitors of other protein kinases such as, for instance, protein kinase C in different isoforms, Met, PAK4, PAK-5, ZC-1, STLK-2, DDR-2, Aurora 1, Aurora 2, Bub-1, PLK, Chk1, Chk2, HER2, rafl, MEK1, MAPK, EGF-R, PDGF-R, FGF-R, IGF-R, VEGF-R, PI3K, weel kinase, Src, Abl, Akt, ILK, MK-2, IKK-2, Cdc7, Nek, and thus be effective in the treatment of diseases associated with other protein kinases.

Accordingly, embodiments of the present invention provide a method for treating a mammal, including humans, suffering from a disease caused by and/or associated with an altered protein kinase activity, by administering to said mammal in need thereof a therapeutically effective amount of a bicyclo-pyrazole compound of formula (I):

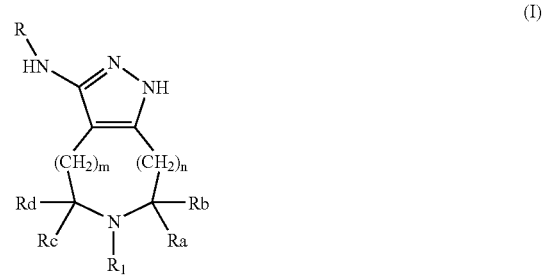

(I)

wherein

R and R1, being the same or different, are independently a hydrogen atom or an optionally substituted group selected from R', —COR', —COOR', —CONHR', —CONR'R", —NH—C(=NH)NHR', —C(=NH)NHR', —SO$_2$R', —SO$_2$NHR' or —SO$_2$NR'R"; wherein R' and R", the same or different, are independently selected from hydrogen or optionally further substituted straight or branched $C_1$-$C_6$ alkyl, aryl, $C_3$-$C_6$ cycloalkyl and aryl $C_1$-$C_6$ alkyl or R' and R" taken together form a $C_4$-$C_6$ alkylene chain;

Ra, Rb, Rc and Rd, being the same or different, are independently selected among hydrogen, optionally further substituted straight or branched $C_1$-$C_6$ alkyl, aryl, aryl $C_1$-$C_6$ alkyl or —$CH_2OR'$ groups, wherein R' is as above defined, or Ra and Rb and/or Rc and Rd, taken together with the carbon atom to which they are bonded, form an optionally substituted $C_3$-$C_6$ cycloalkyl group;

m and n, each independently, represents 0 or an integer from 1 to 2, provided that m+n is lower than, or equal to, 2 (m+n≦2);

or a pharmaceutically acceptable salt thereof.

In a preferred embodiment of the method described above, the disease caused by an altered protein kinase activity is selected from the group consisting of cancer, cell proliferative disorders, Alzheimer's disease, viral infections, auto-immune diseases and neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthomas, thyroid follicular cancer and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis. In addition, certain method embodiments of the present invention, also provide tumor angiogenesis and metastasis inhibition.

A limited number of bicyclic derivatives structurally related to the compounds of formula (I) are known in the art. See, as an example, Gadekar, Sheekrishna M. et al. in J. Med. Chem.; 1968, 11(3), 616-618; which discloses bicyclic derivatives, not showing any kinase inhibitory activity, characterized by the presence of a nitrogen substitutent in position 1.

The 1-unsubstituted bicyclo-pyrazole derivatives of formula (I) embodiment of the present invention, on the contrary, are novel compounds, obtainable through a new and extremely versatile solid-phase combinatorial process, that is also comprised within the scope of the invention.

An embodiment of the present invention thus provides a bicyclo-pyrazole compound of formula (I):

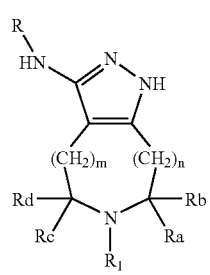

(I)

wherein

R and $R_1$, being the same or different, are independently a hydrogen atom or an optionally substituted group selected from R', —COR', —COOR', —CONHR', —CONR'R", —NH—C(=NH)NHR', —C(=NH)NHR', —$SO_2$R', —$SO_2$NHR' or —$SO_2$NR'R"; wherein R' and R", the same or different, are independently selected from hydrogen or optionally further substituted straight or branched $C_1$-$C_6$ alkyl, aryl, $C_3$-$C_6$ cycloalkyl or aryl $C_1$-$C_6$ alkyl or R' and R" taken together form a $C_4$-$C_6$ alkylene chain;

Ra, Rb, Rc and Rd, being the same or different, are independently selected among hydrogen, optionally further substituted straight or branched $C_1$-$C_6$ alkyl, aryl, aryl $C_1$-$C_6$ alkyl or —$CH_2OR'$ groups, wherein R' is as above defined, or Ra and Rb and/or Rc and Rd, taken together with the carbon atom to which they are bonded, form an optionally substituted $C_3$-$C_6$ cycloalkyl group;

m and n, each independently, represent 0 or an integer from 1 to 2, provided that m+n is lower than, or equal to, 2 (m+n≦2);

and the pharmaceutically acceptable salt thereof.

Embodiments of the invention provide a compound of formula (I) or a pharmaceutically acceptable salt thereof for use as a medicament.

Embodiments of the invention also provide the use of a compound of formula (I) or a pharmaceutically acceptable salt thereof in the manufacture of a medicament for treating a patient suffering from a disease caused by and/or associated with an altered protein kinase activity.

The compounds of formula (I), embodiment of the present invention may have asymmetric carbon atoms and may therefore exist either as racemic admixtures or as individual optical isomers. Accordingly, all the possible isomers and their admixtures and of both the metabolites and the pharmaceutically acceptable bio-precursors (otherwise referred to as pro-drugs) of the compounds of formula (I), as well as any therapeutic method of treatment comprising them, are also within the scope of the present invention.

In addition to the above, as will be readily appreciated, the unsubstituted ring nitrogen pyrazoles in the compounds of the invention are known to rapidly equilibrate, in solution, as admixtures of both tautomers:

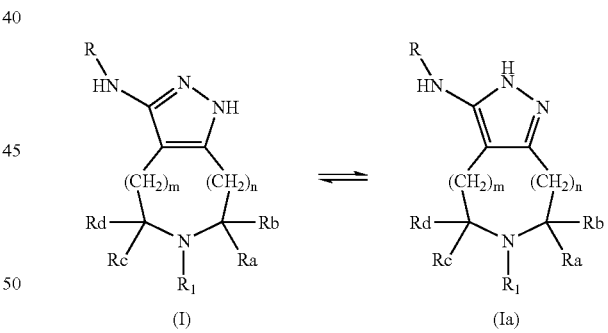

(I)  (Ia)

Accordingly, embodiments of the present invention, where only one tautomer is indicated for the compounds of formula (I), the other, (Ia), are also within the scope of the present invention, unless specifically noted otherwise.

As used herein, unless otherwise specified, with the term straight or branched $C_1$-$C_6$ alkyl, either as such or as arylalkyl, we intend a group such as, for instance, methyl, ethyl, n.propyl, isopropyl, n.butyl, isobutyl, sec-butyl, tert-butyl, n.pentyl, n.hexyl and the like. Preferably it is a $C_1$-$C_4$ alkyl, e.g. methyl, ethyl, n.propyl, isopropyl, n.butyl, isobutyl, sec-butyl, tert-butyl.

When R' and R" taken together form a $C_4$-$C_6$ alkylene chain, they with the nitrogen atom to which they are linked preferably form a piperidino or pyrrolidino group.

With the term $C_3$-$C_6$ cycloalkyl group we intend cyclopropyl, cyclobutyl, cyclopentyl, and cyclohexyl.

With the term aryl, either as such or as arylalkyl group, we intend a mono-, bi- or poly-either carbocyclic as well as heterocyclic hydrocarbon with from 1 to 4 ring moieties, either fused or linked to each other by single bonds, wherein at least one of the carbocyclic or heterocyclic rings is aromatic.

Non limiting examples of aryl groups are, for instance, henyl, indanyl, biphenyl, α- or β-naphthyl, fluorenyl, 9,10-dihydroanthracenyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, tetrazolyl, tetrazolylphenyl, pyrrolidinyl-tetrazolyl, isoindolinyl-phenyl, quinolinyl, isoquinolinyl, 2,6-diphenyl-pyridyl, quinoxalinyl, pyrazinyl, phenyl-quinolinyl, benzofurazanyl, 1,2,3-triazolyl, 1-phenyl-1,2,3-triazolyl, and the like.

Clearly, as above indicated, aryl groups may also refer to aromatic carbocyclic or heterocyclic rings, further fused or linked to non aromatic heterocyclic rings, typically 5 to 7 membered heterocycles.

With the term 5 to 7 membered heterocycle, hence encompassing aromatic heterocycles also referred to as aryl groups, we further intend a saturated or partially unsaturated 5 to 7 membered carbocycle wherein one or more carbon atoms are replaced by heteroatoms such as nitrogen, oxygen and sulphur.

Examples of 5 to 7 membered heterocycles, optionally benzocondensed or further substituted, are 1,3-dioxolane, pyran, pyrrolidine, pyrroline, imidazolidine, pyrazolidine, pyrazoline, piperidine, piperazine, morpholine, tetrahydrofuran, azabicyclononane and the like.

According to the above meanings provided to R, $R_1$, R', R", Ra, Rb, Rc, and Rd, any of the above groups may be further optionally substituted, in any of the free positions, by one or more groups, for instance 1 to 6 groups, selected from: halogen, nitro, oxo groups (=O), carboxy, cyano, alkyl, perfluorinated alkyl, alkenyl, alkynyl, cycloalkyl, aryl, heterocyclyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino, sulfonamido, alkylsulfonamido and arylsulfonamido, hydroxy groups and derivatives thereof such as, for instance, alkoxy, aryloxy, alkylcarbonyloxy, arylcarbonyloxy, cycloalkenyloxy or alkylideneaminooxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulphonyl, arylsulphonyl, alkylsulphinyl, arylsulphinyl, arylsulphonyloxy, aminosulfonyl, alkylaminosulphonyl or dialkylaminosulphonyl. In their turn, whenever appropriate, each of the above substitutents may be further substituted by one or more of the aforementioned groups.

Pharmaceutically acceptable salts of the compounds of formula (I) are the acid addition salts with inorganic or organic, e.g. nitric, hydrochloric, hydrobromic, sulphuric, perchloric, phosphoric, acetic, trifluoroacetic, propionic, glycolic, lacetic, oxalic, malonic, malic, maleic, tartaric, citric, benzoic, cinnamic, mandelic, methanesulphonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

Preferred embodiment compounds of the invention are the compounds of formula (I) wherein R is —COR' or —CONHR' and $R_1$ is R', —COR', —CONHR', —CONR'R", —$SO_2$R', —$SO_2$NHR' or —$SO_2$NR'R", wherein R' and R", the same or different, are selected from hydrogen or optionally substituted straight or branched $C_1$-$C_6$ alkyl, aryl, $C_3$-$C_6$ cycloalkyl and aryl $C_1$-$C_6$ alkyl or R' and R" taken together form a $C_4$-$C_6$ alkylene chain; Ra and Rb, the same or different, are selected from hydrogen or straight or branched $C_1$-$C_3$ alkyl or, taken together with the carbon atom to which they are bonded, Ra and Rb form a $C_3$-$C_6$ cycloalkyl group; Rc and Rd are both hydrogen atoms; m is 0 or 1; n is 0 or 1.

Another class of preferred embodiment compounds of the invention are the compounds of formula (I) wherein R is —COR' or —CONHR' and $R_1$ is R', —COR', —CONHR', —CONR'R", —$SO_2$R', —$SO_2$NHR' or —$SO_2$NR'R", wherein R' and R", the same or different, are selected from hydrogen or optionally substituted straight or branched $C_1$-$C_6$ alkyl, aryl, $C_3$-$C_6$ cycloalkyl and aryl $C_1$-$C_6$ alkyl or R' and R" taken together form a $C_4$-$C_6$ alkylene chain; Ra is hydrogen; Rb is a —$CH_2$OR' group wherein R' is as defined above; Rc and Rd are both hydrogen atoms; m is 0 or 1; n is 0.

Another class of preferred embodiment compounds of the invention are the compounds of formula (I) wherein R is —COR' or —CONHR' and $R_1$ is R', —COR', —CONHR', —CONR'R", —$SO_2$R', —$SO_2$NHR' or —$SO_2$NR'R", wherein R' and R", the same or different, are selected from hydrogen or optionally substituted straight or branched $C_1$-$C_6$ alkyl, aryl, $C_3$-$C_6$ cycloalkyl and aryl $C_1$-$C_6$ alkyl or R' and R" taken together form a $C_4$-$C_6$ alkylene chain; Ra, Rb, Rc and Rd are all hydrogen atoms; m and n are both 0.

Most preferred embodiment compounds of the invention are the compounds of formula (I) wherein R is —COR' or —CONHR' and $R_1$ is R', —COR', —CONHR', —CONR'R" or —$SO_2$R', wherein R' and R", the same or different, are selected from hydrogen or optionally substituted straight or branched $C_1$-$C_6$ alkyl, aryl, $C_3$-$C_6$ cycloalkyl and aryl $C_1$-$C_6$ alkyl or R' and R" taken together form a $C_4$-$C_6$ alkylene chain; Ra and Rb, the same or different, are selected from hydrogen or straight or branched $C_1$-$C_3$ alkyl or, taken together with the carbon atom to which they are bonded, Ra and Rb form a $C_3$-$C_6$ cycloalkyl group; Rc and Rd are both hydrogen atoms; m is 1; n is 0.

Most preferred embodiment compounds of the invention are the compounds of formula (I) wherein R is —COR' or —CONHR' and $R_1$ is R', —COR', —CONHR', —CONR'R" or —$SO_2$R', wherein R' and R", the same or different, are selected from hydrogen or optionally substituted straight or branched $C_1$-$C_6$ alkyl, aryl, $C_3$-$C_6$ cycloalkyl and aryl $C_1$-$C_6$ alkyl or R' and R" taken together form a $C_4$-$C_6$ alkylene chain; Ra and Rb, the same or different, are selected from hydrogen or straight or branched $C_1$-$C_3$ alkyl or, taken together with the carbon atom to which they are bonded, Ra and Rb form a $C_3$-$C_6$ cycloalkyl group; Rc and Rd are both hydrogen atoms; m is 0; n is 1.

Most preferred embodiment compounds of the invention are also the compounds of formula (I) wherein R is —COR' or —CONHR' and $R_1$ is R', —COR', —CONHR', —CONR'R", —$SO_2$R', —$SO_2$NHR' or —$SO_2$NR'R", wherein R' and R", the same or different, are selected from hydrogen or optionally substituted straight or branched $C_1$-$C_6$ alkyl, aryl, $C_3$-$C_6$ cycloalkyl and aryl $C_1$-$C_6$ alkyl or R' and R" taken together form a $C_4$-$C_6$ alkylene chain; m and n are both 0; each of Ra and Rb independently is hydrogen or $C_1$-$C_4$ alkyl or Ra and Rb, taken together with the carbon atom to which they are bonded form a $C_3$-$C_6$ cycloalkyl ring; and Rc and Rd are hydrogen.

Most preferred embodiment compounds of the invention are also the compounds of formula (I) wherein R is —COR' or —CONHR' and $R_1$ is R', —COR', —CONHR', —CONR'R'', —$SO_2$R', —$SO_2$NHR' or —$SO_2$NR'R'', wherein R' and R'', the same or different, are selected from hydrogen or optionally substituted straight or branched $C_1$-$C_6$ alkyl, aryl, $C_3$-$C_6$ cycloalkyl and aryl $C_1$-$C_6$ alkyl or R' and R'' taken together form a $C_4$-$C_6$ alkylene chain; m and n are both 0; Ra, Rb, Rc and Rd are hydrogen.

Specific, non limiting, examples of embodiment compounds of the invention, whenever appropriate in the form of pharmaceutically acceptable salts, are the following:

1. N-{5-phenylacetyl-4,6-dihydropyrrolo[3,4-c]pyrazol-3-yl}phenylacetamide;
2. N-{5-acetyl-4,6-dihydropyrrolo[3,4-c]pyrazol-3-yl}phenylacetamide;
3. N-benzyl-N'-{3-phenylacetamido-4,6-dihydropyrrolo[3,4-c]pyrazol-5-yl}urea;
4. N-{5-toluensulfonyl-4,6-dihydropyrrolo[3,4-c]pyrazol-3-yl}phenylacetamide;
5. N-ethyl-N'-{3-phenylacetamido-4,6-dihydropyrrolo[3,4-c]pyrazol-5-yl}urea;
6. N-{5-acetyl-4,6-dihydropyrrolo[3,4-c]pyrazol-3-yl}-4-(phenyl)phenylacetamide;
7. N-{5-acetyl-4,6-dihydropyrrolo[3,4-c]pyrazol-3-yl}-2-naphtylacetamide;
8. N-{5-acetyl-4,6-dihydropyrrolo[3,4-c]pyrazol-3-yl}-furan-2-carboxamide;
9. N-{5-acetyl-4,6-dihydropyrrolo[3,4-c]pyrazol-3-yl}-5-chlorothiophene-2-carboxamide;
10. N-{5-acetyl-4,6-dihydropyrrolo[3,4-c]pyrazol-3-yl}-6-chloronicotinamide;
11. N-{5-acetyl-4,6-dihydropyrrolo[3,4-c]pyrazol-3-yl}-benzofuran-2-carboxamide;
12. N-{5-acetyl-4,6-dihydropyrrolo[3,4-c]pyrazol-3-yl}-4-phenoxybenzamide;
13. N-{5-acetyl-4,6-dihydropyrrolo[3,4-c]pyrazol-3-yl}-4-tertbutylbenzamide;
14. N-{5-acetyl-4,6-dihydropyrrolo[3,4-c]pyrazol-3-yl}-piperonylamide;
15. N-{5-acetyl-4,6-dihydropyrrolo[3,4-c]pyrazol-3-yl}-[2-methyl-5-phenyl-furan-3-carboxamide;];
16. N-{5-acetyl-4,6-dihydropyrrolo[3,4-c]pyrazol-3-yl}-(quinoline-6-carboxamide;);
17. N-{5-acetyl-4,6-dihydropyrrolo[3,4-c]pyrazol-3-yl}-[5-(4-chlorophenyl)furan-2-carboxamide;];
18. N-{5-methansulfonyl-4,6-dihydropyrrolo[3,4-c]pyrazol-3-yl}-4-tertbutylbenzamide;
19. N-{5-benzensulfonyl-4,6-dihydropyrrolo[3,4-c]pyrazol-3-yl}-4-tertbutylbenzamide;
20. N-{5-benzoyl-4,6-dihydropyrrolo[3,4-c]pyrazol-3-yl}-4-tertbutylbenzamide;
21. N-{5-(1-naphthalene)sulfonyl-4,6-dihydropyrrolo[3,4-c]pyrazol-3-yl}-4-tertbutylbenzamide;
22. N-{5-(1-naphtoyl)-4,6-dihydropyrrolo[3,4-c]pyrazol-3-yl}-4-tertbutylbenzamide;
23. N-{5-phenylacetyl-4,6-dihydropyrrolo[3,4-c]pyrazol-3-yl}-4-tertbutylbenzamide;
24. N-phenyl-N'-{3-(4-tertbutyl-benzamido)-4,6-dihydropyrrolo[3,4-c]pyrazol-5-yl}urea;
25. N-isopropyl-N'-{3-(4-tertbutyl-benzamido)-4,6-dihydropyrrolo[3,4-c]pyrazol-5-yl}urea;
26. N-{5-methansulfonyl-4,6-dihydropyrrolo[3,4-c]pyrazol-3-yl}-4-phenoxylbenzamide;
27. N-{5-benzoyl-4,6-dihydropyrrolo[3,4-c]pyrazol-3-yl}-4-phenoxybenzamide;
28. N-{5-(1-naphtoyl)-4,6-dihydropyrrolo[3,4-c]pyrazol-3-yl}-4-phenoxybenzamide;
29. N-isopropyl-N'-{3-(4-phenoxy-benzamido)-4,6-dihydropyrrolo[3,4-c]pyrazol-5-yl}urea;
30. N-{5-acetyl-4,6-dihydropyrrolo[3,4-c]pyrazol-3-yl}-[2-(2-naphtyl)propionamide;];
31. N-isopropyl-N'-{3-piperonylcarboxamido-4,6-dihydropyrrolo[3,4-c]pyrazol-5-yl}urea;
32. N-cyclohexyl-N'-{3-(4-tertbutyl-benzamido)-4,6-dihydropyrrolo[3,4-c]pyrazol-5-yl}urea;
33. N-ethyl-N'-{3-(4-tertbutyl-benzamido)-4,6-dihydropyrrolo[3,4-c]pyrazol-5-yl}urea;
34. N-(2,6-diethylphenyl)-N'-{3-(4-tertbutyl-benzamido)-4,6-dihydropyrrolo[3,4-c]pyrazol-5-yl}urea;
35. N-cyclohexyl-N'-{3-(2-ethyl-butyramido)-4,6-dihydropyrrolo[3,4-c]pyrazol-5-yl}urea;
36. N-(2,6-diethylphenyl)-N'-{3-piperonylcarboxamido-4,6-dihydropyrrolo[3,4-c]pyrazol-5-yl}urea;
37. N-2-methoxyphenyl-N'-{3-(2-naphthalen-2-yl-propionamido)-4,6-dihydropyrrolo[3,4-c]pyrazol-5-yl}urea;
38. N-(1-phenyl)ethyl-N'-{3-(2-naphthalen-2-yl-propionamido)-4,6-dihydropyrrolo[3,4-c]pyrazol-5-yl}urea;
39. N-{5-phenylsulfonyl-4,6-dihydropyrrolo[3,4-c]pyrazol-3-yl}-3-(2-naphthalen-2-yl)-propionamide;
40. N-(2,5-dimethylphenyl)-N'-{3-(4-tertbutyl-benzamido)-4,6-dihydropyrrolo[3,4-c]pyrazol-5-yl}urea;
41. N-(2,5-dimethylphenyl)-N'-{3-(2-ethyl-butyramido)-4,6-dihydropyrrolo[3,4-c]pyrazol-5-yl}urea;
42. N-(4-fluorobenzyl)-N'-{3-(2-ethyl-butyramido)-4,6-dihydropyrrolo[3,4-c]pyrazol-5-yl}urea;
43. N-{5-benzylsulfonyl-4,6-dihydropyrrolo[3,4-c]pyrazol-3-yl}-4-tertbutylbenzamide;
44. N-2-chlorophenyl-N'-{3-(2-naphthalen-2-yl-propionamido)-4,6-dihydropyrrolo[3,4-c]pyrazol-5-yl}urea;
45. N-{5-aminocarbonyl-4,6-dihydropyrrolo[3,4-c]pyrazol-3-yl}-2-(2-naphtyl)propionamide;
46. N-{5-(3-methyl-butanoyl)-4,6-dihydropyrrolo[3,4-c]pyrazol-3-yl}-4-phenoxybenzamide;
47. N-{5-(2-phenyl-thiazol-yl)acetyl-4,6-dihydropyrrolo[3,4-c]pyrazol-3-yl}-4-phenoxybenzamide;
48. N-{5-(2-thienyl-acetyl)-4,6-dihydropyrrolo[3,4-c]pyrazol-3-yl}-4-tertbutylbenzamide;
49. N-{5-(3-pyridinyl-acetyl)-4,6-dihydropyrrolo[3,4-c]pyrazol-3-yl)}tertbutylbenzamide;
50. N-{5-benzylsulfonyl-4,6-dihydropyrrolo[3,4-c]pyrazol-3-yl}-4-phenoxybenzamide;
51. N-{5-(2-methylpropyl)carbonyl-4,6-dihydropyrrolo[3,4-c]pyrazol-3-yl}-4-tertbutylbenzamide;
52. N-{5-(2-phenyl-thiazol-4-yl)acetyl-4,6-dihydropyrrolo[3,4-c]pyrazol-3-yl}-4-tertbutylbenzamide;
53. N-{5-(2-thienyl)acetyl-4,6-dihydropyrrolo[3,4-c]pyrazol-3-yl}-4-phenoxybenzamide;
54. N-{5-(benzo[1,3]dioxol-5-yl)acetyl-4,6-dihydropyrrolo[3,4-c]pyrazol-3-yl}-3-methylbutanamide;
55. N-{5-(1-naphthalene)sulfonyl-4,6-dihydropyrrolo[3,4-c]pyrazol-3-yl}-cyclopropylcarboxamide;
56. N-{5-(2-methoxyphenyl)-4,6-dihydropyrrolo[3,4-c]pyrazol-3-yl}-3-(2-naphthalen-2-yl)-propionylamide;
57. N-{5-(2-furoyl)-4,6-dihydropyrrolo[3,4-c]pyrazol-3-yl}-3-(2-naphthalen-2-yl)-propionylamide;
58. N-{5-[5-(1-morfolinomethyl)furan-2-carbonyl]-4,6-dihydropyrrolo[3,4-c]pyrazol-3-yl}-4-tertbutylbenzamide;

59. N-{5-{4-[2-(1-pyrrolidinyl)ethoxy]phenyl}acetyl-4,6-dihydropyrrolo[3,4-c]pyrazol-3-yl}-4-tertbutylbenzamide;
60. N-{5-(1-H-benzotriazole-5-carbonyl)-4,6-dihydropyrrolo[3,4-c]pyrazol-3-yl}-4-tertbutylbenzamide;
61. N-{5-(pirrole-3-carbonyl)-4,6-dihydropyrrolo[3,4-c]pyrazol-3-yl}-4-tertbutylbenzamide;
62. N-{5-{4-[2-oxo-2-(1-pyrrolidinyl)ethoxy]phenyl}acetyl-4,6-dihydropyrrolo[3,4-c]pyrazol-3-yl}-4-phenoxybenzamide;
63. N-{5-(4-methylsulfonamido-phenyl)acetyl-4,6-dihydropyrrolo[3,4-c]pyrazol-3-yl}-4-phenoxybenzamide;
64. N-{5-[2-(6-oxo-1(6H)-pyridazinyl]acetyl-4,6-dihydropyrrolo[3,4-c]pyrazol-3-yl}-4-phenoxybenzamide;
65. N-{5-(3-carbamoylmethoxy-phenyl)acetyl-4,6-dihydropyrrolo[3,4-c]pyrazol-3-yl}-4-phenoxybenzamide;
66. N-{5-(4-carbamoylmethoxy-phenyl)acetyl-4,6-dihydropyrrolo[3,4-c]pyrazol-3-yl}-4-phenoxybenzamide;
67. N-{5-[4-(1-pirrolidinyl)phenyl]acetyl-4,6-dihydropyrrolo[3,4-c]pyrazol-3-yl}-4-phenoxybenzamide;
68. N-{5-carbamoyloxyacetyl-4,6-dihydropyrrolo[3,4-c]pyrazol-3-yl}-4-phenoxybenzamide;
69. N-{5-{4-[2-(4-methylpiperazin-2-yl)ethoxy]phenyl}acetyl-4,6-dihydropyrrolo[3,4-c]pyrazol-3-yl}-4-phenoxybenzamide;
70. N-{5-{4-[2-(1-pyrrolidinyl)ethoxy]phenyl}acetyl-4,6-dihydropyrrolo[3,4-c]pyrazol-3-yl}-4-phenoxybenzamide;
71. N-{5-{4-[2-oxo-2-(1-pyrrolidinyl)ethoxy]phenyl}acetyl-4,6-dihydropyrrolo[3,4-c]pyrazol-3-yl}-4-tertbutylbenzamide;
72. N-{5-(4-methylsulfonamido-phenyl)acetyl-4,6-dihydropyrrolo[3,4-c]pyrazol-3-yl}-4-tertbutylbenzamide;
73. N-{5-(pyridine-3-carbonyl-4,6-dihydropyrrolo[3,4-c]pyrazol-3-yl}-4-tertbutylbenzamide;
74. N-{5-(pyridine-3-carbonyl)-4,6-dihydropyrrolo[3,4-c]pyrazol-3-yl}-4-tertbutylbenzamide;
75. N-{5-(pyridine-4-carbonyl)-4,6-dihydropyrrolo[3,4-c]pyrazol-3-yl}-4-tertbutylbenzamide;
76. N-{5-(2-methyl-pyridine-3-carbonyl)-4,6-dihydropyrrolo[3,4-c]pyrazol-3-yl}-4-tertbutylbenzamide;
77. N-{5-(2-thiomethyl-pyridine-3-carbonyl)-4,6-dihydropyrrolo[3,4-c]pyrazol-3-yl}-4-tertbutylbenzamide;
78. N-{5-(pyrazine-2-carbonyl)-4,6-dihydropyrrolo[3,4-c]pyrazol-3-yl}-4-tertbutylbenzamide;
79. N-{5-(3-furoyl)-4,6-dihydropyrrolo[3,4-c]pyrazol-3-yl}-4-phenoxybenzamide;
80. N-{5-(2-thenoyl)-4,6-dihydropyrrolo[3,4-c]pyrazol-3-yl}-4-phenoxybenzamide;
81. N-{5-(7-methoxy-benzofuran-2-carbonyl)-4,6-dihydropyrrolo[3,4-c]pyrazol-3-yl}-4-tertbutylbenzamide;
82. N-{5-(benzofuran-2-carbonyl)-4,6-dihydropyrrolo[3,4-c]pyrazol-3-yl}-4-tertbutylbenzamide;
83. N-{5-(2-furoyl)-4,6-dihydropyrrolo[3,4-c]pyrazol-3-yl}-4-tertbutylbenzamide;
84. N-{5-(3-furoyl)-4,6-dihydropyrrolo[3,4-c]pyrazol-3-yl}-4-tertbutylbenzamide;
85. N-{5-(2-furoyl)-4,6-dihydropyrrolo[3,4-c]pyrazol-3-yl}-4-phenoxybenzamide;
86. N-{5-(3-thenoyl)-4,6-dihydropyrrolo[3,4-c]pyrazol-3-yl}-4-tertbutylbenzamide;
87. N-{5-(quinoxaline-2-carbonyl)-4,6-dihydropyrrolo[3,4-c]pyrazol-3-yl}-4-phenoxybenzamide;
88. N-{5-(2-thienyl)acetyl-4,6-dihydropyrrolo[3,4-c]pyrazol-3-yl}-4-tertbutylbenzamide;
89. N-{5-(quinoline-6-carbonyl)-4,6-dihydropyrrolo[3,4-c]pyrazol-3-yl}-4-tertbutylbenzamide;
90. N-{5-(3-furoyl)-4,6-dihydropyrrolo[3,4-c]pyrazol-3-yl}-4-phenoxybenzamide;
91. N-{5-(pyrazine-2-carbonyl)-4,6-dihydropyrrolo[3,4-c]pyrazol-3-yl}-4-phenoxybenzamide;
92. N-{5-[2-(6-oxo-1(6H)-pyridazinyl]acetyl-4,6-dihydropyrrolo[3,4-c]pyrazol-3-yl}-4-tertbutylbenzamide;
93. N-{5-(4-carbamoylmethoxy-phenyl)acetyl-4,6-dihydropyrrolo[3,4-c]pyrazol-3-yl}-4-tertbutylbenzamide;
94. N-{5-carbamoyloxyacetyl-4,6-dihydropyrrolo[3,4-c]pyrazol-3-yl}-4-tertbutylbenzamide;
95. N-{5-{4-[2-(4-methylpiperazin-2-yl)ethoxy]phenyl}acetyl-4,6-dihydropyrrolo[3,4-c]pyrazol-3-yl}-4-tertbutylbenzamide;
96. N-{5-(2-methylsulfonamidothiazole-4-carbonyl)-4,6-dihydropyrrolo[3,4-c]pyrazol-3-yl}-4-tertbutylbenzamide;
97. N-{5-(benzofuran-2-carbonyl)-4,6-dihydropyrrolo[3,4-c]pyrazol-3-yl}-4-phenoxybenzamide;
98. N-{5-(pyridine-2-carbonyl)-4,6-dihydropyrrolo[3,4-c]pyrazol-3-yl}4-phenoxybenzamide;
99. N-{5-(2-methyl-pyridine-3-carbonyl)-4,6-dihydropyrrolo[3,4-c]pyrazol-3-yl}-4-phenoxybenzamide;
100. N-{5-(quinoline-4-carbonyl)-4,6-dihydropyrrolo[3,4-c]pyrazol-3-yl}-4-phenoxybenzamide;
101. N-{5-[4-(1-pyrrolidin-2-on)benzoyl]-4,6-dihydropyrrolo[3,4-c]pyrazol-3-yl}-4-tertbutylbenzamide;
102. N-{5-phenylethyl-4,6-dihydropyrrolo[3,4-c]pyrazol-3-yl}-4-tertbutylbenzamide;
103. N-n-butyl-N'-{3-(2-naphthalen-2-yl-propionamido)-4,6-dihydropyrrolo[3,4-c]pyrazol-5-yl}urea;
104. N-isopropyl-N'-{3-(2-naphthalen-2-yl-propionamido)-4,6-dihydropyrrolo[3,4-c]pyrazol-5-yl}urea;
105. N-{5-ethylaminocarbonyl-4,6-dihydropyrrolo[3,4-c]pyrazol-3-yl}-2-naphtylpropionamide;
106. N-{5-ethoxycarbonyl-4,6-dihydropyrrolo[3,4-c]pyrazol-3-yl}-3-(2-naphthalen-2-yl)-propionamide;
107. N-{5-(3-methylbutyrroyl)-4,6-dihydropyrrolo[3,4-c]pyrazol-3-yl}-3-(2-naphthalen-2-yl)-propionylamide;
108. N-{5-aminocarbonylmethyl-4,6-dihydropyrrolo[3,4-c]pyrazol-3-yl}-3-(2-naphthalen-2-yl)-propionamide;
109. N-{5-(pyrrol-3-ylcarbonyl)-4,6-dihydropyrrolo[3,4-c]pyrazol-3-yl}-3-(2-naphthalen-2-yl)-propionamide;
110. N-{5-ethoxycarbonyl-4,6-dihydropyrrolo[3,4-c]pyrazol-3-yl)}tertbutylbenzamide;
111. N-{5-isopentyl-4,6-dihydropyrrolo[3,4-c]pyrazol-3-yl}-4-tertbutylbenzamide;
112. N-butyl-N'-{3-(4-tertbutyl-benzamido)-4,6-dihydropyrrolo[3,4-c]pyrazol-5-yl}urea;
113. N-{5-(indol-2-yl)carbonyl-4,6-dihydropyrrolo[3,4-c]pyrazol-3-yl}-4-tertbutylbenzamide;
114. N-{5-(1-methyl-indol-3-yl)acetyl-4,6-dihydropyrrolo[3,4-c]pyrazol-3-yl}-4-tertbutylbenzamide;
115. N-{5-[4-(1-imidazolylmethyl)benzoyl]-4,6-dihydropyrrolo[3,4-c]pyrazol-3-yl}-4-phenoxybenzamide;
116. N-{5-[4-(1-imidazolylmethyl)benzoyl]-4,6-dihydropyrrolo[3,4-c]pyrazol-3-yl}-4-phenoxybenzamide;
117. N-{5-[4-(1-pyrrolidin-2-on)benzoyl]-4,6-dihydropyrrolo[3,4-c]pyrazol-3-yl}-4-phenoxybenzamide;
118. N-{5-(2-morfolinomethyl-5-furoyl)-4,6-dihydropyrrolo[3,4-c]pyrazol-3-yl}-4-phenoxybenzamide;
119. N-{5-(5-acetylamino-2-furoyl)-4,6-dihydropyrrolo[3,4-c]pyrazol-3-yl}-3-(2-naphthalen-2-yl)-propionamide;
120. N-{5-(4-methyl-piperazin-1-yl)acetyl-4,6-dihydropyrrolo[3,4-c]pyrazol-3-yl}-3-(2-naphthalen-2-yl)-propionamide;
121. N-{5-(piperidin-1-yl)acetyl-4,6-dihydropyrrolo[3,4-c]pyrazol-3-yl}-3-(2-naphthalen-2-yl)-propionamide;

122. N-{5-(pirrolidin-1-ylcarbonyl)methyl-4,6-dihydropyrrolo[3,4-c]pyrazol-3-yl}-3-(2-naphthalen-2-yl)-propionamide;
123. N-{5-acetyl-4,6-hydropyrrolo[3,4-c]pyrazol-3-yl}-(4-pyrrolidin-1-yl)phenylacetamide;
124. N-{5-acetyl-4,6-dihydropyrrolo[3,4-c]pyrazol-3-yl}-2-((4-pyrrolidin-1-yl)phenyl)propionamide;
125. N-{5-acetyl-4,6-dihydropyrrolo[3,4-c]pyrazol-3-yl}-(4-(2-oxo-pyrrolidin-1-yl)phenyl)acetamide;
126. N-{5-acetyl-4,6-dihydropyrrolo[3,4-c]pyrazol-3-yl}-2-(4-(2-oxo-pyrrolidin-1-yl)phenyl)propionamide;
127. N-2-methoxyphenyl-N'-{2-[4-(2-oxo-pyrrolidin-1-yl)phenyl]-propionamido-4,6-dihydropyrrolo[3,4-c]pyrazol-5-yl}urea;
128. N-2,4-difluorophenyl-N'-{2-[4-(2-oxo-pyrrolidin-1-yl)phenyl]-propionamido-4,6-dihydropyrrolo[3,4-c]pyrazol-5-yl}urea;
129. N-(1-phenyl)ethyl-N'-{2-[4-(2-oxo-pyrrolidin-1-yl)phenyl]-propionamido-4,6-dihydropyrrolo[3,4-c]pyrazol-5-yl}urea;
130. N-2-methoxyphenyl-N'-{2-(4-pyrrolidin-1-yl-phenyl)-propionamido-4,6-dihydropyrrolo[3,4-c]pyrazol-5-yl}urea;
131. N-2,4-difluorophenyl-N'-{2-(4-pyrrolidin-1-yl-phenyl)-propionamido-4,6-dihydropyrrolo[3,4-c]pyrazol-5-yl}urea;
132. N-(1-phenyl)ethyl-N'-{2-(4-pyrrolidin-1-yl-phenyl)-propionamido-4,6-dihydropyrrolo[3,4-c]pyrazol-5-yl}urea;
133. N-{5-phenylsulfonyl-4,6-dihydropyrrolo[3,4-c]pyrazol-3-yl}-2-(4-pyrrolidin-1-yl-phenyl)-propionamide;
134. N-2-methoxyphenyl-N'-{[4-(2-oxo-pyrrolidin-1-yl)-phenyl]-acetamido-4,6-dihydropyrrolo[3,4-c]pyrazol-5-yl}urea;
135. N-2-chlorophenyl-N'-{[4-(2-oxo-pyrrolidin-1-yl)-phenyl]-acetamido-4,6-dihydropyrrolo[3,4-c]pyrazol-5-yl}urea;
136. N-(1-phenyl)ethyl-N'-{[4-(2-oxo-pyrrolidin-1-yl)-phenyl]-acetamido-4,6-dihydropyrrolo[3,4-c]pyrazol-5-yl}urea;
137. N-n-butyl-N'-{[4-(2-oxo-pyrrolidin-1-yl)-phenyl]-acetamido-4,6-dihydropyrrolo[3,4-c]pyrazol-5-yl}urea;
138. N-{5-phenulsulfonyl-4,6-dihydropyrrolo[3,4-c]pyrazol-3-yl}-4-(2-oxo-pyrrolidin-1-yl)-phenyl-acetamide;
139. N-n-butyl-N'-{2-[4-(2-oxo-pyrrolidin-1-yl)phenyl]-propionamido-4,6-dihydropyrrolo[3,4-c]pyrazol-5-yl}urea;
140. N-{5-phenylsulfonyl-4,6-dihydropyrrolo[3,4-c]pyrazol-3-yl}-2-[4-(2-oxo-pyrrolidin-1-yl)-phenyl]-propionamide;
141. N-{5-aminocarbonyl-4,6-dihydropyrrolo[3,4-c]pyrazol-3-yl}-4-(2-oxo-pyrrolidin-1-yl)-phenyl-acetamide;
142. N-n-butyl-N'-{2-(4-pyrrolidin-1-yl-phenyl)-propionamido-4,6-dihydropyrrolo[3,4-c]pyrazol-5-yl}urea;
143. N-{5-aminocarbonyl-4,6-dihydropyrrolo[3,4-c]pyrazol-3-yl}-2-(4-pyrrolidin-1-yl-phenyl)-propionamide;
144. N-2-methoxyphenyl-N'-{(4-pyrrolidin-1-yl-phenyl)-acetamido-4,6-dihydropyrrolo[3,4-c]pyrazol-5-yl}urea;
145. N-2-chlorophenyl-N'-{(4-pyrrolidin-1-yl-phenyl)-acetamido-4,6-dihydropyrrolo[3,4-c]pyrazol-5-yl}urea;
146. N-(1-phenyl)ethyl-N'-{(4-pyrrolidin-1-yl-phenyl)-acetamido-4,6-dihydropyrrolo[3,4-c]pyrazol-5-yl}urea;
147. N-n-butyl-N'-{(4-pyrrolidin-1-yl-phenyl)-acetamido-4,6-dihydropyrrolo[3,4-c]pyrazol-5-yl}urea;
148. N-{5-phenylsulfonyl-4,6-dihydropyrrolo[3,4-c]pyrazol-3-yl}-(4-pyrrolidin-1-yl-phenyl)-acetamide;
149. N-ethyl-N'-{[4-(2-oxo-pyrrolidin-1-yl)-phenyl]-acetamido-4,6-dihydropyrrolo[3,4-c]pyrazol-5-yl}urea;
150. N-i-propyl-N'-{[4-(2-oxo-pyrrolidin-1-yl)-phenyl]-acetamido-4,6-dihydropyrrolo[3,4-c]pyrazol-5-yl}urea;
151. N-{5-(2-furoyl)-4,6-dihydropyrrolo[3,4-c]pyrazol-3-yl}-4-(2-oxo-pyrrolidin-1-yl)-phenyl-acetamide;
152. N-{5-(2-methoxyphenyl)-4,6-dihydropyrrolo[3,4-c]pyrazol-3-yl}-4-(2-oxo-pyrrolidin-1-yl)-phenyl-acetamide;
153. N-{5-aminocarboylmethyl-4,6-dihydropyrrolo[3,4-c]pyrazol-3-yl}-4-(2-oxo-pyrrolidin-1-yl)-phenyl-acetamide;
154. N-i-propyl-N'-{(4-pyrrolidin-1-yl-phenyl)-acetamido-4,6-dihydropyrrolo[3,4-c]pyrazol-5-yl)}urea;
155. N-ethyl-N'-{(4-pyrrolidin-1-yl-phenyl)-acetamido-4,6-dihydropyrrolo[3,4-c]pyrazol-5-yl}urea;
156. N-{5-aminocarbonylmethyl-4,6-dihydropyrrolo[3,4-c]pyrazol-3-yl}-(4-pyrrolidin-1-yl-phenyl)-acetamide;
157. N-{5-(3-methylbutyrroyl)-4,6-dihydropyrrolo[3,4-c]pyrazol-3-yl}-4-(2-oxo-pyrrolidin-1-yl)-phenyl-acetamide;
158. N-n-butyl-N'-{3-(naphth-2-yl)acetamido-4,6-dihydropyrrolo[3,4-c]pyrazol-5-yl}urea;
159. N-n-butyl-N'-{3-(3-methyl-phenyl)acetamido)-4,6-dihydropyrrolo[3,4-c]pyrazol-5-yl}urea;
160. N-n-butyl-N'-{3-(3-fluoro-phenyl)acetamido)-4,6-dihydropyrrolo[3,4-c]pyrazol-5-yl}urea;
161. N-n-butyl-N'-{3-(3-pyridyl)acetamido-4,6-dihydropyrrolo[3,4-c]pyrazol-5-yl}urea;
162. N-n-butyl-N'-{3-(bicyclo[4.2.0]octa-1,3,5-triene-7-carboxamido)-4,6-dihydropyrrolo[3,4-c]pyrazol-5-yl}urea;
163. N-n-butyl-N'-{3-phenoxyacetamido-4,6-dihydropyrrolo[3,4-c]pyrazol-5-yl}urea;
164. N-n-butyl-N'-{3-(4-methyl-phenyl)acetamido)-4,6-dihydropyrrolo[3,4-c]pyrazol-5-yl}urea;
165. N-n-butyl-N'-{3-(4-fluoro-phenyl)acetamido)-4,6-dihydropyrrolo[3,4-c]pyrazol-5-yl}urea;
166. N-n-butyl-N'-{3-(3,4-difluoro-phenyl)acetamido)-4,6-dihydropyrrolo[3,4-c]pyrazol-5-yl}urea;
167. N-n-butyl-N'-{3-(4-trifluoromethoxy-phenyl)acetamido)-4,6-dihydropyrrolo[3,4-c]pyrazol-5-yl}urea;
168. N-n-butyl-N'-{3-(2-methyl-phenyl)acetamido)-4,6-dihydropyrrolo[3,4-c]pyrazol-5-yl}urea;
169. N-n-butyl-N'-{3-(2-bromo-phenyl)acetamido)-4,6-dihydropyrrolo[3,4-c]pyrazol-5-yl}urea;
170. N-n-butyl-N'-{3-(2,5-difluoro-phenyl)acetamido)-4,6-dihydropyrrolo[3,4-c]pyrazol-5-yl}urea;
171. N-n-butyl-N'-{3-(4-(pyrrolidin-1-yl-carbonylmethyloxy)-phenyl)acetamido)-4,6-dihydropyrrolo[3,4-c]pyrazol-5-yl}urea;
172. N-n-butyl-N'-{3-(3-(aminocarbonylmethyloxy)-phenyl)acetamido)-4,6-dihydropyrrolo[3,4-c]pyrazol-5-yl}urea;
173. N-n-butyl-N'-{3-(pyrid-4-yl-acetamido)-4,6-dihydropyrrolo[3,4-c]pyrazol-5-yl}urea;
174. N-n-butyl-N'-{3-(4-(morpholin-1-yl)-phenyl)acetamido)-4,6-dihydropyrrolo[3,4-c]pyrazol-5-yl}urea;
175. N-n-butyl-N'-{3-(2-fluoro-phenyl)acetamido)-4,6-dihydropyrrolo[3,4-c]pyrazol-5-yl}urea;
176. N-n-butyl-N'-{3-(3,5-difluoro-phenyl)acetamido)-4,6-dihydropyrrolo[3,4-c]pyrazol-5-yl}urea;
177. N-n-butyl-N'-{3-(6-oxo-6H-pyridazin-1-yl)acetamido)-4,6-dihydropyrrolo[3,4-c]pyrazol-5-yl}urea;
178. N-{5-picolinoyl-4,6-dihydropyrrolo[3,4-c]pyrazol-3-yl}-4-(2-oxo-oxazolidin-3-yl)-phenyl-acetamide;

179. N-{5-(thien-2-yl)acetyl-4,6-dihydropyrrolo[3,4-c]pyrazol-3-yl}-4-(2-oxo-oxazolidin-3-yl)-phenyl-acetamide;
180. N-{5-(2-furoyl)-4,6-dihydropyrrolo[3,4-c]pyrazol-3-yl}-4-(2-oxo-oxazolidin-3-yl)-phenyl-acetamide;
181. N-{5-ethoxyacetyl-4,6-dihydropyrrolo[3,4-c]pyrazol-3-yl}-4-(2-oxo-oxazolidin-3-yl)-phenyl-acetamide;
182. N-{5-(3-methyl-butyrroyl)-4,6-dihydropyrrolo[3,4-c]pyrazol-3-yl}-4-(2-oxo-oxazolidin-3-yl)-phenyl-acetamide;
183. N-{5-butyrroyl-4,6-dihydropyrrolo[3,4-c]pyrazol-3-yl}-4-(2-oxo-oxazolidin-3-yl)-phenyl-acetamide;
184. N-isopropyl-N'-{3-[4-(2-oxo-oxazolidin-3-yl)-phenyl-acetamido)]-4,6-dihydropyrrolo[3,4-c]pyrazol-5-yl}urea;
185. N-(n-butyl)-N'-{3-[4-(2-oxo-oxazolidin-3-yl)-phenyl-acetamido)]-4,6-dihydropyrrolo[3,4-c]pyrazol-5-yl}urea;
186. N-{5-ethoxycarbonyl-4,6-dihydropyrrolo[3,4-c]pyrazol-3-yl}-4-(2-oxo-oxazolidin-3-yl)-phenyl-acetamide;
187. N-isopropyl-N'-{3-[2-(3-oxo-3,4,4a,8a-tetrahydro-2H-benzo[1,4]oxazin-6-yl)acetamido]-4,6-dihydropyrrolo[3,4-c]pyrazol-5-yl}urea;
188. N-isopropyl-N'-{3-(3-bromo-benzamido)-4,6-dihydropyrrolo[3,4-c]pyrazol-5-yl}urea;
189. N-{5-benzensulfonyl-4,&dihydropyrrolo[3,4-c]pyrazol-3-yl}-3-bromobenzamide;
190. N-{5-acetyl-4,6-dihydropyrrolo[3,4-c]pyrazol-3-yl}-[4-(1-pyrrolidin-2-one)benzamide;];
191. N-ethyl-N'-{3-(3-bromo-benzamido)-4,6-dihydropyrrolo[3,4-c]pyrazol-5-yl}urea
192. N-{5-(8-quinoline)sulfonyl-4,6-dihydropyrrolo[3,4-c]pyrazol-3-yl}-p-toluic amide;
193. N-phenyl-N'-{3-(3-bromo-benzamido)-4,6-dihydropyrrolo[3,4-c]pyrazol-5-yl}urea;
194. N-{5-phenylacetyl-4,6-dihydropyrrolo[3,4-c]pyrazol-3-yl}-3-bromobenzamide;
195. N-{5-methansulfonyl-4,6-dihydropyrrolo[3,4-c]pyrazol-3-yl}-3-bromobenzamide;
196. N-isopropyl-N'-{3-[4-(1-pyrrolidin-2-on)benzamido]-4,6-dihydropyrrolo[3,4-c]pyrazol-5-yl}urea;
197. N-{5-(8-quinoline)carbonyl-4,6-dihydropyrrolo[3,4-c]pyrazol-3-yl}-p-toluic amide;
198. N-{5-(1-naphthalene)sulfonyl-4,6-dihydropyrrolo[3,4-c]pyrazol-3-yl}-4-phenylbenzamide;
199. N-{5-(1-naphtoyl)-4,6-dihydropyrrolo[3,4-c]pyrazol-3-yl}-4-phenylbenzamide;
200. N-{5-(1-naphtoyl)-4,6-dihydropyrrolo[3,4-c]pyrazol-3-yl}-4-phenoxybenzamide;
201. N-phenyl-N'-{3-(4-phenyl-benzamido)-4,6-dihydropyrrolo[3,4-c]pyrazol-5-yl}urea;
202. N-{5-phenylacetyl-4,6-dihydropyrrolo[3,4-c]pyrazol-3-yl}-4-phenylbenzamide;
203. N-{5-(1-naphthalene)sulfonyl-4,6-dihydropyrrolo[3,4-c]pyrazol-3-yl}-p-toluic amide;
204. N-{5-(1-naphtoyl)-4,6-dihydropyrrolo[3,4-c]pyrazol-3-yl}-p-toluic amide;
205. N-{5-acetyl-4,6-dihydropyrrolo[3,4-c]pyrazol-3-yl}-3-phenoxybenzamide;
206. N-[5-(4-chloro-2,5-difluorobenzoyl)-4,6-dihydropyrrolo[3,4-c]pyrazol-3-yl]-2-(2-naphthyl)acetamide;
207. N-{5-[tert-butyl carboxylate]-4,6-dihydropyrrolo[3,4-c]pyrazol-3-yl}-2-(2-naphthyl)acetamide;
208. N-{5-[(1-methylcyclopropyl)carbonyl]-4,6-dihydropyrrolo[3,4-c]pyrazol-3-yl}-2-(2-naphthyl)acetamide;
209. N-[5-(cyclobutylcarbonyl)-4,6-dihydropyrrolo[3,4-c]pyrazol-3-yl]-2-(2-naphthyl)acetamide;
210. N-[5-(2-fluorobenzoyl)-4,6-dihydropyrrolo[3,4-c]pyrazol-3-yl]-2-(2-naphthyl)acetamide;
211. N-[5-(pyridin-3-ylcarbonyl)-4,6-dihydropyrrolo[3,4-c]pyrazol-3-yl]-2-(2-naphthyl)acetamide;
212. N-{5-[(2,2,3,3-tetramethylcyclopropyl)carbonyl]-4,6-dihydropyrrolo[3,4-c]pyrazol-3-yl}-2-(2-naphthyl)acetamide;
213. N-[5-(2,4,5-trifluorobenzoyl)-4,6-dihydropyrrolo[3,4-c]pyrazol-3-yl]-2-(2-naphthyl)acetamide;
214. N-[5-(2-methylpent-4-enoyl)-4,6-dihydropyrrolo[3,4-c]pyrazol-3-yl]-2-(2-naphthyl)acetamide;
215. N-[5-(cyclopropylacetyl)-4,6-dihydropyrrolo[3,4-c]pyrazol-3-yl]-2-(2-naphthyl)acetamide;
216. N-[5-(5-fluoro-2-methylbenzoyl)-4,6-dihydropyrrolo[3,4-c]pyrazol-3-yl]-2-(2-naphthyl)acetamide;
217. N-{5-[2-fluoro-5-(trifluoromethyl)benzoyl]-4,6-dihydropyrrolo[3,4-c]pyrazol-3-yl}-2-(2-naphthyl)acetamide;
218. N-{5-[(3-methoxycyclohexyl)carbonyl]-4,6-dihydropyrrolo[3,4-c]pyrazol-3-yl}-2-(2-naphthyl)acetamide;
219. N-[5-(2,4-dichloro-5-fluorobenzoyl)-4,6-dihydropyrrolo[3,4-c]pyrazol-3-yl]-2-(2-naphthyl)acetamide;
220. N-[5-(2-chloro-4,5-difluorobenzoyl)-4,6-dihydropyrrolo[3,4-c]pyrazol-3-yl]-2-(2-naphthyl)acetamide;
221. N-{5-[4-(1H-imidazol-1-yl)benzoyl]-4,6-dihydropyrrolo[3,4-c]pyrazol-3-yl}-2-(2-naphthyl)acetamide;
222. N-{5-[4-(aminosulfonyl)butanoyl]-4,6-dihydropyrrolo[3,4-c]pyrazol-3-yl}-2-(2-naphthyl)acetamide;
223. N-{5-[(8-oxo-5,6,7,8-tetrahydronaphthalen-2-yl)carbonyl]-4,6-dihydropyrrolo[3,4-c]pyrazol-3-yl}-2-(2-naphthyl)acetamide;
224. N-(5-pyruvoyl-4,6-dihydropyrrolo[3,4-c]pyrazol-3-yl)-2-(2-naphthyl)acetamide;
225. N-[5-(2,2-dimethylpropanoyl)-4,6-dihydropyrrolo[3,4-c]pyrazol-3-yl]-2-(2-naphthyl)acetamide;
226. N-(5-but-2-ynoyl-4,6-dihydropyrrolo[3,4-c]pyrazol-3-yl)-2-(2-naphthyl)acetamide;
227. N-[5-(3-iodo-4-methylbenzoyl)-4,6-dihydropyrrolo[3,4-c]pyrazol-3-yl]-2-(2-naphthyl)acetamide;
228. N-{5-[(benzyloxy)acetyl]-4,6-dihydropyrrolo[3,4-c]pyrazol-3-yl}-2-(2-naphthyl)acetamide;
229. N-{5-(2-fluoro-2-phenylacetyl)-4,6-dihydropyrrolo[3,4-c]pyrazol-3-yl}-4-tertbutylbenzamide;
230. N-{5-(2-fluoro-2-phenylacetyl)-4,6-dihydropyrrolo[3,4-c]pyrazol-3-yl}-4-phenoxybenzamide;
231. N-{5-(2-thienyl-acetyl)-4,6-dihydropyrrolo[3,4-c]pyrazol-3-yl}-4-(4-methylpiperazino)benzamide;
232. N-{5-(3-methyl-butanoyl)-4,6-dihydropyrrolo[3,4-c]pyrazol-3-yl}-4-(4-methylpiperazino)benzamide;
233. N-{5-(2-furoyl)-4,6-dihydropyrrolo[3,4-c]pyrazol-3-yl}-4-(4-methylpiperazino)benzamide;
234. N-{5-phenylacetyl-4,6-dihydropyrrolo[3,4-c]pyrazol-3-yl}(4-methylpiperazino)benzamide;
235. N-{5-benzenesulfonyl-4,6-dihydropyrrolo[3,4-c]pyrazol-3-yl}-4-(4-methylpiperazino)benzamide;
236. N-(2,6-diethylphenyl)-N'-{3-[4-(4-methylpiperazino)benzamide;]-4,6-dihydropyrrolo[3,4-c]pyrazol-5-yl}urea;
237. N-ethyl-N'-{3-[4-(4-methylpiperazino)benzamide;]-4,6-dihydropyrrolo[3,4-c]pyrazol-5-yl}urea;
238. N-{5-(2-fluoro-2-phenylacetyl)-4,6-dihydropyrrolo[3,4-c]pyrazol-3-yl}-[4-(1-pyrrolidin-2-one)benzamide;];
239. N-{5-(2-fluoro-2-phenylacetyl)-4,6-dihydropyrrolo[3,4-c]pyrazol-3-yl}-4-(4-methylpiperazino)benzamide;
240. N-{5-(2-thienyl-acetyl)-4,6-dihydropyrrolo[3,4-c]pyrazol-3-yl}-piperonylamide;
241. N-{5-(3-methyl-butanoyl)-4,6-dihydropyrrolo[3,4-c]pyrazol-3-yl}-piperonylamide;
242. N-{5-(2-furoyl)-4,6-dihydropyrrolo[3,4-c]pyrazol-3-yl}-piperonylamide;

243. N-{5-phenylacetyl-4,6-dihydropyrrolo[3,4-c]pyrazol-3-yl}-piperonylamide;
244. N-{5-benzenesulfonyl-4,6-dihydropyrrolo[3,4-c]pyrazol-3-yl}-piperonylamide;
245. N-{5-(2-trifluoromethyl)benzenesulfonyl-4,6-dihydropyrrolo[3,4-c]pyrazol-3-yl}-piperonylamide;
246. N-ethyl-N'-{3-piperonylcarboxamido-4,6-dihydropyrrolo[3,4-c]pyrazol-5-yl}urea;
247. N-{5-acetyl-4,6-dihydropyrrolo[3,4-c]pyrazol-3-yl}-acetamide;
248. N-{5-acetyl-4,6-dihydropyrrolo[3,4-c]pyrazol-3-yl}-cyclopropanecarboxamide;
249. N-{5-acetyl-4,6-dihydropyrrolo[3,4-c]pyrazol-3-yl}-isobutyramide;
250. N-{5-acetyl-4,6-dihydropyrrolo[3,4-c]pyrazol-3-yl}-cyclopentanecarboxamide;
251. N-{5-acetyl-4,6-dihydropyrrolo[3,4-c]pyrazol-3-yl}-benzamide;
252. N-{5-acetyl-4,6-dihydropyrrolo[3,4-c]pyrazol-3-yl}-picolinic amide;
253. N-{5-acetyl-4,6-dihydropyrrolo[3,4-c]pyrazol-3-yl}-nicotinic amide;
254. N-{5-acetyl-4,6-dihydropyrrolo[3,4-c]pyrazol-3-yl}-isonicotinic amide;
255. N-{5-acetyl-4,6-dihydropyrrolo[3,4-c]pyrazol-3-yl}-3-methyl-2-furoic amide;
256. N-{5-acetyl-4,6-dihydropyrrolo[3,4-c]pyrazol-3-yl}-thiophene-2-carboxamide;
257. N-{5-acetyl-4,6-dihydropyrrolo[3,4-c]pyrazol-3-yl}-thiophene-3-carboxamide;
258. N-{5-acetyl-4,6-dihydropyrrolo[3,4-c]pyrazol-3-yl}-o-toluic amide;
259. N-{5-acetyl-4,6-dihydropyrrolo[3,4-c]pyrazol-3-yl}-m-toluic amide;
260. N-{5-acetyl-4,6-dihydropyrrolo[3,4-c]pyrazol-3-yl}-p-toluic amide;
261. N-{5-acetyl-4,6-dihydropyrrolo[3,4-c]pyrazol-3-yl}-salicylic amide;
262. N-{5-acetyl-4,6-dihydropyrrolo[3,4-c]pyrazol-3-yl}-2-fluorobenzamide;
263. N-{5-acetyl-4,6-dihydropyrrolo[3,4-c]pyrazol-3-yl}-3-fluorobenzamide;
264. N-{5-acetyl-4,6-dihydropyrrolo[3,4-c]pyrazol-3-yl)}-4-fluorobenzamide;
265. N-{5-acetyl-4,6-dihydropyrrolo[3,4-c]pyrazol-3-yl}-thiophene-2-acetamide;
266. N-{5-acetyl-4,6-dihydropyrrolo[3,4-c]pyrazol-3-yl}-thiophene-3-acetamide;
267. N-{5-acetyl-4,6-dihydropyrrolo[3,4-c]pyrazol-3-yl}-phenylpropiolic amide;
268. N-{5-acetyl-4,&dihydropyrrolo[3,4-c]pyrazol-3-yl}-3-cyanobenzamide;
269. N-{5-acetyl-4,6-dihydropyrrolo[3,4-c]pyrazol-3-yl}-4-cyanobenzamide;
270. N-{5-acetyl-4,6-dihydropyrrolo[3,4-c]pyrazol-3-yl}-trans-cinnamic amide;
271. N-{5-acetyl-4,6-dihydropyrrolo[3,4-c]pyrazol-3-yl}-cis-cinnamic amide;
272. N-{5-acetyl-4,6-dihydropyrrolo[3,4-c]pyrazol-3-yl}-3-(3-pyridyl)acrylic amide;
273. N-{5-acetyl-4,6-dihydropyrrolo[3,4-c]pyrazol-3-yl}-3-(4-pyridyl)-acrylic amide;
274. N-{5-acetyl-4,6-dihydropyrrolo[3,4-c]pyrazol-3-yl}-2-phenylpropionamide;
275. N-{5-acetyl-4,6-dihydropyrrolo[3,4-c]pyrazol-3-yl}-o-tolylacetamide;
276. N-{5-acetyl-4,6-dihydropyrrolo[3,4-c]pyrazol-3-yl}-m-tolylacetamide;
277. N-{5-acetyl-4,6-dihydropyrrolo[3,4-c]pyrazol-3-yl}-p-tolylacetamide;
278. N-{5-acetyl-4,6-dihydropyrrolo[3,4-c]pyrazol-3-yl}-o-anisic amide;
279. N-{5-acetyl-4,6-dihydropyrrolo[3,4-c]pyrazol-3-yl}-3-methoxybenzamide;
280. N-{5-acetyl-4,6-dihydropyrrolo[3,4-c]pyrazol-3-yl}-p-anisic amide;
281. N-{5-acetyl-4,6-dihydropyrrolo[3,4-c]pyrazol-3-yl}-phenoxyacetamide;
282. N-{5-acetyl-4,6-dihydropyrrolo[3,4-c]pyrazol-3-yl}-2-fluorophenylacetamide;
283. N-{5-acetyl-4,6-dihydropyrrolo[3,4-c]pyrazol-3-yl}-3-fluorophenylacetamide;
284. N-{5-acetyl-4,6-dihydropyrrolo[3,4-c]pyrazol-3-yl)}-4-fluorophenylacetamide;
285. N-{5-acetyl-4,6-dihydropyrrolo[3,4-c]pyrazol-3-yl}-3-(2-thienyl)acrylic amide;
286. N-{5-acetyl-4,6-dihydropyrrolo[3,4-c]pyrazol-3-yl}-3-(3-thienyl)-acrylic amide;
287. N-{5-acetyl-4,6-dihydropyrrolo[3,4-c]pyrazol-3-yl}-3-(2-thienyl)propanoic amide;
288. N-{5-acetyl-4,6-dihydropyrrolo[3,4-c]pyrazol-3-yl}-2-chlorobenzamide;
289. N-{5-acetyl-4,6-dihydropyrrolo[3,4-c]pyrazol-3-yl}-3-chlorobenzamide;
290. N-{5-acetyl-4,6-dihydropyrrolo[3,4-c]pyrazol-3-yl}-4-chlorobenzamide;
291. N-{5-acetyl-4,6-dihydropyrrolo[3,4-c]pyrazol-3-yl}-1-piperidinepropionamide;
292. N-{5-acetyl-4,6-dihydropyrrolo[3,4-c]pyrazol-3-yl}-2-acetylbenzamide;
293. N-{5-acetyl-4,6-dihydropyrrolo[3,4-c]pyrazol-3-yl}-4-acetylbenzamide;
294. N-{5-acetyl-4,6-dihydropyrrolo[3,4-c]pyrazol-3-yl}-1-naphthoic amide;
295. N-{5-acetyl-4,6-dihydropyrrolo[3,4-c]pyrazol-3-yl}-2-naphthoic amide;
296. N-{5-acetyl-4,6-dihydropyrrolo[3,4-c]pyrazol-3-yl}-3-benzoylpropionamide;
297. N-{5-acetyl-4,6-dihydropyrrolo[3,4-c]pyrazol-3-yl}-4-acetamidobenzamide;
298. N-{5-acetyl-4,6-dihydropyrrolo[3,4-c]pyrazol-3-yl}-2,5-dimethoxybenzamide;
299. N-{5-acetyl-4,6-dihydropyrrolo[3,4-c]pyrazol-3-yl}-2,6-dimethoxybenzamide;
300. N-{5-acetyl-4,6-dihydropyrrolo[3,4-c]pyrazol-3-yl}-3,4-dimethoxybenzamide;
301. N-{5-acetyl-4,6-dihydropyrrolo[3,4-c]pyrazol-3-yl}-3,5-dimethoxybenzamide;
302. N-{5-acetyl-4,6-dihydropyrrolo[3,4-c]pyrazol-3-yl}-3-(2-thenoyl)-propionamide;
303. N-{5-acetyl-4,6-dihydropyrrolo[3,4-c]pyrazol-3-yl}-1-naphtylacetamide;
304. N-{5-acetyl-4,6-dihydropyrrolo[3,4-c]pyrazol-3-yl}-4-phenylbenzamide;
305. N-{5-benzyl-4,6-dihydropyrrolo[3,4-c]pyrazol-3-yl}-acetamide;
306. N-{5-benzyl-4,6-dihydropyrrolo[3,4-c]pyrazol-3-yl}-cyclopropanecarboxamide;
307. N-{5-benzyl-4,6-dihydropyrrolo[3,4-c]pyrazol-3-yl}-isobutyramide;
308. N-{5-benzyl-4,6-dihydropyrrolo[3,4-c]pyrazol-3-yl}-cyclopentanecarboxamide;

309. N-{5-benzyl-4,6-dihydropyrrolo[3,4-c]pyrazol-3-yl}-benzamide;
310. N-{5-benzyl-4,6-dihydropyrrolo[3,4-c]pyrazol-3-yl}-picolinic amide;
311. N-{5-benzyl-4,6-dihydropyrrolo[3,4-c]pyrazol-3-yl}-nicotinic amide;
312. N-{5-benzyl-4,6-dihydropyrrolo[3,4-c]pyrazol-3-yl}-isonicotinic amide;
313. N-{5-benzyl-4,6-dihydropyrrolo[3,4-c]pyrazol-3-yl}-3-methyl-2-furoic amide;
314. N-{5-benzyl-4,6-dihydropyrrolo[3,4-c]pyrazol-3-yl}-thiophene-2-carboxamide;
315. N-{5-benzyl-4,6-dihydropyrrolo[3,4-c]pyrazol-3-yl}-thiophene-3-carboxamide;
316. N-{5-benzyl-4,6-dihydropyrrolo[3,4-c]pyrazol-3-yl}-o-toluic amide;
317. N-{5-benzyl-4,6-dihydropyrrolo[3,4-c]pyrazol-3-yl}-m-toluic amide;
318. N-{5-benzyl-4,6-dihydropyrrolo[3,4-c]pyrazol-3-yl}-p-toluic amide;
319. N-{5-benzyl-4,6-dihydropyrrolo[3,4-c]pyrazol-3-yl}-phenylacetamide;
320. N-{5-benzyl-4,6-dihydropyrrolo[3,4-c]pyrazol-3-yl}-salicylic amide;
321. N-{5-benzyl-4,6-dihydropyrrolo[3,4-c]pyrazol-3-yl}-2-fluorobenzamide;
322. N-{5-benzyl-4,6-dihydropyrrolo[3,4-c]pyrazol-3-yl}-3-fluorobenzamide;
323. N-{5-benzyl-4,6-dihydropyrrolo[3,4-c]pyrazol-3-yl}-4-fluorobenzamide;
324. N-{5-benzyl-4,6-dihydropyrrolo[3,4-c]pyrazol-3-yl}-thiophene-2-acetamide;
325. N-{5-benzyl-4,6-dihydropyrrolo[3,4-c]pyrazol-3-yl}-thiophene-3-acetamide;
326. N-{5-benzyl-4,6-dihydropyrrolo[3,4-c]pyrazol-3-yl}-phenylpropiolic amide;
327. N-{5-benzyl-4,6-dihydropyrrolo[3,4-c]pyrazol-3-yl}-3-cyanobenzamide;
328. N-{5-benzyl-4,6-dihydropyrrolo[3,4-c]pyrazol-3-yl}-4-cyanobenzamide;
329. N-{5-benzyl-4,6-dihydropyrrolo[3,4-c]pyrazol-3-yl
330. N-{5-benzyl-4,6-dihydropyrrolo[3,4-c]pyrazol-3-yl}-cis-cinnamic amide;
331. N-{5-benzyl-4,6-dihydropyrrolo[3,4-c]pyrazol-3-yl}-3-(3-pyridyl)acrylic amide;
332. N-{5-benzyl-4,6-dihydropyrrolo[3,4-c]pyrazol-3-yl}-3-(4-pyridyl)-acrylic amide;
333. N-{5-benzyl-4,6-dihydropyrrolo[3,4-c]pyrazol-3-yl}-2-phenylpropionamide;
334. N-{5-benzyl-4,6-dihydropyrrolo[3,4-c]pyrazol-3-yl}-o-tolylacetamide;
335. N-{5-benzyl-4,6-dihydropyrrolo[3,4-c]pyrazol-3-yl}-m-tolylacetamide;
336. N-{5-benzyl-4,6-dihydropyrrolo[3,4-c]pyrazol-3-yl}-p-tolylacetamide;
337. N-{5-benzyl-4,6-dihydropyrrolo[3,4-c]pyrazol-3-yl}-o-anisic amide;
338. N-{5-benzyl-4,6-dihydropyrrolo[3,4-c]pyrazol-3-yl}-3-methoxybenzamide;
339. N-{5-benzyl-4,6-dihydropyrrolo[3,4-c]pyrazol-3-yl}-p-anisic amide;
340. N-{5-benzyl-4,6-dihydropyrrolo[3,4-c]pyrazol-3-yl}-phenoxyacetamide;
341. N-{5-benzyl-4,6-dihydropyrrolo[3,4-c]pyrazol-3-yl}-2-fluorophenylacetamide;
342. N-{5-benzyl-4,6-dihydropyrrolo[3,4-c]pyrazol-3-yl}-3-fluorophenylacetamide;
343. N-{5-benzyl-4,6-dihydropyrrolo[3,4-c]pyrazol-3-yl}-4-fluorophenylacetamide;
344. N-{5-benzyl-4,6-dihydropyrrolo[3,4-c]pyrazol-3-yl}-3-(2-thienyl)acrylic amide;
345. N-{5-benzyl-4,6-dihydropyrrolo[3,4-c]pyrazol-3-yl}-3-(3-thienyl)-acrylic amide;
346. N-{5-benzyl-4,6-dihydropyrrolo[3,4-c]pyrazol-3-yl}-3-(2-thienyl)propanoic amide;
347. N-{5-benzyl-4,6-dihydropyrrolo[3,4-c]pyrazol-3-yl}-2-chlorobenzamide;
348. N-{5-benzyl-4,6-dihydropyrrolo[3,4-c]pyrazol-3-yl}-3-chlorobenzamide;
349. N-{5-benzyl-4,6-dihydropyrrolo[3,4-c]pyrazol-3-yl}-4-chlorobenzamide;
350. N-{5-benzyl-4,6-dihydropyrrolo[3,4-c]pyrazol-3-yl}-1-piperidinepropionamide;
351. N-{5-benzyl-4,6-dihydropyrrolo[3,4-c]pyrazol-3-yl}-2-acetylbenzamide;
352. N-{5-benzyl-4,6-dihydropyrrolo[3,4-c]pyrazol-3-yl}-4-acetylbenzamide;
353. N-{5-benzyl-4,6-dihydropyrrolo[3,4-c]pyrazol-3-yl}-1-naphthoic amide;
354. N-{5-benzyl-4,6-dihydropyrrolo[3,4-c]pyrazol-3-yl}-2-naphthoic amide;
355. N-{5-benzyl-4,6-dihydropyrrolo[3,4-c]pyrazol-3-yl}-3-benzoylpropionamide;
356. N-{5-benzyl-4,6-dihydropyrrolo[3,4-c]pyrazol-3-yl}-4-acetamidobenzamide;
357. N-{5-benzyl-4,6-dihydropyrrolo[3,4-c]pyrazol-3-yl}-2,5-dimethoxybenzamide;
358. N-{5-benzyl-4,6-dihydropyrrolo[3,4-c]pyrazol-3-yl}-2,6-dimethoxybenzamide;
359. N-{5-benzyl-4,6-dihydropyrrolo[3,4-c]pyrazol-3-yl}-3,4-dimethoxybenzamide;
360. N-{5-benzyl-4,6-dihydropyrrolo[3,4-c]pyrazol-3-yl}-3,5-dimethoxybenzamide;
361. N-{5-benzyl-4,6-dihydropyrrolo[3,4-c]pyrazol-3-yl}-3-(2-thenoyl)-propionamide;
362. N-{5-benzyl-4,6-dihydropyrrolo[3,4-c]pyrazol-3-yl}-2-naphtylacetamide;
363. N-{5-benzyl-4,6-dihydropyrrolo[3,4-c]pyrazol-3-yl}-1-naphtylacetamide;
364. N-{5-benzyl-4,6-dihydropyrrolo[3,4-c]pyrazol-3-yl}-4-phenylbenzamide;
365. N-{5-phenylethyl-4,6-dihydropyrrolo[3,4-c]pyrazol-3-yl}-acetamide;
366. N-{5-phenylethyl-4,6-dihydropyrrolo[3,4-c]pyrazol-3-yl}-cyclopropanecarboxamide;
367. N-{5-phenylethyl-4,6-dihydropyrrolo[3,4-c]pyrazol-3-yl}-isobutyramide;
368. N-{5-phenylethyl-4,6-dihydropyrrolo[3,4-c]pyrazol-3-yl}-cyclopentanecarboxamide;
369. N-{5-phenylethyl-4,6-dihydropyrrolo[3,4-c]pyrazol-3-yl}-benzamide;
370. N-{5-phenylethyl-4,6-dihydropyrrolo[3,4-c]pyrazol-3-yl}-picolinic amide;
371. N-{5-phenylethyl-4,6-dihydropyrrolo[3,4-c]pyrazol-3-yl}-nicotinic amide;
372. N-{5-phenylethyl-4,6-dihydropyrrolo[3,4-c]pyrazol-3-yl}-isonicotinic amide;
373. N-{5-phenylethyl-4,6-dihydropyrrolo[3,4-c]pyrazol-3-yl}-3-methyl-2-furoic amide;
374. N-{5-phenylethyl-4,6-dihydropyrrolo[3,4-c]pyrazol-3-yl}-thiophene-2-carboxamide;
375. N-{5-phenylethyl-4,6-dihydropyrrolo[3,4-c]pyrazol-3-yl}-thiophene-3-carboxamide;

376. N-{5-phenylethyl-4,6-dihydropyrrolo[3,4-c]pyrazol-3-yl}-o-toluic amide;
377. N-{5-phenylethyl-4,6-dihydropyrrolo[3,4-c]pyrazol-3-yl}-m-toluic amide;
378. N-{5-phenylethyl-4,6-dihydropyrrolo[3,4-c]pyrazol-3-yl}-p-toluic amide;
379. N-{5-phenylethyl-4,6-dihydropyrrolo[3,4-c]pyrazol-3-yl}-phenylacetamide;
380. N-{5-phenylethyl-4,6-dihydropyrrolo[3,4-c]pyrazol-3-yl}-salicylic amide;
381. N-{5-phenylethyl-4,6-dihydropyrrolo[3,4-c]pyrazol-3-yl}-2-fluorobenzamide;
382. N-{5-phenylethyl-4,6-dihydropyrrolo[3,4-c]pyrazol-3-yl}-3-fluorobenzamide;
383. N-{5-phenylethyl-4,6-dihydropyrrolo[3,4-c]pyrazol-3-yl}-4-fluorobenzamide;
384. N-{5-phenylethyl-4,6-dihydropyrrolo[3,4-c]pyrazol-3-yl}-thiophene-2-acetamide;
385. N-{5-phenylethyl-4,6-dihydropyrrolo[3,4-c]pyrazol-3-yl}-thiophene-3-acetamide;
386. N-{5-phenylethyl-4,6-dihydropyrrolo[3,4-c]pyrazol-3-yl}-phenylpropiolic amide;
387. N-{5-phenylethyl-4,6-dihydropyrrolo[3,4-c]pyrazol-3-yl}-3-cyanobenzamide;
388. N-{5-phenylethyl-4,6-dihydropyrrolo[3,4-c]pyrazol-3-yl}-4-cyanobenzamide;
389. N-{5-phenylethyl-4,6-dihydropyrrolo[3,4-c]pyrazol-3-yl}-trans-cinnamic amide;
390. N-{5-phenylethyl-4,6-dihydropyrrolo[3,4-c]pyrazol-3-yl}-cis-cinnamic amide;
391. N-{5-phenylethyl-4,6-dihydropyrrolo[3,4-c]pyrazol-3-yl}-3-(3-pyridyl)acrylic amide;
392. N-{5-phenylethyl-4,6-dihydropyrrolo[3,4-c]pyrazol-3-yl}-3-(4-pyridyl)-acrylic amide;
393. N-{5-phenylethyl-4,6-dihydropyrrolo[3,4-c]pyrazol-3-yl}-2-phenylpropionamide;
394. N-{5-phenylethyl-4,6-dihydropyrrolo[3,4-c]pyrazol-3-yl}-o-tolylacetamide;
395. N-{5-phenylethyl-4,6-dihydropyrrolo[3,4-c]pyrazol-3-yl}-m-tolylacetamide;
396. N-{5-phenylethyl-4,6-dihydropyrrolo[3,4-c]pyrazol-3-yl}-p-tolylacetamide;
397. N-{5-phenylethyl-4,6-dihydropyrrolo[3,4-c]pyrazol-3-yl}-o-anisic amide;
398. N-{5-phenylethyl-4,6-dihydropyrrolo[3,4-c]pyrazol-3-yl}-3-methoxybenzamide;
399. N-{5-phenylethyl-4,6-dihydropyrrolo[3,4-c]pyrazol-3-yl}-p-anisic amide;
400. N-{5-phenylethyl-4,6-dihydropyrrolo[3,4-c]pyrazol-3-yl}-phenoxyacetamide;
401. N-{5-phenylethyl-4,6-dihydropyrrolo[3,4-c]pyrazol-3-yl}-2-fluorophenylacetamide;
402. N-{5-phenylethyl-4,6-dihydropyrrolo[3,4-c]pyrazol-3-yl}-3-fluorophenylacetamide;
403. N-{5-phenylethyl-4,6-dihydropyrrolo[3,4-c]pyrazol-3-yl}-4-fluorophenylacetamide;
404. N-{5-phenylethyl-4,6-dihydropyrrolo[3,4-c]pyrazol-3-yl}-3-(2-thienyl)acrylic amide;
405. N-{5-phenylethyl-4,6-dihydropyrrolo[3,4-c]pyrazol-3-yl}-3-(3-thienyl)-acrylic amide;
406. N-{5-phenylethyl-4,6-dihydropyrrolo[3,4-c]pyrazol-3-yl}-3-(2-thienyl)propanoic aide;
407. N-{5-phenylethyl-4,6-dihydropyrrolo[3,4-c]pyrazol-3-yl}-2-chlorobenzamide;
408. N-{5-phenylethyl-4,6-dihydropyrrolo[3,4-c]pyrazol-3-yl}-3-chlorobenzamide;
409. N-{5-phenylethyl-4,6-dihydropyrrolo[3,4-c]pyrazol-3-yl-}4-chlorobenzamide;
410. N-{5-phenylethyl-4,6-dihydropyrrolo[3,4-c]pyrazol-3-yl}-1-piperidinepropionamide;
411. N-{5-phenylethyl-4,6-dihydropyrrolo[3,4-c]pyrazol-3-yl}-2-acetylbenzamide;
412. N-{5-phenylethyl-4,6-dihydropyrrolo[3,4-c]pyrazol-3-yl}-4-acetylbenzamide;
413. N-{5-phenylethyl-4,6-dihydropyrrolo[3,4-c]pyrazol-3-yl}-1-naphthoic amide;
414. N-{5-phenylethyl-4,6-dihydropyrrolo[3,4-c]pyrazol-3-yl}-2-naphthoic amide;
415. N-{5-phenylethyl-4,6-dihydropyrrolo[3,4-c]pyrazol-3-yl}-3-benzoylpropionamide;
416. N-{5-phenylethyl-4,6-dihydropyrrolo[3,4-c]pyrazol-3-yl}-4-acetamidobenzamide;
417. N-{5-phenylethyl-4,6-dihydropyrrolo[3,4-c]pyrazol-3-yl}-2,5-dimethoxybenzamide;
418. N-{5-phenylethyl-4,6-dihydropyrrolo[3,4-c]pyrazol-3-yl}-2,6-dimethoxybenzamide;
419. N-{5-phenylethyl-4,6-dihydropyrrolo[3,4-c]pyrazol-3-yl}-3,4-dimethoxybenzamide;
420. N-{5-phenylethyl-4,6-dihydropyrrolo[3,4-c]pyrazol-3-yl}-3,5-dimethoxybenzamide;
421. N-{5-phenylethyl-4,6-dihydropyrrolo[3,4-c]pyrazol-3-yl}-3-(2-thenoyl)-propionamide;
422. N-{5-phenylethyl-4,6-dihydropyrrolo[3,4-c]pyrazol-3-yl}-2-naphtylacetamide;
423. N-{5-phenylethyl-4,6-dihydropyrrolo[3,4-c]pyrazol-3-yl}-1-naphtylacetamide;
424. N-{5-phenylethyl-4,6-dihydropyrrolo[3,4-c]pyrazol-3-yl}-4-phenylbenzamide;
425. N-{5-methansulfonyl-4,6-dihydropyrrolo[3,4-c]pyrazol-3-yl}-acetamide;
426. N-{5-methansulfonyl-4,6-dihydropyrrolo[3,4-c]pyrazol-3-yl}-cyclopropanecarboxamide;
427. N-{5-methansulfonyl-4,6-dihydropyrrolo[3,4-c]pyrazol-3-yl}-isobutyramide;
428. N-{5-methansulfonyl-4,6-dihydropyrrolo[3,4-c]pyrazol-3-yl}-cyclopentanecarboxamide;
429. N-{5-methansulfonyl-4,6-dihydropyrrolo[3,4-c]pyrazol-3-yl}-benzamide;
430. N-{5-methansulfonyl-4,6-dihydropyrrolo[3,4-c]pyrazol-3-yl}-picolinic amide;
431. N-{5-methansulfonyl-4,6-dihydropyrrolo[3,4-c]pyrazol-3-yl}-nicotinic amide;
432. N-{5-methansulfonyl-4,6-dihydropyrrolo[3,4-c]pyrazol-3-yl}-isonicotinic amide;
433. N-{5-methansulfonyl-4,6-dihydropyrrolo[3,4-c]pyrazol-3-yl}-3-methyl-2-furoic amide;
434. N-{5-methansulfonyl-4,6-dihydropyrrolo[3,4-c]pyrazol-3-yl}-thiophene-2-carboxamide;
435. N-{5-methansulfonyl-4,6-dihydropyrrolo[3,4-c]pyrazol-3-yl}-thiophene-3-carboxamide;
436. N-{5-methansulfonyl-4,6-dihydropyrrolo[3,4-c]pyrazol-3-yl}-o-toluic amide;
437. N-{5-methansulfonyl-4,6-dihydropyrrolo[3,4-c]pyrazol-3-yl}-m-toluic amide;
438. N-{5-methansulfonyl-4,6-dihydropyrrolo[3,4-c]pyrazol-3-yl}-p-toluic amide;
439. N-{5-methansulfonyl-4,6-dihydropyrrolo[3,4-c]pyrazol-3-yl}-phenylacetamide;
440. N-{5-methansulfonyl-4,6-dihydropyrrolo[3,4-c]pyrazol-3-yl}-salicylic amide;
441. N-{5-methansulfonyl-4,6-dihydropyrrolo[3,4-c]pyrazol-3-yl}-2-fluorobenzamide;

442. N-{5-methansulfonyl-4,6-dihydropyrrolo[3,4-c]pyrazol-3-yl}-3-fluorobenzamide;
443. N-{5-methansulfonyl-4,6-dihydropyrrolo[3,4-c]pyrazol-3-yl}-4-fluorobenzamide;
444. N-{5-methansulfonyl-4,6-dihydropyrrolo[3,4-c]pyrazol-3-yl}-thiophene-2-acetamide;
445. N-{5-methansulfonyl-4,6-dihydropyrrolo[3,4-c]pyrazol-3-yl}-thiophene-3-acetamide;
446. N-{5-methansulfonyl-4,6-dihydropyrrolo[3,4-c]pyrazol-3-yl}-phenylpropiolic amide;
447. N-{5-methansulfonyl-4,6-dihydropyrrolo[3,4-c]pyrazol-3-yl}-3-cyanobenzamide;
448. N-{5-methansulfonyl-4,6-dihydropyrrolo[3,4-c]pyrazol-3-yl}-4-cyanobenzamide;
449. N-{5-methansulfonyl-4,6-dihydropyrrolo[3,4-c]pyrazol-3-yl}-trans-cinnamic amide;
450. N-{5-methansulfonyl-4,6-dihydropyrrolo[3,4-c]pyrazol-3-yl}-cis-cinnamic amide;
451. N-{5-methansulfonyl-4,6-dihydropyrrolo[3,4-c]pyrazol-3-yl}-3-(3-pyridyl)acrylic amide;
452. N-{5-methansulfonyl-4,6-dihydropyrrolo[3,4-c]pyrazol-3-yl}-3-(4-pyridyl)-acrylic amide;
453. N-{5-methansulfonyl-4,6-dihydropyrrolo[3,4-c]pyrazol-3-yl}-2-phenylpropionamide;
454. N-{5-methansulfonyl-4,6-dihydropyrrolo[3,4-c]pyrazol-3-yl}-o-tolylacetamide;
455. N-{5-methansulfonyl-4,6-dihydropyrrolo[3,4-c]pyrazol-3-yl}-m-tolylacetamide;
456. N-{5-methansulfonyl-4,6-dihydropyrrolo[3,4-c]pyrazol-3-yl}-p-tolylacetamide;
457. N-{5-methansulfonyl-4,6-dihydropyrrolo[3,4-c]pyrazol-3-yl}-o-anisic amide;
458. N-{5-methansulfonyl-4,6-dihydropyrrolo[3,4-c]pyrazol-3-yl}-3-methoxybenzamide;
459. N-{5-methansulfonyl-4,6-dihydropyrrolo[3,4-c]pyrazol-3-yl}-p-anisic amide;
460. N-{5-methansulfonyl-4,6-dihydropyrrolo[3,4-c]pyrazol-3-yl}-phenoxyacetamide;
461. N-{5-methansulfonyl-4,6-dihydropyrrolo[3,4-c]pyrazol-3-yl}-2-fluorophenylacetamide;
462. N-{5-methansulfonyl-4,6-dihydropyrrolo[3,4-c]pyrazol-3-yl}-3-fluorophenylacetamide;
463. N-{5-methansulfonyl-4,6-dihydropyrrolo[3,4-c]pyrazol-3-yl}-4-fluorophenylacetamide;
464. N-{5-methansulfonyl-4,6-dihydropyrrolo[3,4-c]pyrazol-3-yl}-3-(2-thienyl)acrylic amide;
465. N-{5-methansulfonyl-4,6-dihydropyrrolo[3,4-c]pyrazol-3-yl}-3-(3-thienyl)-acrylic amide;
466. N-{5-methansulfonyl-4,6-dihydropyrrolo[3,4-c]pyrazol-3-yl}-3-(2-thienyl)propanoic amide;
467. N-{5-methansulfonyl-4,6-dihydropyrrolo[3,4-c]pyrazol-3-yl}-2-chlorobenzamide;
468. N-{5-methansulfonyl-4,6-dihydropyrrolo[3,4-c]pyrazol-3-yl}-3-chlorobenzamide;
469. N-{5-methansulfonyl-4,6-dihydropyrrolo[3,4-c]pyrazol-3-yl}-4-chlorobenzamide;
470. N-{5-methansulfonyl-4,6-dihydropyrrolo[3,4-c]pyrazol-3-yl}-1-piperidinepropionamide;
471. N-{5-methansulfonyl-4,6-dihydropyrrolo[3,4-c]pyrazol-3-yl}-2-acetylbenzamide;
472. N-{5-methansulfonyl-4,6-dihydropyrrolo[3,4-c]pyrazol-3-yl}-4-acetylbenzamide;
473. N-{5-methansulfonyl-4,6-dihydropyrrolo[3,4-c]pyrazol-3-yl}-1-naphthoic amide;
474. N-{5-methansulfonyl-4,6-dihydropyrrolo[3,4-c]pyrazol-3-yl}-2-naphthoic amide;
475. N-{5-methansulfonyl-4,6-dihydropyrrolo[3,4-c]pyrazol-3-yl}-3-benzoylpropionamide;
476. N-{5-methansulfonyl-4,6-dihydropyrrolo[3,4-c]pyrazol-3-yl}-4-acetamidobenzamide;
477. N-{5-methansulfonyl-4,6-dihydropyrrolo[3,4-c]pyrazol-3-yl}-2,5-dimethoxybenzamide;
478. N-{5-methansulfonyl-4,6-dihydropyrrolo[3,4-c]pyrazol-3-yl}-2,6-dimethoxybenzamide;
479. N-{5-methansulfonyl-4,6-dihydropyrrolo[3,4-c]pyrazol-3-yl}-3,4-dimethoxybenzamide;
480. N-{5-methansulfonyl-4,6-dihydropyrrolo[3,4-c]pyrazol-3-yl}-3,5-dimethoxybenzamide;
481. N-{5-methansulfonyl-4,6-dihydropyrrolo[3,4-c]pyrazol-3-yl}-3-(2-thenoyl)-propionamide;
482. N-{5-methansulfonyl-4,6-dihydropyrrolo[3,4-c]pyrazol-3-yl}-2-naphtylacetamide;
483. N-{5-methansulfonyl-4,6-dihydropyrrolo[3,4-c]pyrazol-3-yl}-1-naphtylacetamide;
484. N-{5-methansulfonyl-4,6-dihydropyrrolo[3,4-c]pyrazol-3-yl}-4-phenylbenzamide;
485. N-{5-ethylaminocarbonyl-4,6-dihydropyrrolo[3,4-c]pyrazol-3-yl}-acetamide;
486. N-{5-ethylaminocarbonyl-4,6-dihydropyrrolo[3,4-c]pyrazol-3-yl}-cyclopropanecarboxamide;
487. N-{5-ethylaminocarbonyl-4,6-dihydropyrrolo[3,4-c]pyrazol-3-yl}-isobutyramide;
488. N-{5-ethylaminocarbonyl-4,6-dihydropyrrolo[3,4-c]pyrazol-3-yl}-cyclopentanecarboxamide;
489. N-{5-ethylaminocarbonyl-4,6-dihydropyrrolo[3,4-c]pyrazol-3-yl}-benzamide;
490. N-{5-ethylaminocarbonyl-4,6-dihydropyrrolo[3,4-c]pyrazol-3-yl}-picolinic amide;
491. N-{5-ethylaminocarbonyl-4,6-dihydropyrrolo[3,4-c]pyrazol-3-yl}-nicotinic amide;
492. N-{5-ethylaminocarbonyl-4,6-dihydropyrrolo[3,4-c]pyrazol-3-yl}-isonicotinic amide;
493. N-{5-ethylaminocarbonyl-4,6-dihydropyrrolo[3,4-c]pyrazol-3-yl}-3-methyl-2-furoic amide;
494. N-{5-ethylaminocarbonyl-4,6-dihydropyrrolo[3,4-c]pyrazol-3-yl}-thiophene-2-carboxamide;
495. N-{5-ethylaminocarbonyl-4,6-dihydropyrrolo[3,4-c]pyrazol-3-yl}-thiophene-3-carboxamide;
496. N-{5-ethylaminocarbonyl-4,6-dihydropyrrolo[3,4-c]pyrazol-3-yl}-m-toluic amide;
497. N-{5-ethylaminocarbonyl-4,6-dihydropyrrolo[3,4-c]pyrazol-3-yl}-p-toluic amide;
498. N-{5-ethylaminocarbonyl-4,6-dihydropyrrolo[3,4-c]pyrazol-3-yl}-salicylic amide;
499. N-{5-ethylaminocarbonyl-4,6-dihydropyrrolo[3,4-c]pyrazol-3-yl}-2-fluorobenzamide;
500. N-{5-ethylaminocarbonyl-4,6-dihydropyrrolo[3,4-c]pyrazol-3-yl}-3-fluorobenzamide;
501. N-{5-ethylaminocarbonyl-4,6-dihydropyrrolo[3,4-c]pyrazol-3-yl}-4-fluorobenzamide;
502. N-{5-ethylaminocarbonyl-4,6-dihydropyrrolo[3,4-c]pyrazol-3-yl}-thiophene-2-acetamide;
503. N-{5-ethylaminocarbonyl-4,6-dihydropyrrolo[3,4-c]pyrazol-3-yl}-thiophene-3-acetamide;
504. N-{5-ethylaminocarbonyl-4,6-dihydropyrrolo[3,4-c]pyrazol-3-yl}-phenylpropiolic amide;
505. N-{5-ethylaminocarbonyl-4,6-dihydropyrrolo[3,4-c]pyrazol-3-yl}-3-cyanobenzamide;
506. N-{5-ethylaminocarbonyl-4,6-dihydropyrrolo[3,4-c]pyrazol-3-yl}-4-cyanobenzamide;
507. N-{5-ethylaminocarbonyl-4,6-dihydropyrrolo[3,4-c]pyrazol-3-yl}-trans-cinnamic amide;

508. N-{5-ethylaminocarbonyl-4,6-dihydropyrrolo[3,4-c]pyrazol-3-yl}-cis-cinnamic amide;
509. N-{5-ethylaminocarbonyl-4,6-dihydropyrrolo[3,4-c]pyrazol-3-yl}-3-(3-pyridyl)acrylic amide;
510. N-{5-ethylaminocarbonyl-4,6-dihydropyrrolo[3,4-c]pyrazol-3-yl}-3-(4-pyridyl)-acrylic amide;
511. N-{5-ethylaminocarbonyl-4,6-dihydropyrrolo[3,4-c]pyrazol-3-yl}-2-phenylpropionamide;
512. N-{5-ethylaminocarbonyl-4,6-dihydropyrrolo[3,4-c]pyrazol-3-yl}-o-tolylacetamide;
513. N-{5-ethylaminocarbonyl-4,6-dihydropyrrolo[3,4-c]pyrazol-3-yl}-m-tolylacetamide;
514. N-{5-ethylaminocarbonyl-4,6-dihydropyrrolo[3,4-c]pyrazol-3-yl}-p-tolylacetamide;
515. N-{5-ethylaminocarbonyl-4,6-dihydropyrrolo[3,4-c]pyrazol-3-yl}-o-anisic amide;
516. N-{5-ethylaminocarbonyl-4,6-dihydropyrrolo[3,4-c]pyrazol-3-yl}-3-methoxybenzamide;
517. N-{5-ethylaminocarbonyl-4,6-dihydropyrrolo[3,4-c]pyrazol-3-yl}-p-anisic amide;
518. N-{5-ethylaminocarbonyl-4,6-dihydropyrrolo[3,4-c]pyrazol-3-yl}-phenoxyacetamide;
519. N-{5-ethylaminocarbonyl-4,6-dihydropyrrolo[3,4-c]pyrazol-3-yl}-2-fluorophenylacetamide;
520. N-{5-ethylaminocarbonyl-4,6-dihydropyrrolo[3,4-c]pyrazol-3-yl}-3-fluorophenylacetamide;
521. N-{5-ethylaminocarbonyl-4,6-dihydropyrrolo[3,4-c]pyrazol-3-yl}-4-fluorophenylacetamide;
522. N-{5-ethylaminocarbonyl-4,6-dihydropyrrolo[3,4-c]pyrazol-3-yl}-3-(2-thienyl)acrylic amide;
523. N-{5-ethylaminocarbonyl-4,6-dihydropyrrolo[3,4-c]pyrazol-3-yl}-3-(3-thienyl)-acrylic amide;
524. N-{5-ethylaminocarbonyl-4,6-dihydropyrrolo[3,4-c]pyrazol-3-yl}-3-(2-thienyl)propanoic amide;
525. N-{5-ethylaminocarbonyl-4,6-dihydropyrrolo[3,4-c]pyrazol-3-yl}-2-chlorobenzamide;
526. N-{5-ethylaminocarbonyl-4,6-dihydropyrrolo[3,4-c]pyrazol-3-yl}-3-chlorobenzamide;
527. N-{5-ethylaminocarbonyl-4,6-dihydropyrrolo[3,4-c]pyrazol-3-yl}-4-chlorobenzamide;
528. N-{5-ethylaminocarbonyl-4,6-dihydropyrrolo[3,4-c]pyrazol-3-yl}-1-piperidinepropionamide;
529. N-{5-ethylaminocarbonyl-4,6-dihydropyrrolo[3,4-c]pyrazol-3-yl}-2-acetylbenzamide;
530. N-{5-ethylaminocarbonyl-4,6-dihydropyrrolo[3,4-c]pyrazol-3-yl}-4-acetylbenzamide;
531. N-{5-ethylaminocarbonyl-4,6-dihydropyrrolo[3,4-c]pyrazol-3-yl}-1-naphthoic amide;
532. N-{5-ethylaminocarbonyl-4,6-dihydropyrrolo[3,4-c]pyrazol-3-yl}-2-naphthoic amide;
533. N-{5-ethylaminocarbonyl-4,6-dihydropyrrolo[3,4-c]pyrazol-3-yl}-3-benzoylpropionamide;
534. N-{5-ethylaminocarbonyl-4,6-dihydropyrrolo[3,4-c]pyrazol-3-yl}-4-acetamidobenzamide;
535. N-{5-ethylaminocarbonyl-4,6-dihydropyrrolo[3,4-c]pyrazol-3-yl}-2,5-dimethoxybenzamide;
536. N-{5-ethylaminocarbonyl-4,6-dihydropyrrolo[3,4-c]pyrazol-3-yl}-2,6-dimethoxybenzamide;
537. N-{5-ethylaminocarbonyl-4,6-dihydropyrrolo[3,4-c]pyrazol-3-yl}-3,4-dimethoxybenzamide;
538. N-{5-ethylaminocarbonyl-4,6-dihydropyrrolo[3,4-c]pyrazol-3-yl}-3,5-dimethoxybenzamide;
539. N-{5-ethylaminocarbonyl-4,6-dihydropyrrolo[3,4-c]pyrazol-3-yl}-3-(2-thenoyl)-propionamide;
540. N-{5-ethylaminocarbonyl-4,6-dihydropyrrolo[3,4-c]pyrazol-3-yl}-2-naphtylacetamide;
541. N-{5-ethylaminocarbonyl-4,6-dihydropyrrolo[3,4-c]pyrazol-3-yl}-1-naphtylacetamide;
542. N-{5-ethylaminocarbonyl-4,6-dihydropyrrolo[3,4-c]pyrazol-3-yl}-4-phenylbenzamide;
543. N-{5-phenylaminocarbonyl-4,6-dihydropyrrolo[3,4-c]pyrazol-3-yl}-acetamide;
544. N-{5-phenylaminocarbonyl-4,6-dihydropyrrolo[3,4-c]pyrazol-3-yl}-cyclopropanecarboxamide;
545. N-{5-phenylaminocarbonyl-4,6-dihydropyrrolo[3,4-c]pyrazol-3-yl}-isobutyramide;
546. N-{5-phenylaminocarbonyl-4,6-dihydropyrrolo[3,4-c]pyrazol-3-yl}-cyclopentanecarboxamide;
547. N-{5-phenylaminocarbonyl-4,6-dihydropyrrolo[3,4-c]pyrazol-3-yl}-benzamide;
548. N-{5-phenylaminocarbonyl-4,6-dihydropyrrolo[3,4-c]pyrazol-3-yl}-picolinic amide;
549. N-{5-phenylaminocarbonyl-4,6-dihydropyrrolo[3,4-c]pyrazol-3-yl}-nicotinic amide;
550. N-{5-phenylaminocarbonyl-4,6-dihydropyrrolo[3,4-c]pyrazol-3-yl}-isonicotinic amide;
551. N-{5-phenylaminocarbonyl-4,6-dihydropyrrolo[3,4-c]pyrazol-3-yl}-3-methyl-2-furoic amide;
552. N-{5-phenylaminocarbonyl-4,6-dihydropyrrolo[3,4-c]pyrazol-3-yl}-thiophene-2-carboxamide;
553. N-{5-phenylaminocarbonyl-4,6-dihydropyrrolo[3,4-c]pyrazol-3-yl}-thiophene-3-carboxamide;
554. N-{5-phenylaminocarbonyl-4,6-dihydropyrrolo[3,4-c]pyrazol-3-yl}-o-toluic amide;
555. N-{5-phenylaminocarbonyl-4,6-dihydropyrrolo[3,4-c]pyrazol-3-yl}-m-toluic amide;
556. N-{5-phenylaminocarbonyl-4,6-dihydropyrrolo[3,4-c]pyrazol-3-yl}-p-toluic amide;
557. N-{5-phenylaminocarbonyl-4,6-dihydropyrrolo[3,4-c]pyrazol-3-yl}-phenylacetamide;
558. N-{5-phenylaminocarbonyl-4,6-dihydropyrrolo[3,4-c]pyrazol-3-yl}-salicylic amide;
559. N-{5-phenylaminocarbonyl-4,6-dihydropyrrolo[3,4-c]pyrazol-3-yl}-2-fluorobenzamide;
560. N-{5-phenylaminocarbonyl-4,6-dihydropyrrolo[3,4-c]pyrazol-3-yl}-3-fluorobenzamide;
561. N-{5-phenylaminocarbonyl-4,6-dihydropyrrolo[3,4-c]pyrazol-3-yl}-4-fluorobenzamide;
562. N-{5-phenylaminocarbonyl-4,6-dihydropyrrolo[3,4-c]pyrazol-3-yl}-thiophene-2-acetamide;
563. N-{5-phenylaminocarbonyl-4,6-dihydropyrrolo[3,4-c]pyrazol-3-yl}-thiophene-3-acetamide;
564. N-{5-phenylaminocarbonyl-4,6-dihydropyrrolo[3,4-c]pyrazol-3-yl}-phenylpropiolic amide;
565. N-{5-phenylaminocarbonyl-4,6-dihydropyrrolo[3,4-c]pyrazol-3-yl}-3-cyanobenzamide;
566. N-{5-phenylaminocarbonyl-4,6-dihydropyrrolo[3,4-c]pyrazol-3-yl}-4-cyanobenzamide;
567. N-{5-phenylaminocarbonyl-4,6-dihydropyrrolo[3,4-c]pyrazol-3-yl}-trans-cinnamic amide;
568. N-{5-phenylaminocarbonyl-4,6-dihydropyrrolo[3,4-c]pyrazol-3-yl}-cis-cinnamic amide;
569. N-{5-phenylaminocarbonyl-4,6-dihydropyrrolo[3,4-c]pyrazol-3-yl}-3-(3-pyridyl)acrylic amide;
570. N-{5-phenylaminocarbonyl-4,6-dihydropyrrolo[3,4-c]pyrazol-3-yl}-3-(4-pyridyl)-acrylic amide;
571. N-{5-phenylaminocarbonyl-4,6-dihydropyrrolo[3,4-c]pyrazol-3-yl}-2-phenylpropionamide;
572. N-{5-phenylaminocarbonyl-4,6-dihydropyrrolo[3,4-c]pyrazol-3-yl}-o-tolylacetamide;
573. N-{5-phenylaminocarbonyl-4,6-dihydropyrrolo[3,4-c]pyrazol-3-yl}-m-tolylacetamide;

574. N-{5-phenylaminocarbonyl-4,6-dihydropyrrolo[3,4-c]pyrazol-3-yl}-p-tolylacetamide;
575. N-{5-phenylaminocarbonyl-4,6-dihydropyrrolo[3,4-c]pyrazol-3-yl}-o-anisic amide;
576. N-{5-phenylaminocarbonyl-4,6-dihydropyrrolo[3,4-c]pyrazol-3-yl}-3-methoxybenzamide;
577. N-{5-phenylaminocarbonyl-4,6-dihydropyrrolo[3,4-c]pyrazol-3-yl}-p-anisic amide;
578. N-{5-phenylaminocarbonyl-4,6-dihydropyrrolo[3,4-c]pyrazol-3-yl}-phenoxyacetamide;
579. N-{5-phenylaminocarbonyl-4,6-dihydropyrrolo[3,4-c]pyrazol-3-yl}-2-fluorophenylacetamide;
580. N-{5-phenylaminocarbonyl-4,6-dihydropyrrolo[3,4-c]pyrazol-3-yl}-3-fluorophenylacetamide;
581. N-{5-phenylaminocarbonyl-4,6-dihydropyrrolo[3,4-c]pyrazol-3-yl)}-4-fluorophenylacetamide;
582. N-{5-phenylaminocarbonyl-4,6-dihydropyrrolo[3,4-c]pyrazol-3-yl}-3-(2-thienyl)acrylic amide;
583. N-{5-phenylaminocarbonyl-4,6-dihydropyrrolo[3,4-c]pyrazol-3-yl}-3-(3-thienyl)-acrylic amide;
584. N-{5-phenylaminocarbonyl-4,6-dihydropyrrolo[3,4-c]pyrazol-3-yl}-3-(2-thienyl)propanoic amide;
585. N-{5-phenylaminocarbonyl-4,6-dihydropyrrolo[3,4-c]pyrazol-3-yl}-2-chlorobenzamide;
586. N-{5-phenylaminocarbonyl-4,6-dihydropyrrolo[3,4-c]pyrazol-3-yl}-3-chlorobenzamide;
587. N-{5-phenylaminocarbonyl-4,6-dihydropyrrolo[3,4-c]pyrazol-3-yl}-4-chlorobenzamide;
588. N-{5-phenylaminocarbonyl-4,6-dihydropyrrolo[3,4-c]pyrazol-3-yl}-1-piperidinepropionamide;
589. N-{5-phenylaminocarbonyl-4,6-dihydropyrrolo[3,4-c]pyrazol-3-yl}-2-acetylbenzamide;
590. N-{5-phenylaminocarbonyl-4,6-dihydropyrrolo[3,4-c]pyrazol-3-yl}-4-acetylbenzamide;
591. N-{5-phenylaminocarbonyl-4,6-dihydropyrrolo[3,4-c]pyrazol-3-yl}-1-naphthoic amide;
592. N-{5-phenylaminocarbonyl-4,6-dihydropyrrolo[3,4-c]pyrazol-3-yl}-2-naphthoic amide;
593. N-{5-phenylaminocarbonyl-4,6-dihydropyrrolo[3,4-c]pyrazol-3-yl}-3-benzoylpropionamide;
594. N-{5-phenylaminocarbonyl-4,6-dihydropyrrolo[3,4]pyrazol-3-yl}-4-acetamidobenzamide;
595. N-{5-phenylaminocarbonyl-4,6-dihydropyrrolo[3,4-c]pyrazol-3-yl}-2,5-dimethoxybenzamide;
596. N-{5-phenylaminocarbonyl-4,6-dihydropyrrolo[3,4-c]pyrazol-3-yl}-2,6-dimethoxybenzamide;
597. N-{5-phenylaminocarbonyl-4,6-dihydropyrrolo[3,4-c]pyrazol-3-yl}-3,4-dimethoxybenzamide;
598. N-{5-phenylaminocarbonyl-4,6-dihydropyrrolo[3,4-c]pyrazol-3-yl}-3,5-dimethoxybenzamide;
599. N-{5-phenylaminocarbonyl-4,6-dihydropyrrolo[3,4-c]pyrazol-3-yl}-3-(2-thenoyl)-propionamide;
600. N-{5-phenylaminocarbonyl-4,6-dihydropyrrolo[3,4-c]pyrazol-3-yl}-2-naphtylacetamide;
601. N-{5-phenylaminocarbonyl-4,6-dihydropyrrolo[3,4-c]pyrazol-3-yl}-1-naphtylacetamide;
602. N-{5-phenylaminocarbonyl-4,6-dihydropyrrolo[3,4-c]pyrazol-3-yl}-4-phenylbenzamide;
603. N-{5-benzylaminocarbonyl-4,6-dihydropyrrolo[3,4-c]pyrazol-3-yl}-acetamide;
604. N-{5-benzylaminocarbonyl-4,6-dihydropyrrolo[3,4-c]pyrazol-3-yl}-cyclopropanecarboxamide;
605. N-{5-benzylaminocarbonyl-4,6-dihydropyrrolo[3,4-c]pyrazol-3-yl}-isobutyramide;
606. N-{5-benzylaminocarbonyl-4,6-dihydropyrrolo[3,4-c]pyrazol-3-yl}-cyclopentanecarboxamide;
607. N-{5-benzylaminocarbonyl-4,6-dihydropyrrolo[3,4-c]pyrazol-3-yl}-benzamide;
608. N-{5-benzylaminocarbonyl-4,6-dihydropyrrolo[3,4-c]pyrazol-3-yl}-picolinic amide;
609. N-{5-benzylaminocarbonyl-4,6-dihydropyrrolo[3,4-c]pyrazol-3-yl}-nicotinic amide;
610. N-{5-benzylaminocarbonyl-4,6-dihydropyrrolo[3,4-c]pyrazol-3-yl}-isonicotinic amide;
611. N-{5-benzylaminocarbonyl-4,6-dihydropyrrolo[3,4-c]pyrazol-3-yl}-3-methyl-2-furoic amide;
612. N-{5-benzylaminocarbonyl-4,6-dihydropyrrolo[3,4-c]pyrazol-3-yl}-thiophene-2-carboxamide;
613. N-{5-benzylaminocarbonyl-4,6-dihydropyrrolo[3,4-c]pyrazol-3-yl}-thiophene-3-carboxamide;
614. N-{5-benzylaminocarbonyl-4,6-dihydropyrrolo[3,4-c]pyrazol-3-yl}-o-toluic amide;
615. N-{5-benzylaminocarbonyl-4,6-dihydropyrrolo[3,4-c]pyrazol-3-yl}-m-toluic amide;
616. N-{5-benzylaminocarbonyl-4,6-dihydropyrrolo[3,4-c]pyrazol-3-yl}-p-toluic amide;
617. N-{5-benzylaminocarbonyl-4,6-dihydropyrrolo[3,4-c]pyrazol-3-yl}-salicylic amide;
618. N-{5-benzylaminocarbonyl-4,6-dihydropyrrolo[3,4-c]pyrazol-3-yl}-2-fluorobenzamide;
619. N-{5-benzylaminocarbonyl-4,6-dihydropyrrolo[3,4-c]pyrazol-3-yl}-3-fluorobenzamide;
620. N-{5-benzylaminocarbonyl-4,6-dihydropyrrolo[3,4-c]pyrazol-3-yl}-4-fluorobenzamide;
621. N-{5-benzylaminocarbonyl-4,6-dihydropyrrolo[3,4-c]pyrazol-3-yl}-thiophene-2-acetamide;
622. N-{5-benzylaminocarbonyl-4,6-dihydropyrrolo[3,4-c]pyrazol-3-yl}-thiophene-3-acetamide;
623. N-{5-benzylaminocarbonyl-4,6-dihydropyrrolo[3,4-c]pyrazol-3-yl}-phenylpropiolic amide;
624. N-{5-benzylaminocarbonyl-4,6-dihydropyrrolo[3,4-c]pyrazol-3-yl}-3-cyanobenzamide;
625. N-{5-benzylaminocarbonyl-4,6-dihydropyrrolo[3,4-c]pyrazol-3-yl}-4-cyanobenzamide;
626. N-{5-benzylaminocarbonyl-4,6-dihydropyrrolo[3,4-c]pyrazol-3-yl}-trans-cinnamic amide;
627. N-{5-benzylaminocarbonyl-4,6-dihydropyrrolo[3,4-c]pyrazol-3-yl}-cis-cinnamic amide;
628. N-{5-benzylaminocarbonyl-4,6-dihydropyrrolo[3,4-c]pyrazol-3-yl}-3-(3-pyridyl)acrylic amide;
629. N-{5-benzylaminocarbonyl-4,6-dihydropyrrolo[3,4-c]pyrazol-3-yl}-3-(4-pyridyl)-acrylic amide;
630. N-{5-benzylaminocarbonyl-4,6-dihydropyrrolo[3,4-c]pyrazol-3-yl}-2-phenylpropionamide;
631. N-{5-benzylaminocarbonyl-4,6-dihydropyrrolo[3,4-c]pyrazol-3-yl}-o-tolylacetamide;
632. N-{5-benzylaminocarbonyl-4,6-dihydropyrrolo[3,4-c]pyrazol-3-yl}-m-tolylacetamide;
633. N-{5-benzylaminocarbonyl-4,6-dihydropyrrolo[3,4-c]pyrazol-3-yl}-p-tolylacetamide;
634. N-{5-benzylaminocarbonyl-4,6-dihydropyrrolo[3,4-c]pyrazol-3-yl}-o-anisic amide;
635. N-{5-benzylaminocarbonyl-4,6-dihydropyrrolo[3,4-c]pyrazol-3-yl}-3-methoxybenzamide;
636. N-{5-benzylaminocarbonyl-4,6-dihydropyrrolo[3,4-c]pyrazol-3-yl}-p-anisic amide;
637. N-{5-benzylaminocarbonyl-4,6-dihydropyrrolo[3,4-c]pyrazol-3-yl}-phenoxyacetamide;
638. N-{5-benzylaminocarbonyl-4,6-dihydropyrrolo[3,4-c]pyrazol-3-yl}-2-fluorophenylacetamide;
639. N-{5-benzylaminocarbonyl-4,6-dihydropyrrolo[3,4-c]pyrazol-3-yl}-3-fluorophenylacetamide;

640. N-{5-benzylaminocarbonyl-4,6-dihydropyrrolo[3,4-c]pyrazol-3-yl}-4-fluorophenylacetamide;
641. N-{5-benzylaminocarbonyl-4,6-dihydropyrrolo[3,4-c]pyrazol-3-yl}-3-(2-thienyl)acrylic amide;
642. N-{5-benzylaminocarbonyl-4,6-dihydropyrrolo[3,4-c]pyrazol-3-yl}-3-(3-thienyl)-acrylic amide;
643. N-{5-benzylaminocarbonyl-4,6-dihydropyrrolo[3,4-c]pyrazol-3-yl}-3-(2-thienyl)propanoic amide;
644. N-{5-benzylaminocarbonyl-4,6-dihydropyrrolo[3,4-c]pyrazol-3-yl}-2-chlorobenzamide;
645. N-{5-benzylaminocarbonyl-4,6-dihydropyrrolo[3,4-c]pyrazol-3-yl}-3-chlorobenzamide;
646. N-{5-benzylaminocarbonyl-4,6-dihydropyrrolo[3,4-c]pyrazol-3-yl}-4-chlorobenzamide;
647. N-{5-benzylaminocarbonyl-4,6-dihydropyrrolo[3,4-c]pyrazol-3-yl}-1-piperidinepropionamide;
648. N-{5-benzylaminocarbonyl-4,6-dihydropyrrolo[3,4-c]pyrazol-3-yl}-2-acetylbenzamide;
649. N-{5-benzylaminocarbonyl-4,6-dihydropyrrolo[3,4-c]pyrazol-3-yl}-4-acetylbenzamide;
650. N-{5-benzylaminocarbonyl-4,6-dihydropyrrolo[3,4-c]pyrazol-3-yl}-1-naphthoic amide;
651. N-{5-benzylaminocarbonyl-4,6-dihydropyrrolo[3,4-c]pyrazol-3-yl}-2-naphthoic amide;
652. N-{5-benzylaminocarbonyl-4,6-dihydropyrrolo[3,4-c]pyrazol-3-yl}-3-benzoylpropionamide;
653. N-{5-benzylaminocarbonyl-4,6-dihydropyrrolo[3,4-c]pyrazol-3-yl}-4-acetamidobenzamide;
654. N-{5-benzylaminocarbonyl-4,6-dihydropyrrolo[3,4-c]pyrazol-3-yl}-2,5-dimethoxybenzamide;
655. N-{5-benzylaminocarbonyl-4,6-dihydropyrrolo[3,4-c]pyrazol-3-yl}-2,6-dimethoxybenzamide;
656. N-{5-benzylaminocarbonyl-4,6-dihydropyrrolo[3,4-c]pyrazol-3-yl}-3,4-dimethoxybenzamide;
657. N-{5-benzylaminocarbonyl-4,6-dihydropyrrolo[3,4-c]pyrazol-3-yl}-3,5-dimethoxybenzamide;
658. N-{5-benzylaminocarbonyl-4,6-dihydropyrrolo[3,4-c]pyrazol-3-yl}-3-(2-thenoyl)-propionamide;
659. N-{5-benzylaminocarbonyl-4,6-dihydropyrrolo[3,4-c]pyrazol-3-yl}-2-naphthylacetamide;
660. N-{5-benzylaminocarbonyl-4,6-dihydropyrrolo[3,4-c]pyrazol-3-yl}-1-naphthylacetamide;
661. N-{5-benzylaminocarbonyl-4,6-dihydropyrrolo[3,4-c]pyrazol-3-yl}-4-phenylbenzamide;
662. N-{5-benzoylaminocarbonyl-4,6-dihydropyrrolo[3,4-c]pyrazol-3-yl}-acetamide;
663. N-{5-benzoylaminocarbonyl-4,6-dihydropyrrolo[3,4-c]pyrazol-3-yl}-cyclopropanecarboxamide;
664. N-{5-benzoylaminocarbonyl-4,6-dihydropyrrolo[3,4-c]pyrazol-3-yl}-isobutyramide;
665. N-{5-benzoylaminocarbonyl-4,6-dihydropyrrolo[3,4-c]pyrazol-3-yl}-cyclopentanecarboxamide;
666. N-{5-benzoylaminocarbonyl-4,6-dihydropyrrolo[3,4-c]pyrazol-3-yl}-benzamide;
667. N-{5-benzoylaminocarbonyl-4,6-dihydropyrrolo[3,4-c]pyrazol-3-yl}-picolinic amide;
668. N-{5-benzoylaminocarbonyl-4,6-dihydropyrrolo[3,4-c]pyrazol-3-yl}-nicotinic amide;
669. N-{5-benzoylaminocarbonyl-4,6-dihydropyrrolo[3,4-c]pyrazol-3-yl}-isonicotinic amide;
670. N-{5-benzoylaminocarbonyl-4,6-dihydropyrrolo[3,4-c]pyrazol-3-yl}-3-methyl-2-furoic amide;
671. N-{5-benzoylaminocarbonyl-4,6-dihydropyrrolo[3,4-c]pyrazol-3-yl}-thiophene-2-carboxamide;
672. N-{5-benzoylaminocarbonyl-4,6-dihydropyrrolo[3,4-c]pyrazol-3-yl}-thiophene-3-carboxamide;
673. N-{5-benzoylaminocarbonyl-4,6-dihydropyrrolo[3,4-c]pyrazol-3-yl}-o-toluic amide;
674. N-{5-benzoylaminocarbonyl-4,6-dihydropyrrolo[3,4-c]pyrazol-3-yl}-m-toluic amide;
675. N-{5-benzoylaminocarbonyl-4,6-dihydropyrrolo[3,4-c]pyrazol-3-yl}-p-toluic amide;
676. N-{5-benzoylaminocarbonyl-4,6-dihydropyrrolo[3,4-c]pyrazol-3-yl}-phenylacetamide;
677. N-{5-benzoylaminocarbonyl-4,6-dihydropyrrolo[3,4-c]pyrazol-3-yl}-salicylic amide;
678. N-{5-benzoylaminocarbonyl-4,6-dihydropyrrolo[3,4-c]pyrazol-3-yl}-2-fluorobenzamide;
679. N-{5-benzoylaminocarbonyl-4,6-dihydropyrrolo[3,4-c]pyrazol-3-yl}-3-fluorobenzamide;
680. N-{5-benzoylaminocarbonyl-4,6-dihydropyrrolo[3,4-c]pyrazol-3-yl}-4-fluorobenzamide;
681. N-{5-benzoylaminocarbonyl-4,6-dihydropyrrolo[3,4-c]pyrazol-3-yl}-thiophene-2-acetamide;
682. N-{5-benzoylaminocarbonyl-4,6-dihydropyrrolo[3,4-c]pyrazol-3-yl}-thiophene-3-acetamide;
683. N-{5-benzoylaminocarbonyl-4,6-dihydropyrrolo[3,4-c]pyrazol-3-yl}-phenylpropiolic amide;
684. N-{5-benzoylaminocarbonyl-4,6-dihydropyrrolo[3,4-c]pyrazol-3-yl}-3-cyanobenzamide;
685. N-{5-benzoylaminocarbonyl-4,6-dihydropyrrolo[3,4-c]pyrazol-3-yl}-4-cyanobenzamide;
686. N-{5-benzoylaminocarbonyl-4,6-dihydropyrrolo[3,4-c]pyrazol-3-yl}-trans-cinnamic amide;
687. N-{5-benzoylaminocarbonyl-4,6-dihydropyrrolo[3,4-c]pyrazol-3-yl}-cis-cinnamic amide;
688. N-{5-benzoylaminocarbonyl-4,6-dihydropyrrolo[3,4-c]pyrazol-3-yl}-3-(3-pyridyl)acrylic amide;
689. N-{5-benzoylaminocarbonyl-4,6-dihydropyrrolo[3,4-c]pyrazol-3-yl}-3-(4-pyridyl)-acrylic amide;
690. N-{5-benzoylaminocarbonyl-4,6-dihydropyrrolo[3,4-c]pyrazol-3-yl}-2-phenylpropionamide;
691. N-{5-benzoylaminocarbonyl-4,6-dihydropyrrolo[3,4-c]pyrazol-3-yl}-o-tolylacetamide;
692. N-{5-benzoylaminocarbonyl-4,6-dihydropyrrolo[3,4-c]pyrazol-3-yl}-m-tolylacetamide;
693. N-{5-benzoylaminocarbonyl-4,6-dihydropyrrolo[3,4-c]pyrazol-3-yl}-p-tolylacetamide;
694. N-{5-benzoylaminocarbonyl-4,6-dihydropyrrolo[3,4-c]pyrazol-3-yl}-o-anisic amide;
695. N-{5-benzoylaminocarbonyl-4,6-dihydropyrrolo[3,4-c]pyrazol-3-yl}-3-methoxybenzamide;
696. N-{5-benzoylaminocarbonyl-4,6-dihydropyrrolo[3,4-c]pyrazol-3-yl}-p-anisic amide;
697. N-{5-benzoylaminocarbonyl-4,6-dihydropyrrolo[3,4-c]pyrazol-3-yl}-phenoxyacetamide;
698. N-{5-benzoylaminocarbonyl-4,6-dihydropyrrolo[3,4-c]pyrazol-3-yl}-2-fluorophenylacetamide;
699. N-{5-benzoylaminocarbonyl-4,6-dihydropyrrolo[3,4-c]pyrazol-3-yl}-3-fluorophenylacetamide;
700. N-{5-benzoylaminocarbonyl-4,6-dihydropyrrolo[3,4-c]pyrazol-3-yl}-4-fluorophenylacetamide;
701. N-{5-benzoylaminocarbonyl-4,6-dihydropyrrolo[3,4-c]pyrazol-3-yl}-3-(2-thienyl)acrylic amide;
702. N-{5-benzoylaminocarbonyl-4,6-dihydropyrrolo[3,4-c]pyrazol-3-yl}-3-(3-thienyl)-acrylic amide;
703. N-{5-benzoylaminocarbonyl-4,6-dihydropyrrolo[3,4-c]pyrazol-3-yl}-3-(2-thienyl)propanoic amide;
704. N-{5-benzoylaminocarbonyl-4,6-dihydropyrrolo[3,4-c]pyrazol-3-yl}-2-chlorobenzamide;
705. N-{5-benzoylaminocarbonyl-4,6-dihydropyrrolo[3,4-c]pyrazol-3-yl}-3-chlorobenzamide;

706. N-{5-benzoylaminocarbonyl-4,6-dihydropyrrolo[3,4-c]pyrazol-3-yl}-4-chlorobenzamide;
707. N-{5-benzoylaminocarbonyl-4,6-dihydropyrrolo[3,4-c]pyrazol-3-yl}-1-piperidinepropionamide;
708. N-{5-benzoylaminocarbonyl-4,6-dihydropyrrolo[3,4-c]pyrazol-3-yl}-2-acetylbenzamide;
709. N-{5-benzoylaminocarbonyl-4,6-dihydropyrrolo[3,4-c]pyrazol-3-yl}-4-acetylbenzamide;
710. N-{5-benzoylaminocarbonyl-4,6-dihydropyrrolo[3,4-c]pyrazol-3-yl}-1-naphthoic amide;
711. N-{5-benzoylaminocarbonyl-4,6-dihydropyrrolo[3,4-c]pyrazol-3-yl}-2-naphthoic amide;
712. N-{5-benzoylaminocarbonyl-4,6-dihydropyrrolo[3,4-c]pyrazol-3-yl}-3-benzoylpropionamide;
713. N-{5-benzoylaminocarbonyl-4,6-dihydropyrrolo[3,4-c]pyrazol-3-yl}-4-acetamidobenzamide;
714. N-{5-benzoylaminocarbonyl-4,6-dihydropyrrolo[3,4-c]pyrazol-3-yl}-2,5-dimethoxybenzamide;
715. N-{5-benzoylaminocarbonyl-4,6-dihydropyrrolo[3,4-c]pyrazol-3-yl}-2,6-dimethoxybenzamide;
716. N-{5-benzoylaminocarbonyl-4,6-dihydropyrrolo[3,4-c]pyrazol-3-yl}-3,4-dimethoxybenzamide;
717. N-{5-benzoylaminocarbonyl-4,6-dihydropyrrolo[3,4-c]pyrazol-3-yl}-3,5-dimethoxybenzamide;
718. N-{5-benzoylaminocarbonyl-4,6-dihydropyrrolo[3,4-c]pyrazol-3-yl}-3-(2-thenoyl)-propionamide;
719. N-{5-benzoylaminocarbonyl-4,6-dihydropyrrolo[3,4-c]pyrazol-3-yl}-2-naphtylacetamide;
720. N-{5-benzoylaminocarbonyl-4,6-dihydropyrrolo[3,4-c]pyrazol-3-yl}-1-naphtylacetamide;
721. N-{5-benzoylaminocarbonyl-4,6-dihydropyrrolo[3,4-c]pyrazol-3-yl}-4-phenylbenzamide;
722. N-{5-aminocarbonyl-4,6-dihydropyrrolo[3,4-c]pyrazol-3-yl}-acetamide;
723. N-{5-aminocarbonyl-4,6-dihydropyrrolo[3,4-c]pyrazol-3-yl}-cyclopropanecarboxamide;
724. N-{5-aminocarbonyl-4,6-dihydropyrrolo[3,4-c]pyrazol-3-yl}-isobutyramide;
725. N-{5-aminocarbonyl-4,6-dihydropyrrolo[3,4-c]pyrazol-3-yl}-cyclopentanecarboxamide;
726. N-{5-aminocarbonyl-4,6-dihydropyrrolo[3,4-c]pyrazol-3-yl}-benzamide;
727. N-{5-aminocarbonyl-4,6-dihydropyrrolo[3,4-c]pyrazol-3-yl}-picolinic amide;
728. N-{5-aminocarbonyl-4,6-dihydropyrrolo[3,4-c]pyrazol-3-yl}-nicotinic amide;
729. N-{5-aminocarbonyl-4,6-dihydropyrrolo[3,4-c]pyrazol-3-yl}-isonicotinic amide;
730. N-{5-aminocarbonyl-4,6-dihydropyrrolo[3,4-c]pyrazol-3-yl}-3-methyl-2-furoic amide;
731. N-{5-aminocarbonyl-4,6-hydropyrrolo[3,4-c]pyrazol-3-yl}-thiophene-2-carboxamide;
732. N-{5-aminocarbonyl-4,6-dihydropyrrolo[3,4-c]pyrazol-3-yl}-thiophene-3-carboxamide;
733. N-{5-aminocarbonyl-4,6-dihydropyrrolo[3,4-c]pyrazol-3-yl}-o-toluic amide;
734. N-{5-aminocarbonyl-4,6-dihydropyrrolo[3,4-c]pyrazol-3-yl}-m-toluic amide;
735. N-{5-aminocarbonyl-4,6-dihydropyrrolo[3,4-c]pyrazol-3-yl}-p-toluic amide;
736. N-{5-aminocarbonyl-4,6-dihydropyrrolo[3,4-c]pyrazol-3-yl}-phenylacetamide;
737. N-{5-aminocarbonyl-4,6-dihydropyrrolo[3,4-c]pyrazol-3-yl}-salicylic amide;
738. N-{5-aminocarbonyl-4,6-dihydropyrrolo[3,4-c]pyrazol-3-yl}-2-fluorobenzamide;
739. N-{5-aminocarbonyl-4,6-dihydropyrrolo[3,4-c]pyrazol-3-yl}-3-fluorobenzamide;
740. N-{5-aminocarbonyl-4,6-dihydropyrrolo[3,4-c]pyrazol-3-yl}-4-fluorobenzamide;
741. N-{5-aminocarbonyl-4,6-dihydropyrrolo[3,4-c]pyrazol-3-yl}-thiophene-2-acetamide;
742. N-{5-aminocarbonyl-4,6-dihydropyrrolo[3,4-c]pyrazol-3-yl}-thiophene-3-acetamide;
743. N-{5-aminocarbonyl-4,6-dihydropyrrolo[3,4-c]pyrazol-3-yl}-phenylpropiolic amide;
744. N-{5-aminocarbonyl-4,6-dihydropyrrolo[3,4-c]pyrazol-3-yl}-3-cyanobenzamide;
745. N-{5-aminocarbonyl-4,6-dihydropyrrolo[3,4-c]pyrazol-3-yl}-cyanobenzamide;
746. N-{5-aminocarbonyl-4,6-dihydropyrrolo[3,4-c]pyrazol-3-yl}-trans-cinnamic amide;
747. N-{5-aminocarbonyl-4,6-dihydropyrrolo[3,4-c]pyrazol-3-yl}-cis-cinnamic amide;
748. N-{5-aminocarbonyl-4,6-dihydropyrrolo[3,4-c]pyrazol-3-yl}-3-(3-pyridyl)acrylic amide;
749. N-{5-aminocarbonyl-4,6-dihydropyrrolo[3,4-c]pyrazol-3-yl}-3-(4-pyridyl)-acrylic amide;
750. N-{5-aminocarbonyl-4,6-dihydropyrrolo[3,4-c]pyrazol-3-yl}-2-phenylpropionamide;
751. N-{5-aminocarbonyl-4,6-dihydropyrrolo[3,4-c]pyrazol-3-yl}-o-tolylacetamide;
752. N-{5-aminocarbonyl-4,6-dihydropyrrolo[3,4-c]pyrazol-3-yl}-m-tolylacetamide;
753. N-{5-aminocarbonyl-4,6-dihydropyrrolo[3,4-c]pyrazol-3-yl}-p-tolylacetamide;
754. N-{5-aminocarbonyl-4,6-dihydropyrrolo[3,4-c]pyrazol-3-yl}-o-anisic amide;
755. N-{5-aminocarbonyl-4,6-dihydropyrrolo[3,4-c]pyrazol-3-yl}-3-methoxybenzamide;
756. N-{5-aminocarbonyl-4,6-dihydropyrrolo[3,4-c]pyrazol-3-yl}-p-anisic amide;
757. N-{5-aminocarbonyl-4,6-dihydropyrrolo[3,4-c]pyrazol-3-yl}-phenoxyacetamide;
758. N-{5-aminocarbonyl-4,6-dihydropyrrolo[3,4-c]pyrazol-3-yl}-2-fluorophenylacetamide;
759. N-{5-aminocarbonyl-4,6-dihydropyrrolo[3,4-c]pyrazol-3-yl}-3-fluorophenylacetamide;
760. N-{5-aminocarbonyl-4,6-dihydropyrrolo[3,4-c]pyrazol-3-yl})-4-fluorophenylacetamide;
761. N-{5-aminocarbonyl-4,6-dihydropyrrolo[3,4-c]pyrazol-3-yl}-3-(2-thienyl)acrylic amide;
762. N-{5-aminocarbonyl-4,6-dihydropyrrolo[3,4-c]pyrazol-3-yl}-3-(3-thienyl)-acrylic amide;
763. N-{5-aminocarbonyl-4,6-dihydropyrrolo[3,4-c]pyrazol-3-yl}-3-(2-thienyl)propanoic amide;
764. N-{5-aminocarbonyl-4,6-dihydropyrrolo[3,4-c]pyrazol-3-yl}-2-chlorobenzamide;
765. N-{5-aminocarbonyl-4,6-dihydropyrrolo[3,4-c]pyrazol-3-yl}-3-chlorobenzamide;
766. N-{5-aminocarbonyl-4,6-dihydropyrrolo[3,4-c]pyrazol-3-yl}-4-chlorobenzamide;
767. N-{5-aminocarbonyl-4,6-dihydropyrrolo[3,4-c]pyrazol-3-yl}-1-piperidinepropionamide;
768. N-{5-aminocarbonyl-4,6-dihydropyrrolo[3,4-c]pyrazol-3-yl}-2-acetylbenzamide;
769. N-{5-aminocarbonyl-4,6-dihydropyrrolo[3,4-c]pyrazol-3-yl}-4-acetylbenzamide;
770. N-{5-aminocarbonyl-4,6-dihydropyrrolo[3,4-c]pyrazol-3-yl-}-1-napnaphthoic amide;
771. N-{5-aminocarbonyl-4,6-dihydropyrrolo[3,4-c]pyrazol-3-yl}-2-naphthoic amide;

772. N-{5-aminocarbonyl-4,6-dihydropyrrolo[3,4-c]pyrazol-3-yl}-3-benzoylpropionamide;
773. N-{5-aminocarbonyl-4,6-dihydropyrrolo[3,4-c]pyrazol-3-yl}-acetamidobenzamide;
774. N-{5-aminocarbonyl-4,6-dihydropyrrolo[3,4-c]pyrazol-3-yl}-2,5-dimethoxybenzamide;
775. N-{5-aminocarbonyl-4,6-dihydropyrrolo[3,4-c]pyrazol-3-yl}-2,6-dimethoxybenzamide;
776. N-{5-aminocarbonyl-4,6-dihydropyrrolo[3,4-c]pyrazol-3-yl}-3,4-dimethoxybenzamide;
777. N-{5-aminocarbonyl-4,6-dihydropyrrolo[3,4-c]pyrazol-3-yl}-3,5-dimethoxybenzamide;
778. N-{5-aminocarbonyl-4,6-dihydropyrrolo[3,4-c]pyrazol-3-yl}-3-(2-thenoyl)-propionamide;
779. N-{5-aminocarbonyl-4,6-dihydropyrrolo[3,4-c]pyrazol-3-yl}-2-naphtylacetamide;
780. N-{5-aminocarbonyl-4,6-dihydropyrrolo[3,4-c]pyrazol-3-yl}-1-naphtylacetamide;
781. N-{5-aminocarbonyl-4,6-dihydropyrrolo[3,4-c]pyrazol-3-yl}-4-phenylbenzamide;
782. N-{5-aminosulfonyl-4,6-dihydropyrrolo[3,4-c]pyrazol-3-yl}-acetamide;
783. N-{5-aminosulfonyl-4,6-dihydropyrrolo[3,4-c]pyrazol-3-yl}-cyclopropanecarboxamide;
784. N-{5-aminosulfonyl-4,6-dihydropyrrolo[3,4-c]pyrazol-3-yl}-isobutyramide;
785. N-{5-aminosulfonyl-4,6-dihydropyrrolo[3,4-c]pyrazol-3-yl}-cyclopentanecarboxamide;
786. N-{5-aminosulfonyl-4,6-dihydropyrrolo[3,4-c]pyrazol-3-yl}-benzamide;
787. N-{5-aminosulfonyl-4,6-dihydropyrrolo[3,4-c]pyrazol-3-yl}-picolinic amide;
788. N-{5-aminosulfonyl-4,6-dihydropyrrolo[3,4-c]pyrazol-3-yl}-nicotinic amide;
789. N-{5-aminosulfonyl-4,6-dihydropyrrolo[3,4-c]pyrazol-3-yl}-isonicotinic amide;
790. N-{5-aminosulfonyl-4,6-dihydropyrrolo[3,4-c]pyrazol-3-yl}-3-methyl-2-furoic amide;
791. N-{5-aminosulfonyl-4,6-dihydropyrrolo[3,4-c]pyrazol-3-yl}-thiophene-2-carboxamide;
792. N-{5-aminosulfonyl-4,6-dihydropyrrolo[3,4-c]pyrazol-3-yl}-thiophene-3-carboxamide;
793. N-{5-aminosulfonyl-4,6-dihydropyrrolo[3,4-c]pyrazol-3-yl}-o-toluic amide;
794. N-{5-aminosulfonyl-4,6-dihydropyrrolo[3,4-c]pyrazol-3-yl}-m-toluic amide;
795. N-{5-aminosulfonyl-4,6-dihydropyrrolo[3,4-c]pyrazol-3-yl}-p-toluic amide;
796. N-{5-aminosulfonyl-4,6-dihydropyrrolo[3,4-c]pyrazol-3-yl}-phenylacetamide;
797. N-{5-aminosulfonyl-4,6-dihydropyrrolo[3,4-c]pyrazol-3-yl}-salicylic amide;
798. N-{5-aminosulfonyl-4,6-dihydropyrrolo[3,4-c]pyrazol-3-yl}-2-fluorobenzamide;
799. N-{5-aminosulfonyl-4,6-dihydropyrrolo[3,4-c]pyrazol-3-yl}-3-fluorobenzamide;
800. N-{5-aminosulfonyl-4,6-dihydropyrrolo[3,4-c]pyrazol-3-yl)}-4-fluorobenzamide;
801. N-{5-aminosulfonyl-4,6-dihydropyrrolo[3,4-c]pyrazol-3-yl}-thiophene-2-acetamide;
802. N-{5-aminosulfonyl-4,6-dihydropyrrolo[3,4-c]pyrazol-3-yl}-thiophene-3-acetamide;
803. N-{5-aminosulfonyl-4,6-dihydropyrrolo[3,4-c]pyrazol-3-yl}-phenylpropiolic amide;
804. N-{5-aminosulfonyl-4,6-dihydropyrrolo[3,4-c]pyrazol-3-yl}-3-cyanobenzamide;
805. N-{5-aminosulfonyl-4,6-dihydropyrrolo[3,4-c]pyrazol-3-yl}-4-cyanobenzamide;
806. N-{5-aminosulfonyl-4,6-dihydropyrrolo[3,4-c]pyrazol-3-yl}-trans-cinnamic amide;
807. N-{5-aminosulfonyl-4,6-dihydropyrrolo[3,4-c]pyrazol-3-yl}-cis-cinnamic amide;
808. N-{5-aminosulfonyl-4,6-dihydropyrrolo[3,4-c]pyrazol-3-yl}-3-(3-pyridyl)acrylic amide;
809. N-{5-aminosulfonyl-4,6-dihydropyrrolo[3,4-c]pyrazol-3-yl}-3-(4-pyridyl)-acrylic amide;
810. N-{5-aminosulfonyl-4,6-dihydropyrrolo[3,4-c]pyrazol-3-yl}-2-phenylpropionamide;
811. N-{5-aminosulfonyl-4,6-dihydropyrrolo[3,4-c]pyrazol-3-yl}-o-tolylacetamide;
812. N-{5-aminosulfonyl-4,6-dihydropyrrolo[3,4-c]pyrazol-3-yl}-m-tolylacetamide;
813. N-{5-aminosulfonyl-4,6-dihydropyrrolo[3,4-c]pyrazol-3-yl}-p-tolylacetamide;
814. N-{5-aminosulfonyl-4,6-dihydropyrrolo[3,4-c]pyrazol-3-yl}-o-anisic amide;
815. N-{5-aminosulfonyl-4,6-dihydropyrrolo[3,4-c]pyrazol-3-yl}-3-methoxybenzamide;
816. N-{5-aminosulfonyl-4,6-dihydropyrrolo[3,4-c]pyrazol-3-yl}-p-anisic amide;
817. N-{5-aminosulfonyl-4,6-dihydropyrrolo[3,4-c]pyrazol-3-yl}-phenoxyacetamide;
818. N-{5-aminosulfonyl-4,6-dihydropyrrolo[3,4-c]pyrazol-3-yl}-2-fluorophenylacetamide;
819. N-{5-aminosulfonyl-4,6-dihydropyrrolo[3,4-c]pyrazol-3-yl}-3-fluorophenylacetamide;
820. N-{5-aminosulfonyl-4,6-dihydropyrrolo[3,4-c]pyrazol-3-yl}-4-fluorophenylacetamide;
821. N-{5-aminosulfonyl-4,6-dihydropyrrolo[3,4-c]pyrazol-3-yl}-3-(2-thienyl)acrylic amide;
822. N-{5-aminosulfonyl-4,6-dihydropyrrolo[3,4-c]pyrazol-3-yl}-3-(3-thienyl)-acrylic amide;
823. N-{5-aminosulfonyl-4,6-dihydropyrrolo[3,4-c]pyrazol-3-yl}-3-(2-thienyl)propanoic amide;
824. N-{5-aminosulfonyl-4,6-dihydropyrrolo[3,4-c]pyrazol-3-yl}-2-chlorobenzamide;
825. N-{5-aminosulfonyl-4,6-dihydropyrrolo[3,4-c]pyrazol-3-yl}-3-chlorobenzamide;
826. N-{5-aminosulfonyl-4,6-dihydropyrrolo[3,4-c]pyrazol-3-yl}-4-chlorobenzamide;
827. N-{5-aminosulfonyl-4,6-dihydropyrrolo[3,4-c]pyrazol-3-yl}-1-piperidinepropionamide;
828. N-{5-aminosulfonyl-4,6-dihydropyrrolo[3,4-c]pyrazol-3-yl}-2-acetylbenzamide;
829. N-{5-aminosulfonyl-4,6-dihydropyrrolo[3,4-c]pyrazol-3-yl}-4-acetylbenzamide;
830. N-{5-aminosulfonyl-4,6-dihydropyrrolo[3,4-c]pyrazol-3-yl}-1-naphthoic amide;
831. N-{5-aminosulfonyl-4,6-dihydropyrrolo[3,4-c]pyrazol-3-yl}-2-naphthoic amide;
832. N-{5-aminosulfonyl-4,6-dihydropyrrolo[3,4-c]pyrazol-3-yl}-3-benzoylpropionamide;
833. N-{5-aminosulfonyl-4,6-dihydropyrrolo[3,4-c]pyrazol-3-yl}-4-acetamidobenzamide;
834. N-{5-aminosulfonyl-4,6-dihydropyrrolo[3,4-c]pyrazol-3-yl}-2,5-dimethoxybenzamide;
835. N-{5-aminosulfonyl-4,6-dihydropyrrolo[3,4-c]pyrazol-3-yl}-2,6-dimethoxybenzamide;
836. N-{5-aminosulfonyl-4,6-dihydropyrrolo[3,4-c]pyrazol-3-yl}-3,4-dimethoxybenzamide;
837. N-{5-aminosulfonyl-4,6-dihydropyrrolo[3,4-c]pyrazol-3-yl}-3,5-dimethoxybenzamide;

838. N-{5-aminosulfonyl-4,6-dihydropyrrolo[3,4-c]pyrazol-3-yl}-3-(2-thenoyl)-propionamide;
839. N-{5-aminosulfonyl-4,6-dihydropyrrolo[3,4-c]pyrazol-3-yl}-2-naphtylacetamide;
840. N-{5-aminosulfonyl-4,6-dihydropyrrolo[3,4-c]pyrazol-3-yl)}-1-naphtylacetamide;
841. N-{5-aminosulfonyl-4,6-dihydropyrrolo[3,4-c]pyrazol-3-yl}-4-phenylbenzamide;
842. N-{5-toluensulfonyl-4,6-dihydropyrrolo[3,4-c]pyrazol-3-yl}-acetamide;
843. N-{5-toluensulfonyl-4,6-dihydropyrrolo[3,4-c]pyrazol-3-yl}-cyclopropanecarboxamide;
844. N-{5-toluensulfonyl-4,6-dihydropyrrolo[3,4-c]pyrazol-3-yl}-isobutyramide;
845. N-{5-toluensulfonyl-4,6-dihydropyrrolo[3,4-c]pyrazol-3-yl}-cyclopentanecarboxamide;
846. N-{5-toluensulfonyl-4,6-dihydropyrrolo[3,4-c]pyrazol-3-yl}-benzamide;
847. N-{5-toluensulfonyl-4,6-dihydropyrrolo[3,4-c]pyrazol-3-yl}-picolinic amide;
848. N-{5-toluensulfonyl-4,6-dihydropyrrolo[3,4-c]pyrazol-3-yl}-nicotinic amide;
849. N-{5-toluensulfonyl-4,6-dihydropyrrolo[3,4-c]pyrazol-3-yl}-isonicotinic amide;
850. N-{5-toluensulfonyl-4,6-dihydropyrrolo[3,4-c]pyrazol-3-yl}-3-methyl-2-furoic amide;
851. N-{5-toluensulfonyl-4,6-dihydropyrrolo[3,4-c]pyrazol-3-yl}-thiophene-2-carboxamide;
852. N-{5-toluensulfonyl-4,6-dihydropyrrolo[3,4-c]pyrazol-3-yl}-thiophene-3-carboxamide;
853. N-{5-toluensulfonyl-4,6-dihydropyrrolo[3,4-c]pyrazol-3-yl}-o-toluic amide;
854. N-{5-toluensulfonyl-4,6-dihydropyrrolo[3,4-c]pyrazol-3-yl}-m-toluic amide;
855. N-{5-toluensulfonyl-4,6-dihydropyrrolo[3,4-c]pyrazol-3-yl}-p-toluic amide;
856. N-{5-toluensulfonyl-4,6-dihydropyrrolo[3,4-c]pyrazol-3-yl}-salicylic amide;
857. N-{5-toluensulfonyl-4,6-dihydropyrrolo[3,4-c]pyrazol-3-yl}-2-fluorobenzamide;
858. N-{5-toluensulfonyl-4,6-dihydropyrrolo[3,4-c]pyrazol-3-yl}-3-fluorobenzamide;
859. N-{5-toluensulfonyl-4,6-dihydropyrrolo[3,4-c]pyrazol-3-yl}-4-fluorobenzamide;
860. N-{5-toluensulfonyl-4,6-dihydropyrrolo[3,4-c]pyrazol-3-yl}-thiophene-2-acetamide;
861. N-{5-toluensulfonyl-4,6-dihydropyrrolo[3,4-c]pyrazol-3-yl}-thiophene-3-acetamide;
862. N-{5-toluensulfonyl-4,6-dihydropyrrolo[3,4-c]pyrazol-3-yl}-phenylpropiolic amide;
863. N-{5-toluensulfonyl-4,6-dihydropyrrolo[3,4-c]pyrazol-3-yl}-3-cyanobenzamide;
864. N-{5-toluensulfonyl-4,6-dihydropyrrolo[3,4-c]pyrazol-3-yl}-4-cyanobenzamide;
865. N-{5-toluensulfonyl-4,6-dihydropyrrolo[3,4-c]pyrazol-3-yl}-trans-cinnamic amide;
866. N-{5-toluensulfonyl-4,6-dihydropyrrolo[3,4-c]pyrazol-3-yl}-cis-cinnamic amide;
867. N-{5-toluensulfonyl-4,6-dihydropyrrolo[3,4-c]pyrazol-3-yl}-3-(3-pyridyl)acrylic amide;
868. N-{5-toluensulfonyl-4,6-dihydropyrrolo[3,4-c]pyrazol-3-yl}-3-(4-pyridyl)-acrylic amide;
869. N-{5-toluensulfonyl-4,6-dihydropyrrolo[3,4-c]pyrazol-3-yl}-2-phenylpropionamide;
870. N-{5-toluensulfonyl-4,6-dihydropyrrolo[3,4-c]pyrazol-3-yl}-o-tolylacetamide;
871. N-{5-toluensulfonyl-4,6-dihydropyrrolo[3,4-c]pyrazol-3-yl}-m-tolylacetamide;
872. N-{5-toluensulfonyl-4,6-dihydropyrrolo[3,4-c]pyrazol-3-yl}-p-tolylacetamide;
873. N-{5-toluensulfonyl-4,6-dihydropyrrolo[3,4-c]pyrazol-3-yl}-o-anisic amide;
874. N-{5-toluensulfonyl-4,6-dihydropyrrolo[3,4-c]pyrazol-3-yl}-3-methoxybenzamide;
875. N-{5-toluensulfonyl-4,6-dihydropyrrolo[3,4-c]pyrazol-3-yl}-p-anisic amide;
876. N-{5-toluensulfonyl-4,6-dihydropyrrolo[3,4-c]pyrazol-3-yl}-phenoxyacetamide;
877. N-{5-toluensulfonyl-4,6-dihydropyrrolo[3,4-c]pyrazol-3-yl}-2-fluorophenylacetamide;
878. N-{5-toluensulfonyl-4,6-dihydropyrrolo[3,4-c]pyrazol-3-yl}-3-fluorophenylacetamide;
879. N-{5-toluensulfonyl-4,6-dihydropyrrolo[3,4-c]pyrazol-3-yl}-4-fluorophenylacetamide;
880. N-{5-toluensulfonyl-4,6-dihydropyrrolo[3,4-c]pyrazol-3-yl}-3-(2-thienyl)acrylic amide;
881. N-{5-toluensulfonyl-4,6-dihydropyrrolo[3,4-c]pyrazol-3-yl}-3-(3-thienyl)-acrylic amide;
882. N-{5-toluensulfonyl-4,6-dihydropyrrolo[3,4-c]pyrazol-3-yl}-3-(2-thienyl)propanoic amide;
883. N-{5-toluensulfonyl-4,6-dihydropyrrolo[3,4-c]pyrazol-3-yl}-2-chlorobenzamide;
884. N-{5-toluensulfonyl-4,6-dihydropyrrolo[3,4-c]pyrazol-3-yl}-3-chlorobenzamide;
885. N-{5-toluensulfonyl-4,6-dihydropyrrolo[3,4-c]pyrazol-3-yl}-4-chlorobenzamide;
886. N-{5-toluensulfonyl-4,6-dihydropyrrolo[3,4-c]pyrazol-3-yl}-1-piperidinepropionamide;
887. N-{5-toluensulfonyl-4,6-dihydropyrrolo[3,4-c]pyrazol-3-yl}-2-acetylbenzamide;
888. N-{5-toluensulfonyl-4,6-dihydropyrrolo[3,4-c]pyrazol-3-yl}-4-acetylbenzamide;
889. N-{5-toluensulfonyl-4,6-dihydropyrrolo[3,4-c]pyrazol-3-yl}-1-naphthoic amide;
890. N-{5-toluensulfonyl-4,6-dihydropyrrolo[3,4-c]pyrazol-3-yl}-2-naphthoic amide;
891. N-{5-toluensulfonyl-4,6-dihydropyrrolo[3,4-c]pyrazol-3-yl}-3-benzoylpropionamide;
892. N-{5-toluensulfonyl-4,6-dihydropyrrolo[3,4-c]pyrazol-3-yl)}-4-acetamidobenzamide;
893. N-{5-toluensulfonyl-4,6-dihydropyrrolo[3,4-c]pyrazol-3-yl}-2,5-dimethoxybenzamide;
894. N-{5-toluensulfonyl-4,6-dihydropyrrolo[3,4-c]pyrazol-3-yl}-2,6-dimethoxybenzamide;
895. N-{5-toluensulfonyl-4,6-dihydropyrrolo[3,4-c]pyrazol-3-yl}-3,4-dimethoxybenzamide;
896. N-{5-toluensulfonyl-4,6-dihydropyrrolo[3,4-c]pyrazol-3-yl}-3,5-dimethoxybenzamide;
897. N-{5-toluensulfonyl-4,6-dihydropyrrolo[3,4-c]pyrazol-3-yl)}-3-(2-thenoyl)-propionamide;
898. N-{5-toluensulfonyl-4,6-dihydropyrrolo[3,4-c]pyrazol-3-yl}-2-naphtylacetamide;
899. N-{5-toluensulfonyl-4,6-dihydropyrrolo[3,4-c]pyrazol-3-yl}-1-naphtylacetamide;
900. N-{5-toluensulfonyl-4,6-dihydropyrrolo[3,4-c]pyrazol-3-yl}-4-phenylbenzamide;
901. N-{5-benzylsulfonyl-4,6-dihydropyrrolo[3,4-c]pyrazol-3-yl}-acetamide;
902. N-{5-benzylsulfonyl-4,6-dihydropyrrolo[3,4-c]pyrazol-3-yl}-cyclopropanecarboxamide;
903. N-{5-benzylsulfonyl-4,6-dihydropyrrolo[3,4-c]pyrazol-3-yl}-isobutyramide;

904. N-{5-benzylsulfonyl-4,6-dihydropyrrolo[3,4-c]pyrazol-3-yl}-cyclopentanecarboxamide;
905. N-{5-benzylsulfonyl-4,6-dihydropyrrolo[3,4-c]pyrazol-3-yl}-benzamide;
906. N-{5-benzylsulfonyl-4,6-dihydropyrrolo[3,4-c]pyrazol-3-yl}-picolinic amide;
907. N-{5-benzylsulfonyl-4,6-dihydropyrrolo[3,4-c]pyrazol-3-yl}-nicotinic amide;
908. N-{5-benzylsulfonyl-4,6-dihydropyrrolo[3,4-c]pyrazol-3-yl}-isonicotinic amide;
909. N-{5-benzylsulfonyl-4,6-dihydropyrrolo[3,4-c]pyrazol-3-yl}-3-methyl-2-furoic amide;
910. N-{5-benzylsulfonyl-4,&dihydropyrrolo[3,4-c]pyrazol-3-yl}-thiophene-2-carboxamide;
911. N-{5-benzylsulfonyl-4,6-dihydropyrrolo[3,4-c]pyrazol-3-yl}-thiophene-3-carboxamide;
912. N-{5-benzylsulfonyl-4,6-dihydropyrrolo[3,4-c]pyrazol-3-yl}-o-toluic amide;
913. N-{5-benzylsulfonyl-4,6-dihydropyrrolo[3,4-c]pyrazol-3-yl}-m-toluic amide;
914. N-{5-benzylsulfonyl-4,6-dihydropyrrolo[3,4-c]pyrazol-3-yl}-p-toluic amide;
915. N-{5-benzylsulfonyl-4,6-dihydropyrrolo[3,4-c]pyrazol-3-yl}-phenylacetamide;
916. N-{5-benzylsulfonyl-4,6-dihydropyrrolo[3,4-c]pyrazol-3-yl}-salicylic amide;
917. N-{5-benzylsulfonyl-4,6-dihydropyrrolo[3,4-c]pyrazol-3-yl}-2-fluorobenzamide;
918. N-{5-benzylsulfonyl-4,6-dihydropyrrolo[3,4-c]pyrazol-3-yl}-3-fluorobenzamide;
919. N-{5-benzylsulfonyl-4,6-dihydropyrrolo[3,4-c]pyrazol-3-yl}-4-fluorobenzamide;
920. N-{5-benzylsulfonyl-4,6-dihydropyrrolo[3,4-c]pyrazol-3-yl}-thiophene-2-acetamide;
921. N-{5-benzylsulfonyl-4,6-dihydropyrrolo[3,4-c]pyrazol-3-yl}-thiophene-3-acetamide;
922. N-{5-benzylsulfonyl-4,6-dihydropyrrolo[3,4-c]pyrazol-3-yl}-phenylpropiolic amide;
923. N-{5-benzylsulfonyl-4,6-dihydropyrrolo[3,4-c]pyrazol-3-yl}-3-cyanobenzamide;
924. N-{5-benzylsulfonyl-4,6-dihydropyrrolo[3,4-c]pyrazol-3-yl}-4-cyanobenzamide;
925. N-{5-benzylsulfonyl-4,6-dihydropyrrolo[3,4-c]pyrazol-3-yl}-trans-cinnamic amide;
926. N-{5-benzylsulfonyl-4,6-dihydropyrrolo[3,4-c]pyrazol-3-yl}-cis-cinnamic amide;
927. N-{5-benzylsulfonyl-4,6-dihydropyrrolo[3,4-c]pyrazol-3-yl}-3-(3-pyridyl)acrylic amide;
928. N-{5-benzylsulfonyl-4,6-dihydropyrrolo[3,4-c]pyrazol-3-yl}-3-(4-pyridyl)-acrylic amide;
929. N-{5-benzylsulfonyl-4,6-dihydropyrrolo[3,4-c]pyrazol-3-yl}-2-phenylpropionamide;
930. N-{5-benzylsulfonyl-4,6-dihydropyrrolo[3,4-c]pyrazol-3-yl}-m-tolylacetamide;
931. N-{5-benzylsulfonyl-4,6-dihydropyrrolo[3,4-c]pyrazol-3-yl}-p-tolylacetamide;
932. N-{5-benzylsulfonyl-4,6-dihydropyrrolo[3,4-c]pyrazol-3-yl}-o-anisic amide;
933. N-{5-benzylsulfonyl-4,6-dihydropyrrolo[3,4-c]pyrazol-3-yl}-3-methoxybenzamide;
934. N-{5-benzylsulfonyl-4,6-dihydropyrrolo[3,4-c]pyrazol-3-yl}-p-anisic amide;
935. N-{5-benzylsulfonyl-4,6-dihydropyrrolo[3,4-c]pyrazol-3-yl}-phenoxyacetamide;
936. N-{5-benzylsulfonyl-4,6-dihydropyrrolo[3,4-c]pyrazol-3-yl}-2-fluorophenylacetamide;
937. N-{5-benzylsulfonyl-4,6-dihydropyrrolo[3,4-c]pyrazol-3-yl}-3-fluorophenylacetamide;
938. N-{5-benzylsulfonyl-4,6-dihydropyrrolo[3,4-c]pyrazol-3-yl}-4-fluorophenylacetamide;
939. N-{5-benzylsulfonyl-4,6-dihydropyrrolo[3,4-c]pyrazol-3-yl}-3-(2-thienyl)acrylic amide;
940. N-{5-benzylsulfonyl-4,6-dihydropyrrolo[3,4-c]pyrazol-3-yl}-3-(3-thienyl)-acrylic amide;
941. N-{5-benzylsulfonyl-4,6-dihydropyrrolo[3,4-c]pyrazol-3-yl}-3-(2-thienyl)propanoic amide;
942. N-{5-benzylsulfonyl-4,6-dihydropyrrolo[3,4-c]pyrazol-3-yl}-2-chlorobenzamide;
943. N-{5-benzylsulfonyl-4,6-dihydropyrrolo[3,4-c]pyrazol-3-yl}-3-chlorobenzamide;
944. N-{5-benzylsulfonyl-4,6-dihydropyrrolo[3,4-c]pyrazol-3-yl}-4-chlorobenzamide;
945. N-{5-benzylsulfonyl-4,6-dihydropyrrolo[3,4-c]pyrazol-3-yl}-1-piperidinepropionamide;
946. N-{5-benzylsulfonyl-4,6-dihydropyrrolo[3,4-c]pyrazol-3-yl}-2-acetylbenzamide;
947. N-{5-benzylsulfonyl-4,6-dihydropyrrolo[3,4-c]pyrazol-3-yl}-4-acetylbenzamide;
948. N-{5-benzylsulfonyl-4,6-dihydropyrrolo[3,4-c]pyrazol-3-yl}-1-naphthoic amide;
949. N-{5-benzylsulfonyl-4,6-dihydropyrrolo[3,4-c]pyrazol-3-yl}-2-naphthoic amide;
950. N-{5-benzylsulfonyl-4,6-dihydropyrrolo[3,4-c]pyrazol-3-yl}-3-benzoylpropionamide;
951. N-{5-benzylsulfonyl-4,6-dihydropyrrolo[3,4-c]pyrazol-3-yl}-4-acetamidobenzamide;
952. N-{5-benzylsulfonyl-4,6-dihydropyrrolo[3,4-c]pyrazol-3-yl}-2,5-dimethoxybenzamide;
953. N-{5-benzylsulfonyl-4,6-dihydropyrrolo[3,4-c]pyrazol-3-yl}-2,6-dimethoxybenzamide;
954. N-{5-benzylsulfonyl-4,6-dihydropyrrolo[3,4-c]pyrazol-3-yl}-3,4-dimethoxybenzamide;
955. N-{5-benzylsulfonyl-4,6-dihydropyrrolo[3,4-c]pyrazol-3-yl}-3,5-dimethoxybenzamide;
956. N-{5-benzylsulfonyl-4,6-dihydropyrrolo[3,4-c]pyrazol-3-yl}-3-(2-thenoyl)-propionamide;
957. N-{5-benzylsulfonyl-4,6-dihydropyrrolo[3,4-c]pyrazol-3-yl}-2-naphtylacetamide;
958. N-{5-benzylsulfonyl-4,6-dihydropyrrolo[3,4-c]pyrazol-3-yl}-1-naphtylacetamide;
959. N-{5-benzylsulfonyl-4,6-dihydropyrrolo[3,4-c]pyrazol-3-yl}-4-phenylbenzamide;
960. N-{5-acetyl-4,6-dihydropyrrolo[3,4-c]pyrazol-3-yl},N'-(4-chlorobenzyl)urea;
961. N-{5-benzyl-4,6-dihydropyrrolo[3,4-c]pyrazol-3-yl},N'-(4-chlorobenzyl)urea;
962. N-{5-phenyl-4,6-dihydropyrrolo[3,4-c]pyrazol-3-yl},N'-(4-chlorobenzyl)urea;
963. N-{5-aminocarbonyl-4,6-dihydropyrrolo[3,4-c]pyrazol-3-yl},N'-(4-chlorobenzyl)urea;
964. N-{5-ethylaminocarbonyl-4,6-dihydropyrrolo[3,4-c]pyrazol-3-yl},N'-(4-chlorobenzyl) urea;
965. N-{5-methansulfonyl-4,6-dihydropyrrolo[3,4-c]pyrazol-3-yl},N'-(4-chlorobenzyl)urea;
966. N-{5-benzylsulfonyl-4,6-dihydropyrrolo[3,4-c]pyrazol-3-yl},N'-(4-chlorobenzyl)urea;
967. N-{5-toluensulfonyl-4,6-dihydropyrrolo[3,4-c]pyrazol-3-yl},N'-(4-chlorobenzyl)urea;
968. N-{5-benzylaminocarbonyl-4,6-dihydropyrrolo[3,4-c]pyrazol-3-yl},N'-(4-chlorobenzyl) urea; and
969. N-{5-phenylaminocarbonyl-4,6-dihydropyrrolo[3,4-c]pyrazol-3-yl},N'-(4-chlorobenzyl) urea;

970. N-(5-(1-naphthalenecarbonyl)-4,5,6,7-tetrahydropyridine[4,3-c]pyrazol-3-yl)-3-tphenoxy-benzamide;
971. N-(5-(1-naphthalenecarbonyl)-4,5,6,7-tetrahydropyridine[4,3-c]pyrazol-3-yl)-4-tertbutyl-benzamide;
972. N-(5-(2-furoyl)-4,5,6,7-tetrahydropyridine[4,3-c]pyrazol-3-yl)-(4-phenyl)phenylacetamide;
973. N-(5-(2-furoyl)-4,5,6,7-tetrahydropyridine[4,3-c]pyrazol-3-yl)-2-(2-naphthyl)propanamide;
974. N-(5-(2-furoyl)-4,5,6,7-tetrahydropyridine[4,3-c]pyrazol-3-yl)-2-(3-fluoro-4-phenyl-phenyl)propanamide;
975. N-(5-(2-methoxybenzoyl)-4,5,6,7-tetrahydropyridine[4,3-c]pyrazol-3-yl)-(2-naphtalene)acetamide;
976. N-(5-(2-methoxy-benzoyl)-4,5,6,7-tetrahydropyridine[4,3-c]pyrazol-3-yl)-[4-(1-pirrolidin-2-on)]phenylacetamide;
977. N-(5-(2-methoxyphenyl)-4,5,6,7-tetrahydropyridine[4,3-c]pyrazol-3-yl)-(4-phenyl)phenylacetamide;
978. N-(5-(4-fluoro-benzoyl)-4,5,6,7-tetrahydropyridine[4,3-c]pyrazol-3-yl)-4-fluorobenzamide;
979. N-(5-acetyl-4,5,6,7-tetrahydro-1H-pyrazolo[4,3-c]pyridin-3-yl)-3-fluorobenzamide;
980. N-(5-acetyl-4,5,6,7-tetrahydropyridine[4,3-c]pyrazol-3-yl)-(2-naphtalene)acetamide;
981. N-(5-acetyl-4,5,6,7-tetrahydropyridine[4,3-c]pyrazol-3-yl)acetamide;
982. N-(5-acetyl-4,5,6,7-tetrahydropyridine[4,3-c]pyrazol-3-yl)benzamide;
983. N-(5-aminocarbonyl-4,5,6,7-tetrahydropyridine[4,3-c]pyrazol-3-yl)-phenylacetamide;
984. N-(5-benzoyl-4,5,6,7-tetrahydropyridine[4,3-c]pyrazol-3-yl)-(4-phenyl)phenylacetamide;
985. N-(5-benzoyl-4,5,6,7-tetrahydropyridine[4,3-c]pyrazol-3-yl)-3-fluorobenzamide;
986. N-(5-benzoyl-4,5,6,7-tetrahydropyridine[4,3-c]pyrazol-3-yl)-3-phenoxy-benzamide;
987. N-(5-benzoyl-4,5,6,7-tetrahydropyridine[4,3-c]pyrazol-3-yl)-4-fluorobenzamide;
988. N-(5-benzoyl-4,5,6,7-tetrahydropyridine[4,3-c]pyrazol-3-yl)-4-phenoxybenzamide;
989. N-(5-benzoyl-4,5,6,7-tetrahydropyridine[4,3-c]pyrazol-3-yl)-4-tertbutyl-benzamide;
990. N-(5-benzoyl-4,5,6,7-tetrahydropyridine[4,3-c]pyrazol-3-yl)acetamide;
991. N-(5-benzoyl-4,5,6,7-tetrahydropyridine[4,3-c]pyrazol-3-yl)benzamide;
992. N-(5-benzoyl-4,5,6,7-tetrahydropyridine[4,3-c]pyrazol-3-yl)cyclopropanecarboxamide;
993. N-(5-benzoyl-4,5,6,7-tetrahydropyridine[4,3-c]pyrazol-3-yl)-phenylacetamide;
994. N-(5-benzylsulfonyl-4,5,6,7-tetrahydropyridine[4,3-c]pyrazol-3-yl)cyclopropanecarboxamide;
995. N-(5-phenylacetyl-4,5,6,7-tetrahydropyridine[4,3-c]pyrazol-3-yl)-(2-naphtalene)acetamide;
996. N-(5-phenylacetyl-4,5,6,7-tetrahydropyridine[4,3-c]pyrazol-3-yl)-phenylacetamide;
997. N,N-dimethyl-N'-{3-(2-phenyl-thiazol-4-yl)acetamido-4,5,6,7-tetrahydropyridine[4,3-c]pyrazol-5-yl}urea;
998. N,N-dimethyl-N'-{3-(benzo[1,3]dioxol-5-yl)acetamido-4,5,6,7-tetrahydropyridine[4,3-c]pyrazol-5-yl}urea;
999. N,N-isopropyl-N'-{3-(benzo[1,3]dioxol-5-yl)acetamido-4,5,6,7-tetrahydropyridine[4,3-c]pyrazol-5-yl}urea;
1000. N-[5-(1,3-benzodioxol-5-ylcarbonyl)-4,5,6,7-tetrahydropyridine[4,3-c]pyrazol-3-yl]-3-methoxybenzamide;
1001. N-[5-(1,3-benzodioxol-5-ylcarbonyl)-4,5,6,7-tetrahydropyridine[4,3-c]pyrazol-3-yl]-3-phenoxybenzamide;
1002. N-[5-(1,3-benzodioxol-5-ylcarbonyl)-4,5,6,7-tetrahydropyridine[4,3-c]pyrazol-3-yl]-3-phenoxybenzamide;
1003. N-[5-(1,3-benzodioxol-5-ylcarbonyl)(4,5,6,7-tetrahydropyridine[4,3-c]pyrazol-3-yl]-4-tertbutyl-benzamide;
1004. N-[5-(2-phenylacetyl)-4,5,6,7-tetrahydropyridine[4,3-c]pyrazol-3-yl]acetamide;
1005. N-[5-(2-phenylacetyl)-4,5,6,7-tetrahydropyridine[4,3-c]pyrazol-3-yl]benzamide;
1006. N-[5-(benzylsulfonyl)-4,5,6,7-tetrahydropyridine[4,3-c]pyrazol-3-yl]-3-bromobenzamide;
1007. N-[5-(benzylsulfonyl)-4,5,6,7-tetrahydropyridine[4,3-c]pyrazol-3-yl]-3-fluorobenzamide;
1008. N-[5-(benzylsulfonyl)-4,5,6,7-tetrahydropyridine[4,3-c]pyrazol-3-yl]acetamide;
1009. N-[5-(benzylsulfonyl)-4,5,6,7-tetrahydropyridine[4,3-c]pyrazol-3-yl]benzamide;
1010. N-[5-(methylsulfonyl)-4,5,6,7-tetrahydropyridine[4,3-c]pyrazol-3-yl]-3-fluoro-benzamide;
1011. N-[5-(methylsulfonyl)-4,5,6,7-tetrahydropyridine[4,3-c]pyrazol-3-yl]-3-methoxy-benzamide;
1012. N-[5-(methylsulfonyl)-4,5,6,7-tetrahydropyridine[4,3-c]pyrazol-3-yl]-4-fluorobenzamide;
1013. N-[5-(methylsulfonyl)-4,5,6,7-tetrahydropyridine[4,3-c]pyrazol-3-yl]-4-phenoxybenzamide;
1014. N-[5-(methylsulfonyl)-4,5,6,7-tetrahydropyridine[4,3-c]pyrazol-3-yl]-4-phenoxy-benzamide;
1015. N-[5-(methylsulfonyl)-4,5,6,7-tetrahydropyridine[4,3-c]pyrazol-3-yl]-4-tertbutyl-benzamide;
1016. N-[5-(methylsulfonyl)-4,5,6,7-tetrahydropyridine[4,3-c]pyrazol-3-yl]acetamide;
1017. N-[5-(methylsulfonyl)-4,5,6,7-tetrahydropyridine[4,3-c]pyrazol-3-yl]benzamide;
1018. N-[5-(methylsulfonyl)-4,5,6,7-tetrahydropyridine[4,3-c]pyrazol-3-yl]cyclopropanecarboxamide;
1019. N-[5-(methylsulfonyl)-4,5,6,7-tetrahydropyridine[4,3-c]pyrazol-3-yl]-phenylacetamide;
1020. N-[5-(quinoline-8-sulfonyl)-4,5,6,7-tetrahydropyridine[4,3-c]pyrazol-3-yl]-4-phenoxybenzamide;
1021. N-[5-(quinoline-8-sulfonyl)-4,5,6,7-tetrahydropyridine[4,3-c]pyrazol-3-yl]acetamide;
1022. N-[5-benzoyl-4,5,6,7-tetrahydropyridine[4,3-c]pyrazol-3-yl]-(2-naphtalene)acetamide;
1023. N-[5-isobutyryl-4,5,6,7-tetrahydropyridine[4,3-c]pyrazol-3-yl]-4-fluorobenzamide;
1024. N-[5-phenylacetyl-4,5,6,7-tetrahydropyridine[4,3-c]pyrazol-3-yl]-3-fluorobenzamide;
1025. N-[5-phenylacetyl-4,5,6,7-tetrahydropyridine[4,3-c]pyrazol-3-yl]-3-methoxybenzamide;
1026. N-[5-phenylacetyl-4,5,6,7-tetrahydropyridine[4,3-c]pyrazol-3-yl]-3-phenoxybenzamide;
1027. N-[5-phenylacetyl-4,5,6,7-tetrahydropyridine[4,3-c]pyrazol-3-yl]-4-fluorobenzamide;
1028. N-[5-phenylacetyl-4,5,6,7-tetrahydropyridine[4,3-c]pyrazol-3-yl]-4-phenoxybenzamide;
1029. N-[5-phenylacetyl-4,5,6,7-tetrahydropyridine[4,3-c]pyrazol-3-yl]-4-tertbutyl-benzamide;
1030. N-[5-phenylacetyl-4,5,6,7-tetrahydropyridine[4,3-c]pyrazol-3-yl]cyclopropanecarboxamide;
1031. N-{5-(2-furoyl)-4,5,6,7-tetrahydropyridine[4,3-c]pyrazol-3-yl}-4-tertbutyl-benzamide;
1032. N-{5-(2-naphthalene)sulfonyl-4,5,6,7-tetrahydropyridine[4,3-c]pyrazol-3-yl}-3-bromobenzamide;
1033. N-{5-(2-thienyl)acetyl-4,5,6,7-tetrahydropyridine[4,3-c]pyrazol-3-yl}-3-methoxybenzamide;
1034. N-{5-(2-thienyl)acetyl-4,5,6,7-tetrahydropyridine[4,3-c]pyrazol-3-yl}-3-phenoxybenzamide;
1035. N-{5-(2-thienyl)acetyl-4,5,6,7-tetrahydropyridine[4,3-c]pyrazol-3-yl}-4-fluorobenzamide;

1036. N-{5-(2-thienyl)acetyl-4,5,6,7-tetrahydropyridine[4,3-c]pyrazol-3-yl}-4-phenoxybenzamide;
1037. N-{5-(2-thienyl)acetyl-4,5,6,7-tetrahydropyridine[4,3-c]pyrazol-3-yl}-4-tertbutyl-benzamide;
1038. N-{5-(2-thienyl)acetyl-4,5,6,7-tetrahydropyridine[4,3-c]pyrazol-3-yl}-acetamide;
1039. N-{5-(2-thienyl)acetyl-4,5,6,7-tetrahydropyridine[4,3-c]pyrazol-3-yl}-cyclopropanecarboxamide;
1040. N-{5-(3-trifluoromethylbenzene)sulfonyl-4,5,6,7-tetrahydropyridine[4,3-c]pyrazol-3-yl}-3-bromo-benzamide;
1041. N-{5-(4-chlorobenzene)sulfonyl-4,5,6,7-tetrahydropyridine[4,3-c]pyrazol-3-yl}-3-bromobenzamide;
1042. N-{5-(4-fluorobenzene)sulfonyl-4,5,6,7-tetrahydropyridine[4,3-c]pyrazol-3-yl}-3-bromobenzamide;
1043. N-{5-(4-methoxybenzene)sulfonyl-4,5,6,7-tetrahydropyridine[4,3-c]pyrazol-3-yl}-3-bromobenzamide;
1044. N-{5-(4-tertbutylbenzene)sulfonyl-4,5,6,7-tetrahydropyridine[4,3-c]pyrazol-3-yl}-3-bromobenzamide;
1045. N-{5-(4-toluensulfonyl)-4,5,6,7-tetrahydropyridine[4,3-c]pyrazol-3-yl}-3-bromobenzamide;
1046. N-{5-(quinoline-8-sulfonyl)-4,5,6,7-tetrahydropyridine[4,3-c]pyrazol-3-yl}-3-fluorobenzamide;
1047. N-{5-(quinoline-8-sulfonyl)-4,5,6,7-tetrahydropyridine[4,3-c]pyrazol-3-yl}-3-methoxy-benzamide;
1048. N-{5-(quinoline-8-sulfonyl)-4,5,6,7-tetrahydropyridine[4,3-c]pyrazol-3-yl}-4-fluoro-benzamide;
1049. N-{5-(quinoline-8-sulfonyl)-4,5,6,7-tetrahydropyridine[4,3-c]pyrazol-3-yl}-4-phenoxy-benzamide;
1050. N-{5-(quinoline-8-sulfonyl)-4,5,6,7-tetrahydropyridine[4,3-c]pyrazol-3-yl}-4-tertbutyl-benzamide;
1051. N-{5-(quinoline-8-sulfonyl)-4,5,6,7-tetrahydropyridine[4,3-c]pyrazol-3-yl}-benzamide;
1052. N-{5-(quinoline-8-sulfonyl)-4,5,6,7-tetrahydropyridine[4,3-c]pyrazol-3-yl}-cyclopropanecarboxamide;
1053. N-{5-(quinoxaline-2-carbonyl)-4,5,6,7-tetrahydropyridine[4,3-c]pyrazol-3-yl}-3-phenoxybenzamide;
1054. N-{5-(quinoxaline-2-carbonyl)-4,5,6,7-tetrahydropyridine[4,3-c]pyrazol-3-yl}-4-tertbutyl-benzamide;
1055. N-{5-[2-(2-thienyl)acetyl]-4,5,6,7-tetrahydropyridine[4,3-c]pyrazol-3-yl}benzamide;
1056. N-{5-benzensulfonyl-4,5,6,7-tetrahydropyridine[4,3-c]pyrazol-3-yl}-3-bromobenzamide;
1057. N-{5-benzensulfonyl-4,5,6,7-tetrahydropyridine[4,3-c]pyrazol-3-yl}-3-fluorobenzamide;
1058. N-{5-benzensulfonyl-4,5,6,7-tetrahydropyridine[4,3-c]pyrazol-3-yl}-3-phenoxybenzamide;
1059. N-{5-benzensulfonyl-4,5,6,7-tetrahydropyridine[4,3-c]pyrazol-3-yl}-4-fluorobenzamide;
1060. N-{5-benzensulfonyl-4,5,6,7-tetrahydropyridine[4,3-c]pyrazol-3-yl}-4-phenoxybenzamide;
1061. N-{5-benzensulfonyl-4,5,6,7-tetrahydropyridine[4,3-c]pyrazol-3-yl}-4-tertbutyl-benzamide;
1062. N-{5-benzensulfonyl-4,5,6,7-tetrahydropyridine[4,3-c]pyrazol-3-yl}-acetamide;
1063. N-{5-benzensulfonyl-4,5,6,7-tetrahydropyridine[4,3-c]pyrazol-3-yl}benzamide;
1064. N-{5-benzensulfonyl-4,5,6,7-tetrahydropyridine[4,3-c]pyrazol-3-yl}-cyclopropanecarboxamide;
1065. N-{5-benzylsulfonyl-4,5,6,7-tetrahydropyridine[4,3-c]pyrazol-3-yl}-3-methoxybenzamide;
1066. N-{5-benzylsulfonyl-4,5,6,7-tetrahydropyridine[4,3-c]pyrazol-3-yl}-3-phenoxybenzamide;
1067. N-{5-benzylsulfonyl-4,5,6,7-tetrahydropyridine[4,3-c]pyrazol-3-yl}-4-fluorobenzamide;
1068. N-{5-benzylsulfonyl-4,5,6,7-tetrahydropyridine[4,3-c]pyrazol-3-yl}-4-phenoxybenzamide;
1069. N-{5-benzylsulfonyl-4,5,6,7-tetrahydropyridine[4,3-c]pyrazol-3-yl}-4-tertbutyl-benzamide;
1070. N-benzyl-N'-{3-(2-(2-naphthalene)propionamido)-4,5,6,7-tetrahydropyridine[4,3-c]pyrazol-5-yl}urea;
1071. N-benzyl-N'-{3-(2-(6-methoxy-2-naphthalene)propionamido)-4,5,6,7-tetrahydropyridine[4,3-c]pyrazol-5-yl}urea;
1072. N-benzyl-N'-{3-(2-naphthalene)acetamido-4,5,6,7-tetrahydropyridine[4,3-c]pyrazol-5-yl}urea;
1073. N-benzyl-N'-{3-(3-methoxy-benzamido)-4,5,6,7-tetrahydropyridine[4,3-c]pyrazol-5-yl}urea;
1074. N-benzyl-N'-{3-(3-methyl-butanamido)-4,5,6,7-tetrahydropyridine[4,3-c]pyrazol-5-yl}urea;
1075. N-benzyl-N'-{3-(4-phenyl)phenylacetamido-4,5,6,7-tetrahydropyridine[4,3-c]pyrazol-5-yl}urea;
1076. N-butyl-N'-{3-(2-(2-naphthalene)propionamido)-4,5,6,7-tetrahydropyridine[4,3-c]pyrazol-5-yl}urea;
1077. N-butyl-N'-{3-(2-(6-methoxy-2-naphthalene)propionamido)-4,5,6,7-tetrahydropyridine[4,3-c]pyrazol-5-yl}urea;
1078. N-butyl-N'-{3-(2-naphthalene)acetamido-4,5,6,7-tetrahydropyridine[4,3-c]pyrazol-5-yl}urea;
1079. N-butyl-N'-{3-(3-methyl-butanamido)-4,5,6,7-tetrahydropyridine[4,3-c]pyrazol-5-yl}urea;
1080. N-butyl-N'-{3-[2-(4-phenyl-3-fluoro-phenyl)propionamido]-4,5,6,7-tetrahydropyridine[4,3-c]pyrazol-5-yl}urea;
1081. N-butyl-N'-{3-benzamido-4,5,6,7-tetrahydropyridine[4,3-c]pyrazol-5-yl}urea;
1082. N-butyl-N'-{3-phenylacetamido-4,5,6,7-tetrahydropyridine[4,3-c]pyrazol-5-yl}urea;
1083. N-ethyl-N'-{3-(2-(2-naphthalene)propionamido)-4,5,6,7-tetrahydropyridine[4,3-c]pyrazol-5-yl}urea;
1084. N-ethyl-N'-{3-(2-(6-methoxy-2-naphthalene)propionamido)-4,5,6,7-tetrahydropyridine[4,3-c]pyrazol-5-yl}urea;
1085. N-ethyl-N'-{3-(2-naphthalene)acetamido-4,5,6,7-tetrahydropyridine[4,3-c]pyrazol-5-yl}urea;
1086. N-ethyl-N'-{3-(3-methyl-butanamido)-4,5,6,7-tetrahydropyridine[4,3-c]pyrazol-5-yl}urea;
1087. N-ethyl-N'-{3-(4-fluorobenzamido)-4,5,6,7-tetrahydropyridine[4,3-c]pyrazol-5-yl}urea;
1088. N-ethyl-N'-{3-(4-phenyl)phenylacetamido-4,5,6,7-tetrahydropyridine[4,3-c]pyrazol-5-yl}urea;
1089. N-ethyl-N'-{3-[2-(4-phenyl-3-fluoro-phenyl)propionamido]-4,5,6,7-tetrahydropyridine[4,3-c]pyrazol-5-yl}urea;
1090. N-ethyl-N'-{3-benzamido-4,5,6,7-tetrahydropyridine[4,3-c]pyrazol-5-yl}urea;
1091. N-ethyl-N'-{3-phenylacetamido-4,5,6,7-tetrahydropyridine[4,3-c]pyrazol-5-yl}urea;
1092. N-isopropyl-N'-{3-(1-methyl-indol-3-yl)acetamido-4,5,6,7-tetrahydropyridine[4,3-c]pyrazol-5-yl}urea;
1093. N-isopropyl-N'-{3-(2-(2-naphthalene)propionamido)-4,5,6,7-tetrahydropyridine[4,3-c]pyrazol-5-yl}urea;
1094. N-isopropyl-N'-{3-(2-(6-methoxy-2-naphthalene)propionamido)-4,5,6,7-tetrahydropyridine[4,3-c]pyrazol-5-yl}urea;
1095. N-isopropyl-N'-{3-(2-phenyl-1,3-thiazol-4-yl)acetamido-4,5,6,7-tetrahydropyridine[4,3-c]pyrazol-5-yl}urea;
1096. N-isopropyl-N'-{3-(3-fluorobenzamido)-4,5,6,7-tetrahydropyridine[4,3-c]pyrazol-5-yl}urea;
1097. N-isopropyl-N'-{3-(3-methoxy-benzamido)-4,5,6,7-tetrahydropyridine[4,3-c]pyrazol-5-yl}urea;
1098. N-isopropyl-N'-{3-(4-fluoro-benzamido)-4,5,6,7-tetrahydropyridine[4,3-c]pyrazol-5-yl}urea;

1099. N-isopropyl-N'-{3-(4-phenyl)phenylacetamido-4,5,6,7-tetrahydropyridine[4,3-c]pyrazol-5-yl}urea;
1100. N-isopropyl-N'-{3-(4-tertbutyl-benzamido)-4,5,6,7-tetrahydropyridine[4,3-c]pyrazol-5-yl}urea;
1101. N-isopropyl-N'-{3-[2-(4-phenyl-3-fluoro-phenyl)propionamido]-4,5,6,7-tetrahydropyridine[4,3-c]pyrazol-5-yl}urea;
1102. N-isopropyl-N'-{3-[4-(1-pirrolidin-2-on)]phenylacetamido-4,5,6,7-tetrahydropyridine[4,3-c]pyrazol-5-yl}urea;
1103. N-isopropyl-N'-{3-acetamido-4,5,6,7-tetrahydropyridine[4,3-c]pyrazol-5-yl}urea;
1104. N-isopropyl-N'-{3-benzamido-4,5,6,7-tetrahydropyridine[4,3-c]pyrazol-5-yl}urea;
1105. N-isopropyl-N'-{3-cyclopropanecarboxamido-4,5,6,7-tetrahydropyridine[4,3-c]pyrazol-5-yl}urea;
1106. N-isopropyl-N'-{3-phenylacetamido-4,5,6,7-tetrahydropyridine[4,3-c]pyrazol-5-yl}urea;
1107. N-phenyl-N'-{3-(2-naphthalene)acetamido-4,5,6,7-tetrahydropyridine[4,3-c]pyrazol-5-yl}urea;
1108. N-phenyl-N'-{3-(3-fluorobenzamido)-4,5,6,7-tetrahydropyridine[4,3-c]pyrazol-5-yl}urea;
1109. N-phenyl-N'-{3-(3-methyl-butanamido)-4,5,6,7-tetrahydropyridine[4,3-c]pyrazol-5-yl}urea;
1110. N-phenyl-N'-{3-(3-phenoxy-benzamido)-4,5,6,7-tetrahydropyridine[4,3-c]pyrazol-5-yl}urea;
1111. N-phenyl-N'-{3-(4-phenoxy-benzamido)-4,5,6,7-tetrahydropyridine[4,3-c]pyrazol-5-yl}urea;
1112. N-phenyl-N'-{3-(4-tertbutyl-benzamido)-4,5,6,7-tetrahydropyridine[4,3-c]pyrazol-5-yl}urea;
1113. N-phenyl-N'-{3-acetamido-4,5,6,7-tetrahydropyridine[4,3-c]pyrazol-5-yl}urea;
1114. N-phenyl-N'-{3-benzamido-4,5,6,7-tetrahydropyridine[4,3-c]pyrazol-5-yl}urea;
1115. N-phenyl-N'-{3-cyclopropanecarboxamido-4,5,6,7-tetrahydropyridine[4,3-c]pyrazol-5-yl}urea;
1116. N-phenyl-N'-{3-phenylacetamido-4,5,6,7-tetrahydropyridine[4,3-c]pyrazol-5-yl}urea;
1117. N-propyl-N'-{3-(4-phenyl)phenylacetamido-4,5,6,7-tetrahydropyridine[4,3-c]pyrazol-5-yl}urea;
1118. N-butyl-N'-{3-(2-naphthalene)acetamido-6,6-dimethyl-4,6-dihydropyrrolo[3,4-c]pyrazol-1-yl}urea;
1119. N-butyl-N'-{3-(3-bromo)benzamido-6,6-dimethyl-4,6-dihydropyrrolo[3,4-c]pyrazol-1-yl}urea;
1120. N-butyl-N'-{3-(4-fluoro)benzamido-6,6-dimethyl-4,6-dihydropyrrolo[3,4-c]pyrazol-1-yl}urea;
1121. N-butyl-N'-{3-(4-tertbutyl)benzamido-6,6-dimethyl-4,6-dihydropyrrolo[3,4-c]pyrazol-1-yl}
1122. N-butyl-N'-{3-cyclopropanecarboxamido-6,6-dimethyl-4,6-dihydropyrrolo[3,4-c]pyrazol-1-yl}urea;
1123. N-butyl-N'-{3-phenylacetamido-6,6-dimethyl-4,6-dihydropyrrolo[3,4-c]pyrazol-5-yl}urea;
1124. N-ethyl-N'-{3-(2-naphthalene)acetamido-6,6-dimethyl-4,6-dihydropyrrolo[3,4-c]pyrazol-1-yl}urea;
1125. N-ethyl-N'-{3-(3-bromo)benzamido-6,6-dimethyl-4,6-dihydropyrrolo[3,4-c]pyrazol-1-yl}urea;
1126. N-ethyl-N'-{3-(4-fluoro)benzamido-6,6-dimethyl-4,6-dihydropyrrolo[3,4-c]pyrazol-1-yl}urea;
1127. N-ethyl-N'-{3-(4-tertbutyl)benzamido-6,6-dimethyl-4,6-dihydropyrrolo[3,4-c]pyrazol-1-yl}
1128. N-ethyl-N'-{3-cyclopropanecarboxamido-6,6-dimethyl-4,6-dihydropyrrolo[3,4-c]pyrazol-1-yl}urea;
1129. N-ethyl-N'-{3-phenylacetamido-6,6-dimethyl-4,6-dihydropyrrolo[3,4-c]pyrazol-5-yl}urea;
1130. N-{5-(2-thienyl-acetyl)-6,6-dimethyl-4,6-dihydropyrrolo[3,4-c]pyrazol-1-yl}-(3-bromo)benzamide;
1131. N-{5-(2-thienyl-acetyl)-6,6-dimethyl-4,6-dihydropyrrolo[3,4-c]pyrazol-3-yl}-(2-naphthalene)acetamide;
1132. N-{5-(2-thienyl-acetyl)-6,6-dimethyl-4,6-dihydropyrrolo[3,4-c]pyrazol-3-yl}-(4-fluoro)benzamide;
1133. N-{5-(2-thienyl-acetyl)-6,6-dimethyl-4,6-dihydropyrrolo[3,4-c]pyrazol-3-yl}-(4-tertbutyl)benzamide;
1134. N-{5-(2-thienyl-acetyl)-6,6-dimethyl-4,6-dihydropyrrolo[3,4-c]pyrazol-3-yl}cyclopropanecarboxamide;
1135. N-{5-(2-thienyl-acetyl)-6,6-dimethyl-4,6-dihydropyrrolo[3,4-c]pyrazol-3-yl}phenylacetamide;
1136. N-{5-(4-fluorobenzoyl)-6,6-dimethyl-4,6-dihydropyrrolo[3,4-c]pyrazol-1-yl}-(3-bromo)benzamide;
1137. N-{5-(4-fluorobenzoyl)-6,6-dimethyl-4,6-dihydropyrrolo[3,4-c]pyrazol-1-yl}-(4-fluoro)benzamide;
1138. N-{5-(4-fluorobenzoyl)-6,6-dimethyl-4,6-dihydropyrrolo[3,4-c]pyrazol-3-yl}-(2-naphthalene)acetamide;
1139. N-{5-(4-fluorobenzoyl)-6,6-dimethyl-4,6-dihydropyrrolo[3,4-c]pyrazol-3-yl}-(4-tertbutyl)benzamide;
1140. N-{5-(4-fluorobenzoyl)-6,6-dimethyl-4,6-dihydropyrrolo[3,4-c]pyrazol-3-yl}cyclopropanecarboxamide;
1141. N-{5-(4-fluorobenzoyl)-6,6-dimethyl-4,6-dihydropyrrolo[3,4-c]pyrazol-3-yl}phenylacetamide;
1142. N-{5-acetyl-6,6-dimethyl-4,6-dihydropyrrolo[3,4-c]pyrazol-3-yl}-(2-naphthalene)acetamide;
1143. N-{5-acetyl-6,6-dimethyl-4,6-dihydropyrrolo[3,4-c]pyrazol-3-yl}-(3-bromo)benzamide;
1144. N-{5-acetyl-6,6-dimethyl-4,6-dihydropyrrolo[3,4-c]pyrazol-3-yl}-(4-fluoro)benzamide;
1145. N-{5-acetyl-6,6-dimethyl-4,6-dihydropyrrolo[3,4-c]pyrazol-3-yl}-(4-tertbutyl)benzamide;
1146. N-{5-acetyl-6,6-dimethyl-4,6-dihydropyrrolo[3,4-c]pyrazol-3-yl}cyclopropanecarboxamide;
1147. N-{5-acetyl-6,6-dimethyl-4,6-dihydropyrrolo[3,4-c]pyrazol-3-yl}phenylacetamide;
1148. N-{5-phenylacetyl-6,6-dimethyl-4,6-dihydropyrrolo[3,4-c]pyrazol-3-yl}-(2-naphthalene)acetamide;
1149. N-{5-phenylacetyl-6,6-dimethyl-4,6-dihydropyrrolo[3,4-c]pyrazol-3-yl}-(3-bromo)benzamide;
1150. N-{5-phenylacetyl-6,6-dimethyl-4,6-dihydropyrrolo[3,4-c]pyrazol-3-yl}-(4-fluoro)benzamide;
1151. N-{5-phenylacetyl-6,6-dimethyl-4,6-dihydropyrrolo[3,4-c]pyrazol-3-yl}-(4-tertbutyl)benzamide;
1152. N-{5-phenylacetyl-6,6-dimethyl-4,6-dihydropyrrolo[3,4-c]pyrazol-3-yl}cyclopropanecarboxamide;
1153. N-isopropyl-N'-{3-(4-tertbutyl-benzamido)-4,5,6,7-tetrahydropyridine[3,4-c]pyrazol-6-yl}urea;
1154. N-{6-(2-thienyl)acetyl-4,5,6,7-tetrahydropyridine[3,4-c]pyrazol-3-yl}4-tertbutyl-benzamide;
1155. N-{6-acetyl-4,5,6,7-tetrahydropyridine[3,4-c]pyrazol-3-yl}-4-tertbutyl-benzamide;
1156. N-{6-methansulfonyl-4,5,6,7-tetrahydropyridine[3,4-c]pyrazol-3-yl}-4-tertbutyl-benzamide;
1157. N-ethyl-N'-{3-(4-tertbutyl-benzamido)-4,5,6,7-tetrahydropyridine[3,4-c]pyrazol-6-yl}urea;
1158. N-{6-(3-methyl)butyryl-4,5,6,7-tetrahydropyridine[3,4-c]pyrazol-3-yl}-4-tertbutyl-benzamide;
1159. N-{6-(2-furoyl)-4,5,6,7-tetrahydropyridine[3,4-c]pyrazol-3-yl}-4-tertbutyl-benzamide;
1160. N-{6-phenylacetyl-4,5,6,7-tetrahydropyridine[3,4-c]pyrazol-3-yl}-4-tertbutyl-benzamide;
1161. N-{6-phenylsulfonyl-4,5,6,7-tetrahydropyridine[3,4-c]pyrazol-3-yl}-4-tertbutyl-benzamide;
1162. N-{6-(quinoline-8-sulfonyl)-4,5,6,7-tetrahydropyridine[3,4-c]pyrazol-3-yl}-4-tertbutyl-benzamide;
1163. N-{5-isopentyl-4,6-dihydropyrrolo[3,4-c]pyrazol-3-yl}-4-tertbutylbenzamide;

1164. N-{5-phenylethyl-4,6-dihydropyrrolo[3,4-c]pyrazol-3-yl}-4-tertbutylbenzamide;

1165. N-[5-(2-thien-2-ylethyl)-4,6-dihydropyrrolo[3,4-c]pyrazol-3-yl]-4-tertbutyl-benzamide;

1166. N,N-dimethyl-N'-{3-(2-naphthalen-2-yl-propionamido)-4,6-dihydropyrrolo[3,4-c]pyrazol-5-yl}urea;

1167. N-{5-(piperidin-1-yl)carbamoyl)-4,6-dihydropyrrolo[3,4-c]pyrazol-3-yl}-3-(2-naphthalen-2-yl)-propionamide; and 1168. N,N-dimethyl-N'-{3-(2-phenyl-thiazol-4-yl)acetamido-4,5,6,7-tetrahydropyridine[4,3-c]pyrazol-5-yl}urea.

As formerly indicated, the process for preparing the compounds of formula (I) represents a further embodiment of the invention. The compounds of formula (I) and the pharmaceutically acceptable salts thereof can be thus prepared according to a process comprising:

a) reacting a compound of formula (II)

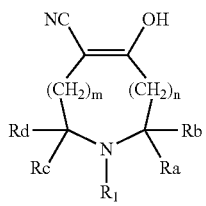

(II)

wherein $R_1$, being as defined above, is not hydrogen, and Ra, Rb, Rc, Rd, m and n are as defined above with hydrazine or hydrazine salt, so as to obtain a compound of formula (I) wherein R is hydrogen and $R_1$, being as being as defined above, is not hydrogen and, if desired, b) converting a thus obtained compound of formula (I) into another compound of formula (I) wherein R, being as defined above, is other than hydrogen and $R_1$, Ra, Rb, Rc, Rd, m and n are as defined above in formula (I), and/or if desired converting a compound of formula (I) into a pharmaceutically acceptable salt thereof.

The above process is an analogy process which can be carried out according to well known methods. It is clear to the person skilled in the art that if a compound of formula (I), prepared according to the above process, is obtained as an admixture of isomers, their separation into the single isomers of formula (I), carried out according to conventional techniques, is still within the scope of the present invention. Likewise, the conversion into the free compound (I) of a corresponding salt thereof, according to well-known procedures in the art, is still within the scope of the invention. An hydrazide salt is e.g. hydrazine dihydrochloride, sulphate or acetate.

According to step a) of the process, the reaction between a compound of formula (II) and hydrazine, or hydrazine salt, can be carried out in the presence of catalytic amounts of an acid, for instance hydrochloric, acetic or sulphuric acid; in a suitable solvent such as, for instance, tetrahydrofuran, 1,4-dioxane, acetonitrile, methanol or ethanol, at a temperature ranging from about room temperature to reflux and for a time varying from about 30 minutes to about 8 hours.

The bicyclo-pyrazoles of formula (I) wherein R is hydrogen, obtained according to step a) of the process, can be easily converted into a variety of derivatives of formula (I) having R other than hydrogen, and/or into salts thereof.

As set forth below, these conversions occur according to conventional techniques by properly reacting the amino derivative (I) with alkylating, acylating, sulfonylating agents and the like.

In this respect it is worth noting that optional by-products, for instance originating by the above reactions also occurring at the nitrogen pyrazole atom, may be obtained. As such, a subsequent step to isolate the desired compound of formula (I) is then required.

According to a preferred embodiment of the process of the invention which avoids the above by-products formation, a compound of formula (I), obtained according to step a) above, is first supported onto a suitable resin and, then, reacted as per step b) above.

It is therefore a further object of the invention a process for preparing a compound of formula (I), in which R, $R_1$, Ra, Rb, Rc, Rd and m and n are as defined above, which comprises:

a) reacting a compound of formula (II)

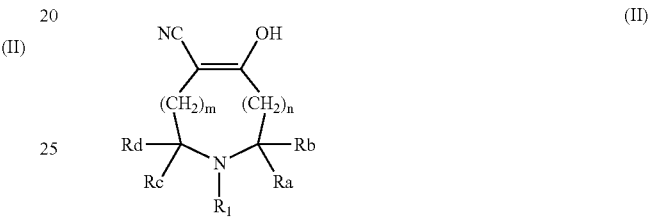

(II)

wherein, $R_1$, being as defined above, is not hydrogen, and Ra, Rb, Rc, Rd, m and n are as defined above, with hydrazine or hydrazine salt, so as to obtain a compound of formula (I) wherein R is hydrogen and $R_1$, being as defined above, is not hydrogen;

a') reacting a thus obtained compound of formula (I) with an isocyanate polystyrenic resin of formula (III)

(III)

so as to obtain a polystyrenemethyl urea; of formula (IV)

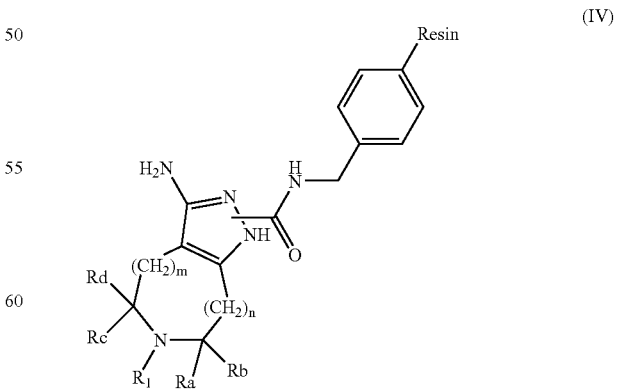

(IV)

wherein Ra, Rb, Rc, Rd, m and n are as defined above and $R_1$, being as defined above, is not hydrogen;

b) converting a thus obtained compound of formula (IV) into a compound of formula (V)

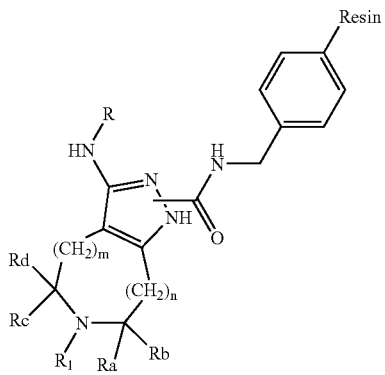
(V)

wherein R has the above reported meanings other than hydrogen and $R_1$, Ra, Rb, Rc, Rd, m and n are as defined above; and c) cleaving under alkaline conditions a compound of formula (V) so as to eliminate the resin and to obtain the desired compound of formula (I) and, optionally, converting a compound of formula (I) into another compound of formula (I) and/or into a pharmaceutically acceptable salt thereof.

Notably, while the previously reported process for the conversion of the aminopyrazole derivatives of formula (I) having R equal to hydrogen does not discriminate between the amino moiety in position 3 of the pyrazole ring and the reactive nitrogen of the pyrazole ring, as formerly indicated, the present reaction according to the above step a) shows an unexpected high selectivity towards the acylation of the ring nitrogen, hence allowing to obtain, in the subsequent step b), the exclusive conversion of the amino group, in position 3 of the pyrazole ring, into the desired compound of formula (V).

In step a'), the reaction between isocyanatomethyl polystyrenic resin of formula (III) and a compound of formula (I), as therein defined, can be carried out in a suitable solvent such as, for instance, N,N-dimethylformamide, dichloromethane, chloroform, acetonitrile, toluene or a mixture thereof, at a temperature ranging from about 5° C. to about 35° C. and for a time varying from about 30 minutes to about 72 hours.

After having carried out the conversion of a compound of formula (IV) into a compound of formula (V), as described below, the subsequent cleavage of the resin, in step c), is carried out under alkaline conditions by working according to conventional techniques.

As an example, aqueous sodium or potassium hydroxides in the presence of a suitable co-solvent such as methanol, ethanol, dimethylformamide, 1,4-dioxane, or acetonitril can be employed.

The reaction occurs under mild conditions, at temperatures from about 5° C. to about 60° C. and for a time varying from about 2 hours to about 7 days.

Also the optional salification of a compound of formula (I) or the conversion of its salt into the free compound, as well as the separation of a mixture of isomers into the single isomers, may all be carried out by conventional methods.

As far as step b) of the process is concerned, the optional conversion of a compound of formula (I) or, more preferably, of formula (IV) having R equal to hydrogen, into a corresponding derivatives of formula (I) or (V) having R other than hydrogen, is carried according to conventional techniques known in the art to alkylate, acylate or sulfonylate amino groups.

In particular, a compound of formula (I) or (V) wherein R is selected from R' other than hydrogen, —COR', —COOR', —SO$_2$R', —SO$_2$NHR' or —SO$_2$NR'R", wherein R' and R" have the above reported meanings; $R_1$ is not hydrogen and Ra, Rb, Rc, Rd, m and n are as above defined, may be prepared by reacting a compound of formula (I), or a compound of formula (IV), having R equal to hydrogen, with a compound of formula (VI)

R—X  (VI)

wherein R is as above indicated except hydrogen and X is a suitable leaving group, preferably chlorine or bromine.

The above reaction can be carried out according to conventional procedures well known in the art for acylating, sulfonylating or alkylating amino groups, for instance in the presence of a tertiary base, such as triethylamine, N,N-diisopropylethylamine or pyridine, in a suitable solvent such as toluene, dichloromethane, chloroform, diethyl ether, tetrahydrofuran, acetonitrile, or N,N-dimethylformamide, at a temperature ranging from about −10° C. to reflux and for a time varying from about 30 minutes to about 96 hours.

From the foregoing it is clear to the person skilled in the art that the preparation of the compounds of formula (I) or (V) having R equal to —SO$_2$NR'R" can be actually performed as above described or, alternatively, by properly reacting a compound of formula (I) or (V) having R equal to —SO$_2$NHR' with any suitable alkylating moiety, according to well known methodologies for preparing di-substituted sulfonamides.

A compound of formula (I) or (V) wherein R is a —CONHR' group, R' has the above reported meanings other than hydrogen, $R_1$ is not hydrogen and Ra, Rb, Rc, Rd, m and n are as above defined, may be prepared by reacting a compound of formula (I) or a compound of formula (IV) having R equal to hydrogen, with a compound of formula (VII)

R'NCO  (VII)

wherein R' is as above defined other than hydrogen, so as to obtain a corresponding compound of formula (I) or (V) which may be optionally further reacted with a compound of formula (VIII)

R"—X  (VIII)

wherein R" is as above defined other than hydrogen and X is a suitable leaving group, preferably chlorine or bromine, so as to obtain a compound of formula (I) or (V) wherein R is —CONR'R", wherein R' and R" are other than hydrogen.

The reaction between the above compounds (I) or (IV) with a compound of formula (VII) can be carried out in the presence of a tertiary base, such as triethylamine, N,N-diisopropylethylamine or pyridine, in a suitable solvent, such as toluene, dichloromethane, chloroform, diethyl ether, tetrahydrofuran, acetonitrile, or N,N-dimethylformamide, at a temperature ranging from about −10° C. to reflux and for a time varying from about 30 minutes to about 72 hours.

The optional subsequent conversion of a compound of formula (I) or (V) having R equal to —CONHR' into a corresponding derivative having R equal to —CONR'R" is carried out according to conventional methods used to prepare di-substituted ureido derivatives.

A compound of formula (I) or (V) wherein R is a —CONR'R" group, R' and R" has the above reported meanings other than hydrogen, $R_1$ is not hydrogen and Ra, Rb, Rc, Rd, m and n are as above defined, may be prepared by reacting a compound of formula (I), or a compound of formula (IV), having R equal to hydrogen with 4-nitrophenylchloroformate and subsequently with a compound of formula (IX)

R'R"NH (IX)

wherein R' and R", being as defined above are not hydrogen.

The reaction is carried out according to conventional methods used to prepare di-substituted ureido derivatives.

Alternatively, a compound of formula (I), or a compound of formula (IV), having R equal to hydrogen may be reacted under reductive conditions with a compound of formula (X)

R'—CHO (X)

wherein R', being as defined above is not hydrogen, so as to obtain a corresponding compound of formula (I) or (V) wherein R is a R'CH$_2$— group and R' being as defined above is not hydrogen.

The reaction is carried out in a suitable solvent such as, for instance, N,N-dimethylformamide, N,N-dimethylacetamide, chloroform, dichloromethane, tetrahydrofuran, or acetonitrile, optionally in the presence of acetic acid, ethanol or methanol as co-solvents, at a temperature ranging from about −10° C. to reflux and for a time varying from about 30 min to about 4 days.

Conventional reducing agents in the reaction medium are, for instance, sodium boron hydride, sodium triacetoxy boron hydride, and the like. From the foregoing, it is clear to the person skilled in the art than any of the above compounds of formula (I), (IV) and (V) may be conveniently converted into other derivatives (I, (IV) or (V) also by properly reacting functional groups other than the R group, extensively described above, in a substantial similar fashion and according to conventional synthetic organic methods.

As an example, the compounds of formula (I), (IV) or (V) wherein R$_1$ is —COO$^t$Bu can be hydrolized to the compounds of formula (V) wherein R$_1$ is H, by treatment with a suitable acid, for instance trifluoroacetic or hydrochloric acid.

So far, any of the above compounds of formula (I), (IV) or (V) wherein R$_1$ is a hydrogen atom can be easily converted into the corresponding derivatives alkylated, acylated or sulfonated, by working substantially as above described for the R group.

In a further example, any of the above compounds wherein one or more of Ra, Rb, Rc and Rd is —CH$_2$OH may be conveniently prepared by starting from a corresponding protected derivative having one or more of Ra, Rb, Rc and Rd as —CH$_2$—O—Si(Me)$_2$tBu or —CH$_2$—O-Ph.

The reaction is carried according to conventional techniques, for instance in a suitable solvent such as, for instance, N,N-dimethylformamide chloroform, dichloromethane, tetrahydrofuran, methanol, ethanol or acetonitrile, at a temperature ranging from about −10° C. to reflux and for a time varying from about 30 min to about 72 hours with a suitable fluoride source, for instance tetrabutylamonium fluoride.

Likewise, the above compounds (I), (IV) or (V) having one or more Ra, Rb, Rc and Rd equal to —CH$_2$OH can be reacted with a compound of formula (VI)

R—X (VI)

wherein R is R' which, being as defined above, is not hydrogen and X is a suitable leaving group, so as to obtain the corresponding compounds having one or more Ra, Rb, Rc and Rd as —CH$_2$OR', R' being other than hydrogen.

This latter reaction can be carried out in the presence of a base, such as sodium hydride, N,N-diisopropylethylamine or pyridine, in a suitable solvent, such as toluene, dichloromethane, chloroform, diethyl ether, tetrahydrofuran, acetonitrile, or N,N-dimethylformamide, at a temperature ranging from about −10° C. to reflux.

As will be appreciated by the person skilled in the art, when preparing the compounds of formula (I) embodiment of the invention, optional functional groups within both the starting materials or the intermediates thereof, which could give rise to unwanted side reactions, need to be properly protected according to conventional techniques. Likewise, the conversion of these latter into the free deprotected compounds may be carried out according to known procedures.

All of the compounds of formula (II), (III), (VI), (VII), (VIII), (IX) and (X), according to process embodiments of the present invention, are known or can be obtained according to known methods. In particular, the compounds of formula from (VI) to (X) are commercially available or readily prepared according to conventional methods and the compounds of formula (II) can be prepared according to the procedures described in the aforementioned Gadekar, Sheekrishna M. et al. in J. Med. Chem.; 1968, 11(3), 616-618; Hong, C. Y; Kim, Y K.; Chang, J. H.; Kim, S. H.; Choi, H.; Nam, D. H.; Kim, Y Z.; Kwak, J. H. J. Med. Chem.; 1997, 40(22) 3584-3593; Pedersen, H.; Brauner-Obsborne, H.; Ball, J. R.; Frydenvang, K.; Meier, E.; Bogeso, K. P.; Krogsgaard-Larsen, P. Bioorg. Med. Chem. 1999, 7, 795-809.

Finally, it is clear to the person skilled in the art that the compounds embodiments of formula (I) of the invention can be prepared, preferably, by performing the above described reactions in a combinatorial fashion. As an example, the compounds of formula (IV) supported onto resin particles, prepared as above described, are reacted with a variety of compounds of formula from (VI) to (X) so as to obtain thousands of different compounds of formula (V), according to combinatorial chemistry methods. These derivatives, in their turn, are then conveniently converted into the derivatives of formula (I) embodiments of the invention.

It is therefore a further object of the invention a combinatorial chemical library comprising a plurality of members of formula (V):

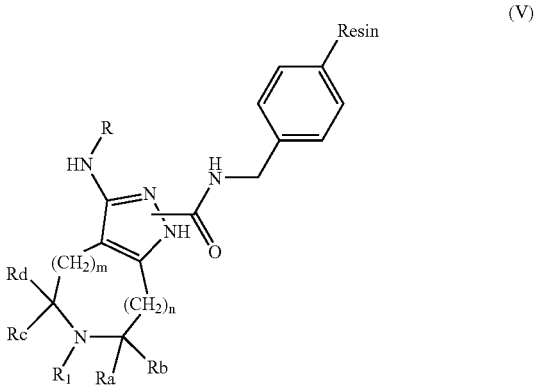

wherein

R and R$_1$, being the same or different, are independently a hydrogen atom or an optionally substituted group selected from R', —COR', —COOR', —CONHR', —CONR'R", —NH—C(=NH)NHR', —C(=NH)NHR', —SO$_2$R', —SO$_2$NHR' or —SO$_2$NR'R"; wherein R' and R", the same or different, are independently selected from hydrogen or optionally further substituted straight or branched C$_1$-C$_6$ alkyl, aryl, C$_3$-C$_6$ cycloalkyl or aryl C$_1$-C$_6$ alkyl or R' and R" taken together form a $C_4$-$C_6$ alkylene chain; Ra, Rb, Rc and Rd, the same or different, are selected among hydrogen, optionally further substituted straight or branched $C_1$-$C_6$ alkyl, aryl, aryl $C_1$-$C_6$ alkyl or —$CH_2OR'$ groups, wherein R' is as above defined or, Ra and Rb and/or Rb and Rc taken together with the carbon atom to which they are bonded, form an optionally substituted $C_3$-$C_6$ cycloalkyl group; m and n, each independently, represent 0 or an integer from 1 to 2, provided that m+n is lower than, or equal to, 2 (m+n$\leq$2).

Preferably, the above resin is a polystyrenic resin, in particular a methylisocyanate polystirene resin.

Pharmacology

The compounds of formula (I) are active as protein kinase inhibitors and are therefore useful, for instance, to restrict the unregulated proliferation of tumor cells. In therapy, they may be used in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease. The inhibiting activity of putative protein kinase inhibitors and the potency of selected compounds was determined through a method of assay based on the use of the MultiScreen-PH 96 well plate (Millipore), in which a phosphocellulose filter paper was placed at each well bottom allowing binding of positive charged substrate after a washing/filtration step. When a radioactivity labeled phosphate moiety was transferred by the ser/threo kinase to the filter-bound histone, light emitted was measured in a scintillation counter.

Inhibition Assay of cdk2/Cyclin A Activity

Kinase reaction: 1.5 µM histone H1 substrate, 25 µM ATP (0.2 µCi P33γ-ATP), 30 ng of baculovirus co-expressed cdk2/Cyclin A, 10 µM inhibitor in a final volume of 100 µl buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS Ca++/Mg++free and filtered by MultiScreen filtration system.

Detection: filters were allowed to dry at 37° C., then 100 µl/well scintillant were added and 33P labeled histone H1 was detected by radioactivity counting in the Top-Count instrument.

Results: data were analyzed and expressed as % inhibition referred to total activity of enzyme (=100%).

All compounds showing inhibition$\geq$50% were further analyzed in order to study and define potency (IC50) as well as the kinetic-profile of inhibitor through Ki calculation.

IC50 determination: the protocol used was the same described above, where inhibitors were tested at different concentrations ranging from 0.0045 to 10 µM. Experimental data were analyzed by the computer program GraphPad Prizm using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

Ki calculation: either the concentration of ATP and histone H1 substrate were varied: 4, 8, 12, 24, 48 µM for ATP (containing proportionally diluted $P^{33}\gamma$-ATP) and 0.4, 0.8, 1.2, 2.4, 4.8 µM for histone were used in absence and presence of two different, properly chosen inhibitor concentrations.

Experimental data were analyzed by the computer program "SigmaPlot" for Ki determination, using a random bireactant system equation:

$$v = \frac{V\max \frac{(A)(B)}{aKAKB}}{1 + \frac{(A)}{KA} + \frac{(B)}{KB} + \frac{(A)(B)}{aKAKB}}$$

where A=ATP and B=histone H1.

In addition the selected compounds have been characterized on a panel of ser/threo kinases strictly related to cell cycle (cdk2/cyclin E, cdk1/cyclin B1, cdk4/Cyclin D1), and also for specificity on MAPK, PKA, EGFR, IGF1-R, Cdc7/dbf4 and aurora-2.

Inhibition Assay of cdk2/Cyclin E Activity

Kinase reaction: 1.5 µM histone H1 (Sigma # H-5505) substrate, 25 µM ATP (0.2 µCi $P^{33}\gamma$-ATP), 15 ng of baculovirus co-expressed cdk2/GST-Cyclin E, suitable concentrations of inhibitor in a final volume of 100 µl buffer (TRIS HCl 10 mM pH 7.5, $MgCl_2$ 10 mM, 7.5 mM DTT+0.2 mg/ml BSA) were added to each well of a 96-U bottom well plate. After 10 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS $Ca^{++}/Mg^{++}$ free and filtered by MultiScreen filtration system.

Detection: filters were allowed to dry at 37° C., then 100 µl/well scintillant were added and $^{33}P$ labeled histone H1 was detected by radioactivity counting in the Top-Count instrument.

Inhibition Assay of cdk1/Cyclin B1 Activity

Kinase reaction: 1.5 µM histone H1 (Sigma # H-5505) substrate, 25 µM ATP (0.2 µCi $P^{33}\gamma$-ATP), 30 ng of baculovirus co-expressed cdk1/Cyclin B1, suitable concentrations of inhibitor in a final volume of 100 µl buffer (TRIS HCl 10 mM pH 7.5, $MgCl_2$ 10 mM, 7.5 mM DTT+0.2 mg/ml BSA) were added to each well of a 96 U bottom well plate. After 10 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS $Ca^{++}/Mg^{++}$ free and filtered by MultiScreen filtration system.

Detection: filters were allowed to dry at 37° C., then 100 µl/well scintillant were added and $^{33}P$ labeled histone H1 was detected by radioactivity counting in the Top-Count instrument.

Inhibition Assay cdk4/Cyclin D1 activity

Kinase reaction: 0.4 uM µM mouse GST-Rb (769-921) (# sc-4112 from Santa Cruz) substrate, 10 µM ATP (0.5 µCi $P^{33}\gamma$-ATP), 100 ng of baculovirus expressed GST-cdk4/GST-Cyclin D1, suitable concentrations of inhibitor in a final volume of 50 µl buffer (TRIS HCl 10 mM pH 7.5, $MgCl_2$ 10 mM, 7.5 mM DTT+0.2 mg/ml BSA) were added to each well of a 96 U bottom well plate. After 40 min at 37° C. incubation, reaction was stopped by 20 µl EDTA 120 mM.

Capture: 60 µl were transferred from each well to Multi-Screen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled Rb fragment was detected by radioactivity counting in the Top-Count instrument.

Inhibition Assay of MAPK Activity

Kinase reaction: 10 µM MBP (Sigma # M-1891) substrate, 25 µM ATP (0.2 µCi p$^{33}$γ-ATP), 25 ng of bacterially expressed GST-MAPK (Upstate Biotechnology # 14-173), suitable concentrations of inhibitor in a final volume of 100 µl buffer (TRIS HCl 10 mM pH 7.5, MgCl$_2$ 10 mM, 7.5 mM DTT+0.1 mg/ml BSA) were added to each well of a 96 U bottom well plate. After 15 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled MBP was detected by radioactivity counting in the Top-Count instrument.

Inhibition Assay of PKA Activity

Kinase reaction: 10 µM histone H1 (Sigma # H-5505) substrate, 10 µM ATP (0.2 µCi P$^{33}$γ-ATP), 1 U of bovine heart PKA (Sigma # 2645), suitable concentrations of inhibitor in a final volume of 100 µl buffer (TRIS HCl 10 mM pH 7.5, MgCl$_2$ 10 mM, 7.5 mM DTT+0.2 mg/ml BSA) were added to each well of a 96 U bottom well plate. After 5 min at 37° C. incubation, reaction was stopped by 20 µl EDTA 120 mM.

Capture: 100 µl were transferred from each well to Multi-Screen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled histone H1 was detected by radioactivity counting in the Top-Count instrument.

Inhibition Assay of EGFR Activity

Kinase reaction: 25 nM in house biotinylated PolyGluTyr (Sigma # 0275) substrate, 2.5 µM ATP (0.3 µCi P$^{33}$γ-ATP), 80 ng baculovirus expressed GST-EGFR, suitable concentrations of inhibitor in a final volume of 100 µl buffer (Hepes 50 mM pH 7.5, MnCl$_2$—MgCl$_2$ 3 mM, 1 mM DTT+3 M µNaVO3, 0.1 mg/ml BSA) were added to each well of a 96 U bottom well plate. After 5 min. at 37° C. incubation, reaction was stopped by 20 µl EDTA 120 mM.

Capture: 100 µl were transferred from each well to streptavidin-Flashplate, to allow biotinylated-substrate binding to plate. Plates were then washed 3 times with 150 µl/well PBS Ca$^{++}$/Mg$^{++}$ free.

Detection: radioactivity counting in the Top-Count instrument.

Inhibition Assay of IGF1-R Activity

The inhibition assay of IGF1-R activity was performed according to the following protocol.

Kinase reaction: 10 µM biotinylated MBP (Sigma cat. # M-1891) substrate, 0-20 µM inhibitor, 6 µM cold ATP, 2 nM $^{33}$P-ATP, and 22.5 ng IGF1-R (pre-incubated for 30 min at room temperature with cold 60 µM cold ATP) in a final volume of 30 µl buffer (50 mM HEPES pH 7.9, 3 mM MnCl$_2$, 1 mM DTT, 3 µM NaVO$_3$) were added to each well of a 96 U bottom well plate. After incubation for 35 min at room temperature, the reaction was stopped by addition of 100 µl PBS buffer containing 32 mM EDTA, 500 µM cold ATP, 0.1% Triton X100 and 10 mg/ml streptavidin coated SPA beads. After 15 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

Results: Experimental data were analyzed with the program GraphPad Prizm.

In addition, the inhibiting activity of putative protein kinase inhibitors and the potency of selected compounds was also determined through a method of assay based on the use of a SPA (Scintillation Proximity Assay) 96 well plate assay. The assay is based on the ability of streptavidin coated SPA beads to capture a biotinylated peptide derived from a phosphorylation site of histone.

When a radioactivity labeled phosphate moiety was transferred by the ser/threo kinase to the biotinylated histone peptide, light emitted was measured in a scintillation counter.

Inhibition Assay of cdk5/p25 Activity

The inhibition assay of cdk5/p25 activity was performed according to the following protocol.

Kinase reaction: 1.0 µM biotinylated histone peptide substrate, 0.25 µCi P33g-ATP, 4 nM cdk5/p25 complex, 0-100 µM inhibitor in a final volume of 100 µl buffer (Hepes 20 mM pH 7.5, MgCl2 15 mM, 1 mM DTT) were added to each well of a 96 U bottom well plate. After 20 min at 37° C. incubation, the reaction was stopped by the addition of 500 ug SPA beads in phosphate-buffered saline containing 0.1% Triton X-100, 50 uM ATP and 5 mM EDTA. The beads were allowed to settle, and the radioactivity incorporated in the $^{33}$P-labelled peptide was detected in a Top Count scintillation counter.

Results: Data were analyzed and expressed as % Inhibition using the formula:

$$100 \times (1-(\text{Unknown}-\text{Bkgd})/(\text{Enz. Control}-\text{Bkgd}))$$

IC50 values were calculated using a variation of the four parameter logistics equation:

$$Y=100/[1+10^{((\log \text{EC50}-X)*\text{Slope})}]$$

Where X=log(uM) and Y=% Inhibition.

Inhibition Assay of Cdc7/dbf4 Activity

The inhibition assay of Cdc7/dbf4 activity was performed according to the following protocol.

The Biotin-MCM2 substrate is trans-phosphorylated by the Cdc7/Dbf4 complex in the presence of ATP traced with γ$^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:

10 µl substrate (biotinylated MCM2, 6 µM final concentration)

10 µl enzyme (Cdc7/Dbf4, 12.5 nM final concentration)

10 µl test compound (12 increasing concentrations in the nM to 1M range to generate a dose-response curve)

10 µl of a mixture of cold ATP (10M final concentration) and radioactive ATP (1/2500 molar ratio with cold ATP) was then used to start the reaction which was allowed to take place at 37° C.

Substrate, enzyme and ATP were diluted in 50 mM HEPES pH 7.9 containing 15 mM MgCl$_2$, 2 mM DTT, 3 µM NaVO$_3$, 2 mM glycerophosphate and 0.2 mg/ml BSA. The solvent for test compounds also contained 10% DMSO.

After incubation for 20 minutes, the reaction was stopped by adding to each well 100 µl of PBS pH 7.4 containing 50 mM EDTA, 1 mM cold ATP, 0.1% Triton X100 and 10 mg/ml streptavidin coated SPA beads.

After 15 minutes of incubation at room temperature to allow the biotinylated MCM2-streptavidin SPA beads interaction to occur, beads were trapped in a 96 wells filter plate (Unifilfer® GF/B™) using a Packard Cell Harvester (Filtermate), washed with distilled water and then counted using a Top Count (Packard).

Counts were blank-subtracted and then the experimental data (each point in triplicate) were analyzed for IC50 determination using a non-linear regression analysis (Sigma Plot).

Inhibition Assay of Aurora-2 Activity

The inhibiting activity and the potency of selected compounds was determined through a method of assay based on the use of the streptavidin scintillation proximity assay beads (amershampharmacia biotech) run in a 96 well plates. At the end of the reaction, the biotinylated peptide substrate was captured with the beads and subsequently allowed to stratify using CsCl$_2$.

When a radioactivity labeled phosphate moiety was transferred by the kinase to the beads-bound peptide, light emitted was measured in a scintillation counter.

The inhibition assay of Aurora-2 activity was performed in 96 wells plate according to the following protocol.

Kinase reaction: 8 µM biotinylated peptide (4 repeats of LRRWSLG), 10 µM ATP (0.5 uCi P$^{33}$g-ATP), 10 nM Aurora2, 10 µM inhibitor in a final volume of 60 µl buffer (HEPES 50 mM pH 7.0, MgCl$_2$ 10 mM, 1 mM DTT, 0.125 mg/ml BSA, 3 µM orthovanadate) were added to each well of a 96 U bottom well plate. After 30 minutes at room temperature incubation, reaction was stopped and biotinylated peptide captured by adding 100 µl of bead suspension.

Stratification: 100 µl of CsCl2 7.5 M were added to each well and let stand one hour before radioactivity was counted in the Top-Count instrument.

Results: data were analyzed and expressed as % inhibition referred to total activity of enzyme (=100%).

All compounds showing inhibition≧60% were further analyzed in order to study the potency of the inhibitor through IC50 calculation.

The protocol used was the same described above, except that serial dilution of the inhibitor was used. Experimental data were fitted by nonlinear regression using the following equation:

$$v = v_0 + \frac{(v_0 - v_b)}{1 + 10^{n(\log IC_{50} - \log[I])}}$$

With $v_b$ as the baseline velocity, $v_o$ as the observed reaction velocity, v as the velocity in the absence of inhibitors, and [I] as the inhibitor concentration.

Compounds of formula (I) of the present invention, suitable for administration to a mammal, e.g. to humans, can be administered by the usual routes and the dosage level depends upon the age, weight, conditions of the patient and the administration route.

For example, a suitable dosage adopted for oral administration of a compound of formula (I) may range from about 10 to about 500 mg pro dose, from 1 to 5 times daily.

Compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

In addition, compounds of the invention can be administered either as single agents or, alternatively, in a combination therapy method comprising additional anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors, in particular celecoxib, rofecoxib, parecoxib and valdecoxib), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, compounds of the invention can be administered in combination with one or more chemotherapeutic agents such as, for instance, exemestane, formestane, anastrozole, letrozole, fadrozole, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, tamoxifen, raloxifen, Sugen SU-5416, Sugen SU-6668, Herceptin, and the like, optionally within liposomal formulations thereof.

If formulated as a fixed dose, such combination products employ the compounds of this invention within the dosage range described above and the other pharmaceutically active agent within the approved dosage range. Compounds of formula (I) may be used sequentially with known anticancer agents when a combination formulation is inappropriate.

Embodiments of the present invention also include pharmaceutical compositions comprising a compound of formula (I) or a pharmaceutically acceptable salt thereof in association with a pharmaceutically acceptable excipient (which can be a carrier or a diluent). The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic, magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions. The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty ester surfactant or lecithin.

Embodiments of the invention may also provide the use of a compound of formula (I), or a pharmaceutically acceptable salt thereof, in the manufacture of a medicament for treating a disease caused by and/or associated with an altered protein kinase activity, in a patient undergoing a simultaneuous, separate or sequential anticancer treatments.

The following examples are herewith intended to illustrate, without posing any limitation to, the present invention.

EXAMPLE 1

Preparation of N-(3-cyanopropyl),N-benzylglicine ethyl ester

N-benzylglycine ethyl ester (0.17 mol, 32.8 g) and anhydrous $K_2CO_3$ (0.187 mol, 25.8 g) were suspended in 300 mL of acetonitril, 4-bromobutyronitrile (0.187 mol, 27.7 g) was added dropwise. The obtained mixture was stirred at reflux for 16 hrs and then filtered. The filtrate was evaporated to dryness to give a pale yellow oil which was purified by flash chromatography over silica gel using hexane/ethyl acetate (2:1)) as eluent, to afford the title compound as a colorless oil (55.3 g, 83%).

EXAMPLE 2

Preparation of N-(3-cyanopropyl),N-(carbo-tbutoxy)-glicine ethyl ester

N-(3-cyanopropyl),N-benzylglicine ethyl ester (0.13 mol, 33.8 g), di-tbutyl dicarbonate (0.26 mol, 56.7 g) and Pd/C (10% p/p, 3.4 g) were suspended in 400 mL of anhydrous EtOH and hydrogenated in a Parr apparatus at 40 PSI for 6 hrs. The obtained mixture was filtered and the filtrate evaporated to dryness to give a pale yellow oil. The crude was purified by flash chromatography over silica gel using hexane/ethyl acetate (7:3)) as eluent, to afford the title compound as a colorless oil (25.3 g, 72%).

EXAMPLE 3

Preparation of tbutyl 4-cyano-3-oxo-1-piperidinecarboxylate

N-(3-cyanopropyl),N-(carbo-tbutoxy)-glicine ethyl ester (0.09 mol, 24.3 g) was dissolved in 350 mL of toluene and the solution cooled at 0° C. Potassium tbutoxide (0.1 mol, 11.2 g) was added portionwise while stirring. After 30', 500 mL of saturated solution of $NH_4Cl$ were added and the pH adjusted to 6 with HCl 2N. The organic phase was separated and the aqueous layer washed twice with DCM. The collected organic layers were dried over $Na_2SO_4$, filtered and evaporated. The obtained yellow oil (19.8 g, 98%) was used in the next step without further purification.

EXAMPLE 4

Preparation of 3-amino-5-(carbo-tbutoxy)-4,6-dihydro-pyrrolo[3,4-c]pyrazole

A mixture of tert-butyl 3-cyano-4-oxo-1-pyrrolidine carboxylate (0.0856 mol, 18.0 g) and hydrazine dihydrochloride (0.1027 mol, 10.8 g) in 450 ml of ethanol was stirred at 60° C., for 4 hours. After cooling the obtained mixture to 0° C., a solution of saturated sodium bicarbonate (100 ml) was slowly added dropwise. The solvent was evaporated under vacuum, the residual water extracted with EtOAc and the organic phase dried over anhydrous Na2SO4. The solvent was evaporated to dryness to give a solid product which was purified by flash chromatography over silica gel using dichloromethane: methanol (46:4) as eluent, to afford the title compound as a white solid (5.91 g, 31%).

m.p. 195-197° C.

$(M+H)^+=224$

Analogously, the following compounds can be prepared, starting from the appropriate 3-cyano-4-oxo-1-pyrrolidine carboxylate:

3-amino-5-acetyl-4,6-dihydropyrrolo[3,4-c]pyrazole m.p. 259-260° C.;

$(M+H)^+=166$ 3-amino-5-(carbo-tbutoxy)-6,6-dimethyl-4,6-dihydropyrrolo[3,4-c]pyrazole m.p. 100-102° C.

$(M+H)^+=252$ 3-amino-5-(carbo-tbutoxy)-6-benzoxymethyl-4,6-dihydro-pyrrolo[3,4-c]pyrazole $(M+1H)^+=345$ Analogously, the following compound was prepared, starting from the appropriate tbutyl 4-cyano-3-oxo-1-piperidinecarboxylate:

tbutyl 3-amino-6-(carbo-tbutoxy)-4,5,6,7-tetrahydro-pyridine[3,4-c]pyrazole m.p. 153-155° C.

$(M+H)^+=238$

Analogously, the following compound was prepared; starting from the appropriate tbutyl 3-cyano-4-oxo-1-piperidinecarboxylate:

tbutyl 3-amino-5-(carbo-tbutoxy)-4,5,6,7-tetrahydro-pyridine[4,3-c]pyrazole m.p. 151-155° C.

$(M+H)^+=238$

EXAMPLE 5

Preparation of N-{3-amino-5-(carbo-tbutoxy)-4,6-dihydropyrrolo[3,4-c]pyrazol-1-yl},N'-methylpolystyrene urea 3-amino-5-(carbo-tbutoxy)-4,6-dihydropyrrolo[3,4-c]pyrazole (10.7 mmol, 2.4 g) dissolved in 20 ml of dichloromethane anhydrous was added under nitrogen atmosphere to methylisocyanate polystyrene resin (200-400 mesh, 2% DVB, loading 1.49 mmol/g, 10 g) previously swelled in 200 ml of anhydrous dichlorometane. The resulting suspension was gently stirred at 22° C. for 18 hours, until no traces of 3-amino-5-(carbo-tbutoxy)-4,6-dihydropyrrolo[3,4-c]pyrazole could be detected in the solution. The resin was filtered, washed with dichloromethane and methanol and dried under vacuum.

Analogously, the following compounds can be prepared:
N-{3-amino-5-acetyl-4,6-dihydropyrrolo[3,4-c]pyrazol-1-yl},N'-methylpolystyrene urea
N-{3-amino-5-(carbo-tbutoxy)-6,6-dimethyl-4,6-dihydropyrrolo[3,4-c]pyrazol-1-yl},N'-methylpolystyrene urea
N-{3-amino-5-(carbo-tbutoxy)-6-benzoxymethyl-4,6-dihydropyrrolo[3,4-c]pyrazol-1-yl},N'-methylpolystyrene urea
N-{3-amino-6-(carbo-tbutoxy)-4,5,6,7-tetrahydropyridine[3,4-c]pyrazol-1-yl},N'-methylpolystyrene urea
N-{3-amino-5-(carbo-tbutoxy)-4,5,6,7-tetrahydropyridine[4,3-c]pyrazol-1-yl},N'-methylpolystyrene urea

EXAMPLE 6

Preparation of N-{3-phenylacetamido-5-(carbo-tbutoxy)-4,6-dihydropyrrolo[3,4-c]pyrazol-1-yl},N'-methylpolystyrene urea A solution of phenylacetyl chloride (24.08 mmol, 3.18 ml) in 10 ml of anhydrous dichlorometane was added dropwise to N-{3-amino-5-(carbo-tbutoxy)-4,6-dihydropyrrolo[3,4-c]pyrazol-1-yl},N'-methylpolystyrene urea (3.01 mmol, 3.5 g) previously swelled in 90 ml of anhydrous dichlorometane and 16.5 ml of DIEA (96.32 mmol). The resulting suspension was gently stirred at 22° C. for 18 hours. The resin was then filtered, washed with dichloromethane, methanol and dried under vacuum.

Analogously, the following compounds can be prepared by using the appropriate acyl chloride:
N-{3-acetamido-5-(carbo-tbutoxy)-4,6-dihydropyrrolo[3,4-c]pyrazol-1-yl},N'-methylpolystyrene urea
N-{3-cyclopropanecarboxamido-5-(carbo-tbutoxy)-4,6-dihydropyrrolo[3,4-c]pyrazol-1-yl},N'-methylpolystyrene urea
N-{3-isobutyramido-5-(carbo-tbutoxy)-4,6-dihydropyrrolo[3,4-c]pyrazol-1-yl},N'-methylpolystyrene urea
N-{3-cyclopentanecarboxado-5-(carbo-tbutoxy)-4,6-dihydropyrrolo[3,4-c]pyrazol-1-yl},N'-methylpolystyrene urea
N-{3-benzamido-5-(carbo-tbutoxy)-4,6-dihydro-pyrrolo[3,4-c]pyrazol-1-yl},N'-methylpolystyrene urea
N-{3-picolinic-amido-5-(carbo-tbutoxy)-4,6-dihydropyrrolo[3,4-c]pyrazol-1-yl},N'-methylpolystyrene urea
N-{3-nicotinic-amido-5-(carbo-tbutoxy)-4,6-dihydropyrrolo[3,4-c]pyrazol-1-yl},N'-methylpolystyrene urea
N-{3-isonicotinic-amido-5-(carbo-tbutoxy)-4,6-dihydropyrrolo[3,4-c]pyrazol-1-yl},N'-methylpolystyrene urea
N-{3-(3-methyl-2-furoic)-amido-5-(carbo-tbutoxy)-4,6-dihydropyrrolo[3,4-c]pyrazol-1-yl)},N'-methylpolystyrene urea
N-{3-(thiophene-2-carboxamido)-5-(carbo-tbutoxy)-4,6-dihydropyrrolo[3,4-c]pyrazol-1-yl},N'-methylpolystyrene urea
N-{3-(thiophene-3-carboxamido)-5-(carbo-tbutoxy)-4,6-dihydropyrrolo[3,4-c]pyrazol-1-yl},N'-methylpolystyrene urea
N-{3-(o-toluic-amido)-5-(carbo-tbutoxy)-4,6-dihydropyrrolo[3,4-c]pyrazol-1-yl},N'-methylpolystyrene urea
N-{3-(m-toluic-amido)-5-(carbo-tbutoxy)-4,6-dihydropyrrolo[3,4-c]pyrazol-1-yl},N'-methylpolystyrene urea
N-{3-(p-toluic-amido)-5-(carbo-tbutoxy)-4,6-dihydropyrrolo[3,4-c]pyrazol-1-yl},N'-methylpolystyrene urea
N-{3-salicylic-amido-5-(carbo-tbutoxy)-4,6-dihydropyrrolo[3,4-c]pyrazol-1-yl},N'-methylpolystyrene urea
N-{3-(2-fluorobenzamido)-5-(carbo-tbutoxy)-4,6-dihydropyrrolo[3,4-c]pyrazol-1-yl},N'-methylpolystyrene urea
N-{3-(3-fluorobenzamido)-5-(carbo-tbutoxy)-4,6-dihydropyrrolo[3,4-c]pyrazol-1-yl},N'-methylpolystyrene urea
N-{3-(4-fluorobenzamido)-5-(carbo-tbutoxy)-4,6-dihydropyrrolo[3,4-c]pyrazol-1-yl},N'-methylpolystyrene urea
N-{3-(thiophene-2-acetamido)-5-(carbo-tbutoxy)-4,6-dihydropyrrolo[3,4-c]pyrazol-1-yl},N'-methylpolystyrene urea
N-{3-(thiophene-3-acetamido)-5-(carbo-tbutoxy)-4,6-dihydropyrrolo[3,4-c]pyrazol-1-yl},N'-methylpolystyrene urea
N-{3-phenylpropiolic-amido-5-(carbo-tbutoxy)-4,6-dihydropyrrolo[3,4-c]pyrazol-1-yl},N'-methylpolystyrene urea
N-{3-(3-cyanobenzamido)-5-(carbo-tbutoxy)-4,6-dihydropyrrolo[3,4-c]pyrazol-1-yl},N'-methylpolystyrene urea
N-{3-(4-cyanobenzamido)-5-(carbo-tbutoxy)-4,6-dihydropyrrolo[3,4-c]pyrazol-1-yl},N'-methylpolystyrene urea
N{-3-trans-cinnamic-amido-5-(carbo-tbutoxy)-4,6-dihydropyrrolo[3,4-c]pyrazol-1-yl},N'-methylpolystyrene urea
N-{3-cis-cinnamic-amido-5-(carbo-tbutoxy)-4,6-dihydropyrrolo[3,4-c]pyrazol-1-yl},N'-methylpolystyrene urea
N{-3-[3-(3-pyridyl)acrylic-amido]-(carbo-tbutoxy)-4,6-dihydropyrrolo[3,4-c]pyrazol-1-yl},N'-methylpolystyrene urea
N-{3-[3-(4-pyridyl)-acrylic-amido]-5-(carbo-tbutoxy)-4,6-dihydropyrrolo[3,4-c]pyrazol-1-yl},N'-methylpolystyrene urea
N-{3-(2-phenylpropionamido)-5-(carbo-tbutoxy)-4,6-dihydropyrrolo[3,4-c]pyrazol-1-yl},N'-methylpolystyrene urea
N-{3-o-tolylacetamido-5-(carbo-tbutoxy)-4,6-dihydropyrrolo[3,4-c]pyrazol-1-yl},N'-methylpolystyrene urea
N-{3-m-tolylacetamido-5-(carbo-tbutoxy)-4,6-dihydropyrrolo[3,4-c]pyrazol-1-yl},N'-methylpolystyrene urea
N-{3-p-tolylacetamido-5-(carbo-tbutoxy)-4,6-dihydropyrrolo[3,4-c]pyrazol-yl},N'-methylpolystyrene urea
N-{3-o-anisic-amido-5-(carbo-tbutoxy)-4,6-dihydropyrrolo[3,4-c]pyrazol-1-yl},N'-methylpolystyrene urea
N-{3-(3-methoxybenzamido)-5-(carbo-tbutoxy)-4,6-dihydropyrrolo[3,4-c]pyrazol-1-yl},N'-methylpolystyrene urea
N-{3-p-anisic-amido-5-(carbo-tbutoxy)-4,6-dihydropyrrolo[3,4-c]pyrazol-1-yl},N'-methylpolystyrene urea
N-{3-phenoxyacetamido-5-(carbo-tbutoxy)-4,6-dihydropyrrolo[3,4-c]pyrazol-1-yl},N'-methylpolystyrene urea
N-{3-(2-fluorophenylacetamido)-5-(carbo-tbutoxy)-4,6-dihydropyrrolo[3,4-c]pyrazol-1-yl},N'-methylpolystyrene urea
N-{3-(3-fluorophenylacetamido)-5-(carbo-tbutoxy)-4,6-dihydropyrrolo[3,4-c]pyrazol-1-yl},N'-methylpolystyrene urea
N-{3-(4-fluorophenylacetamido)-5-(carbo-tbutoxy)-4,6-dihydropyrrolo[3,4-c]pyrazol-1-yl},N'-methylpolystyrene urea
N-{3-[3-(2-thienyl)acrylicamido]-5-(carbo-tbutoxy)-4,6-dihydropyrrolo[3,4-c]pyrazol-1-yl},N'-methylpolystyrene urea
N-{3-[3-(3-thienyl)-acrylicamido]-5-(carbo-tbutoxy)-4,6-dihydropyrrolo[3,4-c]pyrazol-1-yl},N'-methylpolystyrene urea
N-{3-[3-(2-thienyl)propanoic-amido]-5-(carbo-tbutoxy)-4,6-dihydropyrrolo[3,4-c]pyrazol-1-yl},N'-methylpolystyrene urea N-{3-[2-chlorobenzamido]-5-(carbo-tbutoxy)-4,6-dihydropyrrolo[3,4-c]pyrazol-1-yl},N'-methylpolystyrene urea
N-{3-[3-chlorobenzamido]-5-(carbo-tbutoxy)-4,6-dihydropyrrolo[3,4-c]pyrazol-1-yl},N'-methylpolystyrene urea
N-{3-(4-chlorobenzamido)-5-(carbo-tbutoxy)-4,6-dihydropyrrolo[3,4-c]pyrazol-1-yl},N'-methylpolystyrene urea
N-{3-(1-piperidinepropionamido)-5-(carbo-tbutoxy)-4,6-dihydropyrrolo[3,4-c]pyrazol-1-yl},N'-methylpolystyrene urea
N-{3-(2-acetylbenzamido)-5-(carbo-tbutoxy)-4,6-dihydropyrrolo[3,4-c]pyrazol-1-yl},N'-methylpolystyrene urea
N-{3-(4-acetylbenzamido)-5-(carbo-tbutoxy)-4,6-dihydropyrrolo[3,4-c]pyrazol-1-yl},N'-methylpolystyrene urea
N-{3-(1-naphthoicamido)-1-(carbo-tbutoxy)-4,6-dihydropyrrolo[3,4-c]pyrazol-1-yl},N'-methylpolystyrene urea
N-{3-(2-naphthoicamido)-5-(carbo-tbutoxy)-4,6-dihydropyrrolo[3,4-c]pyrazol-1-yl},N'-methylpolystyrene urea
N-{3-(3-benzoylpropionamido)-5-(carbo-tbutoxy)-4,6-dihydropyrrolo[3,4-c]pyrazol-1-yl},N'-methylpolystyrene urea
N-{3-(4-acetamidobenzamido)-5-(carbo-tbutoxy)-4,6-dihydropyrrolo[3,4-c]pyrazol-1-yl},N'-methylpolystyrene urea
N-{3-(2,5-dimethoxybenzamido)-5-(carbo-tbutoxy)-4,6-dihydropyrrolo[3,4-c]pyrazol-1-yl},N'-methylpolystyrene urea
N-{3-(2,6-dimethoxybenzamido)-5-(carbo-tbutoxy)-4,6-dihydropyrrolo[3,4-c]pyrazol-1-yl},N'-methylpolystyrene urea
N-{3-(3,4-dimethoxybenzamido)-5-(carbo-tbutoxy)-4,6-dihydropyrrolo[3,4-c]pyrazol-1-yl},N'-methylpolystyrene urea
N-{3-(3,5-dimethoxybenzamido)-5-(carbo-tbutoxy)-4,6-dihydropyrrolo[3,4-c]pyrazol-1-yl},N'-methylpolystyrene urea
N-{3-3-(2-thenoyl)-propionamido-5-(carbo-tbutoxy)-4,6-dihydropyrrolo[3,4-c]pyrazol-1-yl},N'-methylpolystyrene urea
N-{3-(2-naphtylacetamide)-5-(carbo-tbutoxy)-4,6-dihydropyrrolo[3,4-c]pyrazol-1-yl},N'-methylpolystyrene urea
N-{3-(1-naphtylacetamido)-5-(carbo-tbutoxy)-4,6-dihydropyrrolo[3,4-c]pyrazol-1-yl},N'-methylpolystyrene urea
N-{3-(4-phenylbenzamido)-5-(carbo-tbutoxy)-4,6-dihydropyrrolo[3,4-c]pyrazol-1-yl},N'-methylpolystyrene urea
N-{3-(2-furamido)-5-(carbo-tbutoxy)-4,6-dihydropyrrolo[3,4-c]pyrazol-1-yl},N'-methylpolystyrene urea
N-{3-(4-phenoxybenzamido)-5-(carbo-tbutoxy)-4,6-dihydropyrrolo[3,4-c]pyrazol-1-yl},N'-methylpolystyrene urea
N-{3-(3-phenoxybenzamido)-5-(carbo-tbutoxy)-4,6-dihydropyrrolo[3,4-c]pyrazol-1-yl},N'-methylpolystyrene urea
N-{3-(4-tertbutyl-benzamido)-5-(carbo-tbutoxy)-4,6-dihydropyrrolo[3,4-c]pyrazol-1-yl},N'-methylpolystyrene urea
N-{3-piperonylcarboxamido-5-(carbo-tbutoxy)-4,6-dihydropyrrolo[3,4-c]pyrazol-1-yl},N'-methylpolystyrene urea
N-{3-(2-naphtalene)propionamido-5-(carbo-tbutoxy)-4,6-dihydropyrrolo[3,4-c]pyrazol-1-yl},N'-methylpolystyrene urea
N-{3-(6-methoxy-2-naphtalene)propionamido-5-(carbo-tbutoxy)-4,6-dihydropyrrolo[3,4-c]pyrazol-1-yl},N'-methylpolystyrene urea
N-{3-(2-ethylbutyramido)-5-(carbo-tbutoxy)-4,6-dihydropyrrolo[3,4-c]pyrazol-1-yl},N'-methylpolystyrene urea
N-{3-(4-pyrrolidin-1-yl-phenyl)propionamido-5-(carbo-tbutoxy)-4,6-dihydropyrrolo[3,4-c]pyrazol-1-yl},N'-methylpolystyrene urea
N-{3-(2-oxo-pyrrolidin-1-yl)phenyl]propionamido-5-(carbo-tbutoxy)-4,6-dihydropyrrolo[3,4-c]pyrazol-1-yl},N'-methylpolystyrene urea
N-{3-(bicyclo[4.2.0]octa-1,3,5-triene-7-carboxamido)-5-(carbo-tbutoxy)-4,6-dihydropyrrolo[3,4-c]pyrazol-1-yl},N'-methylpolystyrene urea
N-{3-(2-oxo-pyrrolidin-1-yl)phenylacetamido-5-(carbo-tbutoxy)-4,6-dihydropyrrolo[3,4-c]pyrazol-1-yl},N'-methylpolystyrene urea
N-{3-(4-pyrrolidin-1-yl-phenylacetamido-5-(carbo-tbutoxy)-4,6-dihydropyrrolo[3,4-c]pyrazol-1-yl},N'-methylpolystyrene urea
N-{3-(4-trifluoromethyl)phenylacetamido-5-(carbo-tbutoxy)-4,6-dihydropyrrolo[3,4-c]pyrazol-1-yl},N'-methylpolystyrene urea
N-{3-(2-bromo)phenylacetamido-5-(carbo-tbutoxy)-4,6-dihydropyrrolo[3,4-c]pyrazol-1-yl},N'-methylpolystyrene urea
N-{3-[4-(pyrrolidin-1-yl-carbonylmethyloxy)]phenylacetamido-5-(carbo-tbutoxy)-4,6-dihydropyrrolo[3,4-c]pyrazol-1-yl},N'-methylpolystyrene urea
N-{3-[3-(aminocarbonylmethyloxy)phenylacetamido]-5-(carbo-tbutoxy)-4,6-dihydropyrrolo[3,4-c]pyrazol-1-yl},N'-methylpolystyrene urea
N-{3-[4-(2-oxo-oxazolidin-3-yl)phenylacetamido]-5-(carbo-tbutoxy)-4,6-dihydropyrrolo[3,4-c]pyrazol-1-yl},N'-methylpolystyrene urea
N-{3-[4-(4-methylpiperazino)benzamide]-5-(carbo-tbutoxy)-4,6-dihydropyrrolo[3,4-c]pyrazol-1-yl},N'-methylpolystyrene urea
N-{3-(benzo[1,3]dioxol-5-yl)acetamido-5-(carbo-tbutoxy)-4,6-dihydropyrrolo[3,4-c]pyrazol-1-yl},N'-methylpolystyrene urea
N-{3-[4-(2-oxo-oxazolidin-3-yl)phenylacetamido]-5-(carbo-tbutoxy)-4,6-dihydropyrrolo[3,4-c]pyrazol-1-yl},N'-methylpolystyrene urea
N-{3-(2-phenyl-1,3-thiazol-4-yl)acetamido-5-(carbo-tbutoxy)-4,6-dihydropyrrolo[3,4-c]pyrazol-1-yl},N'-methylpolystyrene urea
N-{3-[4-(1-pyrrolidin-2-one)benzamido]-5-(carbo-tbutoxy)-4,6-dihydropyrrolo[3,4-c]pyrazol-1-yl},N'-methylpolystyrene urea
N-{3-[2-(3-oxo-3,4,4a,8a-tetrahydro-2H-benzo[1,4]oxazin-6-yl)acetamido]-5-(carbo-tbutoxy)-4,6-dihydropyrrolo[3,4-c]pyrazol-1-yl},N'-methylpolystyrene urea
N-{3-(1-methyl-indol-3-yl)acetamido-5-(carbo-tbutoxy)-4,6-dihydropyrrolo[3,4-c]pyrazol-1-yl},N'-methylpolystyrene urea
N-{3-(6-oxo-6H-pyridazin-1-yl)acetamido-5-(carbo-tbutoxy)-4,6-dihydropyrrolo[3,4-c]pyrazol-1-yl},N'-methylpolystyrene urea
N-{3-(4-(morpholin-1-yl)-phenyl)acetamido-5-(carbo-tbutoxy)-4,6-dihydropyrrolo[3,4-c]pyrazol-1-yl},N'-methylpolystyrene urea
N-{3-(4-pyridylacetamido)-5-(carbo-tbutoxy)-4,6-dihydropyrrolo[3,4-c]pyrazol-1-yl},N'-methylpolystyrene urea
N-{3-phenoxyacetamido-5-(carbo-tbutoxy)-4,6-dihydropyrrolo[3,4-c]pyrazol-1-yl},N'-methylpolystyrene urea
N-{3-(3-pyridylacetamido)-5-(carbo-tbutoxy)-4,6-dihydropyrrolo[3,4-c]pyrazol-1-yl},N'-methylpolystyrene urea
N-{3-[5-(4-chlorophenyl)furan-2-carboxamido]-5-(carbo-tbutoxy)-4,6-dihydropyrrolo[3,4-c]pyrazol-1-yl},N'-methylpolystyrene urea N-{3-[quinoline-6-carboxamido]-5-(carbo-tbutoxy)-4,6-dihydropyrrolo[3,4-c]pyrazol-1-yl},N'-methylpolystyrene urea N-{3-[2-methyl-5-phenyl-furan-3-carboxamido]-5-(carbo-tbutoxy)-4,6-dihydropyrrolo[3,4-c]pyrazol-1-yl},N'-methylpolystyrene urea N-{3-[benzofuran-2-carboxamido]-5-(carbo-tbutoxy)-4,6-dihydropyrrolo[3,4-c]pyrazol-1-yl},N'-methylpolystyrene urea N-{3-[6-chloronicotinamido]-5-(carbo-tbutoxy)-4,6-dihydropyrrolo[3,4-c]pyrazol-1-yl},N'-methylpolystyrene urea N-{3-[5-chlorothiophene-2-carboxamido]-5-(carbo-tbutoxy)-4,6-dihydropyrrolo[3,4-c]pyrazol-1-yl},N'-methylpolystyrene urea

EXAMPLE 7

Preparation of N-{3-phenylacetamido-4,6-dihydropyrrolo[3,4-c]pyrazol-1-yl},N'-methylpolystyrene urea N-{3-phenylacetamido-5-(carbo-tbutoxy)-4,6-dihydropyrrolo[3,4-c]pyrazol-1-yl},N'-methylpolystyrene urea (3.01 mmol) was treated with a solution of TFA 50% in anhydrous dichloromethane. The resulting suspension was gently stirred at 22° C. for 2 hours, then washed with a solution of TEA 10% in anhydrous dichloromethane, dichloromethane, methanol and dried under vacuum.

Analogously, the following compounds can be prepared by using the appropriate N-{3-amido-5-(carbo-tbutoxy)-4,6-dihydropyrrolo[3,4-c]pyrazol-1-yl},N'-methylpolystyrene urea:

N-{3-acetamido-4,6-dihydropyrrolo[3,4-c]pyrazol-1-yl},N'-methylpolystyrene urea

N-{3-cyclopropanecarboxamido-4,6-dihydropyrrolo[3,4-c]pyrazol-1-yl},N'-methylpolystyrene urea N-{3-isobutyramido-4,6-dihydropyrrolo[3,4-c]pyrazol-1-yl},N'-methylpolystyrene urea N-{3-cyclopentanecarboxamido-4,6-dihydropyrrolo[3,4-c]pyrazol-1-yl},N'-methylpolystyrene urea N-{3-benzamido-4,6-dihydropyrrolo[3,4-c]pyrazol-1-yl},N'-methylpolystyrene urea N-{3-picolinic-amido-4,6-dihydropyrrolo[3,4-c]pyrazol-1-yl},N'-methylpolystyrene urea N-{3-nicotinic-amido-4,6-dihydropyrrolo[3,4-c]pyrazol-1-yl},N'-methylpolystyrene urea N-{3-isonicotinic-amido-4,6-dihydropyrrolo[3,4-c]pyrazol-1-yl},N'-methylpolystyrene urea N-{3-(3-methyl-2-furoic)-amido-4,6-dihydropyrrolo[3,4-c]pyrazol-1-yl},N'-methylpolystyrene urea N-{3-(thiophene-2-carboxamido)-4,6-dihydropyrrolo[3,4-c]pyrazol-1-yl},N'-methylpolystyrene urea N-{3-(thiophene-3-carboxamido)-4,6-dihydropyrrolo[3,4-c]pyrazol-1-yl},N'-methylpolystyrene urea N-{3-(o-toluic-amido)-4,6-dihydropyrrolo[3,4-c]pyrazol-1-yl},N'-methylpolystyrene urea N-{3-(m-toluic-amido)-4,6-dihydropyrrolo[3,4-c]pyrazol-1-yl},N'-methylpolystyrene urea N-{3-(p-toluic-amido)-4,6-dihydropyrrolo[3,4-c]pyrazol-1-yl},N'-methylpolystyrene urea N-{3-salicylic-amido-4,6-dihydropyrrolo[3,4-c]pyrazol-1-yl},N'-methylpolystyrene urea N-{3-(2-fluorobenzamido)-4,6-dihydropyrrolo[3,4-c]pyrazol-1-yl},N'-methylpolystyrene urea N-{3-(3-fluorobenzamido)-4,6-dihydropyrrolo[3,4-c]pyrazol-1-yl},N'-methylpolystyrene urea N-{3-(4-fluorobenzamido)-4,6-dihydropyrrolo[3,4-c]pyrazol-1-yl},N'-methylpolystyrene urea N-{3-(thiophene-2-acetamido)-4,6-dihydropyrrolo[3,4-c]pyrazol-1-yl},N'-methylpolystyrene urea N-{3-(thiophene-3-acetamido)-4,6-dihydropyrrolo[3,4-c]pyrazol-1-yl},N'-methylpolystyrene urea N-{3-phenylpropiolic-amido-4,6-dihydropyrrolo[3,4-c]pyrazol-1-yl},N'-methylpolystyrene urea N-{3-(3-cyanobenzamido)-4,6-dihydropyrrolo[3,4-c]pyrazol-1-yl},N'-methylpolystyrene urea N-{3-(4-cyanobenzamido)-4,6-dihydropyrrolo[3,4-c]pyrazol-1-yl},N'-methylpolystyrene urea N-{3-trans-cinnamic-amido-4,6-dihydropyrrolo[3,4-c]pyrazol-1-yl},N'-methylpolystyrene urea N-{3-cis-cinnamic-amido-4,6-dihydropyrrolo[3,4-c]pyrazol-1-yl},N'-methylpolystyrene urea N-{3-[3-(3-pyridyl)acrylic-amido]-4,6-dihydropyrrolo[3,4-c]pyrazol-1-yl},N'-methylpolystyrene urea N-{3-[3-(4-pyridyl)-acrylic-amido]-4,6-dihydropyrrolo[3,4-c]pyrazol-1-yl},N'-methylpolystyrene urea N-{3-(2-phenylpropionamido)-4,6-dihydropyrrolo[3,4-c]pyrazol-1-yl},N'-methylpolystyrene urea N-{3-o-tolylacetamido-4,6-dihydropyrrolo[3,4-c]pyrazol-1-yl},N'-methylpolystyrene urea N-{3-m-tolylacetamido-4,6-dihydropyrrolo[3,4-c]pyrazol-1-yl},N'-methylpolystyrene urea N-{3-p-tolylacetamido-4,6-dihydropyrrolo[3,4-c]pyrazol-1-yl},N'-methylpolystyrene urea N-{3-o-anisic-amido-4,6-dihydropyrrolo[3,4-c]pyrazol-1-yl},N'-methylpolystyrene urea N-{3-(3-methoxybenzamido)-4,6-dihydropyrrolo[3,4-c]pyrazol-1-yl},N'-methylpolystyrene urea N-{3-p-anisic-amido-4,6-dihydropyrrolo[3,4-c]pyrazol-1-yl},N'-methylpolystyrene urea N-{3-phenoxyacetamido-4,6-dihydropyrrolo[3,4-c]pyrazol-1-yl},N'-methylpolystyrene urea N-{3-(2-fluorophenylacetamido)-4,6-dihydropyrrolo[3,4-c]pyrazol-1-yl},N'-methylpolystyrene urea N-{3-(3-fluorophenylacetamido)-4,6-dihydropyrrolo[3,4-c]pyrazol-1-yl},N'-methylpolystyrene urea N-{3-(4-fluorophenylacetamido)-4,6-dihydropyrrolo[3,4-c]pyrazol-1-yl},N'-methylpolystyrene urea N-{3-[3-(2-thienyl)acrylicamido]-4,6-dihydropyrrolo[3,4-c]pyrazol-1-yl},N'-methylpolystyrene urea N-{3-[3-(3-thienyl)-acrylicamido]-4,6-dihydropyrrolo[3,4-c]pyrazol-1-yl},N'-methylpolystyrene urea N-{3-[3-(2-thienyl)propanoic-amido]-4,6-dihydropyrrolo[3,4-c]pyrazol-1-yl},N'-methylpolystyrene urea N-{3-[2-chlorobenzamido]-4,6-dihydropyrrolo[3,4-c]pyrazol-1-yl},N'-methylpolystyrene urea N-{3-[3-chlorobenzamido]-4,6-dihydropyrrolo[3,4-c]pyrazol-1-yl},N'-methylpolystyrene urea N-{3-(4-chlorobenzamido)-4,6-dihydropyrrolo[3,4-c]pyrazol-1-yl},N'-methylpolystyrene urea N-{3-(1-piperidinepropionamido)-4,6-dihydropyrrolo[3,4-c]pyrazol-1-yl},N'-methylpolystyrene urea N-{3-(2-acetylbenzamido)-4,6-dihydropyrrolo[3,4-c]pyrazol-1-yl},N'-methylpolystyrene urea N-{3-(4-acetylbenzamido)-4,6-dihydropyrrolo[3,4-c]pyrazol-1-yl},N'-methylpolystyrene urea N-{3-(1-naphthoicamido)-4,6-dihydropyrrolo[3,4-c]pyrazol-1-yl},N'-methylpolystyrene urea N-{3-(2-naphthoicamido)-4,6-dihydropyrrolo[3,4-c]pyrazol-1-yl},N'-methylpolystyrene urea N-{3-(3-benzoylpropionamido)-4,6-dihydropyrrolo[3,4-c]pyrazol-1-yl},N'-methylpolystyrene urea N-{3-(4-acetamidobenzamido)-4,6-dihydropyrrolo[3,4-c]pyrazol-1-yl},N'-methylpolystyrene urea
N-{3-(2,5-dimethoxybenzamido)-4,6-dihydropyrrolo[3,4-c]pyrazol-1-yl},N'-methylpolystyrene urea
N-{3-(2,6-dimethoxybenzamido)-4,6-dihydropyrrolo[3,4-c]pyrazol-1-yl},N'-methylpolystyrene urea
N-{3-(3,4-dimethoxybenzamido)-4,6-dihydropyrrolo[3,4-c]pyrazol-1-yl},N'-methylpolystyrene urea
N-{3-(3,5-dimethoxybenzamido)-4,6-dihydropyrrolo[3,4-c]pyrazol-1-yl},N'-methylpolystyrene urea
N-{3-3-(2-thenoyl)-propionamido-4,6-dihydropyrrolo[3,4-c]pyrazol-1-yl},N'-methylpolystyrene urea
N-{3-(2-naphtylacetamide)-4,6-dihydropyrrolo[3,4-c]pyrazol-1-yl},N'-methylpolystyrene urea
N-{3-(1-naphtylacetamido)-4,6-dihydropyrrolo[3,4-c]pyrazol-1-yl},N'-methylpolystyrene urea
N-{3-(4-phenylbenzamido)-4,6-dihydropyrrolo[3,4-c]pyrazol-1-yl},N'-methylpolystyrene urea
N-{3-(2-furamido)-4,6-dihydropyrrolo[3,4-c]pyrazol-1-yl},N'-methylpolystyrene urea
N-{3-(4-phenoxybenzamido)-4,6-dihydropyrrolo[3,4-c]pyrazol-1-yl},N'-methylpolystyrene urea
N-{3-(3-phenoxybenzamido)-4,6-dihydropyrrolo[3,4-c]pyrazol-1-yl},N'-methylpolystyrene urea
N-{3-(4-tertbutyl-benzamido)-4,6-dihydropyrrolo[3,4-c]pyrazol-1-yl},N'-methylpolystyrene urea
N-{3-piperonylcarboxamido-4,6-dihydropyrrolo[3,4-c]pyrazol-1-yl},N'-methylpolystyrene urea
N-{3-(2-naphtalene)propionamido-4,6-dihydropyrrolo[3,4-c]pyrazol-1-yl},N'-methylpolystyrene urea
N-{3-(6-methoxy-2-naphtalene)propionamido-4,6-dihydropyrrolo[3,4-c]pyrazol-1-yl},N'-methylpolystyrene urea
N-{3-(2-ethylbutyramido)-4,6-dihydropyrrolo[3,4-c]pyrazol-1-yl},N'-methylpolystyrene urea
N-{3-(4-pyrrolidin-1-yl-phenyl)propionamido-4,6-dihydropyrrolo[3,4-c]pyrazol-1-yl},N'-methylpolystyrene urea
N-{3-(2-oxo-pyrrolidin-1-yl)phenyl]propionamido-4,6-dihydropyrrolo[3,4-c]pyrazol-1-yl},N'-methylpolystyrene urea
N-{3-(bicyclo[4.2.0]octa-1,3,5-triene-7-carboxamido)-4,6-dihydropyrrolo[3,4-c]pyrazol-1-yl},N'-methylpolystyrene urea
N-{3-(2-oxo-pyrrolidin-1-yl)phenylacetamido-4,6-dihydropyrrolo[3,4-c]pyrazol-1-yl},N'-methylpolystyrene urea
N-{3-(4-pyrrolidin-1-yl-phenylacetamido-4,6-dihydropyrrolo[3,4-c]pyrazol-1-yl},N'-methylpolystyrene urea
N-{3-(4-trifluoromethyl)phenylacetamido-4,6-dihydropyrrolo[3,4-c]pyrazol-1-yl},N'-methylpolystyrene urea
N-{3-(2-bromo)phenylacetamido-4,6-dihydropyrrolo[3,4-c]pyrazol-1-yl},N'-methylpolystyrene urea
N-{3-[4-(pyrrolidin-1-yl-carbonylmethyloxy)]phenylacetamido-4,6-dihydropyrrolo[3,4-c]pyrazol-1-yl},N'-methylpolystyrene urea
N-{3-[3-(aminocarbonylmethyloxy)phenylacetamido]-4,6-dihydropyrrolo[3,4-c]pyrazol-1-yl},N'-methylpolystyrene urea
N-{3-[4-(2-oxo-oxazolidin-3-yl)phenylacetamido]-4,6-dihydropyrrolo[3,4-c]pyrazol-1-yl},N'-methylpolystyrene urea
N-[3-(4-(4-methylpiperazino)benzamide]-4,6-dihydropyrrolo[3,4-c]pyrazol-1-yl},N'-methylpolystyrene urea
N-{3-(benzo[1,3]dioxol-5-yl)acetamido-4,6-dihydropyrrolo[3,4-c]pyrazol-1-yl},N'-methylpolystyrene urea
N-{3-[4-(2-oxo-oxazolidin-3-yl)phenylacetamido]-4,6-dihydropyrrolo[3,4-c]pyrazol-1-yl},N'-methylpolystyrene urea N-{3-(2-phenyl-1,3-thiazol-4-yl)acetamido-4,6-dihydropyrrolo[3,4-c]pyrazol-1-yl},N'-methylpolystyrene urea
N-{3-[4-(1-pyrrolidin-2-one)benzamido]-4,6-dihydropyrrolo[3,4-c]pyrazol-1-yl},N'-methylpolystyrene urea
N-{3-[2-(3-oxo-3,4,4a,8a-tetrahydro-2H-benzo[1,4]oxazin-6-yl)acetamido]-4,6-dihydropyrrolo[3,4-c]pyrazol-1-yl},N'-methylpolystyrene urea
N-{3-(1-methyl-indol-3-yl)acetamido-4,6-dihydropyrrolo[3,4-c]pyrazol-1-yl},N'-methylpolystyrene urea
N-{3-(6-oxo-6H-pyridazin-1-yl)acetamido)-4,6-dihydropyrrolo[3,4-c]pyrazol-1-yl},N'-methylpolystyrene urea
N-{3-(4-(morpholin-1-yl)-phenyl)acetamido-4,6-dihydropyrrolo[3,4-c]pyrazol-1-yl},N'-methylpolystyrene urea
N-{3-(4-pyridylacetamido)-4,6-dihydropyrrolo[3,4-c]pyrazol-1-yl},N'-methylpolystyrene urea
N-{3-phenoxyacetamido-4,6-dihydropyrrolo[3,4-c]pyrazol-1-yl},N'-methylpolystyrene urea
N-{3-(3-pyridylacetamido)-4,6-dihydropyrrolo[3,4-c]pyrazol-1-yl},N'-methylpolystyrene urea
N-{3-[5-(4-chlorophenyl)furan-2-carboxamido]-4,6-dihydropyrrolo[3,4-c]pyrazol-1-yl},N'-methylpolystyrene urea
N-{3-[quinoline-6-carboxamido]-4,6-dihydropyrrolo[3,4-c]pyrazol-1-yl},N'-methylpolystyrene urea
N-{3-[2-methyl-5-phenyl-furan-3-carboxamido]-4,6-dihydropyrrolo[3,4-c]pyrazol-1-yl},N'-methylpolystyrene urea
N-{3-[benzofuran-2-carboxamido]-4,6-dihydropyrrolo[3,4-c]pyrazol-1-yl},N'-methylpolystyrene urea
N-{3-[6-chloronicotinamido]-4,6-dihydropyrrolo[3,4-c]pyrazol-1-yl},N'-methylpolystyrene urea
N-{3-[5-chlorothiophene-2-carboxamido]-4,6-dihydropyrrolo[3,4-c]pyrazol-1-yl},N'-methylpolystyrene urea

EXAMPLE 8

Preparation of N-{3-phenylacetamido-5-phenylacetyl-4,6-dihydropyrrolo[3,4-c]pyrazol-1-yl},N'-methylpolystyrene urea Phenylacetic acid (0.43 mmol, 58.5 mg), NMM (0.43 mmol, 47.3 mcl) and PyBop (0.43 mmol, 223.8 mg) were added to N-{3-phenylacetamido-4,6-dihydropyrrolo[3,4-c]pyrazol-1-yl},N'-methylpolystyrene urea (0.086 mmol, 100 mg) previously swelled in 4 ml of anhydrous N,N-dimethylformamide. The resulting suspension was gently stirred at 22° C. for 24 hours. The resin was then filtered, washed with N,N-dimethylformamide, dichloromethane, methanol, and dried under vacuum.

Analogously, the following compounds can be prepared by using the appropriate carboxylic acid:
N-{3-phenylacetamido-5-acetyl-4,6-dihydropyrrolo[3,4-c]pyrazol-1-yl},N'-methylpolystyrene urea
N-{3-phenylacetamido-5-benzoyl-4,6-dihydropyrrolo[3,4-c]pyrazol-1-yl},N'-methylpolystyrene urea
N-{3-phenylacetamido-5-(2,6-dimethoxybenzoyl)-4,6-dihydropyrrolo[3,4-c]pyrazol-1-yl},N'-methylpolystyrene urea
N-{3-phenylacetamido-5-(2,6-dimethoxybenzoyl)-4,6-dihydropyrrolo[3,4-c]pyrazol-1-yl},N'-methylpolystyrene urea
N-{3-phenylacetamido-5-(2-chlorobenzoyl)-4,6-dihydropyrrolo[3,4-c]pyrazol-1-yl},N'-methylpolystyrene urea
N-{3-phenylacetamido-5-(2-chlorophenylacetyl)-4,6-dihydropyrrolo[3,4-c]pyrazol-1-yl},N'-methylpolystyrene urea N-{3-phenylacetamido-5-(2-fluorobenzoyl)-4,6-dihydropyrrolo[3,4-c]pyrazol-1-yl},N'-methylpolystyrene urea
N-{3-phenylacetamido-5-(4-fluorobenzoyl)-4,6-dihydropyrrolo[3,4-c]pyrazol-1-yl},N'-methylpolystyrene urea
N-{3-phenylacetamido-5-(2-furoyl)-4,6-dihydropyrrolo[3,4-c]pyrazol-1-yl},N'-methylpolystyrene urea
N-{3-phenylacetamido-5-(3-furoyl)-4,6-dihydropyrrolo[3,4-c]pyrazol-1-yl},N'-methylpolystyrene urea
N-{3-phenylacetamido-5-(2-methoxybenzoyl)-4,6-dihydropyrrolo[3,4-c]pyrazol-1-yl},N'-methylpolystyrene urea
N-{3-phenylacetamido-5-(2-methoxyphenylacetyl)-4,6-dihydropyrrolo[3,4-c]pyrazol-1-yl},N'-methylpolystyrene urea
N-{3-phenylacetamido-5-(2-methylphenylacetyl)-4,6-dihydropyrrolo[3,4-c]pyrazol-1-yl},N'-methylpolystyrene urea
N-{3-phenylacetamido-5-(2-quinoxaloyl)-4,6-dihydropyrrolo[3,4-c]pyrazol-1-yl},N'-methylpolystyrene urea
N-{3-phenylacetamido-5-(2-thiopheneacetyl)-4,6-dihydropyrrolo[3,4-c]pyrazol-1-yl},N'-methylpolystyrene urea
N-{3-phenylacetamido-5-(2-toluoyl)-4,6-dihydropyrrolo[3,4-c]pyrazol-1-yl},N'-methylpolystyrene urea
N-{3-phenylacetamido-5-(5-fluoro-2-toluoyl)-4,6-dihydropyrrolo[3,4-c]pyrazol-1-yl},N'-methylpolystyrene urea
N-{3-phenylacetamido-5-(3-chlorobenzoyl)-4,6-dihydropyrrolo[3,4-c]pyrazol-1-yl},N'-methylpolystyrene urea
N-{3-phenylacetamido-5-(3-chlorophenylacetyl)-4,6-dihydropyrrolo[3,4-c]pyrazol-1-yl},N'-methylpolystyrene urea
N-{3-phenylacetamido-5-(3-cyclopentylpropionyl)-4,6-dihydropyrrolo[3,4-c]pyrazol-1-yl},N'-methylpolystyrene urea
N-{3-phenylacetamido-5-(3-fluorobenzoyl)-4,6-dihydropyrrolo[3,4-c]pyrazol-1-yl},N'-methylpolystyrene urea
N-{3-phenylacetamido-5-(3-methoxyphenylacetyl)-4,6-dihydropyrrolo[3,4-c]pyrazol-1-yl},N'-methylpolystyrene urea
N-{3-phenylacetamido-5-(3-methylphenylacetyl)-4,6-dihydropyrrolo[3,4-c]pyrazol-1-yl},N'-methylpolystyrene urea
N-{3-phenylacetamido-5-(3-toluoyl)-4,6-dihydropyrrolo[3,4-c]pyrazol-1-yl},N'-methylpolystyrene urea
N-{3-phenylacetamido-5-(4-bromophenylacetyl)-4,6-dihydropyrrolo[3,4-c]pyrazol-1-yl},N'-methylpolystyrene urea
N-{3-phenylacetamido-5-(4-chlorobenzoyl)-4,6-dihydropyrrolo[3,4-c]pyrazol-1-yl},N'-methylpolystyrene urea
N-{3-phenylacetamido-5-(4-chlorophenylacetyl)-4,6-dihydropyrrolo[3,4-c]pyrazol-1-yl},N'-methylpolystyrene urea
N-{3-phenylacetamido-5-(4-dimethylaminobenzoyl)-4,6-dihydropyrrolo[3,4-c]pyrazol-1-yl},N'-methylpolystyrene urea
N-{3-phenylacetamido-5-(4-fluorobenzoyl)-4,6-dihydropyrrolo[3,4-c]pyrazol-1-yl},N'-methylpolystyrene urea
N-{3-phenylacetamido-5-(4-methoxyphenylacetyl)-4,6-dihydropyrrolo[3,4-c]pyrazol-1-yl},N'-methylpolystyrene urea
N-{3-phenylacetamido-5-(4-methylphenylacetyl)-4,6-dihydropyrrolo[3,4-c]pyrazol-1-yl},N'-methylpolystyrene urea
N-{3-phenylacetamido-5-(4-toluoyl)-4,6-dihydropyrrolo[3,4-c]pyrazol-1-yl},N'-methylpolystyrene urea
N-{3-phenylacetamido-5-(thiophene-2-carbonyl)-4,6-dihydropyrrolo[3,4-c]pyrazol-1-yl},N'-methylpolystyrene urea
N-{3-phenylacetamido-5-(trans-2-phenyl-1-cyclopropanecarbonyl)-4,6-dihydropyrrolo[3,4-c]pyrazol-1-yl},N'-methylpolystyrene urea
N-{3-phenylacetamido-5-butyryl-4,6-dihydropyrrolo[3,4-c]pyrazol-1-yl},N'-methylpolystyrene urea
N-{3-phenylacetamido-5-cyclopropanecarbonyl-4,6-dihydropyrrolo[3,4-c]pyrazol-1-yl},N'-methylpolystyrene urea
N-{3-phenylacetamido-5-(1-methylcyclopropane)carbonyl-4,6-dihydropyrrolo[3,4-c]pyrazol-1-yl},N'-methylpolystyrene urea
N-{3-phenylacetamido-5-(2,2,3,3-methylcyclopropane)carbonyl-4,6-dihydropyrrolo[3,4-c]pyrazol-1-yl},N'-methylpolystyrene urea
N-{3-phenylacetamido-5-isovaleryl-4,6-dihydropyrrolo[3,4-c]pyrazol-1-yl},N'-methylpolystyrene urea
N-{3-phenylacetamido-5-isoxazole-5-carbonyl-4,6-dihydropyrrolo[3,4-c]pyrazol-1-yl},N'-methylpolystyrene urea
N-{3-phenylacetamido-5-m-anisoyl-4,6-dihydropyrrolo[3,4-c]pyrazol-1-yl},N'-methylpolystyrene urea
N-{3-phenylacetamido-5-nicotinoyl-4,6-dihydropyrrolo[3,4-c]pyrazol-1-yl},N'-methylpolystyrene urea
N-{3-phenylacetamido-5-p-anisoyl-4,6-dihydropyrrolo[3,4-c]pyrazol-1-yl},N'-methylpolystyrene urea
N-{3-phenylacetamido-5-phenoxyacetyl-4,6-dihydropyrrolo[3,4-c]pyrazol-1-yl},N'-methylpolystyrene urea
N-{3-phenylacetamido-5-benzoxyacetyl-4,6-dihydropyrrolo[3,4-c]pyrazol-1-yl},N'-methylpolystyrene urea
N-{3-phenylacetamido-5-(1-naphthoyl)-4,6-dihydropyrrolo[3,4-c]pyrazol-1-yl},N'-methylpolystyrene urea
N-{3-phenylacetamido-5-but-2-ynoyl-4,6-dihydropyrrolo[3,4-c]pyrazol-1-yl},N'-methylpolystyrene urea
N-{3-phenylacetamido-5-pyruvoyl-4,6-dihydropyrrolo[3,4-c]pyrazol-1-yl},N'-methylpolystyrene urea
N-{3-phenylacetamido-5-(1,3-benzodioxol-5-ylcarbonyl)-4,6-dihydropyrrolo[3,4-c]pyrazol-1-yl},N'-methylpolystyrene urea
N-{3-phenylacetamido-5-(2,2-dimethylpropanoyl)-4,6-dihydropyrrolo[3,4-c]pyrazol-1-yl},N'-methylpolystyrene urea
N-{3-phenylacetamido-5-(2,4-dichloro-5-fluorobenzoyl)-4,6-dihydropyrrolo[3,4-c]pyrazol-1-yl},N'-methylpolystyrene urea
N-{3-phenylacetamido-5-(2-methylpent-4-enoyl)-4,6-dihydropyrrolo[3,4-c]pyrazol-1-yl},N'-methylpolystyrene urea
N-{3-phenylacetamido-5-(3-iodo-4-methylbenzoyl)-4,6-dihydropyrrolo[3,4-c]pyrazol-1-yl},N'-methylpolystyrene urea
N-{3-phenylacetamido-5-(4-chloro-2,5-difluorobenzoyl)-4,6-dihydropyrrolo[3,4-c]pyrazol-1-yl},N'-methylpolystyrene urea
N-{3-phenylacetamido-5-(cyclobutylcarbonyl)-4,6-dihydropyrrolo[3,4-c]pyrazol-1-yl},N'-methylpolystyrene urea
N-{3-phenylacetamido-5-(pyridin-3-ylcarbonyl)-4,6-dihydropyrrolo[3,4-c]pyrazol-1-yl},N'-methylpolystyrene urea
N-{3-phenylacetamido-5-sobutyryl-4,6-dihydropyrrolo[3,4-c]pyrazol-1-yl},N'-methylpolystyrene urea
N-{3-phenylacetamido-5-(1-H-benzotriazole-5-carbonyl)-4,6-dihydropyrrolo[3,4-c]pyrazol-1-yl},N'-methylpolystyrene urea
N-{3-phenylacetamido-5-(1-methyl-indol-3-yl)acetyl-4,6-dihydropyrrolo[3,4-c]pyrazol-1-yl},N'-methylpolystyrene urea N-{3-phenylacetamido-5-(2-methyl-pyridine-3-carbonyl)-4,6-dihydropyrrolo[3,4-c]pyrazol-1-yl},N'-methylpolystyrene urea N-{3-phenylacetamido-5-(2-methylsulfonamidothiazole-4-carbonyl)-4,6-dihydropyrrolo[3,4-c]pyrazol-1-yl},N'-methylpolystyrene urea N-{3-phenylacetamido-5-(2-morfolinomethyl-5-furoyl)-4,6-dihydropyrrolo[3,4-c]pyrazol-1-yl},N'-methylpolystyrene urea N-{3-phenylacetamido-5-(2-phenyl-thiazol-4-yl)acetyl-4,6-dihydropyrrolo[3,4-c]pyrazol-1-yl},N'-methylpolystyrene urea N-{3-phenylacetamido-5-(2-thiomethyl-pyridine-3-carbonyl)-4,6-dihydropyrrolo[3,4-c]pyrazol-1-yl},N'-methylpolystyrene urea N-{3-phenylacetamido-5-(3-furoyl)-4,6-dihydropyrrolo[3,4-c]pyrazol-1-yl},N'-methylpolystyrene urea N-{3-phenylacetamido-5-(3-pyridinyl-acetyl)-4,6-dihydropyrrolo[3,4-c]pyrazol-1-yl},N'-methylpolystyrene urea N-{3-phenylacetamido-5-(3-thenoyl)-4,6-dihydropyrrolo[3,4-c]pyrazol-1-yl},N'-methylpolystyrene urea N-{3-phenylacetamido-5-(4-methyl-piperazin-1-yl)acetyl-4,6-dihydropyrrolo[3,4-c]pyrazol-1-yl},N'-methylpolystyrene urea N-{3-phenylacetamido-5-(5-acetylamino-2-furoyl)-4,6-dihydropyrrolo[3,4-c]pyrazol-1-yl},N'-methylpolystyrene urea N-{3-phenylacetamido-5-(7-methoxy-benzofuran-2-carbonyl)-4,6-dihydropyrrolo[3,4-c]pyrazol-1-yl},N'-methylpolystyrene urea N-{3-phenylacetamido-5-(8-quinoline)carbonyl-4,6-dihydropyrrolo[3,4-c]pyrazol-1-yl},N'-methylpolystyrene urea N-{3-phenylacetamido-5-(benzofuran-2-carbonyl)-4,6-dihydropyrrolo[3,4-c]pyrazol-1-yl},N'-methylpolystyrene urea N-{3-phenylacetamido-5-(indol-2-yl)carbonyl-4,6-dihydropyrrolo[3,4-c]pyrazol-1-yl},N'-methylpolystyrene urea N-{3-phenylacetamido-5-(piperidin-1-yl)acetyl-4,6-dihydropyrrolo[3,4-c]pyrazol-1-yl},N'-methylpolystyrene urea N-{3-phenylacetamido-5-(pirrole-3-carbonyl)-4,6-dihydropyrrolo[3,4-c]pyrazol-1-yl},N'-methylpolystyrene urea N-{3-phenylacetamido-5-(pirrolidin-1-ylcarbonyl)methyl-4,6-dihydropyrrolo[3,4-c]pyrazol-1-yl},N'-methylpolystyrene urea N-{3-phenylacetamido-5-(pyrazine-2-carbonyl)-4,6-dihydropyrrolo[3,4-c]pyrazol-1-yl},N'-methylpolystyrene urea N-{3-phenylacetamido-5-(pyridine-3-carbonyl)-4,6-dihydropyrrolo[3,4-c]pyrazol-1-yl},N'-methylpolystyrene urea N-{3-phenylacetamido-5-(pyridine-4-carbonyl)-4,6-dihydropyrrolo[3,4-c]pyrazol-1-yl},N'-methylpolystyrene urea N-{3-phenylacetamido-5-(pyrrol-3-ylcarbonyl)-4,6-dihydropyrrolo[3,4-c]pyrazol-1-yl},N'-methylpolystyrene urea N-{3-phenylacetamido-5-(quinoline-4-carbonyl)-4,6-dihydropyrrolo[3,4-c]pyrazol-1-yl},N'-methylpolystyrene urea N-{3-phenylacetamido-5-(quinoline-6-carbonyl)-4,6-dihydropyrrolo[3,4-c]pyrazol-1-yl},N'-methylpolystyrene urea N-{3-phenylacetamido-5-(3-methoxycyclohexyl)carbonyl-4,6-dihydropyrrolo[3,4-c]pyrazol-1-yl},N'-methylpolystyrene urea N-{3-phenylacetamido-5-(8-oxo-5,6,7,8-tetrahydronaphthalen-2-yl)carbonyl-4,6-dihydropyrrolo[3,4-c]pyrazol-1-yl},N'-methylpolystyrene urea N-{3-phenylacetamido-5-[2-(6-oxo-1(6H)-pyridazinyl]acetyl-4,6-dihydropyrrolo[3,4-c]pyrazol-1-yl},N'-methylpolystyrene urea N-{3-phenylacetamido-5-[2-fluoro-5-(trifluoromethyl)benzoyl]-4,6-dihydropyrrolo[3,4-c]pyrazol-1-yl},N'-methylpolystyrene urea N-{3-phenylacetamido-5-[4-(1H-imidazol-1-yl)benzoyl]-4,6-dihydropyrrolo[3,4-c]pyrazol-1-yl},N'-methylpolystyrene urea N-{3-phenylacetamido-5-[4-(1-imidazolylmethyl)benzoyl]-4,6-dihydropyrrolo[3,4-c]pyrazol-1-yl},N'-methylpolystyrene urea N-{3-phenylacetamido-5-[4-(1-pyrrolidin-2-on)benzoyl]-4,6-dihydropyrrolo[3,4-c]pyrazol-1-yl},N'-methylpolystyrene urea N-{3-phenylacetamido-5-[4-(aminosulfonyl)butanoyl]-4,6-dihydropyrrolo[3,4-c]pyrazol-1-yl},N'-methylpolystyrene urea N-{3-phenylacetamido-5-[5-(1-morfolinomethyl)furan-2-carbonyl]-4,6-dihydropyrrolo[3,4-c]pyrazol-1-yl},N'-methylpolystyrene urea N-{3-phenylacetamido-5-carbamoyloxyacetyl-4,6-dihydropyrrolo[3,4-c]pyrazol-1-yl},N'-methylpolystyrene urea N-{3-phenylacetamido-5-ethoxyacetyl-4,6-dihydropyrrolo[3,4-c]pyrazol-1-yl},N'-methylpolystyrene urea N-{3-phenylacetamido-5-picolinoyl-4,6-dihydropyrrolo[3,4-c]pyrazol-1-yl},N'-methylpolystyrene urea

EXAMPLE 9

Preparation of N-{3-phenylacetamido-5-p-toluenesulfonyl-4,6-dihydropyrrolo[3,4-c]pyrazol-1-yl},N'-methylpolystyrene urea p-Toluenesulfonyl chloride (0.43 mmol, 82.0 mg) and DIEA (2.58 mmol, 441.7 mcl) were added to N-{3-phenylacetamido-4,6-dihydropyrrolo[3,4-c]pyrazol-1-yl},N'-methylpolystyrene urea (0.086 mmol, 100 mg) previously swelled in 4 ml of anhydrous dichloromethane. The resulting suspension was gently stirred at 22° C. for 24 hours. The resin was then filtered, washed with dichloromethane and methanol, and dried under vacuum.

Analogously, the following compounds can be prepared by using the appropriate sulfonyl chloride:

N-{3-phenylacetamido-5-methanesulfonyl-4,6-dihydropyrrolo[3,4-c]pyrazol-1-yl},N'-methylpolystyrene urea N-{3-phenylacetamido-5-benzylsulfonyl-4,6-dihydropyrrolo[3,4-c]pyrazol-1-yl},N'-methylpolystyrene urea N-{3-phenylacetamido-5-benzenesulfonyl-4,6-dihydropyrrolo[3,4-c]pyrazol-1-yl},N'-methylpolystyrene urea N-{3-phenylacetamido-5-isobutanesulfonyl-4,6-dihydropyrrolo[3,4-c]pyrazol-1-yl},N'-methylpolystyrene urea N-{3-phenylacetamido-5-(quinoline-8-sulfonyl)-4,6-dihydropyrrolo[3,4-c]pyrazol-1-yl},N'-methylpolystyrene urea N-{3-phenylacetamido-5-(naphthalene-1-sulfonyl)-4,6-dihydropyrrolo[3,4-c]pyrazol-1-yl},N'-methylpolystyrene urea N-{3-phenylacetamido-5-(4-fluorobenzene-sulfonyl)-4,6-dihydropyrrolo[3,4-c]pyrazol-1-yl},N'-methylpolystyrene urea N-{3-phenylacetamido-5-(4-methoxybenzene-sulfonyl)-4,6-dihydropyrrolo[3,4-c]pyrazol-1-yl},N'-methylpolystyrene urea N-{3-phenylacetamido-5-(4-trifluoromethylbenzene-sulfonyl)-4,6-dihydropyrrolo[3,4-c]pyrazol-1-yl},N'-methylpolystyrene urea N-{3-phenylacetamido-5-(3-trifluoromethylbenzene-sulfonyl)-4,6-dihydropyrrolo[3,4-c]pyrazol-1-yl},N'-methylpolystyrene urea N-{3-phenylacetamido-5-(2-trifluoromethylbenzene-sulfonyl)-4,6-dihydropyrrolo[3,4-c]pyrazol-1-yl},N'-methylpolystyrene urea N-{3-phenylacetamido-5-(4-chlorobenzene-sulfonyl)-4,6-dihydropyrrolo[3,4-c]pyrazol-1-yl},N'-methylpolystyrene urea N-{3-phenylacetamido-5-(4-tertbutylbenzene-sulfonyl)-4,6-dihydropyrrolo[3,4-c]pyrazol-1-yl},N'-methylpolystyrene urea N-{3-phenylacetamido-5-(2-cyanobenzene-sulfonyl)-4,6-dihydropyrrolo[3,4-c]pyrazol-1-yl},N'-methylpolystyrene urea

EXAMPLE 10

Preparation of N-{3-phenylacetamido-5-ethylaminocarbonyl-4,6-dihydropyrrolo[3,4-c]pyrazol-1-yl}, N'-methylpolystyrene urea Ethylisocyanate (0.43 mmol, 33.8 mcl) was added to N-{3-phenylacetamido-4,6-dihydropyrrolo[3,4-c]pyrazol-1-yl}, N'-methylpolystyrene urea (0.086 mmol, 100 mg) previously swelled in 4 ml of anhydrous dichloromethane. The resulting suspension was gently stirred at 22° C. for 24 hours. The resin was then filtered, washed with dichloromethane, methanol, and dried under vacuum.

Analogously, the following compounds can be prepared by using the appropriate isocyanate:

N-{3-phenylacetamido-5-(1-naphthyl)aminocarbonyl-4,6-dihydropyrrolo[3,4-c]pyrazol-1-yl},N'-methylpolystyrene urea N-{3-phenylacetamido-5-(2,4-difluorophenyl)aminocarbonyl-4,6-dihydropyrrolo[3,4-c]pyrazol-1-yl},N'-methylpolystyrene urea N-{3-phenylacetamido-5-(2,5-dimethoxyphenyl)aminocarbonyl-4,6-dihydropyrrolo[3,4-c]pyrazol-1-yl},N'-methylpolystyrene urea N-{3-phenylacetamido-5-(2,6-difluorobenzoyl)aminocarbonyl-4,6-dihydropyrrolo[3,4-c]pyrazol-1-yl},N'-methylpolystyrene urea N-{3-phenylacetamido-5-(2,6-dimethylphenyl)aminocarbonyl-4,6-dihydropyrrolo[3,4-c]pyrazol-1-yl},N'-methylpolystyrene urea N-{3-phenylacetamido-5-(2-chlorophenyl)aminocarbonyl-4,6-dihydropyrrolo[3,4-c]pyrazol-1-yl},N'-methylpolystyrene urea N-{3-phenylacetamido-5-(2-ethoxyphenyl)aminocarbonyl-4,6-dihydropyrrolo[3,4-c]pyrazol-1-yl},N'-methylpolystyrene urea N-{3-phenylacetamido-5-(2-fluoro-3-(trifluoromethyl)phenyl)aminocarbonyl-4,6-dihydropyrrolo[3,4-c]pyrazol-1-yl},N'-methylpolystyrene urea N-{3-phenylacetamido-5-(2-isopropylphenyl)-aminocarbonyl-4,6-dihydropyrrolo[3,4-c]pyrazol-1-yl},N'-methylpolystyrene urea N-{3-phenylacetamido-5-(2-methoxyphenyl)aminocarbonyl-4,6-dihydropyrrolo[3,4-c]pyrazol-1-yl},N'-methylpolystyrene urea N-{3-phenylacetamido-5-(2-methylbenzyl)aminocarbonyl-4,6-dihydropyrrolo[3,4-c]pyrazol-1-yl},N'-methylpolystyrene urea N-{3-phenylacetamido-5-(2-naphthyl)aminocarbonyl-4,6-dihydropyrrolo[3,4-c]pyrazol-1-yl},N'-methylpolystyrene urea N-{3-phenylacetamido-5-(3,4-dichlorophenyl)aminocarbonyl-4,6-dihydropyrrolo[3,4-c]pyrazol-1-yl},N'-methylpolystyrene urea N-{3-phenylacetamido-5-(3-chlorophenyl)aminocarbonyl-4,6-dihydropyrrolo[3,4-c]pyrazol-1-yl},N'-methylpolystyrene urea N-{3-phenylacetamido-5-(3-fluorophenyl)aminocarbonyl-4,6-dihydropyrrolo[3,4-c]pyrazol-1-yl},N'-methylpolystyrene urea N-{3-phenylacetamido-5-(3-methoxyphenyl)aminocarbonyl-4,6-dihydropyrrolo[3,4-c]pyrazol-1-yl},N'-methylpolystyrene urea N-{3-phenylacetamido-5-(4-biphenylyl)aminocarbonyl-4,6-dihydropyrrolo[3,4-c]pyrazol-1-yl},N'-methylpolystyrene urea N-{3-phenylacetamido-5-(4-chlorophenyl)aminocarbonyl-4,6-dihydropyrrolo[3,4-c]pyrazol-1-yl},N'-methylpolystyrene urea N-{3-phenylacetamido-5-(4-fluorobenzoyl)aminocarbonyl-4,6-dihydropyrrolo[3,4-c]pyrazol-1-yl},N'-methylpolystyrene urea N-{3-phenylacetamido-5-(4-fluorophenyl)aminocarbonyl-4,6-dihydropyrrolo[3,4-c]pyrazol-1-yl},N'-methylpolystyrene urea N-{3-phenylacetamido-5-(4-methoxybenzyl)aminocarbonyl-4,6-dihydropyrrolo[3,4-c]pyrazol-1-yl},N'-methylpolystyrene urea N-{3-phenylacetamido-5-(4-methoxyphenyl)aminocarbonyl-4,6-dihydropyrrolo[3,4-c]pyrazol-1-yl},N'-methylpolystyrene urea N-{3-phenylacetamido-5-(trans-2-phenylcyclopropyl)aminocarbonyl-4,6-dihydropyrrolo[3,4-c]pyrazol-1-yl},N'-methylpolystyrene urea N-{3-phenylacetamido-5-[(R)-(+)-1-phenylethyl]aminocarbonyl-4,6-dihydropyrrolo[3,4-c]pyrazol-1-yl},N'-methylpolystyrene urea N-{3-phenylacetamido-5-[(S)-(−)-1-phenylethyl]aminocarbonyl-4,6-dihydropyrrolo[3,4-c]pyrazol-1-yl},N'-methylpolystyrene urea N-{3-phenylacetamido-5-[3-(trifluoromethyl)phenyl]aminocarbonyl-4,6-dihydropyrrolo[3,4-c]pyrazol-1-yl},N'-methylpolystyrene urea N-{3-phenylacetamido-5-[4-(trifluoromethoxy)phenyl]aminocarbonyl-4,6-dihydropyrrolo[3,4-c]pyrazol-1-yl},N'-methylpolystyrene urea N-{3-phenylacetamido-5-benzoylaminocarbonyl-4,6-dihydropyrrolo[3,4-c]pyrazol-1-yl},N'-methylpolystyrene urea N-{3-phenylacetamido-5-cyclohexylaminocarbonyl-4,6-dihydropyrrolo[3,4-c]pyrazol-1-yl},N'-methylpolystyrene urea N-{3-phenylacetamido-5-isopropylaminocarbonyl-4,6-dihydropyrrolo[3,4-c]pyrazol-1-yl},N'-methylpolystyrene urea N-{3-phenylacetamido-5-n-butylaminocarbonyl-4,6-dihydropyrrolo[3,4-c]pyrazol-1-yl},N'-methylpolystyrene urea N-{3-phenylacetamido-5-phenylaminocarbonyl-4,6-dihydropyrrolo[3,4-c]pyrazol-1-yl},N'-methylpolystyrene urea N-{3-phenylacetamido-5-p-tolylaminocarbonyl-4,6-dihydropyrrolo[3,4-c]pyrazol-1-yl},N'-methylpolystyrene urea N-{3-phenylacetamido-5-trichloroacetylaminocarbonyl-4,6-dihydropyrrolo[3,4-c]pyrazol-1-yl},N'-methylpolystyrene urea N-{3-phenylacetamido-5-phenethylaminocarbonyl-4,6-dihydropyrrolo[3,4-c]pyrazol-1-yl},N'-methylpolystyrene urea N-{3-phenylacetamido-5-[3,5-bis(trifluoromethyl)phenyl]aminocarbonyl-4,6-dihydropyrrolo[3,4-c]pyrazol-1-yl},N'-methylpolystyrene urea N-{3-phenylacetamido-5-tert-butylaminocarbonyl-4,6-dihydropyrrolo[3,4-c]pyrazol-1-yl},N'-methylpolystyrene urea N-{3-phenylacetamido-5-[2,6-diisopropylphenyl]aminocarbonyl-4,6-dihydropyrrolo[3,4-c]pyrazol-1-yl},N'-methylpolystyrene urea N-{3-phenylacetamido-5-[2,6-diethylphenyl]aminocarbonyl-4,6-dihydropyrrolo[3,4-c]pyrazol-1-yl},N'-methylpolystyrene urea N-{3-phenylacetamido-5-benzylaminocarbonyl-4,6-dihydropyrrolo[3,4-c]pyrazol-1-yl},N'-methylpolystyrene urea N-{3-phenylacetamido-5-[(r)-(−)-1-(1-naphthyl)ethyl]aminocarbonyl-4,6-dihydropyrrolo[3,4-c]pyrazol-1-yl},N'-methylpolystyrene urea.

EXAMPLE 11

Preparation of N-{5-phenylacetyl-4,6-dihydropyrrolo[3,4-c]pyrazol-3-yl}phenylacetamide Aqueous NaOH 35% (1.72 mmol, 143 mcl) was added to N-{3-phenylacetamido-5-phenylacetyl-4,6-dihydropyrrolo[3,4-c]pyrazol-1-yl},N'-methylpolystyrene urea (0.086 mmol) obtained in example 5, previously swelled in 4 ml of methanol. The resulting suspension was gently stirred at 40° C. for 72 hours. The resin was then filtered, the filtrate neutralized with HCl 25% and evaporated to dryness. The residue was partitioned between chloroform (4 ml) and a solution of saturated sodium bicarbonate (200 mcl). The organic layer was dried over sodium sulfate and evaporated to give the title compound as a yellow solid (21.0 mg, 65%).

$^1$H-NMR (DMSO-$d_6$) δ ppm: 7.3-7.1 (m); 4.6-4.4 (m); 3.67 (s); 3.6 (s).

(M+H)$^+$=360

Analogously, by using the appropriate methylpolystyrene ureas described in examples 6 and 7 were obtained:

N-{5-acetyl-4,6-dihydropyrrolo[3,4-c]pyrazol-3-yl}phenylacetamide $^1$H-NMR (DMSO-$d_6$) δ ppm: 12.23 (s); 7.3-7.2 (m); 4.6-4.3 (m); 3.59 (s); 1.97 (s).

(M+H)$^+$=284

N-benzyl-N'-{3-phenylacetamido-4,6-dihydropyrrolo[3,4-c]pyrazol-5-yl}urea $^1$H-NMR (DMSO-$d_6$) δ ppm: 10.6 (s); 7.3-7.1 (m); 6.85 (t broad); 4.37 (s broad); 4.23 (d); 3.6 (s).

(M+H)$^+$=375

N-{5-toluensulfonyl-4,6-dihydropyrrolo[3,4-c]pyrazol-3-yl}phenylacetamide $^1$H-NMR (DMSO-$d_6$) δ ppm: 7.7 (d); 7.39 (d); 7.3-7.2 (m); 4.4-4.2 (m); 3.56 (s); 2.34 (s).

(M+H)$^+$=396

N-ethyl-N'-{3-phenylacetamido-4,6-dihydropyrrolo[3,4-c]pyrazol-5-yl}urea $^1$H-NMR (DMSO-$d_6$) δ ppm: 7.3-7.1 (m); 6.2 (t broad); 4.3 (s broad); 3.59 (s); 3.03 (m); 1 (t).

(M+H)$^+$=313

N-{5-acetyl-4,6-dihydropyrrolo[3,4-c]pyrazol-3-yl}-4-(phenyl)phenylacetamide $^1$H-NMR (DMSO-$d_6$) δ ppm: 7.6-7.3 (m); 4.6-4.3 (m); 3.64 (s); 1.98 (s).

(M+H)$^+$=360

N-{5-acetyl-4,6-dihydropyrrolo[3,4-c]pyrazol-3-yl}-2-naphtylacetamide $^1$H-NMR (DMSO-$d_6$) δ ppm: 7.9-7.5 (m); 4.6-4.3 (m); 3.78 (s); 1.97 (s).

(M+H)$^+$=334

EXAMPLE 12

Preparation of a Library of 4,6-dihydropyrrolo[3,4-c]pyrazol-3-yl derivatives

Step a:

540 g of 3-amino-5-(carbo-tbutoxy)-4,6-dihydropyrrolo[3,4-c]pyrazole were prepared according to the procedure reported in example 4.

Step b:

The obtained 3-amino-5-(carbo-tbutoxy)-4,6-dihydropyrrolo[3,4-c]pyrazole was supported on methylisocyanate polystyrene resin (200-400 mesh, 2% DVB, loading 1.49 mmol/g, 900 g) according to the procedure reported in example 5.

Step c

The obtained N-{3-amino-5-(carbo-tbutoxy)-4,6-dihydropyrrolo[3,4-c]pyrazol-1-yl},N'-methylpolystyrene urea was partioned in 96 different batches (15 g each). Each batch was reacted with the appropriate acyl chloride, according to the procedure described in example 6, to obtain the products listed in example 6.

Step d

The 96 batches of N-{3-acyl-amido-5-(carbo-tbutoxy)-4,6-dihydropyrrolo[3,4-c]pyrazol-1-yl},N'-methylpolystyrene ureas were individually treated with a solution of TFA 50% in anhydrous dichloromethane according to the procedure described in example 7, to obtain the products listed in example 7.

Step e

One out of the 96 lots obtained in step d was partioned in 149 batches (50 mg each). These 149 batches were individually reacted with the 95 carboxylic acids used in example 8, 15 sulfonylchlorides used in example 9, and 15 isocyanates used in example 10.

Step f

Each of the 149 batches obtained in step e was hydrolysed according to the procedure reported in example 11 to give 149 single 4,6-dihydropyrrolo[3,4-c]pyrazol-3-yl derivatives (7-14 mg each).

Step g

Each of the remaining 95 lots of step d underwent steps e, and f.

The overall combinatorial chemistry process gave a library of 96×149=14304 individual 4,6-dihydropyrrolo[3,4-c]pyrazol-3-yl derivatives.

Representative compounds of the above combinatorial library are:

N-{5-acetyl-4,6-dihydropyrrolo[3,4-c]pyrazol-3-yl}-furan-2-carboxamide; 1H-NMR (DMSO-d6) d ppm: 7.9 (m); 7.4 (m); 6.7 (m); 4.6-4.4 (m); 2.02 (s).

N-{5-acetyl-4,6-dihydropyrrolo[3,4-c]pyrazol-3-yl}-5-chlorothiophene-2-carboxamide; 1H-NMR (DMSO-d6) d ppm: 8.0-7.9 (m); 7.2 (m); 4.6-4.4 (m); 2.03 (s).

N-{5-acetyl-4,6-dihydropyrrolo[3,4-c]pyrazol-3-yl}-6-chloronicotinamide; 1H-NMR (DMSO-d6) d ppm: 8.95 (s); 8.4 (m); 7.6 (m); 4.7-4.4 (m); 2.03 (s).

N-{5-acetyl-4,6-dihydropyrrolo[3,4-c]pyrazol-3-yl}-benzofuran-2-carboxamide; 1H-NMR (DMSO-d6) d ppm: 7.8-7.3 (m); 4.7-4.4 (m); 2.03 (s).

N-{5-acetyl-4,6-dihydropyrrolo[3,4-c]pyrazol-3-yl}-4-phenoxybenzamide; 1H-NMR (DMSO-d6) d ppm: 7.5-7.2 (m); 4.7-4.4 (m); 2.0 (s).

N-{5-acetyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 4.7-4.4 (m); 2.03 (s); 1.30 (s).

N-{5-acetyl-4,6-dihydropyrrolo[3,4-c]pyrazol-3-yl}-piperonylamide;

N-{5-acetyl-4,6-dihydropyrrolo[3,4-c]pyrazol-3-yl}-[2-methyl-5-phenyl-furan-3-carboxamide]; 1H-NMR (DMSO-d6) d ppm: 7.6-7.3 (m); 4.7-4.4 (m); 2.62 (s); 2.03 (s).

N-{5-acetyl-4,6-dihydropyrrolo[3,4-c]pyrazol-3-yl}-(quinoline-6-carboxamide); 1H-NMR (DMSO-d6) d ppm: 9.0 (m); 8.7-8.5 (m); 8.3-7.9 (m); 7.6 (m); 4.7-4.2 (m); 2.05 (s).

N-{5-acetyl-4,6-dihydropyrrolo[3,4-c]pyrazol-3-yl}-[5-(4-chlorophenyl)furan-2-carboxamide]; 1H-NMR (DMSO-d6) d ppm: 8.0-7.2 (m); 4.7-4.4 (m); 2.03 (s).

N-{5-methansulfonyl-4,6-dihydropyrrolo[3,4-c]pyrazol-3-yl}-4-tertbutylbenzamide 1H-NMR (DMSO-d6) d ppm: 7.9-7.8 (m); 7.5-7.4 (m); 4.5-4.4 (m); 2.96 (s); 1.28 (s).

N-{5-benzensulfonyl-4,6-dihydropyrrolo[3,4-c]pyrazol-3-yl}-4-tertbutylbenzamide 1H-NMR (DMSO-d6) d ppm: 7.9-7.8 (m); 7.7-7.6 (m); 7.5-7.4 (m); 4.5-4.3 (m); 1.28 (s).

N-{5-benzoyl-4,6-dihydropyrrolo[3,4-c]pyrazol-3-yl}-4-tertbutylbenzamide 1H-NMR (DMSO-d6) d ppm: 7.9-7.8 (m); 7.6-7.4 (m); 4.7-4.5 (m); 1.26 (s).

N-{5-(1-naphthalene)sulfonyl-4,6-dihydropyrrolo[3,4-c]pyrazol-3-yl}-4-tertbutylbenzamide 1H-NMR (DMSO-d6) d ppm: 8.3-8.2 (m); 8.1-8.0 (m); 7.9-7.8 (m); 7.8-7.6 (m); 7.5-7.4 (m); 4.6-4.5 (m); 1.27 (s).

N-{5-(1-naphtoyl)-4,6-dihydropyrrolo[3,4-c]pyrazol-3-yl}-4-tertbutylbenzamide; 1H-NMR (DMSO-d6) d ppm: 8.0-7.9 (m); 7.9-7.7 (m); 7.6-7.4 (m); 4.8-4.2 (m); 1.23 (s).

N-{5-phenylacetyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.3-7.2 (m); 4.7-4.4 (m); 3.7-3.6 (m); 1.29 (s).

N-phenyl-N'-{3-(4-tertbutyl-benzamido)-4,6-dihydropyrrolo[3,4-c]pyrazol-5-yl}urea 1H-NMR (DMSO-d6) d ppm: 7.9-7.8 (m); 7.5-7.4 (m); 7.3-7.2 (m); 6.9-6.8 (m); 4.6-4.5 (m); 1.27 (s).

N-isopropyl-N'-{3-(4-tertbutyl-benzamido)-4,6-dihydropyrrolo[3,4-c]pyrazol-5-yl}urea 1H-NMR (DMSO-d6) d ppm: 7.9-7.8 (m); 7.5-7.4 (m); 4.4-4.3 (m); 3.8-3.7 (m); 1.29 (s); 1.07 (d).

N-{5-methansulfonyl-4,6-dihydropyrrolo[3,4-c]pyrazol-3-yl}-4-phenoxylbenzamide 1H-NMR (DMSO-d6) d ppm: 7.5-7.4 (m); 4.5-4.4 (m); 3.0 (s).

N-{5-benzoyl-4,6-dihydropyrrolo[3,4-c]pyrazol-3-yl}-4-phenoxybenzamide; 1H-NMR (DMSO-d6) d ppm: 7.6-7.4 (m); 7.1-6.9 (m); 4.65-4.5 (m)

N-{5-(1-naphtoyl)-4,6-dihydropyrrolo[3,4-c]pyrazol-3-yl}-4-phenoxybenzamide; 1H-NMR (DMSO-d6) d ppm: 8.1-7.8 (m); 7.2-6.9 (m); 4.9-4.7 (m); 4.4-4.2 (m)

N-isopropyl-N'-{3-(4-phenoxy-benzamido)-4,6-dihydropyrrolo[3,4-c]pyrazol-5-yl}urea 1H-NMR (DMSO-d6) d ppm: 7.5-7.4 (m); 4.3-4.2 (m); 3.8 (m); 1.1 (d).

N-{5-acetyl-4,6-dihydropyrrolo[3,4-c]pyrazol-3-yl}-[2-(2-naphtyl)propionamide];
1H-NMR (DMSO-d6) d ppm: 7.8-7.5 (m); 4.6-4.3 (m); 4.0 (m); 2.0 (s); 1.5 (m)."

N-isopropyl-N'-{3-piperonylcarboxamido-4,6-dihydropyrrolo[3,4-c]pyrazol-5-yl}urea
1H-NMR (DMSO-d6) d ppm: 7.4-7.7 (m), 6.1 (s), 4.7-4.9 (m), 1.0-1.1 (m).

N-cyclohexyl-N'-{3-(4-tertbutyl-benzamido)-4,6-dihydropyrrolo[3,4-c]pyrazol-5-yl}urea 1H-NMR (DMSO-d6) d ppm: 7.9-7.8 (m); 7.5-7.4 (m); 4.4-4.3 (m); 1.8-1.0 (m); 1.23 (s).

N-ethyl-N'-{3-(4-tertbutyl-benzamido)-4,6-dihydropyrrolo[3,4-c]pyrazol-5-yl}urea 1H-NMR (DMSO-d6) d ppm: 7.9-7.8 (m); 7.5-7.4 (m); 4.4-4.3 (m); 3.3-3.0 (m); 1.30 (s); 1.1-1.0 (m);

N-(2,6-diethylphenyl)-N'-{3-(4-tertbutyl-benzamido)-4,6-dihydropyrrolo[3,4-c]pyrazol-5-yl}urea 1H-NMR (DMSO-d6) d ppm: 7.9-7.8 (m); 7.5-7.4 (m); 7.1-7.0 (m); 4.6-4.5 (m); 2.56 (q); 1.30 (s); 1.11 (t).

N-cyclohexyl-N'-{3-(2-ethyl-butyramido)-4,6-dihydropyrrolo[3,4-c]pyrazol-5-yl}urea 1H-NMR (DMSO-d6) d ppm: 4.3 (m); 3.4 (m); 2.24 (m); 1.6-1.4 (m); 0.8 (m).

N-(2,6-diethylphenyl)-N'-{3-piperonylcarboxamido-4,6-dihydropyrrolo[3,4-c]pyrazol-5-yl}urea
1H-NMR (DMSO-d6) d ppm: 7.5-7.7 (m) 7.0-7.2 (m), 6.1 (s), 4.4-4.6 (m), 2.5-2.6 (m), 1.0-1.1 (t).

N-2-methoxyphenyl-N'-{3-(2-naphthalen-2-yl-propionamido)-4,6-dihydropyrrolo[3,4-c]pyrazol-5-yl}urea
1H-NMR (DMSO-d6) d ppm: 7.8-6.8 (m); 4.5 (m); 4.0 (m); 3.8 (s); 1.5 (d).

N-(1-phenyl)ethyl-N'-{3-(2-naphthalen-2-yl-propionamido)-4,6-dihydropyrrolo[3,4-c]pyrazol-5-yl}urea
1H-NMR (DMSO-d6) d ppm: 10.6 (s); 7.8-7.2 (m); 6.6 (m); 4.8 (m); 4.4 (m); 4.0 (m); 1.5 (d); 1.4 (d).

N-{5-phenylsulfonyl-4,6-dihydropyrrolo[3,4-c]pyrazol-3-yl}-3-(2-naphthalen-2-yl)-propionamide 1H-NMR (DMSO-d6) d ppm: 7.8-7.5 (m); 4.4 (m); 4.0 (m); 1.4 (d).

N-(2,5-dimethylphenyl)-N'-{3-(4-tertbutyl-benzamido)-4,6-dihydropyrrolo[3,4-c]pyrazol-5-yl}urea 1H-NMR (DMSO-d6) d ppm: 7.9-7.8 (m); 7.5-7.4 (m); 7.1-6.8 (m); 4.6-4.5 (m); 2.23 (s); 2.16 (s); 1.30 (s).

N-(2,5-dimethylphenyl)-N'-{3-(2-ethyl-butyramido)-4,6-dihydropyrrolo[3,4-c]pyrazol-5-yl}urea 1H-NMR (DMSO-d6) d ppm: 7.1-6.8 (m); 4.5 (m); 1.5-1.4 (m); 0.8 (m).

N-(4-fluorobenzyl)-N'-{3-(2-ethyl-butyramido)-4,6-dihydropyrrolo[3,4-c]pyrazol-5-yl}urea 1H-NMR (DMSO-d6) d ppm: 7.3-7.1 (m); 4.4 (m); 4.2 (m); 1.5-1.4 (m); 0.8 (m).

N-{5-benzylsulfonyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.4-7.3 (m); 4.6-4.3 (m); 1.30 (s).

N-2-chlorophenyl-N'-{3-(2-naphthalen-2-yl-propionamido)-4,6-dihydropyrrolo[3,4-c]pyrazol-5-yl}urea
1H-NMR (DMSO-d6) d ppm: 7.9-7.1 (m); 4.5 (m); 4.0 (m); 1.5 (d).

"N-{5-aminocarbonyl-4,6-dihydropyrrolo[3,4-c]pyrazol-3-yl}-2-(2-naphtyl)propionamide;
1H-NMR (DMSO-d6) d ppm: 10.6 (s); 7.8-7.5 (m); 5.8 (bs); 4.3 (m); 4.0 (m); 1.5 (d)."

N-{5-(3-methyl-butanoyl)-4,6-dihydropyrrolo[3,4-c]pyrazol-3-yl}-4-phenoxybenzamide; 1H-NMR (DMSO-d6) d ppm: 8.0-7.4 (m); 4.7-4.4 (m); 0.9 (d).

N-{5-(2-phenyl-thiazol-4-yl)acetyl-4,6-dihydropyrrolo[3,4-c]pyrazol-3-yl}-4-phenoxybenzamide; 1H-NMR (DMSO-d6) d ppm: 8.1-7.9 (m); 7.5-7.1 (m); 4.9-4.4 (m); 3.3 (s)

N-{-(2-thienyl-acetyl)-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.4-7.3 (m); 7.0-6.9 (m); 4.8-4.4 (m); 4.0-3.9 (m); 1.30 (s).

N-{5-(3-pyridinyl-acetyl)-4,6-dihydropyrrolo[3,4-c]pyrazol-3-yl}-4-tertbutylbenzamide; 1H-NMR (DMSO-d6) d ppm: 8.4-8.3 (m); 7.9-7.8 (m); 7.7-7.3 (m); 4.8-4.4 (m); 3.8-3.7 (m); 1.30 (s).

N-{5-benzylsulfonyl-4,6-dihydropyrrolo[3,4-c]pyrazol-3-yl}-4-phenoxybenzamide; 1H-NMR (DMSO-d6) d ppm: 8.1-7.9 (m); 7.45-7.1 (m); 4.5-4.3 (m); 4.6 (s)

N-{5-(2-methylpropyl)carbonyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 4.7-4.4 (m); 2.2-2.1 (m); 2.1-2.0 (m); 1.30 (s); 0.94 (d).

N-5-(2-phenyl-thiazol-4-yl)acetyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 4.9-4.5 (m); 3.94 (s); 1.30 (s).

N-{5-(2-thienyl)acetyl-4,6-dihydropyrrolo[3,4-c]pyrazol-3-yl}-4-phenoxybenzamide; 1H-NMR (DMSO-d6) d ppm: 7.9-7.4 (m); 4.8-4.4 (m); 3.9 (s);

N-{5-(1-naphthalene)sulfonyl-4,6-dihydropyrrolo[3,4-c]pyrazol-3-yl}-cyclopropylcarboxamide 1H-NMR (DMSO-d6) d ppm: 8.7 (m); 8.2-8.1 (m); 7.8-7.6 (m); 4.6-4.3 (m); 0.8-0.7 (m).

N-{5-(2-methoxyphenyl)-4,6-dihydropyrrolo[3,4-c]pyrazol-3-yl}-3-(2-naphthalen-2-yl)-propionylamide 1H-NMR (DMSO-d6) d ppm: 10.6 (s); 7.8-7.0 (m); 4.6-4.2 (m); 4.0 (m); 3.8 (s); 1.4 (d).

N-{5-(2-furoyl)-4,6-dihydropyrrolo[3,4-c]pyrazol-3-yl}-3-(2-naphthalen-2-yl)-propionylamide 1H-NMR (DMSO-d6) d ppm: 7.8-6.6 (m); 4.9-4.6 (m); 4.0 (m); 1.5 (d).

N-{5-[5-(1-morfolinomethyl)furan-2-carbonyl]-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 5.0-4.7 (m); 3.57 (bs); 2.42 (bs); 1.30 (s).

N-{5-{4-[2-(1-pyrrolidinyl)ethoxy]phenyl}acetyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.2-7.1 (m); 6.9-6.8 (m); 4.7-4.4 (m); 4.11 (bs); 3.7-3.6 (m); 1.77 (bs); 1.30 (s).

N-{5-(1-H-benzotriazole-5-carbonyl)-4,6-dihydropyrrolo[3,4-c]pyrazol-3-yl}-4-tertbutylbenzamide; 1H-NMR (DMSO-d6) d ppm: 8.2-7.4 (m); 4.7-4.6 (m); 1.26 (s).

N-{5-(pirrole-3-carbonyl)-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.3-7.2 (m); 6.81 (bs); 6.5-6.4 (m); 4.9-4.5 (m); 1.30 (s).

N-{5-{4-[2-oxo-2-(1-pyrrolidinyl)ethoxy]phenyl}acetyl-4,6-dihydropyrrolo[3,4-c]pyrazol-3-yl}-4-phenoxybenzamide; 1H-NMR (DMSO-d6) d ppm: 8.02 (m); 4.66 (s); 4.8-4.4 (m); 1.9-1.6 (m)

N-{5-(4-methylsulfonamido-phenyl)acetyl-4,6-dihydropyrrolo[3,4-c]pyrazol-3-yl}-4-phenoxybenzamide; 1H-NMR (DMSO-d6) d ppm: 8.0 (m); 4.8-4.4 (m); 2.95 (s)

N-{5-[2-(6-oxo-1(6H)-pyridazinyl]acetyl-4,6-dihydropyrrolo[3,4-c]pyrazol-3-yl}-4-phenoxybenzamide; 1H-NMR (DMSO-d6) d ppm: 8.0-7.4 (m); 4.97 (m); 4.8-4.4 (m)

N-{5-(3-carbamoylmethoxy-phenyl)acetyl-4,6-dihydropyrrolo[3,4-c]pyrazol-3-yl}-4-phenoxybenzamide; 1H-NMR (DMSO-d6) d ppm: 7.4-7.2 (m); 4.8-4.4 (m); 4.38 (s).

N-{5-(4-carbamoylmethoxy-phenyl)acetyl-4,6-dihydropyrrolo[3,4-c]pyrazol-3-yl}-4-phenoxybenzamide; 1H-NMR (DMSO-d6) d ppm: 7.44 (s); 7.32 (s) 7.44-7.22 (m); 7.16-7.19 (m); 4.85-4.4 (m)

N-{5-[4-(1-pirrolidinyl)phenyl]acetyl-4,6-dihydropyrrolo[3,4-c]pyrazol-3-yl}-4-phenoxybenzamide; 1H-NMR (DMSO-d6) d ppm: 8.01 (d); 7.44 (dd); 4.8-4.2 (m); 3.56 (m); 3.16 (m); 1.91 (m)

N-{5-carbamoyloxyacetyl-4,6-dihydropyrrolo[3,4-c]pyrazol-3-yl}-4-phenoxybenzamide; 1H-NMR (DMSO-d6) d ppm: 7.4-7.2 (m); 7.1 (d); 4.8-4.2 (m)

N-{5-{4-[2-(4-methylpiperazin-2-yl)ethoxy]phenyl}acetyl-4,6-dihydropyrrolo[3,4-c]pyrazol-3-yl}-4-phenoxybenzamide; 1H-NMR (DMSO-d6) d ppm: 8.0 (m); 4.8-4.4 (m); 4.02 (m); 3.64 (m); 2.18 (s)

N-{5-{4-[2-(1-pyrrolidinyl)ethoxy]phenyl}acetyl-4,6-dihydropyrrolo[3,4-c]pyrazol-3-yl}-4-phenoxybenzamide; 1H-NMR (DMSO-d6) d ppm: 8.02 (m); 6.88 (m); 3.65 (m); 2.66 (m); 7.1 (m)

N-{5-{4-[2-oxo-2-(1-pyrrolidinyl)ethoxy]phenyl}acetyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.2-6.8 (m); 4.8-4.4 (m); 4.66 (s); 3.7-3.4 (m); 1.9-1.7 (m); 1.30 (s).

N-{5-(4-methylsulfonamido-phenyl)acetyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.2-7.1 (m); 4.8-4.4 (m); 3.7-3.6 (m); 2.94 (s); 1.30 (s).

N-{5-(pyridine-3-carbonyl-4,6-dihydropyrrolo[3,4-c]pyrazol-3-yl}-4-tertbutylbenzamide; 1H-NMR (DMSO-d6) d ppm: 8.7-8.6 (m); 8.0-7.7 (m); 7.5-7.4 (m); 4.8-4.6 (m); 1.28 (s).

N-{5-(pyridine-3-carbonyl)-4,6-dihydropyrrolo[3,4-c]pyrazol-3-yl}-4-tertbutylbenzamide; 1H-NMR (DMSO-d6) d ppm: 8.8-8.6 (m); 8.1-7.8 (m); 7.5-7.4 (m); 4.8-4.5 (m); 1.27 (s).

N-{5-(pyridine-4-carbonyl)-4,6-dihydropyrrolo[3,4-c]pyrazol-3-yl}-4-tertbutylbenzamide; 1H-NMR (DMSO-d6) d ppm: 8.8-8.7 (m); 7.9-7.7 (m); 7.6-7.4 (m); 4.7-4.5 (m); 1.27 (s).

N-{5-(2-methyl-pyridine-3-carbonyl)-4,6-dihydropyrrolo[3,4-c]pyrazol-3-yl}-4-tertbutylbenzamide; 1H-NMR (DMSO-d6) d ppm: 8.5-8.4 (m); 8.0-7.7 (m); 7.6-7.2 (m); 4.7-4.4 (m); 2.44 (s); 1.27 (s).

N-{5-(2-thiomethyl-pyridine-3-carbonyl)-4,6-dihydropyrrolo[3,4-c]pyrazol-3-yl}-4-tertbutylbenzamide; 1H-NMR (DMSO-d6) d ppm: 8.6-8.5 (m); 7.9-7.2 (m); 4.7-4.4 (m); 2.51 (s); 1.27 (s).

N-{5-(pyrazine-2-carbonyl)-4,6-dihydropyrrolo[3,4-c]pyrazol-3-yl}-4-tertbutylbenzamide; 1H-NMR (DMSO-d6) d ppm: 9.1-9.0 (m); 8.8-8.7 (m); 7.9-7.8 (m); 7.6-7.4 (m); 4.9-4.7 (m); 1.29 (s).

N-{5-(3-furoyl)-4,6-dihydropyrrolo[3,4-c]pyrazol-3-yl}-4-phenoxybenzamide; 1H-NMR (DMSO-d6) d ppm: 7.8-7.7 (m); 7.2-7.0 (m); 4.9-4.6 (m)

N-{5-(2-thenoyl)-4,6-dihydropyrrolo[3,4-c]pyrazol-3-yl}-4-phenoxybenzamide; 1H-NMR (DMSO-d6) d ppm: 8.0-7.7 (m); 7.4-7.0 (m); 5.0-4.6 (m)

N-{5-(7-methoxy-benzofuran-2-carbonyl)-4,6-dihydropyrrolo[3,4-c]pyrazol-3-yl}-4-tertbutylbenzamide 1H-NMR (DMSO-d6) d ppm: 7.9-7.8 (m); 7.7-7.0 (m); 5.2-4.6 (m); 4.0-3.9 (m); 1.31 (s).

N-{5-(benzofuran-2-carbonyl)-4,6-dihydropyrrolo[3,4-c]pyrazol-3-yl}-4-tertbutylbenzamide; 1H-NMR (DMSO-d6) d ppm: 7.9-7.3 (m); 5.2-4.7 (m); 1.31 (s).

N-{5-(2-furoyl)-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.2-7.1 (m); 6.7-6.6 (m); 5.0-4.6 (m); 1.30 (s).

N-{5-(3-furoyl)-4,6-dihydropyrrolo[3,4-c]pyrazol-3-yl}-4-tertbutylbenzamide; 1H-NMR (DMSO-d6) d ppm: 8.3-8.2 (m); 7.9-7.5 (m); 6.9-6.8 (m); 4.8-4.6 (m); 1.30 (s).

N-{5-(2-furoyl)-4,6-dihydropyrrolo[3,4-c]pyrazol-3-yl}-4-phenoxybenzamide; 1H-NMR (DMSO-d6) d ppm: 8.1-7.9 (m); 7.4-7.0 (m); 5.0-4.6 (m)

N-{5-(3-thenoyl)-4,6-dihydropyrrolo[3,4-c]pyrazol-3-yl}-4-tertbutylbenzamide; 1H-NMR (DMSO-d6) d ppm: 8.1-7.8 (m); 7.6-7.3 (m); 4.8-4.6 (m); 1.29 (s).

N-{5-(quinoxaline-2-carbonyl)-4,6-dihydropyrrolo[3,4-c]pyrazol-3-yl}-4-phenoxybenzamide; 1H-NMR (DMSO-d6) d ppm: 8.2-8.15 (m); 7.5-7.4 (m); 5.2-4.8 (m)

N-{5-(2-thienyl)acetyl-4,6-dihydropyrrolo[3,4-c]pyrazol-3-yl}-4-tertbutylbenzamide; 1H-NMR (DMSO-d6) d ppm: 8.0-7.9 (m); 7.5-7.3 (m); 7.0-6.9 (m); 4.9-4.5 (m); 4.40 (q); 3.99 (s); 1.34 (t); 1.30 (s).

N-{5-(quinoline-6-carbonyl)-4,6-dihydropyrrolo[3,4-c]pyrazol-3-yl}-4-tertbutylbenzamide; 1H-NMR (DMSO-d6) d ppm: 9.0-8.95 (m); 7.1-6.9 (m); 4.8-4.6 (m)

N-{5-(3-furoyl)-4,6-dihydropyrrolo[3,4-c]pyrazol-3-yl}-4-phenoxybenzamide; 1H-NMR (DMSO-d6) d ppm: 7.5-7.2 (m); 4.8-4.5 (m);

N-{5-(pyrazine-2-carbonyl)-4,6-dihydropyrrolo[3,4-c]pyrazol-3-yl}-4-phenoxybenzamide 1H-NMR (DMSO-d6) d ppm: 9.1-8.7 (m); 4.9-4.7 (m);

N-{5-[2-(6-oxo-1(6H)-pyridazinyl]acetyl-4,6-dihydropyrrolo[3,4-c]pyrazol-3-yl}-4-tertbutylbenzamide; 1H-NMR (DMSO-d6) d ppm: 8.0-7.9 (m); 7.5-7.4 (m); 7.0-6.9 (m); 5.0-4.9 (m); 4.8-4.5 (m); 1.30 (s).

N-{5-(4-carbamoylmethoxy-phenyl)acetyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.2-7.1 (m); 6.9-6.8 (m); 4.7-4.4 (m); 4.37 (s); 3.7-3.6 (m); 1.30 (s)

N-{5-carbamoyloxyacetyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 4.7-4.4 (m); 1.30 (s).

N-{5-{4-[2-(4-methylpiperazin-2-yl)ethoxy]phenyl}acetyl-4,6-dihydropyrrolo[3,4-c]pyrazol-3-yl}-4-tertbutylbenzamide;
1H-NMR (DMSO-d6) d ppm: 7.9-7.8 (m); 7.5-7.4 (m); 7.2-6.8 (m); 4.7-4.4 (m); 4.1-4.0 (m); 3.7-3.6 (m); 2.7-2.6 (m); 2.5-2.3 (m); 2.13 (s); 1.30 (s)

N-{5-(2-methylsulfonamidothiazole-4-carbonyl)-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 7.11 (s); 5.1-4.5 (m); 2.71 (s); 1.30 (s).

N-{5-(benzofuran-2-carbonyl)-4,6-dihydropyrrolo[3,4-c]pyrazol-3-yl}-4-phenoxybenzamide; 1H-NMR (DMSO-d6) d ppm: 7.8-7.6 (m); 7.3-7.1 (m); 5.1-4.7 (m)

N-{5-(pyridine-2-carbonyl)-4,6-dihydropyrrolo[3,4-c]pyrazol-3-yl}-4-phenoxybenzamide 1H-NMR (DMSO-d6) d ppm: 8.7-8.6 (m); 8.1-7.8 (m); 5.0-4.6 (m)

N-{5-(2-methyl-pyridine-3-carbonyl)-4,6-dihydropyrrolo[3,4-c]pyrazol-3-yl}-4-phenoxybenzamide 1H-NMR (DMSO-d6) d ppm: 8.6-8.5 (m); 4.7-4.3 (m); 2.5-2.4 (s)

N-{5-(quinoline-4-carbonyl)-4,6-dihydropyrrolo[3,4-c]pyrazol-3-yl}-4-phenoxybenzamide; 1H-NMR (DMSO-d6) d ppm: 9 (m); 8.1-7 (m); 4.8-4.3 (m)

N-{5-[4-(1-pyrrolidin-2-on)benzoyl]-4,6-dihydropyrrolo[3,4-c]pyrazol-3-yl}-4-tertbutylbenzamide; 1H-NMR (DMSO-d6) d ppm: 7.9-7.4 (m); 4.7-4.5 (m); 3.9-3.8 (m); 2.5-2.4 (m); 2.1-2.0 (m); 1.27 (s).

N-{5-phenylethyl-4,6-dihydropyrrolo[3,4-c]pyrazol-3-yl}-4-tertbutylbenzamide 1H-NMR (DMSO-d6) d ppm: 7.9-7.8 (m); 7.5-7.4 (m); 7.3-7.1 (m); 4.0-3.8 (m); 3.1-2.8 (m); 1.30 (s).

N-n-butyl-N'-{3-(2-naphthalen-2-yl-propionamido)-4,6-dihydropyrrolo[3,4-c]pyrazol-5-yl}urea 1H-NMR (DMSO-d6) d ppm: 7.8-7.5 (m); 6.2 (m); 4.3 (m); 4.0 (m); 3.0 (m); 1.5-1.3 (m); 0.8 (t).

N-isopropyl-N'-{3-(2-naphthalen-2-yl-propionamido)-4,6-dihydropyrrolo[3,4-c]pyrazol-5-yl}urea 1H-NMR (DMSO-d6) d ppm: 10.6 (s); 7.8-7.5 (m); 5.9 (m); 4.3 (m); 4.0 (m); 3.8 (m); 1.5 (d); 1.0 (d).

N-{5-ethylaminocarbonyl-4,6-dihydropyrrolo[3,4-c]pyrazol-3-yl}-2-naphtylpropionamide
1H-NMR (DMSO-d6) d ppm: 7.8-7.5 (m); 6.2 (m); 4.3 (m); 4.0 (m); 3.1 (m); 1.5 (d); 1.0 (t)."

N-{5-ethoxycarbonyl-4,6-dihydropyrrolo[3,4-c]pyrazol-3-yl}-3-(2-naphthalen-2-yl)-propionamide 1H-NMR (DMSO-d6) d ppm: 7.8-7.5 (m); 4.4 (m); 4.0 (m); 1.5 (d); 1.2-1.0 (m).

N-{5-(3-methylbutyrroyl)-4,6-dihydropyrrolo[3,4-c]pyrazol-3-yl}-3-(2-naphthalen-2-yl)-propionylamide 1H-NMR (DMSO-d6) d ppm: 10.6 (s); 7.8-7.5 (m); 4.6-4.4 (m); 4.0 (m); 2.2-2.0 (m); 1.5 (d); 0.9 (m).

N-{5-aminocarbonylmethyl-4,6-dihydropyrrolo[3,4-c]pyrazol-3-yl}-3-(2-naphthalen-2-yl)-propionamide 1H-NMR (DMSO-d6) d ppm: 7.8-7.5 (m); 7.2 (bs); 7.0 (bs); 4.0 (m); 3.8 (m); 3.2 (s); 1.4 (d).

N-{5-(pyrrol-3-ylcarbonyl)-4,6-dihydropyrrolo[3,4-c]pyrazol-3-yl}-3-(2-naphthalen-2-yl)-propionamide 1H-NMR (DMSO-d6) d ppm: 7.8-6.5 (m); 4.8-4.5 (m); 4.0 (m); 1.5 (d).

N-{5-ethoxycarbonyl-4,6-dihydropyrrolo[3,4-c]pyrazol-3-yl}-4-tertbutylbenzamide; 1H-NMR (DMSO-d6) d ppm: 7.9-7.8 (m); 7.5-7.4 (m); 4.5-4.4 (m); 4.09 (q); 1.30 (s); 1.22 (t).

N-{5-isopentyl-4,6-dihydropyrrolo[3,4-c]pyrazol-3-yl}-4-tertbutylbenzamide 1H-NMR (DMSO-d6) d ppm: 7.9-7.8 (m); 7.5-7.4 (m); 4.0-3.8 (m); 1.7-1.6 (m); 1.5-1.4 (m); 1.30 (s); 0.90 (d).

N-butyl-N'-{3-(4-tertbutyl-benzamido)-4,6-dihydropyrrolo[3,4-c]pyrazol-5-yl}urea 1H-NMR (DMSO-d6) d ppm: 7.9-7.8 (m); 7.5-7.4 (m); 4.4-4.3 (m); 3.04 (q); 1.5-1.4 (m); 1.30 (s); 0.87 (t).

N-{5-(indol-2-yl)carbonyl-4,6-dihydropyrrolo[3,4-c]pyrazol-3-yl}-4-tertbutylbenzamide; 1H-NMR (DMSO-d6) d ppm: 7.9-7.0 (m); 5.1-4.7 (m); 1.31 (s).

N-{5-(1-methyl-indol-3-yl)acetyl-4,6-dihydropyrrolo[3,4-c]pyrazol-3-yl}-4-tertbutylbenzamide; 1H-NMR (DMSO-d6) d ppm: 7.6-7.0 (m); 3.77 (s); 3.8-3.7 (m); 1.30 (s).

N-{5-[4-(1-imidazolylmethyl)benzoyl]-4,6-dihydropyrrolo[3,4-c]pyrazol-3-yl}-4-phenoxybenzamide; 1H-NMR (DMSO-d6) d ppm: 8.1-7.86 (m); 7.5-6.95 (m); 5.2 (m); 4.7-4.4 (m)

N-{5-[4-(1-imidazolylmethyl)benzoyl]-4,6-dihydropyrrolo[3,4-c]pyrazol-3-yl}-4-phenoxybenzamide; 1H-NMR (DMSO-d6) d ppm: 7.9-7.1 (m); 5.2 (s); 4.7-4.5 (m)

N-{5-[4-(1-pyrrolidin-2-on)benzoyl]-4,6-dihydropyrrolo[3,4-c]pyrazol-3-yl}-4-phenoxybenzamide; 1H-NMR (DMSO-d6) d ppm: 8.1-7.6 (m); 7.5-6.95 (m); 4.7-4.55 (m); 3.85 (m); 2.45 (m); 2.1 (m)

N-{5-(2-morfolinomethyl-5-furoyl)-4,6-dihydropyrrolo[3,4-c]pyrazol-3-yl}-4-phenoxybenzamide 1H-NMR (DMSO-d6) d ppm: 7.4-7.0 (m); 4.9-4.6 (m); 2.6-2.4 (m)

N-{5-(5-acetylamino-2-furoyl)-4,6-dihydropyrrolo[3,4-c]pyrazol-3-yl}-3-(2-naphthalen-2-yl)-propionamide 1H-NMR (DMSO-d6) d ppm: 7.8-7.5 (m); 7.1-6.3 (m); 4.8-4.6 (m); 4.0 (m); 2.0 (s); 1.5 (d).

N,N-dimethyl-N'-3-(2-naphthalen-2-yl-propionamido)-4,6-dihydropyrrolo[3,4-c]pyrazol-5-yl}urea 1H-NMR (DMSO-d6) d ppm: 7.8-7.5 (m); 4.4 (m); 4.0 (m); 2.8 (s); 1.5 (d).

N-{5-(piperidin-1-yl)carbamoyl)-4,6-dihydropyrrolo[3,4-c]pyrazol-3-yl}-3-(2-naphthalen-2-yl)-propionamide 1H-NMR (DMSO-d6) d ppm: 7.8-7.5 (m); 4.4 (m); 4.0 (m); 3.1 (m); 1.5 (m).

N-{5-(4-methyl-piperazin-1-yl)acetyl-4,6-dihydropyrrolo[3,4-c]pyrazol-3-yl}-3-(2-naphthalen-2-yl)-propionamide 1H-NMR (DMSO-d6) d ppm: 7.8-7.5 (m); 4.7-4.4 (m); 4.0 (m); 3.1 (m); 2.6-2.2 (m); 1.5 (m).

N-{5-(piperidin-1-yl)acetyl-4,6-dihydropyrrolo[3,4-c]pyrazol-3-yl}-3-(2-naphthalen-2-yl)-propionamide 1H-NMR (DMSO-d6) d ppm: 7.8-7.5 (m); 4.7-4.4 (m); 4.0 (m); 3.1 (m); 2.4 (m); 1.4 (m).

N-{5-(pirrolidin-1-ylcarbonyl)methyl-4,6-dihydropyrrolo[3,4-c]pyrazol-3-yl}-3-(2-naphthalen-2-yl)-propionamide 1H-NMR (DMSO-d6) d ppm: 7.8-7.5 (m); 4.0 (m); 3.8 (m); 3.5 (s); 3.4-3.3 (m); 1.8 (m); 1.4 (d).

N-{5-acetyl-4,6-dihydropyrrolo[3,4-c]pyrazol-3-yl}-(4-pyrrolidin-1-yl)phenylacetamide; 1H-NMR (DMSO-d6) d ppm: 7.1-6.5 (m); 4.6-4.3 (m); 3.4 (s); 3.2 (m); 2.0 (s); 1.9 (m).

N-{5-acetyl-4,6-dihydropyrrolo[3,4-c]pyrazol-3-yl}-2-((4-pyrrolidin-1-yl)phenyl)propionamide; 1H-NMR (DMSO-d6) d ppm: 7.1-6.5 (m); 4.6-4.3 (m); 3.7 (m); 3.2 (m); 2.0 (s); 1.9 (m); 1.3 (m).

N-{5-acetyl-4,6-dihydropyrrolo[3,4-c]pyrazol-3-yl}-(4-(2-oxo-pyrrolidin-1-yl)phenyl)acetamide; 1H-NMR (DMSO-d6) d ppm: 7.1-6.5 (m); 4.6-4.3 (m); 3.8 (m); 3.4 (s); 2.5 (m); 2.1 (m); 2.0 (s).

N-{5-acetyl-4,6-dihydropyrrolo[3,4-c]pyrazol-3-yl}-2-(4-(2-oxo-pyrrolidin-1-yl)phenyl)propionamide; 1H-NMR (DMSO-d6) d ppm: 7.1-6.5 (m); 4.6-4.3 (m); 3.8 (m); 2.4 (m); 2.0 (s); 1.9 (m); 1.4 (m).

N-2-methoxyphenyl-N'-{2-[4-(2-oxo-pyrrolidin-1-yl)phenyl]-propionamido-4,6-dihydropyrrolo[3,4-c]pyrazol-5-yl}urea 1H-NMR (DMSO-d6) d ppm: 7.6-7.3 (m); 7.0-6.8 (m); 4.5 (m); 3.8 (m); 2.4 (m); 2.0 (m); 1.4 (d).

N-2,4-difluorophenyl-N'-{2-[4-(2-oxo-pyrrolidin-1-yl)phenyl]-propionamido-4,6-dihydropyrrolo[3,4-c]pyrazol-5-yl}urea 1H-NMR (DMSO-d6) d ppm: 7.6-7.0 (m); 4.5 (m); 3.8 (m); 2.4 (m); 2.0 (m); 1.4 (d).

N-(1-phenyl)ethyl-N'-{2-[4-(2-oxo-pyrrolidin-1-yl)phenyl]-propionamido-4,6-dihydropyrrolo[3,4-c]pyrazol-5-yl}urea 1H-NMR (DMSO-d6) d ppm: 7.6-7.2 (m); 4.8 (m); 4.4 (m); 3.8 (m); 2.4 (m); 2.0 (m); 1.4 (m).

N-2-methoxyphenyl-N'-{2-(4-pyrrolidin-1-yl-phenyl)-propionamido-4,6-dihydropyrrolo[3,4-c]pyrazol-5-yl}urea 1H-NMR (DMSO-d6) d ppm: 7.2-6.5 (m); 4.5 (m); 3.8 (s); 3.7 (m); 3.2 (m); 1.9 (m); 1.3 (d).

N-2,4-difluorophenyl-N'-{2-(4-pyrrolidin-1-yl-phenyl)-propionamido-4,6-dihydropyrrolo[3,4-c]pyrazol-5-yl}urea 1H-NMR (DMSO-d6) d ppm: 7.5-6.4 (m); 4.5 (m); 3.7 (m); 3.2 (m); 1.9 (m); 1.3 (d).

N-(1-phenyl)ethyl-N'-{2-(4-pyrrolidin-1-yl-phenyl)-propionamido-4,6-dihydropyrrolo[3,4-c]pyrazol-5-yl}urea 1H-NMR (DMSO-d6) d ppm: 7.4-6.4 (m); 4.8 (m); 4.4 (m); 3.7 (m); 3.2 (m); 1.9 (m); 1.4 (d); 1.3 (d).

N-{5-phenylsulfonyl-4,6-dihydropyrrolo[3,4-c]pyrazol-3-yl}-2-(4-pyrrolidin-1-yl-phenyl)-propionamide 1H-NMR (DMSO-d6) d ppm: 7.8-6.4 (m); 4.4 (m); 3.6 (m); 3.2 (m); 1.9 (m); 1.3 (d).

N-2-methoxyphenyl-N'-{[4-(2-oxo-pyrrolidin-1-yl)-phenyl]-acetamido-4,6-dihydropyrrolo[3,4-c]pyrazol-5-yl}urea 1H-NMR (DMSO-d6) d ppm: 7.6-6.8 (m); 4.5 (m); 3.8 (m); 3.6 (s); 2.5 (m); 2.0 (m).

N-2-chlorophenyl-N'-{[4-(2-oxo-pyrrolidin-1-yl)-phenyl]-acetamido-4,6-dihydropyrrolo[3,4-c]pyrazol-5-yl}urea 1H-NMR (DMSO-d6) d ppm: 7.8-7.1 (m); 4.5 (m); 3.8 (m); 3.6 (s); 2.5 (m); 2.0 (m).

N-(1-phenyl)ethyl-N'-{[4-(2-oxo-pyrrolidin-1-yl)-phenyl]-acetamido-4,6-dihydropyrrolo[3,4-c]pyrazol-5-yl}urea 1H-NMR (DMSO-d6) d ppm: 7.6-7.2 (m); 6.6 (m); 4.8 (m); 4.4 (m); 3.8 (m); 3.7 (s); 2.5 (m); 2.0 (m); 1.4 (d).

N-n-butyl-N'-{[4-(2-oxo-pyrrolidin-1-yl)-phenyl]-acetamido-4,6-dihydropyrrolo[3,4-c]pyrazol-5-yl}urea 1H-NMR (DMSO-d6) d ppm: 7.6-7.3 (m); 6.2 (m); 4.3 (m); 3.8 (m); 3.7 (s); 3.0 (m); 2.5 (m); 2.0 (m); 1.4 (m); 1.2 (m); 0.8 (t).

N-{5-phenulsulfonyl-4,6-dihydropyrrolo[3,4-c]pyrazol-3-yl}-4-(2-oxo-pyrrolidin-1-yl)-phenyl-acetamide 1H-NMR (DMSO-d6) d ppm: 7.8-7.2 (m); 4.4 (m); 3.8 (m); 3.6 (s); 2.5 (m); 2.0 (m).

N-n-butyl-N'-{2-[4-(2-oxo-pyrrolidin-1-yl)phenyl]-propionamido-4,6-dihydropyrrolo[3,4-c]pyrazol-5-yl}urea 1H-NMR (DMSO-d6) d ppm: 7.6-7.3 (m); 6.2 (m); 4.3 (m); 3.8 (m); 3.0 (m); 2.4 (m); 2.0 (m); 1.4-1.2 (m); 0.9 (t).

N-{5-phenylsulfonyl-4,6-dihydropyrrolo[3,4-c]pyrazol-3-yl}-2-[4-(2-oxo-pyrrolidin-1-yl)-phenyl]-propionamide 1H-NMR (DMSO-d6) d ppm: 7.8-7.3 (m); 4.4 (m); 3.8 (m); 2.5 (m); 2.0 (m); 1.3 (d).

N-{5-aminocarbonyl-4,6-dihydropyrrolo[3,4-c]pyrazol-3-yl}-4-(2-oxo-pyrrolidin-1-yl)-phenyl-acetamide 1H-NMR (DMSO-d6) d ppm: 7.6-7.2 (m); 5.8 (s); 4.3 (m); 3.8 (m); 3.6 (s); 2.5 (m); 2.0 (m).

N-n-butyl-N'-{2-(4-pyrrolidin-1-yl-phenyl)-propionamido-4,6-dihydropyrrolo[3,4-c]pyrazol-5-yl}urea 1H-NMR (DMSO-d6) d ppm: 7.1-6.5 (m); 6.2 (m); 4.3 (m); 3.7 (m); 3.2 (m); 3.0 (m); 1.9 (m); 1.4-1.2 (m); 0.8 (t).

N-{5-aminocarbonyl-4,6-dihydropyrrolo[3,4-c]pyrazol-3-yl}-2-(4-pyrrolidin-1-yl-phenyl)-propionamide 1H-NMR (DMSO-d6) d ppm: 7.1-6.5 (m); 5.8 (bs); 4.3 (m); 3.7 (m); 3.2 (m); 1.9 (m); 1.3 (d).

N-2-methoxyphenyl-N'-{(4-pyrrolidin-1-yl-phenyl)-acetamido-4,6-dihydropyrrolo[3,4-c]pyrazol-5-yl}urea 1H-NMR (DMSO-d6) d ppm: 10.5 (s); 7.8-6.5 (m); 4.5 (m); 3.8 (m); 3.5 (s); 3.2 (m); 1.9 (m).

N-2-chlorophenyl-N'-{(4-pyrrolidin-1-yl-phenyl)-acetamido-4,6-dihydropyrrolo[3,4-c]pyrazol-5-yl}urea 1H-NMR (DMSO-d6) d ppm: 10.5 (s); 7.8-6.5 (m); 4.5 (m); 3.4 (s); 3.2 (m); 1.9 (m).

N-(1-phenyl)ethyl-N'-{(4-pyrrolidin-1-yl-phenyl)-acetamido-4,6-dihydropyrrolo[3,4-c]pyrazol-5-yl}urea 1H-NMR (DMSO-d6) d ppm: 10.4 (s); 7.3-6.4 (m); 4.8 (m); 4.4 (s); 3.5 (m); 3.2 (m); 1.9 (m); 1.4 (d).

N-n-butyl-N'-{(4-pyrrolidin-1-yl-phenyl)-acetamido-4,6-dihydropyrrolo[3,4-c]pyrazol-5-yl}urea 1H-NMR (DMSO-d6) d ppm: 10.4 (s); 7.1-6.5 (m); 6.2 (t); 4.3 (m); 3.4 (s); 3.2 (m); 3.0 (m); 1.9 (m); 1.4-1.2 (m); 0.8 (t).

N-{5-phenylsulfonyl-4,6-dihydropyrrolo[3,4-c]pyrazol-3-yl}-(4-pyrrolidin-1-yl-phenyl)-acetamide 1H-NMR (DMSO-d6) d ppm: 7.8-7.6 (m); 7.0-6.4 (m); 4.4 (m); 3.3 (s); 3.2 (m); 1.9 (m).

N-ethyl-N'-{[4-(2-oxo-pyrrolidin-1-yl)-phenyl]-acetamido-4,6-dihydropyrrolo[3,4-c]pyrazol-5-yl}urea 1H-NMR (DMSO-d6) d ppm: 7.9-7.3 (m); 6.2 (m); 4.5-4.3 (m); 3.8 (m); 3.6 (s); 3.0 (m); 2.5 (m); 2.0 (m); 1.0 (t).

N-i-propyl-N'-{[4-(2-oxo-pyrrolidin-1-yl)-phenyl]-acetamido-4,6-dihydropyrrolo[3,4-c]pyrazol-5-yl}urea 1H-NMR (DMSO-d6) d ppm: 7.6-7.3 (m); 5.9 (m); 4.3 (m); 3.8 (m); 3.6 (s); 2.5 (m); 2.0 (m); 1.0 (d).

N-{5-(2-furoyl)-4,6-dihydropyrrolo[3,4-c]pyrazol-3-yl}-4-(2-oxo-pyrrolidin-1-yl)-phenyl-acetamide 1H-NMR (DMSO-d6) d ppm: 7.9-6.6 (m); 4.9-4.6 (m); 3.8 (m); 3.6 (s); 2.5 (m); 2.0 (m).

N-{5-(2-methoxyphenyl)-4,6-dihydropyrrolo[3,4-c]pyrazol-3-yl}-4-(2-oxo-pyrrolidin-1-yl)-phenyl-acetamide 1H-NMR (DMSO-d6) d ppm: 10.6 (s); 7.6-7.0 (m); 4.6-4.2 (m); 3.8 (m); 3.5 (s); 2.5 (m); 2.0 (m).

N-{5-aminocarboylmethyl-4,6-dihydropyrrolo[3,4-c]pyrazol-3-yl}-4-(2-oxo-pyrrolidin-1-yl)-phenyl-acetamide 1H-NMR (DMSO-d6) d ppm: 7.6-7.0 (m); 3.8 (m); 3.5 (s); 3.3 (m); 2.5 (m); 2.0 (m).

N-i-propyl-N'-{(4-pyrrolidin-1-yl-phenyl)-acetamido-4,6-dihydropyrrolo[3,4-c]pyrazol-5-yl}urea 1H-NMR (DMSO-d6) d ppm: 7.1-6.4 (m); 5.9 (m); 4.3 (m); 3.8 (m); 3.4 (s); 3.2 (m); 1.9 (m); 1.0 (d).

N-ethyl-N'-{(4-pyrrolidin-1-yl-phenyl)-acetamido-4,6-dihydropyrrolo[3,4-c]pyrazol-5-yl}urea 1H-NMR (DMSO-d6) d ppm: 10.4 (s); 7.1-6.4 (m); 6.2 (m); 4.3 (m); 3.4 (s); 3.2 (m); 3.0 (m); 1.9 (m); 1.0 (t).

N-{5-aminocarbonylmethyl-4,6-dihydropyrrolo[3,4-c]pyrazol-3-yl}-(4-pyrrolidin-1-yl-phenyl)-acetamide 1H-NMR (DMSO-d6) d ppm: 10.3 (s); 7.0-6.4 (m); 3.8 (m); 3.4 (s); 3.3 (s); 3.2 (m); 1.9 (m).

N-{5-(3-methylbutyrroyl)-4,6-dihydropyrrolo[3,4-c]pyrazol-3-yl}-4-(2-oxo-pyrrolidin-1-yl)-phenyl-acetamide 1H-NMR (DMSO-d6) d ppm: 7.6-7.3 (m); 4.6-4.3 (m); 3.8 (m); 3.6 (s); 2.5 (m); 2.2-2.0 (m); 0.9 (m).

N-n-butyl-N'-{3-(naphth-2-yl)acetamido-4,6-dihydropyrrolo[3,4-c]pyrazol-5-yl}urea 1H-NMR (DMSO-d6) d ppm: 7.9-7.4 (m); 6.2 (t); 4.3 (s); 3.8 (s); 3.0 (m); 1.4-1.2 (m); 0.8 (t).

N-n-butyl-N'-{3-(3-methyl-phenyl)acetamido-4,6-dihydropyrrolo[3,4-c]pyrazol-5-yl}urea 1H-NMR (DMSO-d6) d ppm: 7.2-7.0 (m); 6.2 (t); 4.3 (bs); 3.6 (s); 3.0 (m); 2.3 (s); 1.4-1.2 (m); 0.8 (t).

N-n-butyl-N'-{3-(3-fluoro-phenyl)acetamido-4,6-dihydropyrrolo[3,4-c]pyrazol-5-yl}urea 1H-NMR (DMSO-d6) d ppm: 7.4-7.0 (m); 6.2 (t); 4.3 (bs); 3.6 (s); 3.0 (m); 1.4-1.2 (m); 0.8 (t).

N-n-butyl-N'-{3-(3-pyridyl)acetamido-4,6-dihydropyrrolo[3,4-c]pyrazol-5-yl}urea 1H-NMR (DMSO-d6) d ppm: 8.5 (m); 7.7-7.3 (m); 6.2 (t); 4.3 (bs); 3.7 (m); 3.0 (m); 1.4-1.2 (m); 0.8 (t).

N-n-butyl-N'-{3-(bicyclo[4.2.0]octa-1,3,5-triene-7-carboxamido)-4,6-dihydropyrrolo[3,4-c]pyrazol-5-yl}urea 1H-NMR (DMSO-d6) d ppm: 7.2-7.0 (m); 6.2 (t); 4.4 (m); 4.3 (m); 3.3 (s); 3.0 (m); 1.4-1.2 (m); 0.8 (t).

N-n-butyl-N'-{3-phenoxyacetamido-4,6-dihydropyrrolo[3,4-c]pyrazol-5-yl}urea 1H-NMR (DMSO-d6) d ppm: 7.3-6.9 (m); 6.2 (t); 4.7 (s); 4.3 (bs); 3.0 (m); 1.4-1.2 (m); 0.8 (t).

N-n-butyl-N'-{3-(4-methyl-phenyl)acetamido-4,6-dihydropyrrolo[3,4-c]pyrazol-5-yl}urea 1H-NMR (DMSO-d6) d ppm: 7.2-7.1 (m); 6.2 (t); 4.3 (bs); 3.5 (s); 3.0 (m); 2.2 (s); 1.4-1.2 (m); 0.8 (t).

N-n-butyl-N'-{3-(4-fluoro-phenyl)acetamido-4,6-dihydropyrrolo[3,4-c]pyrazol-5-yl}urea 1H-NMR (DMSO-d6) d ppm: 7.3-7.1 (m); 6.2 (t); 4.3 (bs); 3.6 (s); 3.0 (m); 1.4-1.2 (m); 0.8 (t).

N-n-butyl-N'-{3-(3,4-difluoro-phenyl)acetamido-4,6-dihydropyrrolo[3,4-c]pyrazol-5-yl}urea 1H-NMR (DMSO-d6) d ppm: 7.4-7.1 (m); 6.2 (t); 4.3 (bs); 3.6 (s); 3.0 (m); 1.4-1.2 (m); 0.8 (t).

N-n-butyl-N'-{3-(4-trifluoromethoxy-phenyl)acetamido-4,6-dihydropyrrolo[3,4-c]pyrazol-5-yl}urea 1H-NMR (DMSO-d6) d ppm: 7.4-7.3 (m); 6.2 (t); 4.3 (bs); 3.6 (s); 3.0 (m); 1.4-1.2 (m); 0.8 (t).

N-n-butyl-N'-{3-(2-methyl-phenyl)acetamido-4,6-dihydropyrrolo[3,4-c]pyrazol-5-yl}urea 1H-NMR (DMSO-d6) d ppm: 7.2-7.1 (m); 6.2 (t); 4.3 (bs); 3.6 (s); 3.0 (m); 2.2 (s); 1.4-1.2 (m); 0.8 (t).

N-n-butyl-N'-{3-(2-bromo-phenyl)acetamido-4,6-dihydropyrrolo[3,4-c]pyrazol-5-yl}urea 1H-NMR (DMSO-d6) d ppm: 7.6-7.2 (m); 6.2 (t); 4.3 (m); 3.8 (s); 3.0 (m); 1.4-1.2 (m); 0.8 (t).

N-n-butyl-N'-{3-(2,5-difluoro-phenyl)acetamido-4,6-dihydropyrrolo[3,4-c]pyrazol-5-yl}urea 1H-NMR (DMSO-d6) d ppm: 7.2-7.1 (m); 6.2 (t); 4.3 (m); 3.7 (s); 3.0 (m); 1.4-1.2 (m); 0.8 (t).

N-n-butyl-N'-{3-(4-(pyrrolidin-1-yl-carbonylmethyloxy)-phenyl)acetamido)-4,6-dihydropyrrolo[3,4-c]pyrazol-5-yl}urea 1H-NMR (DMSO-d6) d ppm: 7.2-6.8 (m); 6.2 (t); 4.6 (s); 4.3 (bs); 3.4 (m); 3.0 (m); 1.9-1.7 (m); 1.4-1.2 (m); 0.8 (t).

N-n-butyl-N'-{3-(3-(aminocarbonylmethyloxy)-phenyl)acetamido)-4,6-dihydropyrrolo[3,4-c]pyrazol-5-yl}urea 1H-NMR (DMSO-d6) d ppm: 7.5-7.3 (m); 7.2-6.8 (m); 6.2 (t); 4.4 (s); 4.3 (bs); 3.6 (s); 3.0 (m); 1.4-1.2 (m); 0.8 (t).

N-n-butyl-N'-{3-(pyrid-4-yl-acetamido)-4,6-dihydropyrrolo[3,4-c]pyrazol-5-yl}urea 1H-NMR (DMSO-d6) d ppm: 8.6 (m); 7.4 (m); 6.2 (t); 4.3 (bs); 3.7 (s); 3.0 (m); 1.4-1.2 (m); 0.8 (t).

N-n-butyl-N'-{3-(4-(morpholin-1-yl)-phenyl)acetamido)-4,6-dihydropyrrolo[3,4-c]pyrazol-5-yl}urea 1H-NMR (DMSO-d6) d ppm: 7.2-6.8 (m); 6.2 (t); 4.3 (bs); 3.7 (m); 3.5 (s); 3.0 (m); 1.4-1.2 (m); 0.8 (t).

N-n-butyl-N'-{3-(2-fluoro-phenyl)acetamido-4,6-dihydropyrrolo[3,4-c]pyrazol-5-yl}urea 1H-NMR (DMSO-d6) d ppm: 7.4-7.1 (m); 6.2 (t); 4.3 (bs); 3.7 (s); 3.0 (m); 1.4-1.2 (m); 0.8 (t).

N-n-butyl-N'-{3-(3,5-difluoro-phenyl)acetamido-4,6-dihydropyrrolo[3,4-c]pyrazol-5-yl}urea 1H-NMR (DMSO-d6) d ppm: 7.1-6.9 (m); 6.2 (t); 4.3 (bs); 3.7 (s); 3.0 (m); 1.4-1.2 (m); 0.8 (t).

N-n-butyl-N'-{3-(6-oxo-6H-pyridazin-1-yl)acetamido)-4,6-dihydropyrrolo[3,4-c]pyrazol-5-yl}urea 1H-NMR (DMSO-d6) d ppm: 7.9 (m); 7.4 (m); 6.9 (m); 6.2 (t); 4.9 (s); 4.3 (m); 3.0 (m); 1.4-1.2 (m); 0.8 (t).

N-{5-picolinoyl-4,6-dihydropyrrolo[3,4-c]pyrazol-3-yl}-4-(2-oxo-oxazolidin-3-yl)-phenyl-acetamide 1H-NMR (DMSO-d6) d ppm: 8.6-7.25 (m); 4.9-4.6 (m); 4.4-4.0 (m); 3.6 (s).

N-{5-(thien-2-yl)acetyl-4,6-dihydropyrrolo[3,4-c]pyrazol-3-yl}-4-(2-oxo-oxazolidin-3-yl)-phenyl-acetamide 1H-NMR (DMSO-d6) d ppm: 7.5-6.9 (m); 4.7-4.0 (m); 3.9 (s); 3.6 (s).

N-{5-(2-furoyl)-4,6-dihydropyrrolo[3,4-c]pyrazol-3-yl}-4-(2-oxo-oxazolidin-3-yl)-phenyl-acetamide 1H-NMR (DMSO-d6) d ppm: 7.9-6.6 (m); 4.9-4.6 (m); 4.4-4.0 (m); 3.6 (s).

N-{5-ethoxyacetyl-4,6-dihydropyrrolo[3,4-c]pyrazol-3-yl}-4-(2-oxo-oxazolidin-3-yl)-phenyl-acetamide 1H-NMR (DMSO-d6) d ppm: 7.4 (m); 4.6-3.5 (m); 1.1 (m).

N-{5-(3-methyl-butyrroyl)-4,6-dihydropyrrolo[3,4-c]pyrazol-3-yl}-4-(2-oxo-oxazolidin-3-yl)-phenyl-acetamide 1H-NMR (DMSO-d6) d ppm: 7.4 (m); 4.6-4.0 (m); 3.6 (s); 2.2 (d); 2.0 (m); 0.9 (m).

N-{5-butyrroyl-4,6-dihydropyrrolo[3,4-c]pyrazol-3-yl}-4-(2-oxo-oxazolidin-3-yl)-phenyl-acetamide 1H-NMR (DMSO-d6) d ppm: 7.4 (m); 4.6-4.0 (m); 3.6 (s); 2.4 (m); 1.5 (m); 0.9 (m).

N-isopropyl-N'-{3-[4-(2-oxo-oxazolidin-3-yl)-phenyl-acetamido)]-4,6-dihydropyrrolo[3,4-c]pyrazol-5-yl}urea 1H-NMR (DMSO-d6) d ppm: 7.4 (m); 5.9 (d); 4.4-4.0 (m); 3.8 (m); 3.6 (s); 1.0 (m).

N-(n-butyl)-N'-{3-[4-(2-oxo-oxazolidin-3-yl)-phenyl-acetamido)]-4,6-dihydropyrrolo[3,4-c]pyrazol-5-yl}urea 1H-NMR (DMSO-d6) d ppm: 7.4 (m); 6.2 (t); 4.4-4.0 (m); 3.6 (s); 3.0 (m); 1.4-1.2 (m); 0.8 (t).

N-{5-ethoxycarbonyl-4,6-dihydropyrrolo[3,4-c]pyrazol-3-yl}-4-(2-oxo-oxazolidin-3-yl)-phenyl-acetamide 1H-NMR (DMSO-d6) d ppm: 7.4 (m); 4.4-4.0 (m); 3.6 (s); 1.2 (t).

N-isopropyl-N'-{3-[2-(3-oxo-3,4,4a,8a-tetrahydro-2H-benzo[1,4]oxazin-6-yl)acetamido]-4,6-dihydropyrrolo[3,4-c]pyrazol-5-yl}urea 1H-NMR (DMSO-d6) d ppm: 6.8 (m); 5.9 (d); 4.5 (s); 4.3 (bs); 3.8 (m); 3.5 (bs); 1.0 (m).

N-isopropyl-N'-{3-(3-bromo-benzamido)-4,6-dihydropyrrolo[3,4-c]pyrazol-5-yl}urea N-{5-benzensulfonyl-4,6-dihydropyrrolo[3,4-c]pyrazol-3-yl}-3-bromobenzamide N-{5-acetyl-4,6-dihydropyrrolo[3,4-c]pyrazol-3-yl}-[4-(1-pyrrolidin-2-one)benzamide];

N-ethyl-N'-{3-(3-bromo-benzamido)-4,6-dihydropyrrolo[3,4-c]pyrazol-5-yl}

N-{5-(8-quinoline)sulfonyl-4,6-dihydropyrrolo[3,4-c]pyrazol-3-yl}-p-toluic amide N-phenyl-N'-{3-(3-bromo-benzamido)-4,6-dihydropyrrolo[3,4-c]pyrazol-5-yl}urea N-{5-phenylacetyl-4,6-dihydropyrrolo[3,4-c]pyrazol-3-yl}-3-bromobenzamide;

N-{5-methansulfonyl-4,6-dihydropyrrolo[3,4-c]pyrazol-3-yl}-3-bromobenzamide;

N-isopropyl-N'-{3-[4-(1-pyrrolidin-2-on)benzamido]-4,6-dihydropyrrolo[3,4-c]pyrazol-5-yl}urea N-{5-(8-quinoline)carbonyl-4,6-dihydropyrrolo[3,4-c]pyrazol-3-yl}-p-toluic amide N-{5-(1-naphthalene)sulfonyl-4,6-dihydropyrrolo[3,4-c]pyrazol-3-yl}-4-phenylbenzamide N-{5-(1-naphtoyl)-4,6-dihydropyrrolo[3,4-c]pyrazol-3-yl}-4-phenylbenzamide;

N-{5-(1-naphtoyl)-4,6-dihydropyrrolo[3,4-c]pyrazol-3-yl}-4-phenoxybenzamide;

N-phenyl-N'-{3-(4-phenyl-benzamido)-4,6-dihydropyrrolo[3,4-c]pyrazol-5-yl}urea

N-{5-phenylacetyl-4,6-dihydropyrrolo[3,4-c]pyrazol-3-yl}-4-phenylbenzamide;

N-{5-(1-naphthalene)sulfonyl-4,6-dihydropyrrolo[3,4-c]pyrazol-3-yl}-p-toluic amide N-{5-(1-naphtoyl)-4,6-dihydropyrrolo[3,4-c]pyrazol-3-yl}-p-toluic amide;

N-{5-acetyl-4,6-dihydropyrrolo[3,4-c]pyrazol-3-yl}-3-phenoxybenzamide;

N-[5-(4-chloro-2,5-difluorobenzoyl)-4,6-dihydropyrrolo[3,4-c]pyrazol-3-yl]-2-(2-naphthyl)acetamide 1H-NMR (DMSO-d6) d ppm: 7.90-7.30 (m); 4.59 (s); 4.39 (s); 3.72 (s).

N-{5-[tert-butyl carboxylate]-4,6-dihydropyrrolo[3,4-c]pyrazol-3-yl}-2-(2-naphthyl)acetamide 1H-NMR (DMSO-d6) d ppm: 7.90-7.75 (m); 7.55-7.40 (m); 4.33 (s); 4.31 (s); 3.78 (s), 1.40 (s).

N-{5-[(1-methylcyclopropyl)carbonyl]-4,6-dihydropyrrolo[3,4-c]pyrazol-3-yl}-2-(2-naphthyl)acetamide 1H-NMR (DMSO-d6) d ppm: 7.87 (m); 7.79 (s); 7.45 (m); 4.73 (s); 4.36 (s); 3.79 (s); 1.24 (s); 0.83 (s); 0.52 (t).

N-[5-(cyclobutylcarbonyl)-4,6-dihydropyrrolo[3,4-c]pyrazol-3-yl]-2-(2-naphthyl)acetamide 1H-NMR (DMSO-d6) d ppm: 7.85 (m); 7.78 (s); 7.46 (m); 4.46 (s); 3.78 (s); 2.20-1.70 (m).

N-[5-(2-fluorobenzoyl)-4,6-dihydropyrrolo[3,4-c]pyrazol-3-yl]-2-(2-naphthyl)acetamide 1H-NMR (DMSO-d6) d ppm: 10.74 (s); 7.90-7.23 (m); 4.32 (s); 3.80 (s).

N-[5-(pyridin-3-ylcarbonyl)-4,6-dihydropyrrolo[3,4-c]pyrazol-3-yl]-2-(2-naphthyl)acetamide 1H-NMR (DMSO-d6) d ppm: 8.75 (dd); 8.65 (m); 8.05-7.35 (m); 4.46 (s); 3.72 (s).

N-{5-[(2,2,3,3-tetramethylcyclopropyl)carbonyl]-4,6-dihydropyrrolo[3,4-c]pyrazol-3-yl}-2-(2-naphthyl)acetamide 1H-NMR (DMSO-d6) d ppm: 7.86 (m); 7.79 (s); 7.45 (m); 4.73 (s); 4.57 (s); 3.79 (s); 1.22 (m); 1.12 (m).

N-[5-(2,4,5-trifluorobenzoyl)-4,6-dihydropyrrolo[3,4-c]pyrazol-3-yl]-2-(2-naphthyl)acetamide 1H-NMR (DMSO-d6) d ppm: 10.76 (s); 7.90-7.35 (m); 4.47 (s); 4.37 (s); 3.72 (s).

N-[5-(2-methylpent-4-enoyl)-4,6-dihydropyrrolo[3,4-c]pyrazol-3-yl]-2-(2-naphthyl)acetamide 1H-NMR (DMSO-d6) d ppm: 7.86 (m); 7.78 (s); 7.46 (m); 5.71 (m); 4.97 (m); 4.61 (s); 4.35 (s); 3.78 (s); 2.63 (m); 2.28 (m); 2.05 (m) 1.22 (m); 1.0 (t).

N-[5-(cyclopropylacetyl)-4,6-dihydropyrrolo[3,4-c]pyrazol-3-yl]-2-(2-naphthyl)acetamide 1H-NMR (DMSO-d6) d ppm: 7.90-7.40 (m); 3.77 (s); 2.21 (t); 0.96 (m); 0.42 (m).

N-[5-(5-fluoro-2-methylbenzoyl)-4,6-dihydropyrrolo[3,4-c]pyrazol-3-yl]-2-(2-naphthyl)acetamide 1H-NMR (DMSO-d6) d ppm: 7.90-7.10 (m); 4.20 (s); 2.16 (s).

N-{5-[2-fluoro-5-(trifluoromethyl)benzoyl]-4,6-dihydropyrrolo[3,4-c]pyrazol-3-yl}-2-(2-naphthyl)acetamide 1H-NMR (DMSO-d6) d ppm: 10.75 (s); 7.97-7.35 (m); 4.60 (s); 4.35 (s); 3.71 (s).

N-{5-[(3-methoxycyclohexyl)carbonyl]-4,6-dihydropyrrolo[3,4-c]pyrazol-3-yl}-2-(2-naphthyl)acetamide 1H-NMR (DMSO-d6) d ppm: 10.78 (s); 7.85 (m); 7.78 (s); 7.45 (m); 3.78 (s); 3.21 (s); 2.40-2.65 (m); 2.05-0.95 (m).

N-{5-(2,4-dichloro-5-fluorobenzoyl)-4,6-dihydropyrrolo[3,4-c]pyrazol-3-yl}-2-(2-naphthyl)acetamide 1H-NMR (DMSO-d6) d ppm: 10.76 (s); 7.96-7.38 (m); 4.57 (s); 4.27 (s); 3.80 (s).

N-[5-(2-chloro-4,5-difluorobenzoyl)-4,6-dihydropyrrolo[3,4-c]pyrazol-3-yl]-2-(2-naphthyl)acetamide 1H-NMR (DMSO-d6) d ppm: 10.78 (s); 7.90-7.35 (m); 4.58 (s); 4.27 (s); 3.71 (s).

N-{5-[4-(1H-imidazol-1-yl)benzoyl]-4,6-dihydropyrrolo[3,4-c]pyrazol-3-yl}-2-(2-naphthyl)acetamide 1H-NMR (DMSO-d6) d ppm: 7.90-7.20 (m); 4.52 s); 3.78 (s).

N-{5-[4-(aminosulfonyl)butanoyl]-4,6-dihydropyrrolo[3,4-c]pyrazol-3-yl}-2-(2-naphthyl)acetamide 1H-NMR (DMSO-d6) d ppm: 7.85 (m); 7.78 (s); 7.46 (m); 4.53 (s); 3.78 (s); 2.98 (m); 2.25 (t); 1.93 (m).

N-{5-[(8-oxo-5,6,7,8-tetrahydronaphthalen-2-yl)carbonyl]-4,6-dihydropyrrolo[3,4-c]pyrazol-3-yl}-2-(2-naphthyl)acetamide 1H-NMR (DMSO-d6) d ppm: 8.05-7.33 (m); 4.44 (s); 3.80 (s); 2.95 (m); 2.60 (m); 2.05 (m).

N-(5-pyruvoyl-4,6-dihydropyrrolo[3,4-c]pyrazol-3-yl)-2-(2-naphthyl)acetamide

N-[5-(2,2-dimethylpropanoyl)-4,6-dihydropyrrolo[3,4-c]pyrazol-3-yl]-2-(2-naphthyl)acetamide 1H-NMR (DMSO-d6) d ppm: 7.90-7.40 (m); 3.80 (s); 1.20 (s).

N-(5-but-2-ynoyl-4,6-dihydropyrrolo[3,4-c]pyrazol-3-yl)-2-(2-naphthyl)acetamide 1H-NMR (DMSO-d6) d ppm: 7.90-7.40 (m); 3.80 (s); 1.20 (s).

N-[5-(3-iodo-4-methylbenzoyl)-4,6-dihydropyrrolo[3,4-c]pyrazol-3-yl-2-(2-naphthyl)acetamide 1H-NMR (DMSO-d6) d ppm: 10.72 (s); 8.05-7.35 (m); 4.45 (s); 3.710 (s); 2.37 (s).

N-{5-[(benzyloxy)acetyl]-4,6-dihydropyrrolo[3,4-c]pyrazol-3-yl}-2-(2-naphthyl)acetamide 1H-NMR (DMSO-d6) d ppm: 7.90-7.20 (m); 4.25-4.70 (m); 4.20 (s); 3.80 (s).

N-{5-(2-fluoro-2-phenylacetyl)-4,6-dihydropyrrolo[3,4-c]pyrazol-3-yl}-4-tertbutylbenzamide; 1H-NMR (DMSO-d6) d ppm: 7.8-8.0 (m), 7.4-7.6 (m), 6.0-6.5 (m), 4.2-5.0 (m).

N-{5-(2-fluoro-2-phenylacetyl)-4,6-dihydropyrrolo[3,4-c]pyrazol-3-yl}-4-phenoxybenzamide; 1H-NMR (DMSO-d6) d ppm: 7.8-8.0 (m), 7.4-7.6 (m), 4.2-5.0 (m).

N-{5-(2-thienyl-acetyl)-4,6-dihydropyrrolo[3,4-c]pyrazol-3-yl}-4-(4-methylpiperazino)benzamide; 1H-NMR (DMSO-d6) d ppm: 7.8-8.0 (m), 6.8-7.0 (m), 4.6-4.8 (d), 4.4-4.5 (d), 3.7 (s), 2.3 (s).

N-{5-(3-methyl-butanoyl)-4,6-dihydropyrrolo[3,4-c]pyrazol-3-yl}-4-(4-methylpiperazino)benzamide; 1H-NMR (DMSO-d6) d ppm: 7.8-8.0 (m), 6.8-7.0 (m), 4.6-4.8 (m), 4.4-4.5 (m), 2.3 (t), 2.1-2.0 (m).

N-{5-(2-furoyl)-4,6-dihydropyrrolo[3,4-c]pyrazol-3-yl}-4-(4-methylpiperazino)benzamide; 1H-NMR (DMSO-d6) d ppm: 7.8-8.0 (m), 7.2-7.4 (m), 6.8-7.0 (m), 5.0-4.8 (d), 4.6-4.7 (d), 2.1 (s).

N-{5-phenylacetyl-4,6-dihydropyrrolo[3,4-c]pyrazol-3-yl}-4-(4-methylpiperazino)benzamide; 1H-NMR (DMSO-d6) d ppm: 7.8-8.0 (m), 6.8-7.0 (m), 5.0-4.8 (m), 4.6-4.7 (m), 3.7 (s).

N-{5-benzenesulfonyl-4,6-dihydropyrrolo[3,4-c]pyrazol-3-yl}-4-(4-methylpiperazino)benzamide; 1H-NMR (DMSO-d6) d ppm: 7.8-8.0 (m), 7.5-7.7 (m), 7.2-7.3 (m).

N-(2,6-diethylphenyl)-N'-{3-[4-(4-methylpiperazino)benzamide]-4,6-dihydropyrrolo[3,4-c]pyrazol-5-yl}urea 1H-NMR (DMSO-d6) d ppm: 7.8-8.0 (m), 7.0-7.2 (m), 2.5-2.6 (m), 1.1-1.2 (m).

N-ethyl-N'-{3-[4-(4-methylpiperazino)benzamide]-4,6-dihydropyrrolo[3,4-c]pyrazol-5-yl}urea 1H-NMR (DMSO-d6) d ppm: 7.8-8.0 (m), 6.9-7.1 (m), 3.0-3.1 (m), 1.1-1.2 (m).

N-{5-(2-fluoro-2-phenylacetyl)-4,6-dihydropyrrolo[3,4-c]pyrazol-3-yl}-[4-(1-pyrrolidin-2-one)benzamide]; 1H-NMR (DMSO-d6) d ppm: 7.9-8.1 (m), 7.7-7.8 (m), 3.8-4.0 (m), 2.5-2.6 (m), 2.1-2.0 (m).

N-{5-(2-fluoro-2-phenylacetyl)-4,6-dihydropyrrolo[3,4-c]pyrazol-3-yl}-4-(4-methylpiperazino)benzamide;

N-{5-(2-thienyl-acetyl)-4,6-dihydropyrrolo[3,4-c]pyrazol-3-yl}-piperonylamide; 1H-NMR (DMSO-d6) d ppm: 7.60-6.96 (m, 6H), 6.11 (s, 2H), 4.77-4.48 (m, 4H), 3.95 (m, 2H).

N-{5-(3-methyl-butanoyl)-4,6-dihydropyrrolo[3,4-c]pyrazol-3-yl}-piperonylamide; 1H-NMR (DMSO-d6) d ppm: 12.35 (1H), 10.70 (m, 1H), 7.56-7.00 (m, 3H), 6.10 (s, 2H), 4.65-4.45 (m, 4H), 2.21-2.05 (m, 3H), 0.93 (6H).

N-{5-(2-furoyl)-4,6-dihydropyrrolo[3,4-c]pyrazol-3-yl}-piperonylamide; 1H-NMR (DMSO-d6) d ppm: 7.93-7.89 (m, 1H), 7.57-7.49 (m, 2H), 7.14-7.00 (m, 2H), 6.67 (m, 1H), 6.10 (s, 2H), 5.01-4.67 (m, 4H).

N-{5-phenylacetyl-4,6-dihydropyrrolo[3,4-c]pyrazol-3-yl}-piperonylamide; 1H-NMR (DMSO-d6) d ppm: 7.61-7.00 (m, 8H), 6.10 (s, 2H), 4.74-4.47 (m, 4H), 3.72 (2H).

N-{5-benzenesulfonyl-4,6-dihydropyrrolo[3,4-c]pyrazol-3-yl}-piperonylamide; 1H-NMR (DMSO-d6) d ppm: 7.88-6.98 (m, 8H), 6.11 (s, 2H), 4.48-4.34 (m, 4H).

N-{5-(2-trifluoromethyl)benzenesulfonyl-4,6-dihydropyrrolo[3,4-c]pyrazol-3-yl}-piperonylamide; 1H-NMR (DMSO-d6) d ppm: 8.04-6.98 (m, 7H), 6.12 (m, 2H), 4.64-4.49 (m, 4H).

N-ethyl-N'-{3-piperonylcarboxamido-4,6-dihydropyrrolo[3,4-c]pyrazol-5-yl}urea 1H-NMR (DMSO-d6) d ppm: 7.62-6.98 (m, 3H), 6.1 (s, 2H), 4.41-4.38 (m, 4H), 3.2 (m, 2H), 1.01 (t, 3H).

N-{5-acetyl-4,6-dihydropyrrolo[3,4-c]pyrazol-3-yl}-acetamide;

N-{5-acetyl-4,6-dihydropyrrolo[3,4-c]pyrazol-3-yl}-cyclopropanecarboxamide;

N-{5-acetyl-4,6-dihydropyrrolo[3,4-c]pyrazol-3-yl}-isobutyramide;

N-{5-acetyl-4,6-dihydropyrrolo[3,4-c]pyrazol-3-yl}-cyclopentanecarboxamide;

N-{5-acetyl-4,6-dihydropyrrolo[3,4-c]pyrazol-3-yl}-benzamide;

N-{5-acetyl-4,6-dihydropyrrolo[3,4-c]pyrazol-3-yl}-picolinic amide;

N-{5-acetyl-4,6-dihydropyrrolo[3,4-c]pyrazol-3-yl}-nicotinic amide;

N-{5-acetyl-4,6-dihydropyrrolo[3,4-c]pyrazol-3-yl}-isonicotinic amide;

N-{5-acetyl-4,6-dihydropyrrolo[3,4-c]pyrazol-3-yl}-3-methyl-2-furoic amide;

N-{5-acetyl-4,6-dihydropyrrolo[3,4-c]pyrazol-3-yl}-thiophene-2-carboxamide;

N-{5-acetyl-4,6-dihydropyrrolo[3,4-c]pyrazol-3-yl}-thiophene-3-carboxamide;

N-{5-acetyl-4,6-dihydropyrrolo[3,4-c]pyrazol-3-yl}-o-toluic amide;

N-{5-acetyl-4,6-dihydropyrrolo[3,4-c]pyrazol-3-yl}-m-toluic amide;

N-{5-acetyl-4,6-dihydropyrrolo[3,4-c]pyrazol-3-yl}-p-toluic amide;

N-{5-acetyl-4,6-dihydropyrrolo[3,4-c]pyrazol-3-yl}-salicylic amide;

N-{5-acetyl-4,6-dihydropyrrolo[3,4-c]pyrazol-3-yl}-2-fluorobenzamide;

N-{5-acetyl-4,6-dihydropyrrolo[3,4-c]pyrazol-3-yl}-3-fluorobenzamide;

N-{5-acetyl-4,6-dihydropyrrolo[3,4-c]pyrazol-3-yl}-4-fluorobenzamide;

N-{5-acetyl-4,6-dihydropyrrolo[3,4-c]pyrazol-3-yl}-thiophene-2-acetamide;

N-{5-acetyl-4,6-dihydropyrrolo[3,4-c]pyrazol-3-yl}-thiophene-3-acetamide;

N-{5-acetyl-4,6-dihydropyrrolo[3,4-c]pyrazol-3-yl}-phenylpropiolic amide;

N-{5-acetyl-4,6-dihydropyrrolo[3,4-c]pyrazol-3-yl}-3-cyanobenzamide;

N-{5-acetyl-4,6-dihydropyrrolo[3,4-c]pyrazol-3-yl}cyanobenzamide;

N-{5-acetyl-4,6-dihydropyrrolo[3,4-c]pyrazol-3-yl}-trans-cinnamic amide;

N-{5-acetyl-4,6-dihydropyrrolo[3,4-c]pyrazol-3-yl}-cis-cinnamic amide;

N-{5-acetyl-4,6-dihydropyrrolo[3,4-c]pyrazol-3-yl}-3-(3-pyridyl)acrylic amide;

N-{5-acetyl-4,6-dihydropyrrolo[3,4-c]pyrazol-3-yl}-3-(4-pyridyl)-acrylic amide;

N-{5-acetyl-4,6-dihydropyrrolo[3,4-c]pyrazol-3-yl}-2-phenylpropionamide;

N-{5-acetyl-4,6-dihydropyrrolo[3,4-c]pyrazol-3-yl}-o-tolylacetamide;
N-{5-acetyl-4,6-dihydropyrrolo[3,4-c]pyrazol-3-yl}-m-tolylacetamide;
N-{5-acetyl-4,6-dihydropyrrolo[3,4-c]pyrazol-3-yl}-p-tolylacetamide;
N-{5-acetyl-4,6-dihydropyrrolo[3,4-c]pyrazol-3-yl}-o-anisic amide;
N-{5-acetyl-4,6-dihydropyrrolo[3,4-c]pyrazol-3-yl}-3-methoxybenzamide;
N-{5-acetyl-4,6-dihydropyrrolo[3,4-c]pyrazol-3-yl}-p-anisic amide;
N-{5-acetyl-4,6-dihydropyrrolo[3,4-c]pyrazol-3-yl}-phenoxyacetamide;
N-{5-acetyl-4,6-dihydropyrrolo[3,4-c]pyrazol-3-yl}-2-fluorophenylacetamide;
N-{5-acetyl-4,6-dihydropyrrolo[3,4-c]pyrazol-3-yl}-3-fluorophenylacetamide;
N-{5-acetyl-4,6-dihydropyrrolo[3,4-c]pyrazol-3-yl}-4-fluorophenylacetamide;
N-{5-acetyl-4,6-dihydropyrrolo[3,4-c]pyrazol-3-yl}-3-(2-thienyl)acrylic amide;
N-{5-acetyl-4,6-dihydropyrrolo[3,4-c]pyrazol-3-yl}-3-(3-thienyl)-acrylic amide;
N-{5-acetyl-4,6-dihydropyrrolo[3,4-c]pyrazol-3-yl}-3-(2-thienyl)propanoic amide;
N-{5-acetyl-4,6-dihydropyrrolo[3,4-c]pyrazol-3-yl}-2-chlorobenzamide;
N-{5-acetyl-4,6-dihydropyrrolo[3,4-c]pyrazol-3-yl}-3-chlorobenzamide;
N-{5-acetyl-4,6-dihydropyrrolo[3,4-c]pyrazol-3-yl}-4-chlorobenzamide;
N-{5-acetyl-4,6-dihydropyrrolo[3,4-c]pyrazol-3-yl}-1-piperidinepropionamide;
N-{5-acetyl-4,6-dihydropyrrolo[3,4-c]pyrazol-3-yl}-2-acetylbenzamide;
N-{5-acetyl-4,6-dihydropyrrolo[3,4-c]pyrazol-3-yl}-4-acetylbenzamide;
N-{5-acetyl-4,6-dihydropyrrolo[3,4-c]pyrazol-3-yl}-1-naphthoic amide;
N-{5-acetyl-4,6-dihydropyrrolo[3,4-c]pyrazol-3-yl}-2-naphthoic amide;
N-{5-acetyl-4,6-dihydropyrrolo[3,4-c]pyrazol-3-yl}-3-benzoylpropionamide;
N-{5-acetyl-4,6-dihydropyrrolo[3,4-c]pyrazol-3-yl}-4-acetamidobenzamide;
N-{5-acetyl-4,6-dihydropyrrolo[3,4-c]pyrazol-3-yl}-2,5-dimethoxybenzamide;
N-{5-acetyl-4,6-dihydropyrrolo[3,4-c]pyrazol-3-yl}-2,6-dimethoxybenzamide;
N-{5-acetyl-4,6-dihydropyrrolo[3,4-c]pyrazol-3-yl}-3,4-dimethoxybenzamide;
N-{5-acetyl-4,6-dihydropyrrolo[3,4-c]pyrazol-3-yl}-3,5-dimethoxybenzamide;
N-{5-acetyl-4,6-dihydropyrrolo[3,4-c]pyrazol-3-yl}-3-(2-thenoyl)-propionamide;
N-{5-acetyl-4,6-dihydropyrrolo[3,4-c]pyrazol-3-yl}-1-naphtylacetamide
N-{5-acetyl-4,6-dihydropyrrolo[3,4-c]pyrazol-3-yl}-4-phenylbenzamide
N-{5-benzyl-4,6-dihydropyrrolo[3,4-c]pyrazol-3-yl}-acetamide;
N-{5-benzyl-4,6-dihydropyrrolo[3,4-c]pyrazol-3-yl}-cyclopropanecarboxamide;
N-{5-benzyl-4,6-dihydropyrrolo[3,4-c]pyrazol-3-yl}-isobutyramide;
N-{5-benzyl-4,6-dihydropyrrolo[3,4-c]pyrazol-3-yl}-cyclopentanecarboxamide;
N-{5-benzyl-4,6-dihydropyrrolo[3,4-c]pyrazol-3-yl}-benzamide;
N-{5-benzyl-4,6-hydropyrrolo[3,4-c]pyrazol-3-yl}-picolinic amide;
N-{5-benzyl-4,6-dihydropyrrolo[3,4-c]pyrazol-3-yl}-nicotinic amide;
N-{5-benzyl-4,6-dihydropyrrolo[3,4-c]pyrazol-3-yl}-isonicotinic amide;
N-{5-benzyl-4,6-dihydropyrrolo[3,4-c]pyrazol-3-yl}-3-methyl-2-furoic amide;
N-{5-benzyl-4,6-dihydropyrrolo[3,4-c]pyrazol-3-yl}-thiophene-2-carboxamide;
N-{5-benzyl-4,6-dihydropyrrolo[3,4-c]pyrazol-3-yl}-thiophene-3-carboxamide;
N-{5-benzyl-4,6-dihydropyrrolo[3,4-c]pyrazol-3-yl}-o-toluic amide;
N-{5-benzyl-4,6-dihydropyrrolo[3,4-c]pyrazol-3-yl}-m-toluic amide;
N-{5-benzyl-4,6-dihydropyrrolo[3,4-c]pyrazol-3-yl}-p-toluic amide;
N-{5-benzyl-4,6-dihydropyrrolo[3,4-c]pyrazol-3-yl}-phenylacetamide;
N-{5-benzyl-4,6-dihydropyrrolo[3,4-c]pyrazol-3-yl}-salicylic amide;
N-{5-benzyl-4,6-dihydropyrrolo[3,4-c]pyrazol-3-yl}-2-fluorobenzamide;
N-{5-benzyl-4,6-dihydropyrrolo[3,4-c]pyrazol-3-yl}-3-fluorobenzamide;
N-{5-benzyl-4,6-dihydropyrrolo[3,4-c]pyrazol-3-yl}-4-fluorobenzamide;
N-{5-benzyl-4,6-hydropyrrolo[3,4-c]pyrazol-3-yl}-thiophene-2-acetamide;
N-{5-benzyl-4,6-dihydropyrrolo[3,4-c]pyrazol-3-yl}-thiophene-3-acetamide;
N-{5-benzyl-4,6-dihydropyrrolo[3,4-c]pyrazol-3-yl}-phenylpropiolic amide;
N-{5-benzyl-4,6-dihydropyrrolo[3,4-c]pyrazol-3-yl}-3-cyanobenzamide;
N-{5-benzyl-4,6-dihydropyrrolo[3,4-c]pyrazol-3-yl}-4-cyanobenzamide;
N-{5-benzyl-4,6-dihydropyrrolo[3,4-c]pyrazol-3-yl
N-{5-benzyl-4,6-hydropyrrolo[3,4-c]pyrazol-3-yl}-cis-cinnamic amide;
N-{5-benzyl-4,6-dihydropyrrolo[3,4-c]pyrazol-3-yl}-3-(3-pyridyl)acrylic amide;
N-{5-benzyl-4,6-dihydropyrrolo[3,4-c]pyrazol-3-yl}-3-(4-pyridyl)-acrylic amide;
N-{5-benzyl-4,6-dihydropyrrolo[3,4-c]pyrazol-3-yl}-2-phenylpropionamide;
N-{5-benzyl-4,6-dihydropyrrolo[3,4-c]pyrazol-3-yl}-o-tolylacetamide;
N-{5-benzyl-4,6-dihydropyrrolo[3,4-c]pyrazol-3-yl}-m-tolylacetamide;
N-{5-benzyl-4,6-dihydropyrrolo[3,4-c]pyrazol-3-yl}-p-tolylacetamide;
N-{5-benzyl-4,6-dihydropyrrolo[3,4-c]pyrazol-3-yl}-o-anisic amide;
N-{5-benzyl-4,6-dihydropyrrolo[3,4-c]pyrazol-3-yl}-3-methoxybenzamide;
N-{5-benzyl-4,6-dihydropyrrolo[3,4-c]pyrazol-3-yl}-p-anisic amide;
N-{5-benzyl-4,6-dihydropyrrolo[3,4-c]pyrazol-3-yl}-phenoxyacetamide;
N-{5-benzyl-4,6-dihydropyrrolo[3,4-c]pyrazol-3-yl}-2-fluorophenylacetamide;

N-{5-benzyl-4,6-dihydropyrrolo[3,4-c]pyrazol-3-yl}-3-fluorophenylacetamide;
N-{5-benzyl-4,6-dihydropyrrolo[3,4-c]pyrazol-3-yl}-4-fluorophenylacetamide;
N-{5-benzyl-4,6-dihydropyrrolo[3,4-c]pyrazol-3-yl}-3-(2-thienyl)acrylic amide;
N-{5-benzyl-4,6-dihydropyrrolo[3,4-c]pyrazol-3-yl}-3-(3-thienyl)-acrylic amide;
N-{5-benzyl-4,6-dihydropyrrolo[3,4-c]pyrazol-3-yl}-3-(2-thienyl)propanoic amide;
N-{5-benzyl-4,6-dihydropyrrolo[3,4-c]pyrazol-3-yl}-2-chlorobenzamide;
N-{5-benzyl-4,6-dihydropyrrolo[3,4-c]pyrazol-3-yl}-3-chlorobenzamide;
N-{5-benzyl-4,6-dihydropyrrolo[3,4-c]pyrazol-3-yl}-4-chlorobenzamide;
N-{5-benzyl-4,6-dihydropyrrolo[3,4-c]pyrazol-3-yl}-1-piperidinepropionamide;
N-{5-benzyl-4,6-dihydropyrrolo[3,4-c]pyrazol-3-yl}-2-acetylbenzamide;
N-{5-benzyl-4,6-dihydropyrrolo[3,4-c]pyrazol-3-yl}-4-acetylbenzamide;
N-{5-benzyl-4,6-dihydropyrrolo[3,4-c]pyrazol-3-yl}-1-naphthoic amide;
N-{5-benzyl-4,6-dihydropyrrolo[3,4-c]pyrazol-3-yl}-2-naphthoic amide;
N-{5-benzyl-4,6-dihydropyrrolo[3,4-c]pyrazol-3-yl}-3-benzoylpropionamide;
N-{5-benzyl-4,6-dihydropyrrolo[3,4-c]pyrazol-3-yl}-4-acetamidobenzamide;
N-{5-benzyl-4,6-dihydropyrrolo[3,4-c]pyrazol-3-yl}-2,5-dimethoxybenzamide;
N-{5-benzyl-4,6-dihydropyrrolo[3,4-c]pyrazol-3-yl}-2,6-dimethoxybenzamide;
N-{5-benzyl-4,6-dihydropyrrolo[3,4-c]pyrazol-3-yl}-3,4-dimethoxybenzamide;
N-{5-benzyl-4,6-dihydropyrrolo[3,4-c]pyrazol-3-yl}-3,5-dimethoxybenzamide;
N-{5-benzyl-4,6-dihydropyrrolo[3,4-c]pyrazol-3-yl}-3-(2-thenoyl)-propionamide;
N-{5-benzyl-4,6-dihydropyrrolo[3,4-c]pyrazol-3-yl}-2-naphtylacetamide
N-{5-benzyl-4,6-dihydropyrrolo[3,4-c]pyrazol-3-yl}-1-naphtylacetamide
N-{5-benzyl-4,6-dihydropyrrolo[3,4-c]pyrazol-3-yl}-4-phenylbenzamide
N-{5-phenylethyl-4,6-dihydropyrrolo[3,4-c]pyrazol-3-yl}-acetamide;
N-{5-phenylethyl-4,6-dihydropyrrolo[3,4-c]pyrazol-3-yl}-cyclopropanecarboxamide;
N-{5-phenylethyl-4,6-dihydropyrrolo[3,4-c]pyrazol-3-yl}-isobutyramide;
N-{5-phenylethyl-4,6-dihydropyrrolo[3,4-c]pyrazol-3-yl}-cyclopentanecarboxamide;
N-{5-phenylethyl-4,6-dihydropyrrolo[3,4-c]pyrazol-3-yl}-benzamide;
N-{5-phenylethyl-4,6-dihydropyrrolo[3,4-c]pyrazol-3-yl}-picolinic amide;
N-{5-phenylethyl-4,6-dihydropyrrolo[3,4-c]pyrazol-3-yl}-nicotinic amide;
N-{5-phenylethyl-4,6-dihydropyrrolo[3,4-c]pyrazol-3-yl}-isonicotinic amide;
N-{5-phenylethyl-4,6-dihydropyrrolo[3,4-c]pyrazol-3-yl}-3-methyl-2-furoic amide;
N-{5-phenylethyl-4,6-dihydropyrrolo[3,4-c]pyrazol-3-yl}-thiophene-2-carboxamide;
N-{5-phenylethyl-4,6-dihydropyrrolo[3,4-c]pyrazol-3-yl}-thiophene-3-carboxamide;
N-{5-phenylethyl-4,6-dihydropyrrolo[3,4-c]pyrazol-3-yl}-o-toluic amide;
N-{5-phenylethyl-4,6-dihydropyrrolo[3,4-c]pyrazol-3-yl}-m-toluic amide;
N-{5-phenylethyl-4,6-dihydropyrrolo[3,4-c]pyrazol-3-yl}-p-toluic amide;
N-{5-phenylethyl-4,6-dihydropyrrolo[3,4-c]pyrazol-3-yl}-phenylacetamide;
N-{5-phenylethyl-4,6-dihydropyrrolo[3,4-c]pyrazol-3-yl}-salicylic amide;
N-{5-phenylethyl-4,6-dihydropyrrolo[3,4-c]pyrazol-3-yl}-2-fluorobenzamide;
N-{5-phenylethyl-4,6-dihydropyrrolo[3,4-c]pyrazol-3-yl}-3-fluorobenzamide;
N-{5-phenylethyl-4,6-dihydropyrrolo[3,4-c]pyrazol-3-yl}-4-fluorobenzamide;
N-{5-phenylethyl-4,6-dihydropyrrolo[3,4-c]pyrazol-3-yl}-thiophene-2-acetamide;
N-{5-phenylethyl-4,6-dihydropyrrolo[3,4-c]pyrazol-3-yl}-thiophene-3-acetamide;
N-{5-phenylethyl-4,6-dihydropyrrolo[3,4-c]pyrazol-3-yl}-phenylpropiolic amide;
N-{5-phenylethyl-4,6-dihydropyrrolo[3,4-c]pyrazol-3-yl}-3-cyanobenzamide;
N-{5-phenylethyl-4,6-dihydropyrrolo[3,4-c]pyrazol-3-yl}-4-cyanobenzamide;
N-{5-phenylethyl-4,6-dihydropyrrolo[3,4-c]pyrazol-3-yl}-trans-cinnamic amide;
N-{5-phenylethyl-4,6-dihydropyrrolo[3,4-c]pyrazol-3-yl}-cis-cinnamic amide;
N-{5-phenylethyl-4,6-dihydropyrrolo[3,4-c]pyrazol-3-yl}-3-(3-pyridyl)acrylic amide;
N-{5-phenylethyl-4,6-dihydropyrrolo[3,4-c]pyrazol-3-yl}-3-(4-pyridyl)-acrylic amide;
N-{5-phenylethyl-4,6-dihydropyrrolo[3,4-c]pyrazol-3-yl}-2-phenylpropionamide;
N-{5-phenylethyl-4,6-dihydropyrrolo[3,4-c]pyrazol-3-yl}-o-tolylacetamide;
N-{5-phenylethyl-4,6-dihydropyrrolo[3,4-c]pyrazol-3-yl}-m-tolylacetamide;
N-{5-phenylethyl-4,6-dihydropyrrolo[3,4-c]pyrazol-3-yl}-p-tolylacetamide;
N-{5-phenylethyl-4,6-dihydropyrrolo[3,4-c]pyrazol-3-yl}-o-anisic amide;
N-{5-phenylethyl-4,6-dihydropyrrolo[3,4-c]pyrazol-3-yl}-3-methoxybenzamide;
N-{5-phenylethyl-4,6-dihydropyrrolo[3,4-c]pyrazol-3-yl}-p-anisic amide;
N-{5-phenylethyl-4,6-dihydropyrrolo[3,4-c]pyrazol-3-yl}-phenoxyacetamide;
N-{5-phenylethyl-4,6-dihydropyrrolo[3,4-c]pyrazol-3-yl}-2-fluorophenylacetamide;
N-{5-phenylethyl-4,6-dihydropyrrolo[3,4-c]pyrazol-3-yl}-3-fluorophenylacetamide;
N-{5-phenylethyl-4,6-dihydropyrrolo[3,4-c]pyrazol-3-yl}-4-fluorophenylacetamide;
N-{5-phenylethyl-4,6-dihydropyrrolo[3,4-c]pyrazol-3-yl}-3-(2-thienyl)acrylic amide;
N-{5-phenylethyl-4,6-dihydropyrrolo[3,4-c]pyrazol-3-yl}-3-(3-thienyl)-acrylic amide;
N-{5-phenylethyl-4,6-dihydropyrrolo[3,4-c]pyrazol-3-yl}-3-(2-thienyl)propanoic amide;
N-{5-phenylethyl-4,6-dihydropyrrolo[3,4-c]pyrazol-3-yl}-2-chlorobenzamide;

N-{5-phenylethyl-4,6-dihydropyrrolo[3,4-c]pyrazol-3-yl}-3-chlorobenzamide;
N-{5-phenylethyl-4,6-dihydropyrrolo[3,4-c]pyrazol-3-yl}-4-chlorobenzamide;
N-{5-phenylethyl-4,6-dihydropyrrolo[3,4-c]pyrazol-3-yl}-1-piperidinepropionamide;
N-{5-phenylethyl-4,6-dihydropyrrolo[3,4-c]pyrazol-3-yl}-2-acetylbenzamide;
N-{5-phenylethyl-4,6-dihydropyrrolo[3,4-c]pyrazol-3-yl}-4-acetylbenzamide;
N-{5-phenylethyl-4,6-dihydropyrrolo[3,4-c]pyrazol-3-yl}-1-naphthoic amide;
N-{5-phenylethyl-4,6-dihydropyrrolo[3,4-c]pyrazol-3-yl}-2-naphthoic amide;
N-{5-phenylethyl-4,6-dihydropyrrolo[3,4-c]pyrazol-3-yl}-3-benzoylpropionamide;
N-{5-phenylethyl-4,6-dihydropyrrolo[3,4-c]pyrazol-3-yl}-4-acetamidobenzamide;
N-{5-phenylethyl-4,6-dihydropyrrolo[3,4-c]pyrazol-3-yl}-2,5-dimethoxybenzamide;
N-{5-phenylethyl-4,6-dihydropyrrolo[3,4-c]pyrazol-3-yl}-2,6-dimethoxybenzamide;
N-{5-phenylethyl-4,6-dihydropyrrolo[3,4-c]pyrazol-3-yl}-3,4-dimethoxybenzamide;
N-{5-phenylethyl-4,6-dihydropyrrolo[3,4-c]pyrazol-3-yl}-3,5-dimethoxybenzamide;
N-{5-phenylethyl-4,6-dihydropyrrolo[3,4-c]pyrazol-3-yl}-3-(2-thenoyl)-propionamide;
N-{5-phenylethyl-4,6-dihydropyrrolo[3,4-c]pyrazol-3-yl}-2-naphtylacetamide
N-{5-phenylethyl-4,6-dihydropyrrolo[3,4-c]pyrazol-3-yl}-1-naphtylacetamide
N-{5-phenylethyl-4,6-dihydropyrrolo[3,4-c]pyrazol-3-yl}-4-phenylbenzamide
N-{5-methansulfonyl-4,6-dihydropyrrolo[3,4-c]pyrazol-3-yl}-acetamide;
N-{5-methansulfonyl-4,6-dihydropyrrolo[3,4-c]pyrazol-3-yl}-cyclopropanecarboxamide;
N-{5-methansulfonyl-4,6-dihydropyrrolo[3,4-c]pyrazol-3-yl}-isobutyramide;
N-{5-methansulfonyl-4,6-dihydropyrrolo[3,4-c]pyrazol-3-yl}-cyclopentanecarboxamide;
N-{5-methansulfonyl-4,6-dihydropyrrolo[3,4-c]pyrazol-3-yl}-benzamide;
N-{5-methansulfonyl-4,6-dihydropyrrolo[3,4-c]pyrazol-3-yl}-picolinic amide;
N-{5-methansulfonyl-4,6-dihydropyrrolo[3,4-c]pyrazol-3-yl}-nicotinic amide;
N-{5-methansulfonyl-4,6-dihydropyrrolo[3,4-c]pyrazol-3-yl}-isonicotinic amide;
N-{5-methansulfonyl-4,6-dihydropyrrolo[3,4-c]pyrazol-3-yl}-3-methyl-2-furoic amide;
N-{5-methansulfonyl-4,6-dihydropyrrolo[3,4-c]pyrazol-3-yl}-thiophene-2-carboxamide;
N-{5-methansulfonyl-4,6-dihydropyrrolo[3,4-c]pyrazol-3-yl}-thiophene-3-carboxamide;
N-{5-methansulfonyl-4,6-dihydropyrrolo[3,4-c]pyrazol-3-yl}-o-toluic amide;
N-{5-methansulfonyl-4,6-dihydropyrrolo[3,4-c]pyrazol-3-yl}-m-toluic amide;
N-{5-methansulfonyl-4,6-dihydropyrrolo[3,4-c]pyrazol-3-yl}-p-toluic amide;
N-{5-methansulfonyl-4,6-dihydropyrrolo[3,4-c]pyrazol-3-yl}-phenylacetamide;
N-{5-methansulfonyl-4,6-dihydropyrrolo[3,4-c]pyrazol-3-yl}-salicylic amide;
N-{5-methansulfonyl-4,6-dihydropyrrolo[3,4-c]pyrazol-3-yl}-2-fluorobenzamide;
N-{5-methansulfonyl-4,6-dihydropyrrolo[3,4-c]pyrazol-3-yl}-3-fluorobenzamide;
N-{5-methansulfonyl-4,6-dihydropyrrolo[3,4-c]pyrazol-3-yl}-4-fluorobenzamide;
N-{5-methansulfonyl-4,6-dihydropyrrolo[3,4-c]pyrazol-3-yl}-thiophene-2-acetamide;
N-{5-methansulfonyl-4,6-dihydropyrrolo[3,4-c]pyrazol-3-yl}-thiophene-3-acetamide;
N-{5-methansulfonyl-4,6-dihydropyrrolo[3,4-c]pyrazol-3-yl}-phenylpropiolic amide;
N-{5-methansulfonyl-4,6-dihydropyrrolo[3,4-c]pyrazol-3-yl}-3-cyanobenzamide;
N-{5-methansulfonyl-4,6-dihydropyrrolo[3,4-c]pyrazol-3-yl}-4-cyanobenzamide;
N-{5-methansulfonyl-4,6-dihydropyrrolo[3,4-c]pyrazol-3-yl}-trans-cinnamic amide;
N-{5-methansulfonyl-4,6-dihydropyrrolo[3,4-c]pyrazol-3-yl}-cis-cinnamic amide;
N-{5-methansulfonyl-4,6-dihydropyrrolo[3,4-c]pyrazol-3-yl}-3-(3-pyridyl)acrylic amide;
N-{5-methansulfonyl-4,6-dihydropyrrolo[3,4-c]pyrazol-3-yl}-3-(4-pyridyl)-acrylic amide;
N-{5-methansulfonyl-4,6-dihydropyrrolo[3,4-c]pyrazol-3-yl}-2-phenylpropionamide;
N-{5-methansulfonyl-4,6-dihydropyrrolo[3,4-c]pyrazol-3-yl}-o-tolylacetamide;
N-{5-methansulfonyl-4,6-dihydropyrrolo[3,4-c]pyrazol-3-yl}-m-tolylacetamide;
N-{5-methansulfonyl-4,6-dihydropyrrolo[3,4-c]pyrazol-3-yl}-p-tolylacetamide;
N-{5-methansulfonyl-4,6-dihydropyrrolo[3,4-c]pyrazol-3-yl}-o-anisic amide;
N-{5-methansulfonyl-4,6-dihydropyrrolo[3,4-c]pyrazol-3-yl}-3-methoxybenzamide;
N-{5-methansulfonyl-4,6-dihydropyrrolo[3,4-c]pyrazol-3-yl}-p-anisic amide;
N-{5-methansulfonyl-4,6-dihydropyrrolo[3,4-c]pyrazol-3-yl}-phenoxyacetamide;
N-{5-methansulfonyl-4,6-dihydropyrrolo[3,4-c]pyrazol-3-yl}-2-fluorophenylacetamide;
N-{5-methansulfonyl-4,6-dihydropyrrolo[3,4-c]pyrazol-3-yl}-3-fluorophenylacetamide;
N-{5-methansulfonyl-4,6-dihydropyrrolo[3,4-c]pyrazol-3-yl}-4-fluorophenylacetamide;
N-{5-methansulfonyl-4,6-dihydropyrrolo[3,4-c]pyrazol-3-yl}-3-(2-thienyl)acrylic amide;
N-{5-methansulfonyl-4,6-dihydropyrrolo[3,4-c]pyrazol-3-yl}-3-(3-thienyl)-acrylic amide;
N-{5-methansulfonyl-4,6-dihydropyrrolo[3,4-c]pyrazol-3-yl}-3-(2-thienyl)propanoic amide;
N-{5-methansulfonyl-4,6-dihydropyrrolo[3,4-c]pyrazol-3-yl}-2-chlorobenzamide;
N-{5-methansulfonyl-4,6-dihydropyrrolo[3,4-c]pyrazol-3-yl}-3-chlorobenzamide;
N-{5-methansulfonyl-4,6-dihydropyrrolo[3,4-c]pyrazol-3-yl}-4-chlorobenzamide;
N-{5-methansulfonyl-4,6-dihydropyrrolo[3,4-c]pyrazol-3-yl}-1-piperidinepropionamide;
N-{5-methansulfonyl-4,6-dihydropyrrolo[3,4-c]pyrazol-3-yl}-2-acetylbenzamide;
N-{5-methansulfonyl-4,6-dihydropyrrolo[3,4-c]pyrazol-3-yl}-4-acetylbenzamide;
N-{5-methansulfonyl-4,6-dihydropyrrolo[3,4-c]pyrazol-3-yl}-1-naphthoic amide;

N-{5-methansulfonyl-4,6-dihydropyrrolo[3,4-c]pyrazol-3-yl}-2-naphthoic amide;
N-{5-methansulfonyl-4,6-dihydropyrrolo[3,4-c]pyrazol-3-yl}-3-benzoylpropionamide;
N-{5-methansulfonyl-4,6-dihydropyrrolo[3,4-c]pyrazol-3-yl}-4-acetamidobenzamide;
N-{5-methansulfonyl-4,6-dihydropyrrolo[3,4-c]pyrazol-3-yl}-2,5-dimethoxybenzamide;
N-{5-methansulfonyl-4,6-dihydropyrrolo[3,4-c]pyrazol-3-yl}-2,6-dimethoxybenzamide;
N-{5-methansulfonyl-4,6-dihydropyrrolo[3,4-c]pyrazol-3-yl}-3,4-dimethoxybenzamide;
N-{5-methansulfonyl-4,6-dihydropyrrolo[3,4-c]pyrazol-3-yl}-3,5-dimethoxybenzamide;
N-{5-methansulfonyl-4,6-dihydropyrrolo[3,4-c]pyrazol-3-yl}-3-(2-thenoyl)-propionamide;
N-{5-methansulfonyl-4,6-dihydropyrrolo[3,4-c]pyrazol-3-yl}-2-naphtylacetamide
N-{5-methansulfonyl-4,6-dihydropyrrolo[3,4-c]pyrazol-3-yl}-1-naphtylacetamide
N-{5-methansulfonyl-4,6-dihydropyrrolo[3,4-c]pyrazol-3-yl}-4-phenylbenzamide
N-{5-ethylaminocarbonyl-4,6-dihydropyrrolo[3,4-c]pyrazol-3-yl}-acetamide;
N-{5-ethylaminocarbonyl-4,6-dihydropyrrolo[3,4-c]pyrazol-3-yl}-cyclopropanecarboxamide;
N-{5-ethylaminocarbonyl-4,6-dihydropyrrolo[3,4-c]pyrazol-3-yl}-isobutyramide;
N-{5-ethylaminocarbonyl-4,6-dihydropyrrolo[3,4-c]pyrazol-3-yl}-cyclopentanecarboxamide;
N-{5-ethylaminocarbonyl-4,6-dihydropyrrolo[3,4-c]pyrazol-3-yl}-benzamide;
N-{5-ethylaminocarbonyl-4,6-dihydropyrrolo[3,4-c]pyrazol-3-yl}-picolinic amide;
N-{5-ethylaminocarbonyl-4,6-dihydropyrrolo[3,4-c]pyrazol-3-yl}-nicotinic amide;
N-{5-ethylaminocarbonyl-4,6-dihydropyrrolo[3,4-c]pyrazol-3-yl}-isonicotinic amide;
N-{5-ethylaminocarbonyl-4,6-dihydropyrrolo[3,4-c]pyrazol-3-yl}-3-methyl-2-furoic amide;
N-{5-ethylaminocarbonyl-4,6-dihydropyrrolo[3,4-c]pyrazol-3-yl}-thiophene-2-carboxamide;
N-{5-ethylaminocarbonyl-4,6-dihydropyrrolo[3,4-c]pyrazol-3-yl}-thiophene-3-carboxamide;
N-{5-ethylaminocarbonyl-4,6-dihydropyrrolo[3,4-c]pyrazol-3-yl}-m-toluic amide;
N-{5-ethylaminocarbonyl-4,6-dihydropyrrolo[3,4-c]pyrazol-3-yl}-p-toluic amide;
N-{5-ethylaminocarbonyl-4,6-dihydropyrrolo[3,4-c]pyrazol-3-yl}-salicylic amide;
N-{5-ethylaminocarbonyl-4,6-dihydropyrrolo[3,4-c]pyrazol-3-yl}-2-fluorobenzamide;
N-{5-ethylaminocarbonyl-4,6-dihydropyrrolo[3,4-c]pyrazol-3-yl}-3-fluorobenzamide;
N-{5-ethylaminocarbonyl-4,6-dihydropyrrolo[3,4-c]pyrazol-3-yl}-4-fluorobenzamide;
N-{5-ethylaminocarbonyl-4,6-dihydropyrrolo[3,4-c]pyrazol-3-yl}-thiophene-2-acetamide;
N-{5-ethylaminocarbonyl-4,6-dihydropyrrolo[3,4-c]pyrazol-3-yl}-thiophene-3-acetamide;
N-{5-ethylaminocarbonyl-4,6-dihydropyrrolo[3,4-c]pyrazol-3-yl}-phenylpropiolic amide;
N-{5-ethylaminocarbonyl-4,6-dihydropyrrolo[3,4-c]pyrazol-3-yl}-3-cyanobenzamide;
N-{5-ethylaminocarbonyl-4,6-dihydropyrrolo[3,4-c]pyrazol-3-yl}cyanobenzamide;
N-{5-ethylaminocarbonyl-4,6-dihydropyrrolo[3,4-c]pyrazol-3-yl}-trans-cinnamic amide;
N-{5-ethylaminocarbonyl-4,6-dihydropyrrolo[3,4-c]pyrazol-3-yl}-cis-cinnamic amide;
N-{5-ethylaminocarbonyl-4,6-dihydropyrrolo[3,4-c]pyrazol-3-yl}-3-(3-pyridyl)acrylic amide;
N-{5-ethylaminocarbonyl-4,6-dihydropyrrolo[3,4-c]pyrazol-3-yl}-3-(4-pyridyl)-acrylic amide;
N-{5-ethylaminocarbonyl-4,6-dihydropyrrolo[3,4-c]pyrazol-3-yl}-2-phenylpropionamide;
N-{5-ethylaminocarbonyl-4,6-dihydropyrrolo[3,4-c]pyrazol-3-yl}-o-tolylacetamide;
N-{5-ethylaminocarbonyl-4,6-dihydropyrrolo[3,4-c]pyrazol-3-yl}-m-tolylacetamide;
N-{5-ethylaminocarbonyl-4,6-dihydropyrrolo[3,4-c]pyrazol-3-yl}-p-tolylacetamide;
N-{5-ethylaminocarbonyl-4,6-dihydropyrrolo[3,4-c]pyrazol-3-yl}-o-anisic amide;
N-{5-ethylaminocarbonyl-4,6-dihydropyrrolo[3,4-c]pyrazol-3-yl}-3-methoxybenzamide;
N-{5-ethylaminocarbonyl-4,6-dihydropyrrolo[3,4-c]pyrazol-3-yl}-p-anisic amide;
N-{5-ethylaminocarbonyl-4,6-dihydropyrrolo[3,4-c]pyrazol-3-yl}-phenoxyacetamide;
N-{5-ethylaminocarbonyl-4,6-dihydropyrrolo[3,4-c]pyrazol-3-yl}-2-fluorophenylacetamide;
N-{5-ethylaminocarbonyl-4,6-dihydropyrrolo[3,4-c]pyrazol-3-yl}-3-fluorophenylacetamide;
N-{5-ethylaminocarbonyl-4,6-dihydropyrrolo[3,4-c]pyrazol-3-yl}-4-fluorophenylacetamide;
N-{5-ethylaminocarbonyl-4,6-dihydropyrrolo[3,4-c]pyrazol-3-yl}-3-(2-thienyl)acrylic amide;
N-{5-ethylaminocarbonyl-4,6-dihydropyrrolo[3,4-c]pyrazol-3-yl}-3-(3-thienyl)-acrylic amide;
N-{5-ethylaminocarbonyl-4,6-dihydropyrrolo[3,4-c]pyrazol-3-yl}-3-(2-thienyl)propanoic amide;
N-{5-ethylaminocarbonyl-4,6-dihydropyrrolo[3,4-c]pyrazol-3-yl}-2-chlorobenzamide;
N-{5-ethylaminocarbonyl-4,6-dihydropyrrolo[3,4-c]pyrazol-3-yl}-3-chlorobenzamide;
N-{5-ethylaminocarbonyl-4,6-dihydropyrrolo[3,4-c]pyrazol-3-yl}-4-chlorobenzamide;
N-{5-ethylaminocarbonyl-4,6-dihydropyrrolo[3,4-c]pyrazol-3-yl}-1-piperidinepropionamide;
N-{5-ethylaminocarbonyl-4,6-dihydropyrrolo[3,4-c]pyrazol-3-yl}-2-acetylbenzamide;
N-{5-ethylaminocarbonyl-4,6-dihydropyrrolo[3,4-c]pyrazol-3-yl}-4-acetylbenzamide;
N-{5-ethylaminocarbonyl-4,6-dihydropyrrolo[3,4-c]pyrazol-3-yl}-1-naphthoic amide;
N-{5-ethylaminocarbonyl-4,6-dihydropyrrolo[3,4-c]pyrazol-3-yl}-2-naphthoic amide;
N-{5-ethylaminocarbonyl-4,6-dihydropyrrolo[3,4-c]pyrazol-3-yl}-3-benzoylpropionamide;
N-{5-ethylaminocarbonyl-4,6-dihydropyrrolo[3,4-c]pyrazol-3-yl}-4-acetamidobenzamide;
N-{5-ethylaminocarbonyl-4,6-dihydropyrrolo[3,4-c]pyrazol-3-yl}-2,5-dimethoxybenzamide;
N-{5-ethylaminocarbonyl-4,6-dihydropyrrolo[3,4-c]pyrazol-3-yl}-2,6-dimethoxybenzamide;
N-{5-ethylaminocarbonyl-4,6-dihydropyrrolo[3,4-c]pyrazol-3-yl}-3,4-dimethoxybenzamide;
N-{5-ethylaminocarbonyl-4,6-dihydropyrrolo[3,4-c]pyrazol-3-yl}-3,5-dimethoxybenzamide;
N-{5-ethylaminocarbonyl-4,6-dihydropyrrolo[3,4-c]pyrazol-3-yl}-3-(2-thenoyl)-propionamide;

N-{5-ethylaminocarbonyl-4,6-dihydropyrrolo[3,4-c]pyrazol-3-yl}-2-naphtylacetamide
N-{5-ethylaminocarbonyl-4,6-dihydropyrrolo[3,4-c]pyrazol-3-yl}-1-naphtylacetamide
N-{5-ethylaminocarbonyl-4,6-dihydropyrrolo[3,4-c]pyrazol-3-yl}-4-phenylbenzamide
N-{5-phenylaminocarbonyl-4,6-dihydropyrrolo[3,4-c]pyrazol-3-yl}-acetamide;
N-{5-phenylaminocarbonyl-4,6-dihydropyrrolo[3,4-c]pyrazol-3-yl}-cyclopropanecarboxamide;
N-{5-phenylaminocarbonyl-4,6-dihydropyrrolo[3,4-c]pyrazol-3-yl}-isobutyramide;
N-{5-phenylaminocarbonyl-4,6-dihydropyrrolo[3,4-c]pyrazol-3-yl}-cyclopentanecarboxamide;
N-{5-phenylaminocarbonyl-4,6-dihydropyrrolo[3,4-c]pyrazol-3-yl}-benzamide;
N-{5-phenylaminocarbonyl-4,6-dihydropyrrolo[3,4-c]pyrazol-3-yl}-picolinic amide;
N-{5-phenylaminocarbonyl-4,6-dihydropyrrolo[3,4-c]pyrazol-3-yl}-nicotinic amide;
N-{5-phenylaminocarbonyl-4,6-dihydropyrrolo[3,4-c]pyrazol-3-yl}-isonicotinic amide;
N-{5-phenylaminocarbonyl-4,6-dihydropyrrolo[3,4-c]pyrazol-3-yl}-3-methyl-2-furoic amide;
N-{5-phenylaminocarbonyl-4,6-dihydropyrrolo[3,4-c]pyrazol-3-yl}-thiophene-2-carboxamide;
N-{5-phenylaminocarbonyl-4,6-dihydropyrrolo[3,4-c]pyrazol-3-yl}-thiophene-3-carboxamide;
N-{5-phenylaminocarbonyl-4,6-dihydropyrrolo[3,4-c]pyrazol-3-yl}-o-toluic amide;
N-{5-phenylaminocarbonyl-4,6-dihydropyrrolo[3,4-c]pyrazol-3-yl}-m-toluic amide;
N-{5-phenylaminocarbonyl-4,6-dihydropyrrolo[3,4-c]pyrazol-3-yl}-p-toluic amide;
N-{5-phenylaminocarbonyl-4,6-dihydropyrrolo[3,4-c]pyrazol-3-yl}-phenylacetamide;
N-{5-phenylaminocarbonyl-4,6-dihydropyrrolo[3,4-c]pyrazol-3-yl}-salicylic amide;
N-{5-phenylaminocarbonyl-4,6-dihydropyrrolo[3,4-c]pyrazol-3-yl}-2-fluorobenzamide;
N-{5-phenylaminocarbonyl-4,6-dihydropyrrolo[3,4-c]pyrazol-3-yl}-3-fluorobenzamide;
N-{5-phenylaminocarbonyl-4,6-dihydropyrrolo[3,4-c]pyrazol-3-yl}-4-fluorobenzamide;
N-{5-phenylaminocarbonyl-4,6-dihydropyrrolo[3,4-c]pyrazol-3-yl}-thiophene-2-acetamide;
N-{5-phenylaminocarbonyl-4,6-dihydropyrrolo[3,4-c]pyrazol-3-yl}-thiophene-3-acetamide;
N-{5-phenylaminocarbonyl-4,6-dihydropyrrolo[3,4-c]pyrazol-3-yl}-phenylpropiolic amide;
N-{5-phenylaminocarbonyl-4,6-dihydropyrrolo[3,4-c]pyrazol-3-yl}-3-cyanobenzamide;
N-{5-phenylaminocarbonyl-4,6-dihydropyrrolo[3,4-c]pyrazol-3-yl}-4-cyanobenzamide;
N-{5-phenylaminocarbonyl-4,6-dihydropyrrolo[3,4-c]pyrazol-3-yl}-trans-cinnamic amide;
N-{5-phenylaminocarbonyl-4,6-dihydropyrrolo[3,4-c]pyrazol-3-yl}-cis-cinnamic amide;
N-{5-phenylaminocarbonyl-4,6-dihydropyrrolo[3,4-c]pyrazol-3-yl}-3-(3-pyridyl)acrylic amide;
N-{5-phenylaminocarbonyl-4,6-dihydropyrrolo[3,4-c]pyrazol-3-yl}-3-(4-pyridyl)-acrylic amide;
N-{5-phenylaminocarbonyl-4,6-dihydropyrrolo[3,4-c]pyrazol-3-yl}-2-phenylpropanamide;
N-{5-phenylaminocarbonyl-4,6-dihydropyrrolo[3,4-c]pyrazol-3-yl}-o-tolylacetamide;
N-{5-phenylaminocarbonyl-4,6-dihydropyrrolo[3,4-c]pyrazol-3-yl}-m-tolylacetamide;
N-{5-phenylaminocarbonyl-4,6-dihydropyrrolo[3,4-c]pyrazol-3-yl}-p-tolylacetamide;
N-{5-phenylaminocarbonyl-4,6-dihydropyrrolo[3,4-c]pyrazol-3-yl}-o-anisic amide;
N-{5-phenylaminocarbonyl-4,6-dihydropyrrolo[3,4-c]pyrazol-3-yl}-3-methoxybenzamide;
N-{5-phenylaminocarbonyl-4,6-dihydropyrrolo[3,4-c]pyrazol-3-yl}-p-anisic amide;
N-{5-phenylaminocarbonyl-4,6-dihydropyrrolo[3,4-c]pyrazol-3-yl}-phenoxyacetamide;
N-{5-phenylaminocarbonyl-4,6-dihydropyrrolo[3,4-c]pyrazol-3-yl}-2-fluorophenylacetamide;
N-{5-phenylaminocarbonyl-4,6-dihydropyrrolo[3,4-c]pyrazol-3-yl}-3-fluorophenylacetamide;
N-{5-phenylaminocarbonyl-4,6-dihydropyrrolo[3,4-c]pyrazol-3-yl}-4-fluorophenylacetamide;
N-{5-phenylaminocarbonyl-4,6-dihydropyrrolo[3,4-c]pyrazol-3-yl}-3-(2-thienyl)acrylic amide;
N-{5-phenylaminocarbonyl-4,6-dihydropyrrolo[3,4-c]pyrazol-3-yl}-3-(3-thienyl)-acrylic amide;
N-{5-phenylaminocarbonyl-4,6-dihydropyrrolo[3,4-c]pyrazol-3-yl}-3-(2-thienyl)propanoic amide;
N-{5-phenylaminocarbonyl-4,6-dihydropyrrolo[3,4-c]pyrazol-3-yl}-2-chlorobenzamide;
N-{5-phenylaminocarbonyl-4,6-dihydropyrrolo[3,4-c]pyrazol-3-yl}-3-chlorobenzamide;
N-{5-phenylaminocarbonyl-4,6-dihydropyrrolo[3,4-c]pyrazol-3-yl}-4-chlorobenzamide;
N-{5-phenylaminocarbonyl-4,6-dihydropyrrolo[3,4-c]pyrazol-3-yl}-1-piperidinepropionamide;
N-{5-phenylaminocarbonyl-4,6-dihydropyrrolo[3,4-c]pyrazol-3-yl}-2-acetylbenzamide;
N-{5-phenylaminocarbonyl-4,6-dihydropyrrolo[3,4-c]pyrazol-3-yl}-4-acetylbenzamide;
N-{5-phenylaminocarbonyl-4,6-dihydropyrrolo[3,4-c]pyrazol-3-yl}-1-naphthoic amide;
N-{5-phenylaminocarbonyl-4,6-dihydropyrrolo[3,4-c]pyrazol-3-yl}-2-naphthoic amide;
N-{5-phenylaminocarbonyl-4,6-dihydropyrrolo[3,4-c]pyrazol-3-yl}-3-benzoylpropionamide;
N-{5-phenylaminocarbonyl-4,6-dihydropyrrolo[3,4-c]pyrazol-3-yl}-4-acetamidobenzamide;
N-{5-phenylaminocarbonyl-4,6-dihydropyrrolo[3,4-c]pyrazol-3-yl}-2,5-dimethoxybenzamide;
N-{5-phenylaminocarbonyl-4,6-dihydropyrrolo[3,4-c]pyrazol-3-yl}-2,6-dimethoxybenzamide;
N-{5-phenylaminocarbonyl-4,6-dihydropyrrolo[3,4-c]pyrazol-3-yl}-3,4-dimethoxybenzamide;
N-{5-phenylaminocarbonyl-4,6-dihydropyrrolo[3,4-c]pyrazol-3-yl}-3,5-dimethoxybenzamide;
N-{5-phenylaminocarbonyl-4,6-dihydropyrrolo[3,4-c]pyrazol-3-yl}-3-(2-thenoyl)-propionamide;
N-{5-phenylaminocarbonyl-4,6-dihydropyrrolo[3,4-c]pyrazol-3-yl}-2-naphtylacetamide
N-{5-phenylaminocarbonyl-4,6-dihydropyrrolo[3,4-c]pyrazol-3-yl}-1-naphtylacetamide
N-{5-phenylaminocarbonyl-4,6-dihydropyrrolo[3,4-c]pyrazol-3-yl}-4-phenylbenzamide
N-{5-benzylaminocarbonyl-4,6-dihydropyrrolo[3,4-c]pyrazol-3-yl}-acetamide;
N-{5-benzylaminocarbonyl-4,6-dihydropyrrolo[3,4-c]pyrazol-3-yl}-cyclopropanecarboxamide;
N-{5-benzylaminocarbonyl-4,6-dihydropyrrolo[3,4-c]pyrazol-3-yl}-isobutyramide;

N-{5-benzylaminocarbonyl-4,6-dihydropyrrolo[3,4-c]pyrazol-3-yl}-cyclopentanecarboxamide;
N-{5-benzylaminocarbonyl-4,6-dihydropyrrolo[3,4-c]pyrazol-3-yl}-benzamide;
N-{5-benzylaminocarbonyl-4,6-dihydropyrrolo[3,4-c]pyrazol-3-yl}-picolinic amide;
N-{5-benzylaminocarbonyl-4,6-dihydropyrrolo[3,4-c]pyrazol-3-yl}-nicotinic amide;
N-{5-benzylaminocarbonyl-4,6-dihydropyrrolo[3,4-c]pyrazol-3-yl}-isonicotinic amide;
N-{5-benzylaminocarbonyl-4,6-dihydropyrrolo[3,4-c]pyrazol-3-yl}-3-methyl-2-furoic amide;
N-{5-benzylaminocarbonyl-4,6-dihydropyrrolo[3,4-c]pyrazol-3-yl}-thiophene-2-carboxamide;
N-{5-benzylaminocarbonyl-4,6-dihydropyrrolo[3,4-c]pyrazol-3-yl}-thiophene-3-carboxamide;
N-{5-benzylaminocarbonyl-4,6-dihydropyrrolo[3,4-c]pyrazol-3-yl}-o-toluic amide;
N-{5-benzylaminocarbonyl-4,6-dihydropyrrolo[3,4-c]pyrazol-3-yl}-m-toluic amide;
N-{5-benzylaminocarbonyl-4,6-dihydropyrrolo[3,4-c]pyrazol-3-yl}-p-toluic amide;
N-{5-benzylaminocarbonyl-4,6-dihydropyrrolo[3,4-c]pyrazol-3-yl}-salicylic amide;
N-{5-benzylaminocarbonyl-4,6-dihydropyrrolo[3,4-c]pyrazol-3-yl}-2-fluorobenzamide;
N-{5-benzylaminocarbonyl-4,6-dihydropyrrolo[3,4-c]pyrazol-3-yl}-3-fluorobenzamide;
N-{5-benzylaminocarbonyl-4,6-dihydropyrrolo[3,4-c]pyrazol-3-yl}-4-fluorobenzamide;
N-{5-benzylaminocarbonyl-4,6-dihydropyrrolo[3,4-c]pyrazol-3-yl}-thiophene-2-acetamide;
N-{5-benzylaminocarbonyl-4,6-dihydropyrrolo[3,4-c]pyrazol-3-yl}-thiophene-3-acetamide;
N-{5-benzylaminocarbonyl-4,6-dihydropyrrolo[3,4-c]pyrazol-3-yl}-phenylpropiolic amide;
N-{5-benzylaminocarbonyl-4,6-dihydropyrrolo[3,4-c]pyrazol-3-yl}-3-cyanobenzamide;
N-{5-benzylaminocarbonyl-4,6-dihydropyrrolo[3,4-c]pyrazol-3-yl}-4-cyanobenzamide;
N-{5-benzylaminocarbonyl-4,6-dihydropyrrolo[3,4-c]pyrazol-3-yl}-trans-cinnamic amide;
N-{5-benzylaminocarbonyl-4,6-dihydropyrrolo[3,4-c]pyrazol-3-yl}-cis-cinnamic amide;
N-{5-benzylaminocarbonyl-4,6-dihydropyrrolo[3,4-c]pyrazol-3-yl}-3-(3-pyridyl)acrylic amide;
N-{5-benzylaminocarbonyl-4,6-dihydropyrrolo[3,4-c]pyrazol-3-yl}-3-(4-pyridyl)-acrylic amide;
N-{5-benzylaminocarbonyl-4,6-dihydropyrrolo[3,4-c]pyrazol-3-yl}-2-phenylpropionamide;
N-{5-benzylaminocarbonyl-4,6-dihydropyrrolo[3,4-c]pyrazol-3-yl}-o-tolylacetamide;
N-{5-benzylaminocarbonyl-4,6-dihydropyrrolo[3,4-c]pyrazol-3-yl}-m-tolylacetamide;
N-{5-benzylaminocarbonyl-4,6-dihydropyrrolo[3,4-c]pyrazol-3-yl}-p-tolylacetamide;
N-{5-benzylaminocarbonyl-4,6-dihydropyrrolo[3,4-c]pyrazol-3-yl}-o-anisic amide;
N-{5-benzylaminocarbonyl-4,6-dihydropyrrolo[3,4-c]pyrazol-3-yl}-3-methoxybenzamide;
N-{5-benzylaminocarbonyl-4,6-dihydropyrrolo[3,4-c]pyrazol-3-yl}-p-anisic amide;
N-{5-benzylaminocarbonyl-4,6-dihydropyrrolo[3,4-c]pyrazol-3-yl}-phenoxyacetamide;
N-{5-benzylaminocarbonyl-4,6-dihydropyrrolo[3,4-c]pyrazol-3-yl}-2-fluorophenylacetamide;
N-{5-benzylaminocarbonyl-4,6-dihydropyrrolo[3,4-c]pyrazol-3-yl}-3-fluorophenylacetamide;
N-{5-benzylaminocarbonyl-4,6-dihydropyrrolo[3,4-c]pyrazol-3-yl}-4-fluorophenylacetamide;
N-{5-benzylaminocarbonyl-4,6-dihydropyrrolo[3,4-c]pyrazol-3-yl}-3-(2-thienyl)acrylic amide;
N-{5-benzylaminocarbonyl-4,6-dihydropyrrolo[3,4-c]pyrazol-3-yl}-3-(3-thienyl)-acrylic amide;
N-{5-benzylaminocarbonyl-4,6-dihydropyrrolo[3,4-c]pyrazol-3-yl}-3-(2-thienyl)propanoic amide;
N-{5-benzylaminocarbonyl-4,6-dihydropyrrolo[3,4-c]pyrazol-3-yl}-2-chlorobenzamide;
N-{5-benzylaminocarbonyl-4,6-dihydropyrrolo[3,4-c]pyrazol-3-yl}-3-chlorobenzamide;
N-{5-benzylaminocarbonyl-4,6-dihydropyrrolo[3,4-c]pyrazol-3-yl}-4-chlorobenzamide;
N-{5-benzylaminocarbonyl-4,6-dihydropyrrolo[3,4-c]pyrazol-3-yl}-1-piperidinepropionamide;
N-{5-benzylaminocarbonyl-4,6-dihydropyrrolo[3,4-c]pyrazol-3-yl}-2-acetylbenzamide;
N-{5-benzylaminocarbonyl-4,6-dihydropyrrolo[3,4-c]pyrazol-3-yl}-4-acetylbenzamide;
N-{5-benzylaminocarbonyl-4,6-dihydropyrrolo[3,4-c]pyrazol-3-yl}-1-naphthoic amide;
N-{5-benzylaminocarbonyl-4,6-dihydropyrrolo[3,4-c]pyrazol-3-yl}-2-naphthoic amide;
N-{5-benzylaminocarbonyl-4,6-dihydropyrrolo[3,4-c]pyrazol-3-yl}-3-benzoylpropionamide;
N-{5-benzylaminocarbonyl-4,6-dihydropyrrolo[3,4-c]pyrazol-3-yl}-4-acetamidobenzamide;
N-{5-benzylaminocarbonyl-4,6-dihydropyrrolo[3,4-c]pyrazol-3-yl}-2,5-dimethoxybenzamide;
N-{5-benzylaminocarbonyl-4,6-dihydropyrrolo[3,4-c]pyrazol-3-yl}-2,6-dimethoxybenzamide;
N-{5-benzylaminocarbonyl-4,6-dihydropyrrolo[3,4-c]pyrazol-3-yl}-3,4-dimethoxybenzamide;
N-{5-benzylaminocarbonyl-4,6-dihydropyrrolo[3,4-c]pyrazol-3-yl}-3,5-dimethoxybenzamide;
N-{5-benzylaminocarbonyl-4,6-dihydropyrrolo[3,4-c]pyrazol-3-yl}-3-(2-thenoyl)-propionamide;
N-{5-benzylaminocarbonyl-4,6-dihydropyrrolo[3,4-c]pyrazol-3-yl}-2-naphtylacetamide
N-{5-benzylaminocarbonyl-4,6-dihydropyrrolo[3,4-c]pyrazol-3-yl}-1-naphtylacetamide
N-{5-benzylaminocarbonyl-4,6-dihydropyrrolo[3,4-c]pyrazol-3-yl}-4-phenylbenzamide
N-{5-benzoylaminocarbonyl-4,6-dihydropyrrolo[3,4-c]pyrazol-3-yl}-acetamide;
N-{5-benzoylaminocarbonyl-4,6-dihydropyrrolo[3,4-c]pyrazol-3-yl}-cyclopropanecarboxamide;
N-{5-benzoylaminocarbonyl-4,6-dihydropyrrolo[3,4-c]pyrazol-3-yl}-isobutyramide;
N-{5-benzoylaminocarbonyl-4,6-dihydropyrrolo[3,4-c]pyrazol-3-yl}-cyclopentanecarboxamide;
N-{5-benzoylaminocarbonyl-4,6-dihydropyrrolo[3,4-c]pyrazol-3-yl}-benzamide;
N-{5-benzoylaminocarbonyl-4,6-dihydropyrrolo[3,4-c]pyrazol-3-yl}-picolinic amide;
N-{5-benzoylaminocarbonyl-4,6-dihydropyrrolo[3,4-c]pyrazol-3-yl}-nicotinic amide;
N-{5-benzoylaminocarbonyl-4,6-dihydropyrrolo[3,4-c]pyrazol-3-yl}-isonicotinic amide;
N-{5-benzoylaminocarbonyl-4,6-dihydropyrrolo[3,4-c]pyrazol-3-yl}-3-methyl-2-furoic amide;
N-{5-benzoylaminocarbonyl-4,6-dihydropyrrolo[3,4-c]pyrazol-3-yl}-thiophene-2-carboxamide;

N-{5-benzoylaminocarbonyl-4,6-dihydropyrrolo[3,4-c]
pyrazol-3-yl}-thiophene-3-carboxamide;
N-{5-benzoylaminocarbonyl-4,6-dihydropyrrolo[3,4-c]
pyrazol-3-yl}-o-toluic amide;
N-{5-benzoylaminocarbonyl-4,6-dihydropyrrolo[3,4-c]
pyrazol-3-yl}-m-toluic amide;
N-{5-benzoylaminocarbonyl-4,6-dihydropyrrolo[3,4-c]
pyrazol-3-yl}-p-toluic amide;
N-{5-benzoylaminocarbonyl-4,6-dihydropyrrolo[3,4-c]
pyrazol-3-yl}-phenylacetamide;
N-{5-benzoylaminocarbonyl-4,6-dihydropyrrolo[3,4-c]
pyrazol-3-yl}-salicylic amide;
N-{5-benzoylaminocarbonyl-4,6-dihydropyrrolo[3,4-c]
pyrazol-3-yl}-2-fluorobenzamide;
N-{5-benzoylaminocarbonyl-4,6-dihydropyrrolo[3,4-c]
pyrazol-3-yl}-3-fluorobenzamide;
N-{5-benzoylaminocarbonyl-4,6-dihydropyrrolo[3,4-c]
pyrazol-3-yl}-4-fluorobenzamide;
N-{5-benzoylaminocarbonyl-4,6-dihydropyrrolo[3,4-c]
pyrazol-3-yl}-thiophene-2-acetamide;
N-{5-benzoylaminocarbonyl-4,6-dihydropyrrolo[3,4-c]
pyrazol-3-yl}-thiophene-3-acetamide;
N-{5-benzoylaminocarbonyl-4,6-dihydropyrrolo[3,4-c]
pyrazol-3-yl}-phenylpropiolic amide;
N-{5-benzoylaminocarbonyl-4,6-dihydropyrrolo[3,4-c]
pyrazol-3-yl}-3-cyanobenzamide;
N-{5-benzoylaminocarbonyl-4,6-dihydropyrrolo[3,4-c]
pyrazol-3-yl}-4-cyanobenzamide;
N-{5-benzoylaminocarbonyl-4,6-dihydropyrrolo[3,4-c]
pyrazol-3-yl}-trans-cinnamic amide;
N-{5-benzoylaminocarbonyl-4,6-dihydropyrrolo[3,4-c]
pyrazol-3-yl}-cis-cinnamic amide;
N-{5-benzoylaminocarbonyl-4,6-dihydropyrrolo[3,4-c]
pyrazol-3-yl}-3-(3-pyridyl)acrylic amide;
N-{5-benzoylaminocarbonyl-4,6-dihydropyrrolo[3,4-c]
pyrazol-3-yl}-3-(4-pyridyl)-acrylic amide;
N-{5-benzoylaminocarbonyl-4,6-dihydropyrrolo[3,4-c]
pyrazol-3-yl}-2-phenylpropionamide;
N-{5-benzoylaminocarbonyl-4,6-dihydropyrrolo[3,4-c]
pyrazol-3-yl}-o-tolylacetamide;
N-{5-benzoylaminocarbonyl-4,6-dihydropyrrolo[3,4-c]
pyrazol-3-yl}-m-tolylacetamide;
N-{5-benzoylaminocarbonyl-4,6-dihydropyrrolo[3,4-c]
pyrazol-3-yl}-p-tolylacetamide;
N-{5-benzoylaminocarbonyl-4,6-dihydropyrrolo[3,4-c]
pyrazol-3-yl}-o-anisic amide;
N-{5-benzoylaminocarbonyl-4,6-dihydropyrrolo[3,4-c]
pyrazol-3-yl}-3-methoxybenzamide;
N-{5-benzoylaminocarbonyl-4,6-dihydropyrrolo[3,4-c]
pyrazol-3-yl}-p-anisic amide;
N-{5-benzoylaminocarbonyl-4,6-dihydropyrrolo[3,4-c]
pyrazol-3-yl}-phenoxyacetamide;
N-{5-benzoylaminocarbonyl-4,6-dihydropyrrolo[3,4-c]
pyrazol-3-yl}-2-fluorophenylacetamide;
N-{5-benzoylaminocarbonyl-4,6-dihydropyrrolo[3,4-c]
pyrazol-3-yl}-3-fluorophenylacetamide;
N-{5-benzoylaminocarbonyl-4,6-dihydropyrrolo[3,4-c]
pyrazol-3-yl}-4-fluorophenylacetamide;
N-{5-benzoylaminocarbonyl-4,6-dihydropyrrolo[3,4-c]
pyrazol-3-yl}-3-(2-thienyl)acrylic amide;
N-{5-benzoylaminocarbonyl-4,6-dihydropyrrolo[3,4-c]
pyrazol-3-yl}-3-(3-thienyl)-acrylic amide;
N-{5-benzoylaminocarbonyl-4,6-dihydropyrrolo[3,4-c]
pyrazol-3-yl}-3-(2-thienyl)propanoic amide;
N-{5-benzoylaminocarbonyl-4,6-dihydropyrrolo[3,4-c]
pyrazol-3-yl}-2-chlorobenzamide;
N-{5-benzoylaminocarbonyl-4,6-dihydropyrrolo[3,4-c]
pyrazol-3-yl}-3-chlorobenzamide;
N-{5-benzoylaminocarbonyl-4,6-dihydropyrrolo[3,4-c]
pyrazol-3-yl}-4-chlorobenzamide;
N-{5-benzoylaminocarbonyl-4,6-dihydropyrrolo[3,4-c]
pyrazol-3-yl}-1-piperidinepropionamide;
N-{5-benzoylaminocarbonyl-4,6-dihydropyrrolo[3,4-c]
pyrazol-3-yl}-2-acetylbenzamide;
N-{5-benzoylaminocarbonyl-4,6-dihydropyrrolo[3,4-c]
pyrazol-3-yl}-4-acetylbenzamide;
N-{5-benzoylaminocarbonyl-4,6-dihydropyrrolo[3,4-c]
pyrazol-3-yl}-1-naphthoic amide;
N-{5-benzoylaminocarbonyl-4,6-dihydropyrrolo[3,4-c]
pyrazol-3-yl}-2-naphthoic amide;
N-{5-benzoylaminocarbonyl-4,6-dihydropyrrolo[3,4-c]
pyrazol-3-yl}-3-benzoylpropionamide;
N-{5-benzoylaminocarbonyl-4,6-dihydropyrrolo[3,4-c]
pyrazol-3-yl}-4-acetamidobenzamide;
N-{5-benzoylaminocarbonyl-4,6-dihydropyrrolo[3,4-c]
pyrazol-3-yl}-2,5-dimethoxybenzamide;
N-{5-benzoylaminocarbonyl-4,6-dihydropyrrolo[3,4-c]
pyrazol-3-yl}-2,6-dimethoxybenzamide;
N-{5-benzoylaminocarbonyl-4,6-dihydropyrrolo[3,4-c]
pyrazol-3-yl}-3,4-dimethoxybenzamide;
N-{5-benzoylaminocarbonyl-4,6-dihydropyrrolo[3,4-c]
pyrazol-3-yl}-3,5-dimethoxybenzamide;
N-{5-benzoylaminocarbonyl-4,6-dihydropyrrolo[3,4-c]
pyrazol-3-yl}-3-(2-thenoyl)-propionamide;
N-{5-benzoylaminocarbonyl-4,6-dihydropyrrolo[3,4-c]
pyrazol-3-yl}-2-naphtylacetamide
N-{5-benzoylaminocarbonyl-4,6-dihydropyrrolo[3,4-c]
pyrazol-3-yl}-1-naphtylacetamide
N-{5-benzoylaminocarbonyl-4,6-dihydropyrrolo[3,4-c]
pyrazol-3-yl}-4-phenylbenzamide
N-{5-aminocarbonyl-4,6-dihydropyrrolo[3,4-c]pyrazol-3-
yl}-acetamide;
N-{5-aminocarbonyl-4,6-dihydropyrrolo[3,4-c]pyrazol-3-
yl}-cyclopropanecarboxamide;
N-{5-aminocarbonyl-4,6-dihydropyrrolo[3,4-c]pyrazol-3-
yl}-isobutyramide;
N-{5-aminocarbonyl-4,6-dihydropyrrolo[3,4-c]pyrazol-3-
yl}-cyclopentanecarboxamide;
N-{5-aminocarbonyl-4,6-dihydropyrrolo[3,4-c]pyrazol-3-
yl}-benzamide;
N-{5-aminocarbonyl-4,6-dihydropyrrolo[3,4-c]pyrazol-3-
yl}-picolinic amide;
N-{5-aminocarbonyl-4,6-dihydropyrrolo[3,4-c]pyrazol-3-
yl}-nicotinic amide;
N-{5-aminocarbonyl-4,6-dihydropyrrolo[3,4-c]pyrazol-3-
yl}-isonicotinic amide;
N-{5-aminocarbonyl-4,6-dihydropyrrolo[3,4-c]pyrazol-3-
yl}-3-methyl-2-furoic amide;
N-{5-aminocarbonyl-4,6-dihydropyrrolo[3,4-c]pyrazol-3-
yl}-thiophene-2-carboxamide;
N-{5-aminocarbonyl-4,6-dihydropyrrolo[3,4-c]pyrazol-3-
yl}-thiophene-3-carboxamide;
N-{5-aminocarbonyl-4,6-dihydropyrrolo[3,4-c]pyrazol-3-
yl}-o-toluic amide;
N-{5-aminocarbonyl-4,6-dihydropyrrolo[3,4-c]pyrazol-3-
yl}-m-toluic amide;
N-{5-aminocarbonyl-4,6-dihydropyrrolo[3,4-c]pyrazol-3-
yl}-p-toluic amide;
N-{5-aminocarbonyl-4,6-dihydropyrrolo[3,4-c]pyrazol-3-
yl}-phenylacetamide;
N-{5-aminocarbonyl-4,6-dihydropyrrolo[3,4-c]pyrazol-3-
yl}-salicylic amide;

N-{5-aminocarbonyl-4,6-dihydropyrrolo[3,4-c]pyrazol-3-yl}-2-fluorobenzamide;
N-{5-aminocarbonyl-4,6-dihydropyrrolo[3,4-c]pyrazol-3-yl}-3-fluorobenzamide;
N-{5-aminocarbonyl-4,6-dihydropyrrolo[3,4-c]pyrazol-3-yl}-4-fluorobenzamide;
N-{5-aminocarbonyl-4,6-dihydropyrrolo[3,4-c]pyrazol-3-yl}-thiophene-2-acetamide;
N-{5-aminocarbonyl-4,6-dihydropyrrolo[3,4-c]pyrazol-3-yl}-thiophene-3-acetamide;
N-{5-aminocarbonyl-4,6-dihydropyrrolo[3,4-c]pyrazol-3-yl}-phenylpropiolic amide;
N-{5-aminocarbonyl-4,6-dihydropyrrolo[3,4-c]pyrazol-3-yl}-3-cyanobenzamide;
N-{5-aminocarbonyl-4,6-dihydropyrrolo[3,4-c]pyrazol-3-yl}-4-cyanobenzamide;
N-{5-aminocarbonyl-4,6-dihydropyrrolo[3,4-c]pyrazol-3-yl}-trans-cinnamic amide;
N-{5-aminocarbonyl-4,6-dihydropyrrolo[3,4-c]pyrazol-3-yl}-cis-cinnamic amide;
N-{5-aminocarbonyl-4,6-dihydropyrrolo[3,4-c]pyrazol-3-yl}-3-(3-pyridyl)acrylic amide;
N-{5-aminocarbonyl-4,6-dihydropyrrolo[3,4-c]pyrazol-3-yl}-3-(4-pyridyl)-acrylic amide;
N-{5-aminocarbonyl-4,6-dihydropyrrolo[3,4-c]pyrazol-3-yl}-2-phenylpropionamide;
N-{5-aminocarbonyl-4,6-dihydropyrrolo[3,4-c]pyrazol-3-yl}-o-tolylacetamide;
N-{5-aminocarbonyl-4,6-dihydropyrrolo[3,4-c]pyrazol-3-yl}-m-tolylacetamide;
N-{5-aminocarbonyl-4,6-dihydropyrrolo[3,4-c]pyrazol-3-yl}-p-tolylacetamide;
N-{5-aminocarbonyl-4,6-dihydropyrrolo[3,4-c]pyrazol-3-yl}-o-anisic amide;
N-{5-aminocarbonyl-4,6-dihydropyrrolo[3,4-c]pyrazol-3-yl}-3-methoxybenzamide;
N-{5-aminocarbonyl-4,6-dihydropyrrolo[3,4-c]pyrazol-3-yl}-p-anisic amide;
N-{5-aminocarbonyl-4,6-dihydropyrrolo[3,4-c]pyrazol-3-yl}-phenoxyacetamide;
N-{5-aminocarbonyl-4,6-dihydropyrrolo[3,4-c]pyrazol-3-yl}-2-fluorophenylacetamide;
N-{5-aminocarbonyl-4,6-dihydropyrrolo[3,4-c]pyrazol-3-yl}-3-fluorophenylacetamide;
N-{5-aminocarbonyl-4,6-dihydropyrrolo[3,4-c]pyrazol-3-yl}-4-fluorophenylacetamide;
N-{5-aminocarbonyl-4,6-dihydropyrrolo[3,4-c]pyrazol-3-yl}-3-(2-thienyl)acrylic amide;
N-{5-aminocarbonyl-4,6-dihydropyrrolo[3,4-c]pyrazol-3-yl}-3-(3-thienyl)-acrylic amide;
N-{5-aminocarbonyl-4,6-dihydropyrrolo[3,4-c]pyrazol-3-yl}-3-(2-thienyl)propanoic amide;
N-{5-aminocarbonyl-4,6-dihydropyrrolo[3,4-c]pyrazol-3-yl}-2-chlorobenzamide;
N-{5-aminocarbonyl-4,6-dihydropyrrolo[3,4-c]pyrazol-3-yl}-3-chlorobenzamide;
N-{5-aminocarbonyl-4,6-dihydropyrrolo[3,4-c]pyrazol-3-yl}-4-chlorobenzamide;
N-{5-aminocarbonyl-4,6-dihydropyrrolo[3,4-c]pyrazol-3-yl}-1-piperidinepropionamide;
N-{5-aminocarbonyl-4,6-dihydropyrrolo[3,4-c]pyrazol-3-yl}-2-acetylbenzamide;
N-{5-aminocarbonyl-4,6-dihydropyrrolo[3,4-c]pyrazol-3-yl}-4-acetylbenzamide;
N-{5-aminocarbonyl-4,6-dihydropyrrolo[3,4-c]pyrazol-3-yl}-1-naphthoic amide;
N-{5-aminocarbonyl-4,6-dihydropyrrolo[3,4-c]pyrazol-3-yl}-2-naphthoic amide;
N-{5-aminocarbonyl-4,6-dihydropyrrolo[3,4-c]pyrazol-3-yl}-3-benzoylpropionamide;
N-{5-aminocarbonyl-4,6-dihydropyrrolo[3,4-c]pyrazol-3-yl}-4-acetamidobenzamide;
N-{5-aminocarbonyl-4,6-dihydropyrrolo[3,4-c]pyrazol-3-yl}-2,5-dimethoxybenzamide;
N-{5-aminocarbonyl-4,6-dihydropyrrolo[3,4-c]pyrazol-3-yl}-2,6-dimethoxybenzamide;
N-{5-aminocarbonyl-4,6-dihydropyrrolo[3,4-c]pyrazol-3-yl}-3,4-dimethoxybenzamide;
N-{5-aminocarbonyl-4,6-dihydropyrrolo[3,4-c]pyrazol-3-yl}-3,5-dimethoxybenzamide;
N-{5-aminocarbonyl-4,6-dihydropyrrolo[3,4-c]pyrazol-3-yl}-3-(2-thenoyl)-propionamide;
N-{5-aminocarbonyl-4,6-dihydropyrrolo[3,4-c]pyrazol-3-yl}-2-naphtylacetamide
N-{5-aminocarbonyl-4,6-dihydropyrrolo[3,4-c]pyrazol-3-yl}-1-naphtylacetamide
N-{5-aminocarbonyl-4,6-dihydropyrrolo[3,4-c]pyrazol-3-yl}-4-phenylbenzamide
N-{5-aminosulfonyl-4,6-dihydropyrrolo[3,4-c]pyrazol-3-yl}-acetamide;
N-{5-aminosulfonyl-4,6-dihydropyrrolo[3,4-c]pyrazol-3-yl}-cyclopropanecarboxamide;
N-{5-aminosulfonyl-4,6-dihydropyrrolo[3,4-c]pyrazol-3-yl}-isobutyramide;
N-{5-aminosulfonyl-4,6-dihydropyrrolo[3,4-c]pyrazol-3-yl}-cyclopentanecarboxamide;
N-{5-aminosulfonyl-4,6-dihydropyrrolo[3,4-c]pyrazol-3-yl}-benzamide;
N-{5-aminosulfonyl-4,6-dihydropyrrolo[3,4-c]pyrazol-3-yl}-picolinic amide;
N-{5-aminosulfonyl-4,6-dihydropyrrolo[3,4-c]pyrazol-3-yl}-nicotinic amide;
N-{5-aminosulfonyl-4,6-dihydropyrrolo[3,4-c]pyrazol-3-yl}-isonicotinic amide;
N-{5-aminosulfonyl-4,6-dihydropyrrolo[3,4-c]pyrazol-3-yl}-3-methyl-2-furoic amide;
N-{5-aminosulfonyl-4,6-dihydropyrrolo[3,4-c]pyrazol-3-yl}-thiophene-2-carboxamide;
N-{5-aminosulfonyl-4,6-dihydropyrrolo[3,4-c]pyrazol-3-yl}-thiophene-3-carboxamide;
N-{5-aminosulfonyl-4,6-dihydropyrrolo[3,4-c]pyrazol-3-yl}-o-toluic amide;
N-{5-aminosulfonyl-4,6-dihydropyrrolo[3,4-c]pyrazol-3-yl}-m-toluic amide;
N-{5-aminosulfonyl-4,6-dihydropyrrolo[3,4-c]pyrazol-3-yl}-p-toluic amide;
N-{5-aminosulfonyl-4,6-dihydropyrrolo[3,4-c]pyrazol-3-yl}-phenylacetamide;
N-{5-aminosulfonyl-4,6-dihydropyrrolo[3,4-c]pyrazol-3-yl}-salicylic amide;
N-{5-aminosulfonyl-4,6-dihydropyrrolo[3,4-c]pyrazol-3-yl}-2-fluorobenzamide;
N-{5-aminosulfonyl-4,6-dihydropyrrolo[3,4-c]pyrazol-3-yl}-3-fluorobenzamide;
N-{5-aminosulfonyl-4,6-dihydropyrrolo[3,4-c]pyrazol-3-yl}-4-fluorobenzamide;
N-{5-aminosulfonyl-4,6-dihydropyrrolo[3,4-c]pyrazol-3-yl}-thiophene-2-acetamide;
N-{5-aminosulfonyl-4,6-dihydropyrrolo[3,4-c]pyrazol-3-yl}-thiophene-3-acetamide;
N-{5-aminosulfonyl-4,6-dihydropyrrolo[3,4-c]pyrazol-3-yl}-phenylpropiolic amide;

N-{5-aminosulfonyl-4,6-dihydropyrrolo[3,4-c]pyrazol-3-yl}-3-cyanobenzamide;
N-{5-aminosulfonyl-4,6-dihydropyrrolo[3,4-c]pyrazol-3-yl}-4-cyanobenzamide;
N-{5-aminosulfonyl-4,6-dihydropyrrolo[3,4-c]pyrazol-3-yl}-trans-cinnamic amide;
N-{5-aminosulfonyl-4,6-dihydropyrrolo[3,4-c]pyrazol-3-yl}-cis-cinnamic amide;
N-{5-aminosulfonyl-4,6-dihydropyrrolo[3,4-c]pyrazol-3-yl}-3-(3-pyridyl)acrylic amide;
N-{5-aminosulfonyl-4,6-dihydropyrrolo[3,4-c]pyrazol-3-yl}-3-(4-pyridyl)-acrylic amide;
N-{5-aminosulfonyl-4,6-dihydropyrrolo[3,4-c]pyrazol-3-yl}-2-phenylpropionamide;
N-{5-aminosulfonyl-4,6-dihydropyrrolo[3,4-c]pyrazol-3-yl}-o-tolylacetamide;
N-{5-aminosulfonyl-4,6-dihydropyrrolo[3,4-c]pyrazol-3-yl}-m-tolylacetamide;
N-{5-aminosulfonyl-4,6-dihydropyrrolo[3,4-c]pyrazol-3-yl}-p-tolylacetamide;
N-{5-aminosulfonyl-4,6-dihydropyrrolo[3,4-c]pyrazol-3-yl}-o-anisic amide;
N-{5-aminosulfonyl-4,6-dihydropyrrolo[3,4-c]pyrazol-3-yl}-3-methoxybenzamide;
N-(5-aminosulfonyl-4,6-dihydropyrrolo[3,4-c]pyrazol-3-yl)-p-anisic amide;
N-{5-aminosulfonyl-4,6-dihydropyrrolo[3,4-c]pyrazol-3-yl}-phenoxyacetamide;
N-{5-aminosulfonyl-4,6-dihydropyrrolo[3,4-c]pyrazol-3-yl}-2-fluorophenylacetamide;
N-{5-aminosulfonyl-4,6-dihydropyrrolo[3,4-c]pyrazol-3-yl}-3-fluorophenylacetamide;
N-{5-aminosulfonyl-4,6-dihydropyrrolo[3,4-c]pyrazol-3-yl}-4-fluorophenylacetamide;
N-{5-aminosulfonyl-4,6-dihydropyrrolo[3,4-c]pyrazol-3-yl}-3-(2-thienyl)acrylic amide;
N-{5-aminosulfonyl-4,6-dihydropyrrolo[3,4-c]pyrazol-3-yl}-3-(3-thienyl)-acrylic amide;
N-{5-aminosulfonyl-4,6-dihydropyrrolo[3,4-c]pyrazol-3-yl}-3-(2-thienyl)propanoic amide;
N-{5-aminosulfonyl-4,6-dihydropyrrolo[3,4-c]pyrazol-3-yl}-2-chlorobenzamide;
N-{5-aminosulfonyl-4,6-dihydropyrrolo[3,4-c]pyrazol-3-yl}-3-chlorobenzamide;
N-{5-aminosulfonyl-4,6-dihydropyrrolo[3,4-c]pyrazol-3-yl}-4-chlorobenzamide;
N-{5-aminosulfonyl-4,6-dihydropyrrolo[3,4-c]pyrazol-3-yl}-1-piperidinepropionamide;
N-{5-aminosulfonyl-4,6-dihydropyrrolo[3,4-c]pyrazol-3-yl}-2-acetylbenzamide;
N-{5-aminosulfonyl-4,6-dihydropyrrolo[3,4-c]pyrazol-3-yl}-4-acetylbenzamide;
N-{5-aminosulfonyl-4,6-dihydropyrrolo[3,4-c]pyrazol-3-yl}-1-naphthoic amide;
N-{5-aminosulfonyl-4,6-dihydropyrrolo[3,4-c]pyrazol-3-yl}-2-naphthoic amide;
N-{5-aminosulfonyl-4,6-dihydropyrrolo[3,4-c]pyrazol-3-yl}-3-benzoylpropionamide;
N-{5-aminosulfonyl-4,6-dihydropyrrolo[3,4-c]pyrazol-3-yl}-4-acetamidobenzamide;
N-{5-aminosulfonyl-4,6-dihydropyrrolo[3,4-c]pyrazol-3-yl}-2,5-dimethoxybenzamide;
N-{5-aminosulfonyl-4,6-dihydropyrrolo[3,4-c]pyrazol-3-yl}-2,6-dimethoxybenzamide;
N-{5-aminosulfonyl-4,6-dihydropyrrolo[3,4-c]pyrazol-3-yl}-3,4-dimethoxybenzamide;
N-{5-aminosulfonyl-4,6-dihydropyrrolo[3,4-c]pyrazol-3-yl}-3,5-dimethoxybenzamide;
N-{5-aminosulfonyl-4,6-dihydropyrrolo[3,4-c]pyrazol-3-yl}-3-(2-thenoyl)-propionamide;
N-{5-aminosulfonyl-4,6-dihydropyrrolo[3,4-c]pyrazol-3-yl}-2-naphtylacetamide
N-{5-aminosulfonyl-4,6-dihydropyrrolo[3,4-c]pyrazol-3-yl}-1-naphtylacetamide
N-{5-aminosulfonyl-4,6-dihydropyrrolo[3,4-c]pyrazol-3-yl}-4-phenylbenzamide
N-{5-toluensulfonyl-4,6-dihydropyrrolo[3,4-c]pyrazol-3-yl}-acetamide;
N-{5-toluensulfonyl-4,6-dihydropyrrolo[3,4-c]pyrazol-3-yl}-cyclopropanecarboxamide;
N-{5-toluensulfonyl-4,6-dihydropyrrolo[3,4-c]pyrazol-3-yl}-isobutyramide;
N-{5-toluensulfonyl-4,6-dihydropyrrolo[3,4-c]pyrazol-3-yl}-cyclopentanecarboxamide;
N-{5-toluensulfonyl-4,6-dihydropyrrolo[3,4-c]pyrazol-3-yl}-benzamide;
N-{5-toluensulfonyl-4,6-dihydropyrrolo[3,4-c]pyrazol-3-yl}-picolinic amide;
N-{5-toluensulfonyl-4,6-dihydropyrrolo[3,4-c]pyrazol-3-yl}-nicotinic amide;
N-{5-toluensulfonyl-4,6-dihydropyrrolo[3,4-c]pyrazol-3-yl}-isonicotinic amide;
N-{5-toluensulfonyl-4,6-dihydropyrrolo[3,4-c]pyrazol-3-yl}-3-methyl-2-furoic amide;
N-{5-toluensulfonyl-4,6-dihydropyrrolo[3,4-c]pyrazol-3-yl}-thiophene-2-carboxamide;
N-{5-toluensulfonyl-4,6-dihydropyrrolo[3,4-c]pyrazol-3-yl}-thiophene-3-carboxamide;
N-{5-toluensulfonyl-4,6-dihydropyrrolo[3,4-c]pyrazol-3-yl}-o-toluic amide;
N-{5-toluensulfonyl-4,6-dihydropyrrolo[3,4-c]pyrazol-3-yl}-m-toluic amide;
N-{5-toluensulfonyl-4,6-dihydropyrrolo[3,4-c]pyrazol-3-yl}-p-toluic amide;
N-{5-toluensulfonyl-4,6-dihydropyrrolo[3,4-c]pyrazol-3-yl}-salicylic amide;
N-{5-toluensulfonyl-4,6-dihydropyrrolo[3,4-c]pyrazol-3-yl}-2-fluorobenzamide;
N-{5-toluensulfonyl-4,6-dihydropyrrolo[3,4-c]pyrazol-3-yl}-3-fluorobenzamide;
N-{5-toluensulfonyl-4,6-dihydropyrrolo[3,4-c]pyrazol-3-yl}-4-fluorobenzamide;
N-{5-toluensulfonyl-4,6-dihydropyrrolo[3,4-c]pyrazol-3-yl}-thiophene-2-acetamide;
N-{5-toluensulfonyl-4,6-dihydropyrrolo[3,4-c]pyrazol-3-yl}-thiophene-3-acetamide;
N-{5-toluensulfonyl-4,6-dihydropyrrolo[3,4-c]pyrazol-3-yl}-phenylpropiolic amide;
N-{5-toluensulfonyl-4,6-dihydropyrrolo[3,4-c]pyrazol-3-yl}-3-cyanobenzamide;
N-{5-toluensulfonyl-4,6-dihydropyrrolo[3,4-c]pyrazol-3-yl}-4-cyanobenzamide;
N-{5-toluensulfonyl-4,6-dihydropyrrolo[3,4-c]pyrazol-3-yl}-trans-cinnamic amide;
N-{5-toluensulfonyl-4,6-dihydropyrrolo[3,4-c]pyrazol-3-yl}-cis-cinnamic amide;
N-{5-toluensulfonyl-4,6-dihydropyrrolo[3,4-c]pyrazol-3-yl}-3-(3-pyridyl)acrylic amide;
N-{5-toluensulfonyl-4,6-dihydropyrrolo[3,4-c]pyrazol-3-yl}-3-(4-pyridyl)-acrylic amide;
N-{5-toluensulfonyl-4,6-dihydropyrrolo[3,4-c]pyrazol-3-yl}-2-phenylpropionamide;

N-{5-toluensulfonyl-4,6-dihydropyrrolo[3,4-c]pyrazol-3-yl}-o-tolylacetamide;
N-{5-toluensulfonyl-4,6-dihydropyrrolo[3,4-c]pyrazol-3-yl}-m-tolylacetamide;
N-{5-toluensulfonyl-4,6-dihydropyrrolo[3,4-c]pyrazol-3-yl}-p-tolylacetamide;
N-{5-toluensulfonyl-4,6-dihydropyrrolo[3,4-c]pyrazol-3-yl}-o-anisic amide;
N-{5-toluensulfonyl-4,6-dihydropyrrolo[3,4-c]pyrazol-3-yl}-3-methoxybenzamide;
N-{5-toluensulfonyl-4,6-dihydropyrrolo[3,4-c]pyrazol-3-yl}-p-anisic amide;
N-{5-toluensulfonyl-4,6-dihydropyrrolo[3,4-c]pyrazol-3-yl}-phenoxyacetamide;
N-{5-toluensulfonyl-4,6-dihydropyrrolo[3,4-c]pyrazol-3-yl}-2-fluorophenylacetamide;
N-{5-toluensulfonyl-4,6-dihydropyrrolo[3,4-c]pyrazol-3-yl}-3-fluorophenylacetamide;
N-{5-toluensulfonyl-4,6-dihydropyrrolo[3,4-c]pyrazol-3-yl}-4-fluorophenylacetamide;
N-{5-toluensulfonyl-4,6-dihydropyrrolo[3,4-c]pyrazol-3-yl}-3-(2-thienyl)acrylic amide;
N-{5-toluensulfonyl-4,6-dihydropyrrolo[3,4-c]pyrazol-3-yl}-3-(3-thienyl)-acrylic amide;
N-{5-toluensulfonyl-4,6-dihydropyrrolo[3,4-c]pyrazol-3-yl}-3-(2-thienyl)propanoic amide;
N-{5-toluensulfonyl-4,6-dihydropyrrolo[3,4-c]pyrazol-3-yl}-2-chlorobenzamide;
N-{5-toluensulfonyl-4,6-dihydropyrrolo[3,4-c]pyrazol-3-yl}-3-chlorobenzamide;
N-{5-toluensulfonyl-4,6-dihydropyrrolo[3,4-c]pyrazol-3-yl}-4-chlorobenzamide;
N-{5-toluensulfonyl-4,6-dihydropyrrolo[3,4-c]pyrazol-3-yl}-1-piperidinepropionamide;
N-{5-toluensulfonyl-4,6-dihydropyrrolo[3,4-c]pyrazol-3-yl}-2-acetylbenzamide;
N-{5-toluensulfonyl-4,6-dihydropyrrolo[3,4-c]pyrazol-3-yl}-4-acetylbenzamide;
N-{5-toluensulfonyl-4,6-dihydropyrrolo[3,4-c]pyrazol-3-yl}-1-naphthoic amide;
N-{5-toluensulfonyl-4,6-dihydropyrrolo[3,4-c]pyrazol-3-yl}-2-naphthoic amide;
N-{5-toluensulfonyl-4,6-dihydropyrrolo[3,4-c]pyrazol-3-yl}-3-benzoylpropionamide;
N-{5-toluensulfonyl-4,6-dihydropyrrolo[3,4-c]pyrazol-3-yl}-4-acetamidobenzamide;
N-{5-toluensulfonyl-4,6-dihydropyrrolo[3,4-c]pyrazol-3-yl}-2,5-dimethoxybenzamide;
N-{5-toluensulfonyl-4,6-dihydropyrrolo[3,4-c]pyrazol-3-yl}-2,6-dimethoxybenzamide;
N-{5-toluensulfonyl-4,6-dihydropyrrolo[3,4-c]pyrazol-3-yl}-3,4-dimethoxybenzamide;
N-{5-toluensulfonyl-4,6-dihydropyrrolo[3,4-c]pyrazol-3-yl}-3,5-dimethoxybenzamide;
N-{5-toluensulfonyl-4,6-dihydropyrrolo[3,4-c]pyrazol-3-yl}-3-(2-thenoyl)-propionamide;
N-{5-toluensulfonyl-4,6-dihydropyrrolo[3,4-c]pyrazol-3-yl}-2-naphtylacetamide
N-{5-toluensulfonyl-4,6-dihydropyrrolo[3,4-c]pyrazol-3-yl}-1-naphtylacetamide
N-{5-toluensulfonyl-4,6-dihydropyrrolo[3,4-c]pyrazol-3-yl}-4-phenylbenzamide
N-{5-benzylsulfonyl-4,6-dihydropyrrolo[3,4-c]pyrazol-3-yl}-acetamide;
N-{5-benzylsulfonyl-4,6-dihydropyrrolo[3,4-c]pyrazol-3-yl}-cyclopropanecarboxamide;
N-{5-benzylsulfonyl-4,6-dihydropyrrolo[3,4-c]pyrazol-3-yl}-isobutyramide;
N-{5-benzylsulfonyl-4,6-dihydropyrrolo[3,4-c]pyrazol-3-yl}-cyclopentanecarboxamide;
N-{5-benzylsulfonyl-4,6-dihydropyrrolo[3,4-c]pyrazol-3-yl}-benzamide;
N-{5-benzylsulfonyl-4,6-dihydropyrrolo[3,4-c]pyrazol-3-yl}-picolinic amide;
N-{5-benzylsulfonyl-4,6-dihydropyrrolo[3,4-c]pyrazol-3-yl}-nicotinic amide;
N-{5-benzylsulfonyl-4,6-dihydropyrrolo[3,4-c]pyrazol-3-yl}-isonicotinic amide;
N-{5-benzylsulfonyl-4,6-dihydropyrrolo[3,4-c]pyrazol-3-yl}-3-methyl-2-furoic amide;
N-{5-benzylsulfonyl-4,6-dihydropyrrolo[3,4-c]pyrazol-3-yl}-thiophene-2-carboxamide;
N-{5-benzylsulfonyl-4,6-dihydropyrrolo[3,4-c]pyrazol-3-yl}-thiophene-3-carboxamide;
N-{5-benzylsulfonyl-4,6-dihydropyrrolo[3,4-c]pyrazol-3-yl}-o-toluic amide;
N-{5-benzylsulfonyl-4,6-dihydropyrrolo[3,4-c]pyrazol-3-yl}-m-toluic amide;
N-{5-benzylsulfonyl-4,6-dihydropyrrolo[3,4-c]pyrazol-3-yl}-p-toluic amide;
N-{5-benzylsulfonyl-4,6-dihydropyrrolo[3,4-c]pyrazol-3-yl}-phenylacetamide;
N-{5-benzylsulfonyl-4,6-dihydropyrrolo[3,4-c]pyrazol-3-yl}-salicylic amide;
N-{5-benzylsulfonyl-4,6-dihydropyrrolo[3,4-c]pyrazol-3-yl}-2-fluorobenzamide;
N-{5-benzylsulfonyl-4,6-dihydropyrrolo[3,4-c]pyrazol-3-yl}-3-fluorobenzamide;
N-{5-benzylsulfonyl-4,6-dihydropyrrolo[3,4-c]pyrazol-3-yl}-4-fluorobenzamide;
N-{5-benzylsulfonyl-4,6-dihydropyrrolo[3,4-c]pyrazol-3-yl}-thiophene-2-acetamide;
N-{5-benzylsulfonyl-4,6-dihydropyrrolo[3,4-c]pyrazol-3-yl}-thiophene-3-acetamide;
N-{5-benzylsulfonyl-4,6-dihydropyrrolo[3,4-c]pyrazol-3-yl}-phenylpropiolic amide;
N-{5-benzylsulfonyl-4,6-dihydropyrrolo[3,4-c]pyrazol-3-yl}-3-cyanobenzamide;
N-{5-benzylsulfonyl-4,6-dihydropyrrolo[3,4-c]pyrazol-3-yl}-4-cyanobenzamide;
N-{5-benzylsulfonyl-4,6-dihydropyrrolo[3,4-c]pyrazol-3-yl}-trans-cinnamic amide;
N-{5-benzylsulfonyl-4,6-dihydropyrrolo[3,4-c]pyrazol-3-yl}-cis-cinnamic amide;
N-{5-benzylsulfonyl-4,6-dihydropyrrolo[3,4-c]pyrazol-3-yl}-3-(3-pyridyl)acrylic amide;
N-{5-benzylsulfonyl-4,6-dihydropyrrolo[3,4-c]pyrazol-3-yl}-3-(4-pyridyl)-acrylic amide;
N-{5-benzylsulfonyl-4,6-dihydropyrrolo[3,4-c]pyrazol-3-yl}-2-phenylpropionamide;
N-{5-benzylsulfonyl-4,6-dihydropyrrolo[3,4-c]pyrazol-3-yl}-m-tolylacetamide;
N-{5-benzylsulfonyl-4,6-dihydropyrrolo[3,4-c]pyrazol-3-yl}-p-tolylacetamide;
N-{5-benzylsulfonyl-4,6-dihydropyrrolo[3,4-c]pyrazol-3-yl}-o-anisic amide;
N-{5-benzylsulfonyl-4,6-dihydropyrrolo[3,4-c]pyrazol-3-yl}-3-methoxybenzamide;
N-{5-benzylsulfonyl-4,6-dihydropyrrolo[3,4-c]pyrazol-3-yl}-p-anisic amide;
N-{5-benzylsulfonyl-4,6-dihydropyrrolo[3,4-c]pyrazol-3-yl}-phenoxyacetamide;

N-{5-benzylsulfonyl-4,6-dihydropyrrolo[3,4-c]pyrazol-3-yl}-2-fluorophenylacetamide;
N-{5-benzylsulfonyl-4,6-dihydropyrrolo[3,4-c]pyrazol-3-yl}-3-fluorophenylacetamide;
N-{5-benzylsulfonyl-4,6-dihydropyrrolo[3,4-c]pyrazol-3-yl}-4-fluorophenylacetamide;
N-{5-benzylsulfonyl-4,6-dihydropyrrolo[3,4-c]pyrazol-3-yl}-3-(2-thienyl)acrylic amide;
N-{5-benzylsulfonyl-4,6-dihydropyrrolo[3,4-c]pyrazol-3-yl}-3-(3-thienyl)-acrylic amide;
N-{5-benzylsulfonyl-4,6-dihydropyrrolo[3,4-c]pyrazol-3-yl}-3-(2-thienyl)propanoic amide;
N-{5-benzylsulfonyl-4,6-dihydropyrrolo[3,4-c]pyrazol-3-yl}-2-chlorobenzamide;
N-{5-benzylsulfonyl-4,6-dihydropyrrolo[3,4-c]pyrazol-3-yl}-3-chlorobenzamide;
N-{5-benzylsulfonyl-4,6-dihydropyrrolo[3,4-c]pyrazol-3-yl}-4-chlorobenzamide;
N-{5-benzylsulfonyl-4,6-dihydropyrrolo[3,4-c]pyrazol-3-yl}-1-piperidinepropionamide;
N-{5-benzylsulfonyl-4,6-dihydropyrrolo[3,4-c]pyrazol-3-yl}-2-acetylbenzamide;
N-{5-benzylsulfonyl-4,6-dihydropyrrolo[3,4-c]pyrazol-3-yl}-4-acetylbenzamide;
N-{5-benzylsulfonyl-4,6-dihydropyrrolo[3,4-c]pyrazol-3-yl}-1-naphthoic amide;
N-{5-benzylsulfonyl-4,6-dihydropyrrolo[3,4-c]pyrazol-3-yl}-2-naphthoic amide;
N-{5-benzylsulfonyl-4,6-dihydropyrrolo[3,4-c]pyrazol-3-yl}-3-benzoylpropionamide;
N-{5-benzylsulfonyl-4,6-dihydropyrrolo[3,4-c]pyrazol-3-yl}-4-acetamidobenzamide;
N-{5-benzylsulfonyl-4,6-dihydropyrrolo[3,4-c]pyrazol-3-yl}-2,5-dimethoxybenzamide;
N-{5-benzylsulfonyl-4,6-dihydropyrrolo[3,4-c]pyrazol-3-yl}-2,6-dimethoxybenzamide;
N-{5-benzylsulfonyl-4,6-dihydropyrrolo[3,4-c]pyrazol-3-yl}-3,4-dimethoxybenzamide;
N-{5-benzylsulfonyl-4,6-dihydropyrrolo[3,4-c]pyrazol-3-yl}-3,5-dimethoxybenzamide;
N-{5-benzylsulfonyl-4,6-dihydropyrrolo[3,4-c]pyrazol-3-yl}-3-(2-thenoyl)-propionamide;
N-{5-benzylsulfonyl-4,6-dihydropyrrolo[3,4-c]pyrazol-3-yl}-2-naphtylacetamide
N-{5-benzylsulfonyl-4,6-dihydropyrrolo[3,4-c]pyrazol-3-yl}-1-naphtylacetamide
N-{5-benzylsulfonyl-4,6-dihydropyrrolo[3,4-c]pyrazol-3-yl}-4-phenylbenzamide
N-{5-acetyl-4,6-dihydropyrrolo[3,4-c]pyrazol-3-yl},N'-(4-chlorobenzyl)urea;
N-{5-benzyl-4,6-dihydropyrrolo[3,4-c]pyrazol-3-yl},N'-(4-chlorobenzyl)urea;
N-{5-phenyl-4,6-dihydropyrrolo[3,4-c]pyrazol-3-yl},N'-(4-chlorobenzyl)urea;
N-{5-aminocarbonyl-4,6-dihydropyrrolo[3,4-c]pyrazol-3-yl},N'-(4-chlorobenzyl)urea;
N-{5-ethylaminocarbonyl-4,6-dihydropyrrolo[3,4-c]pyrazol-3-yl},N'-(4-chlorobenzyl) urea;
N-{5-methansulfonyl-4,6-dihydropyrrolo[3,4-c]pyrazol-3-yl},N'-(4-chlorobenzyl)urea;
N-{5-benzensulfonyl-4,6-dihydropyrrolo[3,4-c]pyrazol-3-yl},N'-(4-chlorobenzyl)urea;
N-{5-toluensulfonyl-4,6-dihydropyrrolo[3,4-c]pyrazol-3-yl},N'-(4-chlorobenzyl)urea;
N-{5-benzylaminocarbonyl-4,6-dihydropyrrolo[3,4-c]pyrazol-3-yl},N'-(4-chlorobenzyl) urea; and
N-{5-phenylaminocarbonyl-4,6-dihydropyrrolo[3,4-c]pyrazol-3-yl},N'-(4-chlorobenzyl) urea

EXAMPLE 13

Preparation of N-{3-phenylacetamido-5-(carbo-tbutoxy)-4,5,6,7-tetrahydropyridine[4,3-c]pyrazol-1-yl}, N'-methylpolystyrene urea A solution of phenylacetyl chloride (24.08 mmol, 3.18 ml) in 10 ml of anhydrous dichlorometane was added dropwise to N-{3-amino-5-(carbo-tbutoxy)-4,5,6,7-tetrahydropyridine [4,3-c]pyrazol-1-yl},N'-methylpolystyrene urea (3.01 mmol, 3.5 g) previously swelled in 90 ml of anhydrous dichlorometane and 16.5 ml of DIEA (96.32 mmol). The resulting suspension was gently stirred at 22° C. for 18 hours. The resin was then filtered, washed with dichloromethane, methanol and dried under vacuum.

Analogously, the following compounds can be prepared by using the appropriate acyl chloride:

N-{3-acetamido-5-(carbo-tbutoxy)-4,5,6,7-tetrahydropyridine[4,3-c]pyrazol-1-yl},N'-methylpolystyrene urea
N-{3-cyclopropanecarboxamido-5-(carbo-tbutoxy)-4,5,6,7-tetrahydropyridine[4,3-c]pyrazol-1-yl},N'-methylpolystyrene urea
N-{3-isobutyramido-5-(carbo-tbutoxy)-4,5,6,7-tetrahydropyridine[4,3-c]pyrazol-1-yl},N'-methylpolystyrene urea
N-{3-cyclopentanecarboxamido-5-(carbo-tbutoxy)-4,5,6,7-tetrahydropyridine[4,3-c]pyrazol-1-yl},N'-methylpolystyrene urea
N-{3-benzamido-5-(carbo-tbutoxy)-4,5,6,7-tetrahydropyridine[4,3-c]pyrazol-1-yl},N'-methylpolystyrene urea
N-{3-picolinic-amido-5-(carbo-tbutoxy)-4,5,6,7-tetrahydropyridine[4,3-c]pyrazol-yl}, N'-methylpolystyrene urea
N-{3-nicotinic-amido-5-(carbo-tbutoxy)-4,5,6,7-tetrahydropyridine[4,3-c]pyrazol-1-yl},N'-methylpolystyrene urea
N-{[3-isonicotinic-amido-5-(carbo-tbutoxy)-4,5,6,7-tetrahydropyridine[4,3-c]pyrazol-yl}, N'-methylpolystyrene urea
N-{3-(3-methyl-2-furoic)-amido-5-(carbo-tbutoxy)-4,5,6,7-tetrahydropyridine[4,3-c]pyrazol-1-yl},N'-methylpolystyrene urea
N-{3-(thiophene-2-carboxamido)-5-(carbo-tbutoxy)-4,5,6,7-tetrahydropyridine[4,3-c]pyrazol-1-yl},N'-methylpolystyrene urea
N-{3-(thiophene-3-carboxamido)-5-(carbo-tbutoxy)-4,5,6,7-tetrahydropyridine[4,3-c]pyrazol-1-yl},N'-methylpolystyrene urea
N-{3-(o-toluic-amido)-5-(carbo-tbutoxy)-4,5,6,7-tetrahydropyridine[4,3-c]pyrazol-1-yl},N'-methylpolystyrene urea
N-{3-(m-toluic-amido)-5-(carbo-tbutoxy)-4,5,6,7-tetrahydropyridine[4,3-c]pyrazol-1-yl},N'-methylpolystyrene urea
N-{3-(p-toluic-amido)-5-(carbo-tbutoxy)-4,5,6,7-tetrahydropyridine[4,3-c]pyrazol-1-yl},N'-methylpolystyrene urea
N-{3-salicylic-amido-5-(carbo-tbutoxy)-4,5,6,7-tetrahydropyridine[4,3-c]pyrazol-1-yl},N'-methylpolystyrene urea
N-{3-(2-fluorobenzamido)-5-(carbo-tbutoxy)-4,5,6,7-tetrahydropyridine[4,3-c]pyrazol-1-yl},N'-methylpolystyrene urea
N-{3-(3-fluorobenzamido)-5-(carbo-tbutoxy)-4,5,6,7-tetrahydropyridine[4,3-c]pyrazol-1-yl},N'-methylpolystyrene urea N-{3-(4-fluorobenzamido)-5-(carbo-tbutoxy)-4,5,6,7-tetrahydropyridine[4,3-c]pyrazol-1-yl},N'-methylpolystyrene urea
N-{3-(thiophene-2-acetamido)-5-(carbo-tbutoxy)-4,5,6,7-tetrahydropyridine[4,3-c]pyrazol-1-yl},N'-methylpolystyrene urea
N-{3-(thiophene-3-acetamido)-5-(carbo-tbutoxy)-4,5,6,7-tetrahydropyridine[4,3-c]pyrazol-1-yl},N'-methylpolystyrene urea
N-{3-phenylpropiolic-amido-5-(carbo-tbutoxy)-4,5,6,7-tetrahydropyridine[4,3-c]pyrazol-1-yl},N'-methylpolystyrene urea
N-{3-(3-cyanobenzamido)-5-(carbo-tbutoxy)-4,5,6,7-tetrahydropyridine[4,3-c]pyrazol-1-yl},N'-methylpolystyrene urea
N-{3-(4-cyanobenzamido)-5-(carbo-tbutoxy)-4,5,6,7-tetrahydropyridine[4,3-c]pyrazol-1-yl},N'-methylpolystyrene urea
N-{3-trans-cinnamic-amido-5-(carbo-tbutoxy)-4,5,6,7-tetrahydropyridine[4,3-c]pyrazol-1-yl},N'-methylpolystyrene urea
N-{3-cis-cinnamic-amido-5-(carbo-tbutoxy)-4,5,6,7-tetrahydropyridine[4,3-c]pyrazol-1-yl},N'-methylpolystyrene urea
N-{3-[3-(3-pyridyl)acrylic-amido]-5-(carbo-tbutoxy)-4,5,6,7-tetrahydropyridine[4,3-c]pyrazol-1-yl},N'-methylpolystyrene urea
N-{3-[3-(4-pyridyl)-acrylic-amido]-5-(carbo-tbutoxy)-4,5,6,7-tetrahydropyridine[4,3-c]pyrazol-1-yl},N'-methylpolystyrene urea
N-{3-(2-phenylpropionamido)-5-(carbo-tbutoxy)-4,5,6,7-tetrahydropyridine[4,3-c]pyrazol-1-yl},N'-methylpolystyrene urea
N-{3-o-tolylacetamido-5-(carbo-tbutoxy)-4,5,6,7-tetrahydropyridine[4,3-c]pyrazol-1-yl},N'-methylpolystyrene urea
N-{3-m-tolylacetamido-5-(carbo-tbutoxy)-4,5,6,7-tetrahydropyridine[4,3-c]pyrazol-1-yl},N'-methylpolystyrene urea
N-{-p-tolylacetamido-5-(carbo-tbutoxy)-4,5,6,7-tetrahydropyridine[4,3-c]pyrazol-1-yl},N'-methylpolystyrene urea a
N-{3-o-anisic-amido-5-(carbo-tbutoxy)-4,5,6,7-tetrahydropyridine[4,3-c]pyrazol-1-yl},N'-methylpolystyrene urea
N-{3-(3-methoxybenzamido)-5-(carbo-tbutoxy)-4,5,6,7-tetrahydropyridine[4,3-c]pyrazol-1-yl},N'-methylpolystyrene urea
N-{3-p-anisic-amido-5-(carbo-tbutoxy)-4,5,6,7-tetrahydropyridine[4,3-c]pyrazol-1-yl},N'-methylpolystyrene urea
N-{3-phenoxyacetamido-5-(carbo-tbutoxy)-4,5,6,7-tetrahydropyridine[4,3-c]pyrazol-1-yl},N'-methylpolystyrene urea
N-{3-(2-fluorophenylacetamido)-5-(carbo-tbutoxy)-4,5,6,7-tetrahydropyridine[4,3-c]pyrazol-1-yl},N'-methylpolystyrene urea
N-{3-(3-fluorophenylacetamido)-5-(carbo-tbutoxy)-4,5,6,7-tetrahydropyridine[4,3-c]pyrazol-1-yl},N'-methylpolystyrene urea
N-{3-(4-fluorophenylacetamido)-5-(carbo-tbutoxy)-4,5,6,7-tetrahydropyridine[4,3-c]pyrazol-1-yl},N'-methylpolystyrene urea
N-{3-[3-(2-thienyl)acrylicamido]-5-(carbo-tbutoxy)-4,5,6,7-tetrahydropyridine[4,3-c]pyrazol-1-yl},N'-methylpolystyrene urea
N-{3-[3-(3-thienyl)-acrylicamido]-5-(carbo-tbutoxy)-4,5,6,7-tetrahydropyridine[4,3-c]pyrazol-1-yl},N'-methylpolystyrene urea
N-{3-[3-(2-thienyl)propanoic-amido]-5-(carbo-tbutoxy)-4,5,6,7-tetrahydropyridine[4,3-c]pyrazol-1-yl},N'-methylpolystyrene urea
N-{3-[2-chlorobenzamido]-5-(carbo-tbutoxy)-4,5,6,7-tetrahydropyridine[4,3-c]pyrazol-1-yl},N'-methylpolystyrene urea
N-{3-[3-chlorobenzamido]-5-(carbo-tbutoxy)-4,5,6,7-tetrahydropyridine[4,3-c]pyrazol-1-yl},N'-methylpolystyrene urea
N-{3-(4-chlorobenzamido)-5-(carbo-tbutoxy)-4,5,6,7-tetrahydropyridine[4,3-c]pyrazol-1-yl},N'-methylpolystyrene urea
N-{3-(1-piperidinepropionamido)-5-(carbo-tbutoxy)-4,5,6,7-tetrahydropyridine[4,3-c]pyrazol-1-yl},N'-methylpolystyrene urea
N-{3-(2-acetylbenzamido)-5-(carbo-tbutoxy)-4,5,6,7-tetrahydropyridine[4,3-c]pyrazol-1-yl},N'-methylpolystyrene urea
N-{3-(4-acetylbenzamido)-5-(carbo-tbutoxy)-4,5,6,7-tetrahydropyridine[4,3-c]pyrazol-1-yl},N'-methylpolystyrene urea
N-{3-(1-naphthoicamido)-5-(carbo-tbutoxy)-4,5,6,7-tetrahydropyridine[4,3-c]pyrazol-1-yl},N'-methylpolystyrene urea
N-{3-(2-naphthoicamido)-5-(carbo-tbutoxy)-4,5,6,7-tetrahydropyridine[4,3-c]pyrazol-1-yl},N'-methylpolystyrene urea
N-{3-(3-benzoylpropionamido)-5-(carbo-tbutoxy)-4,5,6,7-tetrahydropyridine[4,3-c]pyrazol-1-yl},N'-methylpolystyrene urea
N-{3-(4-acetamidobenzamido)-5-(carbo-tbutoxy)-4,5,6,7-tetrahydropyridine[4,3-c]pyrazol-1-yl},N'-methylpolystyrene urea
N-{3-(2,5-dimethoxybenzamido)-5-(carbo-tbutoxy)-4,5,6,7-tetrahydropyridine[4,3-c]pyrazol-1-yl},N'-methylpolystyrene urea
N-{3-(2,6-dimethoxybenzamido)-5-(carbo-tbutoxy)-4,5,6,7-tetrahydropyridine[4,3-c]pyrazol-1-yl},N'-methylpolystyrene urea
N-{3-(3,4-dimethoxybenzamido)-5-(carbo-tbutoxy)-4,5,6,7-tetrahydropyridine[4,3-c]pyrazol-1-yl},N'-methylpolystyrene urea
N-{3-(3,5-dimethoxybenzamido)-5-(carbo-tbutoxy)-4,5,6,7-tetrahydropyridine[4,3-c]pyrazol-1-yl},N'-methylpolystyrene urea
N-{3-3-(2-thenoyl)-propionamido-5-(carbo-tbutoxy)-4,5,6,7-tetrahydropyridine[4,3-c]pyrazol-1-yl},N'-methylpolystyrene urea
N-{3-(2-naphtylacetamide)-5-(carbo-tbutoxy)-4,5,6,7-tetrahydropyridine[4,3-c]pyrazol-1-yl},N'-methylpolystyrene urea
N-{3-(1-naphtylacetamido)-5-(carbo-tbutoxy)-4,5,6,7-tetrahydropyridine[4,3-c]pyrazol-1-yl},N'-methylpolystyrene urea
N-{3-(4-phenylbenzamido)-5-(carbo-tbutoxy)-4,5,6,7-tetrahydropyridine[4,3-c]pyrazol-1-yl},N'-methylpolystyrene urea
N-{3-(2-furamido)-5-(carbo-tbutoxy)-4,5,6,7-tetrahydropyridine[4,3-c]pyrazol-1-yl},N'-methylpolystyrene urea
N-{3-(4-phenoxybenzamido)-5-(carbo-tbutoxy)-4,5,6,7-tetrahydropyridine[4,3-c]pyrazol-1-yl},N'-methylpolystyrene urea
N-{3-(3-phenoxybenzamido)-5-(carbo-tbutoxy)-4,5,6,7-tetrahydropyridine[4,3-c]pyrazol-1-yl},N'-methylpolystyrene urea N-{3-(4-tertbutyl-benzamido)-5-(carbo-tbutoxy)-4,5,6,7-tetrahydropyridine[4,3-c]pyrazol-1-yl},N'-methylpolystyrene urea N-{3-piperonylcarboxamido-5-(carbo-tbutoxy)-4,5,6,7-tetrahydropyridine[4,3-c]pyrazol-1-yl},N'-methylpolystyrene urea N-{3-(2-naphtalene)propionamido-5-(carbo-tbutoxy)-4,5,6,7-tetrahydropyridine[4,3-c]pyrazol-1-yl},N'-methylpolystyrene urea N-{3-(6-methoxy-2-naphtalene)propionamido-5-(carbo-tbutoxy)-4,5,6,7-tetrahydropyridine[4,3-c]pyrazol-1-yl},N'-methylpolystyrene urea N-{3-(2-ethylbutyramido)-5-(carbo-tbutoxy)-4,5,6,7-tetrahydropyridine[4,3-c]pyrazol-1-yl},N'-methylpolystyrene urea N-{3-(4-pyrrolidin-1-yl-phenyl)propionamido-5-(carbo-tbutoxy)-4,5,6,7-tetrahydropyridine[4,3-c]pyrazol-1-yl},N'-methylpolystyrene urea N-{3-(2-oxo-pyrrolidin-1-yl)phenyl]propionamido-5-(carbo-tbutoxy)-4,5,6,7-tetrahydropyridine[4,3-c]pyrazol-1-yl},N'-methylpolystyrene urea N-{3-(bicyclo[4.2.0]octa-1,3,5-triene-7-carboxamido)-5-(carbo-tbutoxy)-4,5,6,7-tetrahydropyridine[4,3-c]pyrazol-1-yl},N'-methylpolystyrene urea N-{3-(2-oxo-pyrrolidin-1-yl)phenylacetamido-5-(carbo-tbutoxy)-4,5,6,7-tetrahydropyridine[4,3-c]pyrazol-1-yl},N'-methylpolystyrene urea N-{3-(4-pyrrolidin-1-yl-phenylacetamido-5-(carbo-tbutoxy)-4,5,6,7-tetrahydropyridine[4,3-c]pyrazol-1-yl},N'-methylpolystyrene urea N-{3-(4-trifluoromethyl)phenylacetamido-5-(carbo-tbutoxy)-4,5,6,7-tetrahydropyridine[4,3-c]pyrazol-1-yl},N'-methylpolystyrene urea N-{3-(2-bromo)phenylacetamido-5-(carbo-tbutoxy)-4,5,6,7-tetrahydropyridine[4,3-c]pyrazol-1-yl},N'-methylpolystyrene urea N-{3-[4-(pyrrolidin-1-yl-carbonylmethyloxy)]phenylacetamido-5-(carbo-tbutoxy)-4,5,6,7-tetrahydropyridine[4,3-c]pyrazol-1-yl},N'-methylpolystyrene urea N-{3-[3-(aminocarbonylmethyloxy)phenylacetamido]-5-(carbo-tbutoxy)-4,5,6,7-tetrahydropyridine[4,3-c]pyrazol-1-yl},N'-methylpolystyrene urea N-{3-[4-(2-oxo-oxazolidin-3-yl)phenylacetamido]-5-(carbo-tbutoxy)-4,5,6,7-tetrahydropyridine[4,3-c]pyrazol-1-yl},N'-methylpolystyrene urea N-{3-[4-(4-methylpiperazino)benzamide]-5-(carbo-tbutoxy)-4,5,6,7-tetrahydropyridine[4,3-c]pyrazol-1-yl},N'-methylpolystyrene urea N-{3-(benzo[1,3]dioxol-5-yl)acetamido-5-(carbo-tbutoxy)-4,5,6,7-tetrahydropyridine[4,3-c]pyrazol-1-yl},N'-methylpolystyrene urea N-{3-[4-(2-oxo-oxazolidin-3-yl)phenylacetamido]-5-(carbo-tbutoxy)-4,5,6,7-tetrahydropyridine[4,3-c]pyrazol-1-yl},N'-methylpolystyrene urea N-{3-(2-phenyl-1,3-thiazol-4-yl)acetamido-5-(carbo-tbutoxy)-4,5,6,7-tetrahydropyridine[4,3-c]pyrazol-1-yl},N'-methylpolystyrene urea N-{3-[4-(1-pyrrolidin-2-one)benzamido-5-(carbo-tbutoxy)-4,5,6,7-tetrahydropyridine[4,3-c]pyrazol-1-yl},N'-methylpolystyrene urea N-{3-[2-(3-oxo-3,4,4a,8a-tetrahydro-2H-benzo[1,4]oxazin-6-yl)acetamido]-5-(carbo-tbutoxy)-4,5,6,7-tetrahydropyridine[4,3-c]pyrazol-1-yl},N'-methylpolystyrene urea N-{3-(1-methyl-indol-3-yl)acetamido-5-(carbo-tbutoxy)-4,5,6,7-tetrahydropyridine[4,3-c]pyrazol-1-yl},N'-methylpolystyrene urea N-{3-(6-oxo-6H-pyridazin-1-yl)acetamido)-5-(carbo-tbutoxy)-4,5,6,7-tetrahydropyridine[4,3-c]pyrazol-1-yl},N'-methylpolystyrene urea N-{3-(4-(morpholin-1-yl)-phenyl)acetamido)-5-(carbo-tbutoxy)-4,5,6,7-tetrahydropyridine[4,3-c]pyrazol-1-yl},N'-methylpolystyrene urea N-{3-(4-pyridylacetamido)-5-(carbo-tbutoxy)-4,5,6,7-tetrahydropyridine[4,3-c]pyrazol-1-yl},N'-methylpolystyrene urea.

N-{3-phenoxyacetamido-5-(carbo-tbutoxy)-4,5,6,7-tetrahydropyridine[4,3-c]pyrazol-1-yl},N'-methylpolystyrene urea N-{3-(3-pyridylacetamido)-5-(carbo-tbutoxy)-4,5,6,7-tetrahydropyridine[4,3-c]pyrazol-1-yl},N'-methylpolystyrene urea N-{3-[5-(4-chlorophenyl)furan-2-carboxamido]-5-(carbo-tbutoxy)-4,5,6,7-tetrahydropyridine[4,3-c]pyrazol-1-yl},N'-methylpolystyrene urea N-{3-[quinoline-6-carboxamido]-5-(carbo-tbutoxy)-4,5,6,7-tetrahydropyridine[4,3-c]pyrazol-1-yl},N'-methylpolystyrene urea N-{3-[2-methyl-5-phenyl-furan-3-carboxamido]-5-(carbo-tbutoxy)-4,5,6,7-tetrahydropyridine[4,3-c]pyrazol-1-yl},N'-methylpolystyrene urea N-{3-[benzofuran-2-carboxamido]-5-(carbo-tbutoxy)-4,5,6,7-tetrahydropyridine[4,3-c]pyrazol-1-yl},N'-methylpolystyrene urea N-{3-[6-chloronicotinamido]-5-(carbo-tbutoxy)-4,5,6,7-tetrahydropyridine[4,3-c]pyrazol-1-yl},N'-methylpolystyrene urea N-{3-[5-chlorothiophene-2-carboxamido]-5-(carbo-tbutoxy)-4,5,6,7-tetrahydropyridine[4,3-c]pyrazol-1-yl},N'-methylpolystyrene urea

EXAMPLE 14

Preparation of N-{3-phenylacetamido-4,5,6,7-tetrahydropyridine-[4,3-c]pyrazol-1-yl},N'-methylpolystyrene urea N-{3-phenylacetamido-5-(carbo-tbutoxy)-4,5,6,7-tetrahydropyridine[4,3-c]pyrazol-1-yl},N'-methylpolystyrene urea (3.01 mmol) was treated with a solution of TFA 50% in anhydrous dichloromethane. The resulting suspension was gently stirred at 22° C. for 2 hours, then washed with a solution of TEA 10% in anhydrous dichloromethane, dichloromethane, methanol and dried under vacuum.

Analogously, the following compounds can be prepared by using the appropriate N-{3-amido-5-(carbo-tbutoxy)-4,5,6,7-tetrahydropyridine[4,3-c]pyrazol-1-yl},N'-methylpolystyrene urea:

N-{3-acetamido-4,5,6,7-tetrahydropyridine[4,3-c]pyrazol-1-yl},N'-methylpolystyrene urea N-{3-cyclopropanecarboxamido-4,5,6,7-tetrahydropyridine[4,3-c]pyrazol-1-yl},N'-methylpolystyrene urea N-{3-isobutyramido-4,5,6,7-tetrahydropyridine[4,3-c]pyrazol-1-yl},N'-methylpolystyrene urea N-{3-cyclopentanecarboxamido-4,5,6,7-tetrahydropyridine[4,3-c]pyrazol-1-yl},N'-methylpolystyrene urea N-{3-benzamido-4,5,6,7-tetrahydropyridine[4,3-c]pyrazol-1-yl},N'-methylpolystyrene urea N-{3-picolinic-amido-4,5,6,7-tetrahydropyridine[4,3-c]pyrazol-1-yl},N'-methylpolystyrene urea N-{3-nicotinic-amido-4,5,6,7-tetrahydropyridine[4,3-c]pyrazol-1-yl},N'-methylpolystyrene urea N-{3-isonicotinic-amido-4,5,6,7-tetrahydropyridine[4,3-c]pyrazol-1-yl},N'-methylpolystyrene urea N-{3-(3-methyl-2-furoic)-amido-4,5,6,7-tetrahydropyridine[4,3-c]pyrazol-1-yl},N'-methylpolystyrene urea
N-{3-(thiophene-2-carboxamido)-4,5,6,7-tetrahydropyridine[4,3-c]pyrazol-1-yl},N'-methylpolystyrene urea
N-{3-(thiophene-3-carboxamido)-4,5,6,7-tetrahydropyridine[4,3-c]pyrazol-1-yl},N'-methylpolystyrene urea
N-{3-(o-toluic-amido)-4,5,6,7-tetrahydropyridine[4,3-c]pyrazol-1-yl},N'-methylpolystyrene urea
N-{3-(m-toluic-amido)-4,5,6,7-tetrahydropyridine[4,3-c]pyrazol-1-yl},N'-methylpolystyrene urea
N-{3-(p-toluic-amido)-4,5,6,7-tetrahydropyridine[4,3-c]pyrazol-1-yl},N'-methylpolystyrene urea
N-{3-salicylic-amido-4,5,6,7-tetrahydropyridine[4,3-c]pyrazol-1-yl},N'-methylpolystyrene urea
N-{3-(2-fluorobenzamido)-4,5,6,7-tetrahydropyridine[4,3-c]pyrazol-1-yl},N'-methylpolystyrene urea
N-{3-(3-fluorobenzamido)-4,5,6,7-tetrahydropyridine[4,3-c]pyrazol-1-yl},N'-methylpolystyrene urea
N-{3-(4-fluorobenzamido)-4,5,6,7-tetrahydropyridine[4,3-c]pyrazol-1-yl},N'-methylpolystyrene urea
N-{3-(thiophene-2-acetamido)-4,5,6,7-tetrahydropyridine[4,3-c]pyrazol-1-yl},N'-methylpolystyrene urea
N-{3-(thiophene-3-acetamido)-4,5,6,7-tetrahydropyridine[4,3-c]pyrazol-1-yl},N'-methylpolystyrene urea
N-{3-phenylpropiolic-amido-4,5,6,7-tetrahydropyridine[4,3-c]pyrazol-1-yl},N'-methylpolystyrene urea
N-{3-(3-cyanobenzamido)-4,5,6,7-tetrahydropyridine[4,3-c]pyrazol-1-yl},N'-methylpolystyrene urea
N-{3-(4-cyanobenzamido)-4,5,6,7-tetrahydropyridine[4,3-c]pyrazol-1-yl},N'-methylpolystyrene urea
N-{3-trans-cinnamic-amido-4,5,6,7-tetrahydropyridine[4,3-c]pyrazol-1-yl},N'-methylpolystyrene urea
N-{3-cis-cinnamic-amido-4,5,6,7-tetrahydropyridine[4,3-c]pyrazol-1-yl},N'-methylpolystyrene urea
N-{3-[3-(3-pyridyl)acrylic-amido]-4,5,6,7-tetrahydropyridine[4,3-c]pyrazol-1-yl},N'-methylpolystyrene urea
N-{3-[3-(4-pyridyl)-acrylic-amido]-4,5,6,7-tetrahydropyridine[4,3-c]pyrazol-1-yl},N'-methylpolystyrene urea
N-{3-(2-phenylpropionamido)-4,5,6,7-tetrahydropyridine[4,3-c]pyrazol-1-yl},N'-methylpolystyrene urea
N-{3-o-tolylacetamido-4,5,6,7-tetrahydropyridine[4,3-c]pyrazol-1-yl},N'-methylpolystyrene urea
N-{3-m-tolylacetamido-4,5,6,7-tetrahydropyridine[4,3-c]pyrazol-1-yl},N'-methylpolystyrene urea
N-{3-p-tolylacetamido-4,5,6,7-tetrahydropyridine[4,3-c]pyrazol-1-yl},N'-methylpolystyrene urea
N-{3-o-anisic-amido-4,5,6,7-tetrahydropyridine[4,3-c]pyrazol-1-yl},N'-methylpolystyrene urea
N-{3-(3-methoxybenzamido)-4,5,6,7-tetrahydropyridine[4,3-c]pyrazol-1-yl},N'-methylpolystyrene urea
N-{3-p-anisic-amido-4,5,6,7-tetrahydropyridine[4,3-c]pyrazol-1-yl},N'-methylpolystyrene urea
N-{3-phenoxyacetamido-4,5,6,7-tetrahydropyridine[4,3-c]pyrazol-1-yl},N'-methylpolystyrene urea
N-{3-(2-fluorophenylacetamido)-4,5,6,7-tetrahydropyridine[4,3-c]pyrazol-1-yl},N'-methylpolystyrene urea
N-{3-(3-fluorophenylacetamido)-4,5,6,7-tetrahydropyridine[4,3-c]pyrazol-1-yl},N'-methylpolystyrene urea
N-{3-(4-fluorophenylacetamido)-4,5,6,7-tetrahydropyridine[4,3-c]pyrazol-1-yl},N'-methylpolystyrene urea
N-{3-[3-(2-thienyl)acrylicamido]-4,5,6,7-tetrahydropyridine[4,3-c]pyrazol-1-yl},N'-methylpolystyrene urea
N-{3-[3-(3-thienyl)-acrylicamido]-4,5,6,7-tetrahydropyridine[4,3-c]pyrazol-1-yl},N'-methylpolystyrene urea
N-{3-[3-(2-thienyl)propanoic-amido]-4,5,6,7-tetrahydropyridine[4,3-c]pyrazol-1-yl},N'-methylpolystyrene urea
N-{3-[2-chlorobenzamido]-4,5,6,7-tetrahydropyridine[4,3-c]pyrazol-1-yl},N'-methylpolystyrene urea
N-{3-[3-chlorobenzamido]-4,5,6,7-tetrahydropyridine[4,3-c]pyrazol-1-yl},N'-methylpolystyrene urea
N-{3-(4-chlorobenzamido)-4,5,6,7-tetrahydropyridine[4,3-c]pyrazol-1-yl},N'-methylpolystyrene urea
N-{3-(1-piperidinepropionamido)-4,5,6,7-tetrahydropyridine[4,3-c]pyrazol-1-yl},N'-methylpolystyrene urea
N-{3-(2-acetylbenzamido)-4,5,6,7-tetrahydropyridine[4,3-c]pyrazol-1-yl},N'-methylpolystyrene urea
N-{3-(4-acetylbenzamido)-4,5,6,7-tetrahydropyridine[4,3-c]pyrazol-1-yl},N'-methylpolystyrene urea
N-{3-(1-naphthoicamido)-4,5,6,7-tetrahydropyridine[4,3-c]pyrazol-1-yl},N'-methylpolystyrene urea
N-{3-(2-naphthoicamido)-4,5,6,7-tetrahydropyridine[4,3-c]pyrazol-1-yl},N'-methylpolystyrene urea
N-{3-(3-benzoylpropionamido)-4,5,6,7-tetrahydropyridine[4,3-c]pyrazol-1-yl},N'-methylpolystyrene urea
N-{3-(4-acetamidobenzamido)-4,5,6,7-tetrahydropyridine[4,3-c]pyrazol-1-yl},N'-methylpolystyrene urea
N-{3-(2,5-dimethoxybenzamido)-4,5,6,7-tetrahydropyridine[4,3-c]pyrazol-1-yl},N'-methylpolystyrene urea
N-{3-(2,6-dimethoxybenzamido)-4,5,6,7-tetrahydropyridine[4,3-c]pyrazol-1-yl},N'-methylpolystyrene urea
N-{3-(3,4-dimethoxybenzamido)-4,5,6,7-tetrahydropyridine[4,3-c]pyrazol-1-yl},N'-methylpolystyrene urea
N-{3-(3,5-dimethoxybenzamido)-4,5,6,7-tetrahydropyridine[4,3-c]pyrazol-1-yl},N'-methylpolystyrene urea
N-{3-3-(2-thenoyl)-propionamido-4,5,6,7-tetrahydropyridine[4,3-c]pyrazol-1-yl},N'-methylpolystyrene urea
N-{3-(2-naphtylacetamide)-4,5,6,7-tetrahydropyridine[4,3-c]pyrazol-1-yl},N'-methylpolystyrene urea
N-{3-(1-naphtylacetamido)-4,5,6,7-tetrahydropyridine[4,3-c]pyrazol-1-yl},N'-methylpolystyrene urea
N-{3-(4-phenylbenzamido)-4,5,6,7-tetrahydropyridine[4,3-c]pyrazol-1-yl},N'-methylpolystyrene urea
N-{3-(2-furamido)-4,5,6,7-tetrahydropyridine[4,3-c]pyrazol-1-yl},N'-methylpolystyrene urea
N-{3-(4-phenoxybenzamido)-4,5,6,7-tetrahydropyridine[4,3-c]pyrazol-1-yl},N'-methylpolystyrene urea
N-{3-(3-phenoxybenzamido)-4,5,6,7-tetrahydropyridine[4,3-c]pyrazol-1-yl},N'-methylpolystyrene urea
N-{3-(4-tertbutyl-benzamido)-4,5,6,7-tetrahydropyridine[4,3-c]pyrazol-1-yl},N'-methylpolystyrene urea
N-{3-piperonylcarboxamido-4,5,6,7-tetrahydropyridine[4,3-c]pyrazol-1-yl},N'-methylpolystyrene urea
N-{3-(2-naphtalene)propionamido-4,5,6,7-tetrahydropyridine[4,3-c]pyrazol-1-yl},N'-methylpolystyrene urea
N-{3-(6-methoxy-2-naphtalene)propionamido-4,5,6,7-tetrahydropyridine[4,3-c]pyrazol-1-yl},N'-methylpolystyrene urea
N-{3-(2-ethylbutyramido)-4,5,6,7-tetrahydropyridine[4,3-c]pyrazol-1-yl},N'-methylpolystyrene urea
N-{3-(4-pyrrolidin-1-yl-phenyl)propionamido-4,5,6,7-tetrahydropyridine[4,3-c]pyrazol-1-yl},N'-methylpolystyrene urea
N-{3-(2-oxo-pyrrolidin-1-yl)phenyl]propionamido-4,5,6,7-tetrahydropyridine[4,3-c]pyrazol-1-yl},N'-methylpolystyrene urea
N-{3-(bicyclo[4.2.0]octa-1,3,5-triene-7-carboxamido)-4,5,6,7-tetrahydropyridine[4,3-c]pyrazol-1-yl},N'-methylpolystyrene urea
N-{3-(2-oxo-pyrrolidin-1-yl)phenylacetamido-4,5,6,7-tetrahydropyridine[4,3-c]pyrazol-1-yl},N'-methylpolystyrene urea N-{3-(4-pyrrolidin-1-yl-phenylacetamido-4,5,6,7-tetrahydropyridine[4,3-c]pyrazol-1-yl},N'-methylpolystyrene urea N-{3-(4-trifluoromethyl)phenylacetamido-4,5,6,7-tetrahydropyridine[4,3-c]pyrazol-1-yl},N'-methylpolystyrene urea N-{3-(2-bromo)phenylacetamido-4,5,6,7-tetrahydropyridine[4,3-c]pyrazol-1-yl},N'-methylpolystyrene urea N-{3-[4-(pyrrolidin-1-yl-carbonylmethyloxy)]phenylacetamido-4,5,6,7-tetrahydropyridine[4,3-c]pyrazol-1-yl},N'-methylpolystyrene urea N-{3-[3-(aminocarbonylmethyloxy)phenylacetamido]-4,5,6,7-tetrahydropyridine[4,3-c]pyrazol-1-yl},N'-methylpolystyrene urea N-{3-[4-(2-oxo-oxazolidin-3-yl)phenylacetamido]-4,5,6,7-tetrahydropyridine[4,3-c]pyrazol-1-yl},N'-methylpolystyrene urea N-{3-[4-(4-methylpiperazino)benzamide]-4,5,6,7-tetrahydropyridine[4,3-c]pyrazol-1-yl},N'-methylpolystyrene urea N-{3-(benzo[1,3]dioxol-5-yl)acetamido-4,5,6,7-tetrahydropyridine[4,3-c]pyrazol-1-yl},N'-methylpolystyrene urea N-{3-[4-(2-oxo-oxazolidin-3-yl)phenylacetamido]-4,5,6,7-tetrahydropyridine[4,3-c]pyrazol-1-yl},N'-methylpolystyrene urea N-{3-(2-phenyl-1,3-thiazol-4-yl)acetamido-4,5,6,7-tetrahydropyridine[4,3-c]pyrazol-1-yl},N'-methylpolystyrene urea N-{3-[4-(1-pyrrolidin-2-one)benzamido]-4,5,6,7-tetrahydropyridine[4,3-c]pyrazol-1-yl},N'-methylpolystyrene urea N-{3-[2-(3-oxo-3,4,4a,8a-tetrahydro-2H-benzo[1,4]oxazin-6-yl)acetamido]-4,5,6,7-tetrahydropyridine[4,3-c]pyrazol-1-yl},N'-methylpolystyrene urea N-{3-(1-methyl-indol-3-yl)acetamido-4,5,6,7-tetrahydropyridine[4,3-c]pyrazol-1-yl},N'-methylpolystyrene urea N-{3-(6-oxo-6H-pyridazin-1-yl)acetamido)-4,5,6,7-tetrahydropyridine[4,3-c]pyrazol-1-yl},N'-methylpolystyrene urea N-{3-(4-(morpholin-1-yl)-phenyl)acetamido)-4,5,6,7-tetrahydropyridine[4,3-c]pyrazol-1-yl},N'-methylpolystyrene urea N-{3-(4-pyridylacetamido)-4,5,6,7-tetrahydropyridine[4,3-c]pyrazol-1-yl},N'-methylpolystyrene urea N-{3-phenoxyacetamido-4,5,6,7-tetrahydropyridine[4,3-c]pyrazol-1-yl},N'-methylpolystyrene urea N-{3-(3-pyridylacetamido)-4,5,6,7-tetrahydropyridine[4,3-c]pyrazol-1-yl},N'-methylpolystyrene urea N-{3-[5-(4-chlorophenyl)furan-2-carboxamido]-4,5,6,7-tetrahydropyridine[4,3-c]pyrazol-1-yl},N'-methylpolystyrene urea N-{3-[quinoline-6-carboxamido]-4,5,6,7-tetrahydropyridine[4,3-c]pyrazol-1-yl},N'-methylpolystyrene urea N-{3-[2-methyl-5-phenyl-furan-3-carboxamido]-4,5,6,7-tetrahydropyridine[4,3-c]pyrazol-1-yl},N'-methylpolystyrene urea N-{3-[benzofuran-2-carboxamido]-4,5,6,7-tetrahydropyridine[4,3-c]pyrazol-1-yl},N'-methylpolystyrene urea N-{3-[6-chloronicotinamido]-4,5,6,7-tetrahydropyridine[4,3-c]pyrazol-1-yl},N'-methylpolystyrene urea N-{3-[5-chlorothiophene-2-carboxamido]-4,5,6,7-tetrahydropyridine[4,3-c]pyrazol-1-yl},N'-methylpolystyrene urea

EXAMPLE 15

Preparation of N-{3-phenylacetamido-5-phenylacetyl]-4,5,6,7-tetrahydropyridine[4,3-c]pyrazol-1-yl},N'-methylpolystyrene urea Phenylacetic acid (0.43 mmol, 58.5 mg), NMM (0.43 mmol, 47.3 mcl) and PyBop (0.43 mmol, 223.8 mg) were added to N-{3-phenylacetamido-4,5,6,7-tetrahydropyridine[4,3-c]pyrazol-1-yl},N'-methylpolystyrene urea (0.086 mmol, 100 mg) previously swelled in 4 ml of anhydrous N,N-dimethylformamide. The resulting suspension was gently stirred at 22° C. for 24 hours. The resin was then filtered, washed with N,N-dimethylformamide, dichloromethane, methanol, and dried under vacuum.

EXAMPLE 16

Preparation of a Library of 4,5,6,7-tetrahydropyridine[4,3-c]pyrazol-1-yl derivatives Step a:

540 g of 3-amino-5-(carbo-tbutoxy)-4,5,6,7-tetrahydropyridine[4,3-c]pyrazole were prepared according to the procedure reported in example 4.

Step b:

The obtained 3-amino-5-(carbo-tbutoxy 4,5,6,7-tetrahydropyridine[4,3-c]pyrazole was supported on methylisocyanate polystyrene resin (200-400 mesh, 2% DVB, loading 1.49 mmol/g, 900 g) according to the procedure reported in example 5.

Step c

The obtained N-{3-amino-5-(carbo-tbutoxy)-4,5,6,7-tetrahydropyridine[4,3-c]pyrazol-1-yl},N'-methylpolystyrene urea was partioned in 96 different batches (15 g each). Each batch was reacted with the appropriate acyl chloride, according to the procedure described in example 13, to obtain the products listed in example 13.

Step d

The 96 batches of N-{3-acyl-amido-5-(carbo-tbutoxy)-4,6-dihydropyrrolo[3,4-c]pyrazol-1-yl},N'-methylpolystyrene ureas were individually treated with a solution of TFA 50% in anhydrous dichloromethane according to the procedure described in example 14, to obtain the products listed in example 14.

Step e

One out of the 96 lots obtained in step d was partioned in 149 batches (50 mg each). Each of these 149 batches was individually reacted with all the carboxylic acids, sulfonylchlorides, or isocyanates used for the preparation of the products listed in examples 8, 9, 10.

Step f

One out of the 96 lots obtained in step d was partioned in 149 batches (50 mg each). These 149 batches were individually reacted with the 95 carboxylic acids used in example 8, 15 sulfonylchlorides used in example 9, and 15 isocyanates used in example 10.

Step g

Each of the remaining 95 lots of step d underwent steps e, and f.

The overall combinatorial chemistry process gave a library of 96×149=14304 4,5,6,7-tetrahydropyridine[4,3-c]pyrazol-1-yl derivatives.

Representative compounds of the above combinatorial library are:

N-{5-benzensulfonyl-4,5,6,7-tetrahydropyridine[4,3-c]pyrazol-3-yl}-4-fluorobenzamide 1H-NMR (DMSO-d6) d ppm 2.7 (m); 3.4 (m); 4.1 (s); 7.25-8.1 (m)

N-[5-(methylsulfonyl)-4,5,6,7-tetrahydropyridine[4,3-c]pyrazol-3-yl]benzamide 1H-NMR (DMSO-d6) d ppm 2.78 (m), 2.89 (s), 3.45 (m), 4.15 (s), 7.4-8.0 (m).

N-isopropyl-N'-{3-benzamido-4,5,6,7-tetrahydropyridine[4,3-c]pyrazol-5-yl}urea; 1H-NMR (DMSO-d6) d ppm 1 (d), 2.6 (m), 3.57 (m), 3.75 (m), 4.2 (s), 7.4-8.0 (m).

N-isopropyl-N'-{3-phenylacetamido-4,5,6,7-tetrahydropyridine[4,3-c]pyrazol-5-yl}urea;
1H-NMR (DMSO-d6) d ppm 1 (d) 1.01 (s, 3H), 1.04 (s, 3H), 2.55 (t, 2H), 3.50 (t, 2H), 3.60 (s, 2H), 3.62-3.80 (m, 1H), 4.15 (s, 2H), 6.15 (d, 1H), 7.20-7.40 (m, 5H)."

N-[5-(methylsulfonyl)-4,5,6,7-tetrahydropyridine[4,3-c]pyrazol-3-yl]cyclopropanecarboxamide 1H-NMR (DMSO-d6) d ppm 0.75 (m), 1.8 (m), 2.7 (m), 2.85 (s), 3.4 (m), 4.1 (s).

N-(5-benzoyl-4,5,6,7-tetrahydropyridine[4,3-c]pyrazol-3-yl)cyclopropanecarboxamide 1H-NMR (DMSO-d6) d ppm 0.75 (m), 1.8 (m), 2.7 (m), 3.65 (bs), 4.4 (s), 7.3-7.5 (m).

N-[5-phenylacetyl-4,5,6,7-tetrahydropyridine[4,3-c]pyrazol-3-yl]cyclopropanecarboxamide 1H-NMR (DMSO-d6) d ppm 0.75 (bs), 1.8 (m), 2.6 (bs), 4.2-4.4 (2s), 7.1-7.35 (m).

N-isopropyl-N'-{3-cyclopropanecarboxamido-4,5,6,7-tetrahydropyridine[4,3-c]pyrazol-5-yl}urea;
1H-NMR (DMSO-d6) d ppm 0.75 (bs), 1.0 (d), 1.8 (m), 2.55 (m), 3.5 (m), 3.75 (m), 4.05 (s)."

N-[5-(methylsulfonyl)-4,5,6,7-tetrahydropyridine[4,3-c]pyrazol-3-yl]-4-phenoxybenzamide 1H-NMR (DMSO-d6) d ppm 2.8 (bs), 2.9 (s), 3.5 (m), 4.2 (s), 7.0-8.0 (m).

N-(5-benzoyl-4,5,6,7-tetrahydropyridine[4,3-c]pyrazol-3-yl)-4-phenoxybenzamide 1H-NMR (DMSO-d6) d ppm 2.75 (bs), 3.7 (bs), 4.5 (bs), 7.0-8.0 (m).

N-[5-phenylacetyl-4,5,6,7-tetrahydropyridine[4,3-c]pyrazol-3-yl]-4-phenoxybenzamide 1H-NMR (DMSO-d6) d ppm 2.6 (bs), 3.75 (bs), 4.4 (bs), 7.0-8.0 (m).

N-isopropyl-N'-{3-(4-fluoro-benzamido)-4,5,6,7-tetrahydropyridine[4,3-c]pyrazol-5-yl}urea; 1H-NMR (DMSO-d6) d ppm 1.0 (d); 2.6 (m); 3.55 (m); 3.7 (m); 4.2 (s); 6.2 (d); 7.3-8.1 (m)

N-(5-(4-fluoro-benzoyl)-4,5,6,7-tetrahydropyridine[4,3-c]pyrazol-3-yl)-4-fluorobenzamide 1H-NMR (DMSO-d6) d ppm 2.7 (bs); 3.5-4.0 (2bs); 4.4 (bs); 7.1-8.2 (m)

N-isopropyl-N'-{3-(4-tertbutyl-benzamido)-4,5,6,7-tetrahydropyridine[4,3-c]pyrazol-5-yl}urea;
1H-NMR (DMSO-d6) d ppm 1.0 (d); 1.3 (s); 2.6 (m); 3.6 (m); 3.7 (m); 4.15 (s); 7.45-7.95 (m)"

N-[5-(methylsulfonyl)-4,5,6,7-tetrahydropyridine[4,3-c]pyrazol-3-yl]-4-fluorobenzamide 1H-NMR (DMSO-d6) d ppm 2.8 (m); 2.9 (s); 3.5 (m); 4.2 (s); 7.2-8.1 (m)

N-{5-benzensulfonyl-4,5,6,7-tetrahydropyridine[4,3-c]pyrazol-3-yl}-4-phenoxybenzamide 1H-NMR (DMSO-d6) d ppm 2.7 (m), 3.4 (m), 4.05 (s), 7.0-8.0 (m).

N-{5-benzylsulfonyl-4,5,6,7-tetrahydropyridine[4,3-c]pyrazol-3-yl}-4-phenoxybenzamide 1H-NMR (DMSO-d6) d ppm 2.6 (m), 3.4 (m), 4.2 (s), 4.4 (s), 7.0-8.0 (m).

N-phenyl-N'-{3-(4-phenoxy-benzamido)-4,5,6,7-tetrahydropyridine[4,3-c]pyrazol-5-yl}urea;
1H-NMR (DMSO-d6) d ppm 2.7 (m), 3.7 (m), 4.35 (s), 6.9-8.0 (m)."

N-[5-(quinoline-8-sulfonyl)-4,5,6,7-tetrahydropyridine[4,3-c]pyrazol-3-yl]-4-phenoxybenzamide 1H-NMR (DMSO-d6) d ppm 2.6 (m), 3.75 (m), 4.3 (s), 7.0-9.0 (m).

N-{5-(2-thienyl)acetyl-4,5,6,7-tetrahydropyridine[4,3-c]pyrazol-3-yl}-4-phenoxybenzamide; 1H-NMR (DMSO-d6) d ppm 2.65 (bs), 3.8 (m), 3.9-4.1 (2s), 4.4-4.5 (2s), 6.8-8.0 (m).

N-[5-isobutyryl-4,5,6,7-tetrahydropyridine[4,3-c]pyrazol-3-yl]-4-fluorobenzamide 1H-NMR (DMSO-d6) d ppm 1.0 (d); 2.5-2.7 (2m); 2.9 (m); 3.7 (m); 4.3-4.5 (2s); 7.3-8.1 (m)

N-(5-benzoyl-4,5,6,7-tetrahydropyridine[4,3-c]pyrazol-3-yl)-4-tertbutyl-benzamide 1H-NMR (DMSO-d6) d ppm 1.3 (s); 2.7 (m); 3.7 (m); 4.45 (s); 7.3-7.9 (m)

N-{5-benzensulfonyl-4,5,6,7-tetrahydropyridine[4,3-c]pyrazol-3-yl}-4-tertbutyl-benzamide 1H-NMR (DMSO-d6) d ppm 1.3 (s); 2.7 (m); 3.4 (m); 4.1 (s); 7.45-7.95 (m)

N-phenyl-N'-{3-(4-tertbutyl-benzamido)-4,5,6,7-tetrahydropyridine[4,3-c]pyrazol-5-yl}urea;
1H-NMR (DMSO-d6) d ppm 1.3 (s); 2.7 (m); 3.7 (m); 4.35 (s); 6.8-8.0 (m)"

N-{5-(quinoline-8-sulfonyl)-4,5,6,7-tetrahydropyridine[4,3-c]pyrazol-3-yl}-4-tertbutyl-benzamide 1H-NMR (DMSO-d6) d ppm 1.3 (s); 2.6 (m); 3.7 (m); 4.3 (s); 7.4-9.0 (m)

N-(5-benzylsulfonyl-4,5,6,7-tetrahydropyridine[4,3-c]pyrazol-3-yl)cyclopropanecarboxamide 1H-NMR (DMSO-d6) d ppm 0.75 (m), 1.8 (m), 2.55 (m), 3.35 (m), 4.1 (s), 4.4 (s), 7.2-7.4 (m).

N-phenyl-N'-{3-cyclopropanecarboxamido-4,5,6,7-tetrahydropyridine[4,3-c]pyrazol-5-yl}urea;
1H-NMR (DMSO-d6) d ppm 0.75 (m), 1.8 (m), 2.6 (m), 3.7 (m), 4.3 (s), 4.3 (s), 6.8-7.5 (m)."

N-{5-(2-thienyl)acetyl-4,5,6,7-tetrahydropyridine[4,3-c]pyrazol-3-yl}-cyclopropanecarboxamide 1H-NMR (DMSO-d6) d ppm 0.75 (m), 1.8 (m), 2.6 (m), 3.7 (m), 3.85-4.05 (2s), 4.3-4.5 (2s), 6.8-7.4 (m).

N-{5-(quinoline-8-sulfonyl)-4,5,6,7-tetrahydropyridine[4,3-c]pyrazol-3-yl}-cyclopropanecarboxamide 1H-NMR (DMSO-d6) d ppm 0.75 (bs), 1.8 (m), 2.5 (m), 3.7 (m), 4.25 (s), 7.6-9.0 (m).

N-(5-acetyl-4,5,6,7-tetrahydropyridine[4,3-c]pyrazol-3-yl)benzamide 1H-NMR (DMSO-d6) d ppm 2.05 (s), 2.6-2.8 (2m), 3.6-3.7(2m), 4.3-4.4 (2s), 7.4-8.0 (m).

N-(5-benzoyl-4,5,6,7-tetrahydropyridine[4,3-c]pyrazol-3-yl)benzamide 1H-NMR (DMSO-d6) d ppm 2.75 (m), 3.7 (bs), 4.5 (s), 7.4-8.0 (m).

N-[5-(2-phenylacetyl)-4,5,6,7-tetrahydropyridine[4,3-c]pyrazol-3-yl]benzamide 1H-NMR (DMSO-d6) d ppm 2.6 (bs), 3.75 (bs), 4.5 (bs), 7.1-8.0 (m).

N-{5-benzensulfonyl-4,5,6,7-tetrahydropyridine[4,3-c]pyrazol-3-yl}benzamide 1H-NMR (DMSO-d6) d ppm 2.7 (m), 4.05 (s), 7.4-8.0 (m).

N-butyl-N'-{3-benzamido-4,5,6,7-tetrahydropyridine[4,3-c]pyrazol-5-yl}urea;
1H-NMR (DMSO-d6) d ppm 0.8 (m), 1.2-1.4 (m), 2.6 (m), 3.0 (m), 3.6 (m), 4.2 (s), 7.4-8.0 (m)."

N-ethyl-N'-{3-benzamido-4,5,6,7-tetrahydropyridine[4,3-c]pyrazol-5-yl}urea;
1H-NMR (DMSO-d6) d ppm 1 (m), 2.6 (m), 3.0 (q), 4.2 (s), 7.4-8.0 (m)."

N-{5-(2-furoyl)-4,5,6,7-tetrahydropyridine[4,3-c]pyrazol-3-yl}-4-tertbutyl-benzamide; 1H-NMR (DMSO-d6) d ppm 1.3 (s); 2.8 (m); 3.9 (m); 4.6 (bs); 6.5-8.0 (m)

N-{5-(2-thienyl)acetyl-4,5,6,7-tetrahydropyridine[4,3-c]pyrazol-3-yl}-4-tertbutyl-benzamide; 1H-NMR (DMSO-d6) d ppm 1.3 (s); 2.6 (m); 3.75 (m); 3.9-4.1 (2s); 4.3-4.5 (2s); 6.8-7.9 (m)

N-phenyl-N'-{3-acetamido-4,5,6,7-tetrahydropyridine[4,3-c]pyrazol-5-yl}urea;
1H-NMR (DMSO-d6) d ppm 2.0 (s), 2.7 (m), 3.7 (m), 4.35 (s), 6.8-7.5 (m)."

N-[5-(2-phenylacetyl)-4,5,6,7-tetrahydropyridine[4,3-c]pyrazol-3-yl]acetamide 1H-NMR (DMSO-d6) d ppm 2.0 (s), 2.4-2.6 (2m), 3.6-3.9 (m), 4.3-4.5 (2s), 7.15-7.35 (m).

N-{5-benzensulfonyl-4,5,6,7-tetrahydropyridine[4,3-c]pyrazol-3-yl}-acetamide 1H-NMR (DMSO-d6) d ppm 2.0 (s), 2.65 (m), 3.4 (m), 4.0 (s), 7.5-7.8 (m).

N-[5-(benzylsulfonyl)-4,5,6,7-tetrahydropyridine[4,3-c]pyrazol-3-yl]acetamide 1H-NMR (DMSO-d6) d ppm 2.0 (s), 2.6 (m), 3.4 (m), 4.15 (s), 4.4 (s), 7.35 (s).

N-(5-benzoyl-4,5,6,7-tetrahydropyridine[4,3-c]pyrazol-3-yl)acetamide 1H-NMR (DMSO-d6) d ppm 1.8-2.0 (2bs), 2.7 (bs), 3.4-3.9 (2bs), 4.1-4.5 (2bs), 7.4 (bs).

N-[5-(quinoline-8-sulfonyl)-4,5,6,7-tetrahydropyridine[4,3-c]pyrazol-3-yl]acetamide 1H-NMR (DMSO-d6) d ppm 2.0 (s), 2.55 (m), 3.7 (m), 4.25 (s), 7.4-9.0 (m).

N-{5-(quinoline-8-sulfonyl)-4,5,6,7-tetrahydropyridine[4,3-c]pyrazol-3-yl}-4-fluoro-benzamide 1H-NMR (DMSO-d6) d ppm 2.6 (m); 3.7 (m); 4.3 (s); 7.3-9.0 (m)

N-[5-phenylacetyl-4,5,6,7-tetrahydropyridine[4,3-c]pyrazol-3-yl]-4-tertbutyl-benzamide 1H-NMR (DMSO-d6) d ppm 2.5-2.7 (2m); 3.65-3.8 (m); 4.3-4.5 (2s); 7.15-8.0 (m)

N-{5-benzylsulfonyl-4,5,6,7-tetrahydropyridine[4,3-c]pyrazol-3-yl}-4-tertbutyl-benzamide 1H-NMR (DMSO-d6) d ppm 2.6 (m); 3.4 (m); 4.2 (s); 4.4 (s); 7.3-7.9 (m)

N-isopropyl-N'-{3-acetamido-4,5,6,7-tetrahydropyridine[4,3-c]pyrazol-5-yl}urea;
1H-NMR (DMSO-d6) d ppm 1.0 (d), 1.95 (s), 2.55 (m), 3.55 (m), 3.7 (m), 4.15 (s)."

N-[5-(methylsulfonyl)-4,5,6,7-tetrahydropyridine[4,3-c]pyrazol-3-yl]acetamide 1H-NMR (DMSO-d6) d ppm 1.95 (s), 2.7 (m), 2.85 (s), 3.4 (m), 4.1 (s).

N-(5-acetyl-4,5,6,7-tetrahydropyridine[4,3-c]pyrazol-3-yl)acetamide 1H-NMR (DMSO-d6) d ppm 1.9-2.1 (2s), 2.5-2.7 (2m), 3.55-3.7 (2m), 4.25-4.35 (2s).

N-{5-(2-thienyl)acetyl-4,5,6,7-tetrahydropyridine[4,3-c]pyrazol-3-yl}-acetamide 1H-NMR (DMSO-d6) d ppm 1.95 (s), 2.6 (m), 3.75 (m), 3.9-4.1 (2s), 4.3-4.5 (2s), 6.9-7.5 (m).

N-(5-benzoyl-4,5,6,7-tetrahydropyridine[4,3-c]pyrazol-3-yl)-4-fluorobenzamide 1H-NMR (DMSO-d6) d ppm 2. (bs); 3.3-3.9 (2bs); 4.3-4.6 (2bs); 7.2-8.1 (m)

N-[5-(methylsulfonyl)-4,5,6,7-tetrahydropyridine[4,3-c]pyrazol-3-yl]-4-tertbutyl-benzamide 1H-NMR (DMSO-d6) d ppm 1.3 (s); 2.75 (m); 2.9 (s); 3.5 (m); 4.15 (s); 7.4-7.9 (m)

N-(5-(1-naphthalenecarbonyl)-4,5,6,7-tetrahydropyridine[4,3-c]pyrazol-3-yl)-4-tertbutyl-benzamide 1H-NMR (DMSO-d6) d ppm 1.2-1.3 (2s); 2.45-2.9 (2bs); 3.35 (bs); 4.4-4.8 (m); 7.3-8.0 (m)

N-{5-benzylsulfonyl-4,5,6,7-tetrahydropyridine[4,3-c]pyrazol-3-yl}-4-fluorobenzamide 1H-NMR (DMSO-d6) d ppm 2.6 (m); 3.4 (m); 4.2 (s); 4.4 (s); 7.15-8.1 (m)

N-[5-phenylacetyl-4,5,6,7-tetrahydropyridine[4,3-c]pyrazol-3-yl]-4-fluorobenzamide 1H-NMR (DMSO-d6) d ppm 2.5-2.7 (2m); 3.7-3.8 (2m); 3.85 (s); 4.35-4.5 (2s); 7.1-8.1 (m)

N-[5-(methylsulfonyl)-4,5,6,7-tetrahydropyridine[4,3-c]pyrazol-3-y]-4-phenoxy-benzamide 1H-NMR (DMSO-d6) d ppm 2.75 (m); 2.9 (s); 3.5 (m); 4.15 (s); 7.0-7.8 (m)

N-[5-(methylsulfonyl)-4,5,6,7-tetrahydropyridine[4,3-c]pyrazol-3-yl]-3-methoxy-benzamide 1H-NMR (DMSO-d6) d ppm 2.75 (m); 2.9 (s); 3.5 (m); 3.8 (s); 4.2 (s); 7.1-7.6 (m)

N-{5-(quinoline-8-sulfonyl)-4,5,6,7-tetrahydropyridine[4,3-c]pyrazol-3-yl}-4-phenoxy-benzamide 1H-NMR (DMSO-d6) d ppm 2.6 (m); 3.7 (m); 4.3 (s); 7.0-9.0 (m)

N-{5-(quinoline-8-sulfonyl)-4,5,6,7-tetrahydropyridine[4,3-c]pyrazol-3-yl}-3-methoxy-benzamide 1H-NMR (DMSO-d6) d ppm 2.6 (m); 3.7 (m); 3.8 (s); 4.3 (s); 7.0-9.0 (m)

N-phenyl-N'-{3-benzamido-4,5,6,7-tetrahydropyridine[4,3-c]pyrazol-5-yl}urea; 1H-NMR (DMSO-d6) d ppm 2.7 (m), 3.7 (m), 4.4 (s), 6.9-8.0 (m), 8.6 (s).

N-[5-(methylsulfonyl)-4,5,6,7-tetrahydropyridine[4,3-c]pyrazol-3-yl]-phenylacetamide 2.65 (t, 2H), 2.85 (s, 3H), 3.40 (t, 2H), 3.80 (s, 2H), 4.10 (s, 2H), 7.20-7.40 (m, 5H).

N-{5-[2-(2-thienyl)acetyl]-4,5,6,7-tetrahydropyridine[4,3-c]pyrazol-3-yl}benzamide 1H-NMR (DMSO-d6) d ppm 2.6 (m), 3.77 (m), 3.9-4.1 (2s), 4.4-4.5 (2s), 6.9-8.0 (m).

N-{5-(quinoline-8-sulfonyl)-4,5,6,7-tetrahydropyridine[4,3-c]pyrazol-3-yl}-benzamide 1H-NMR (DMSO-d6) d ppm 2.6 (m), 3.75 (m), 4.35 (s), 7.4-9.0 (m).

N-[5-(methylsulfonyl)-4,5,6,7-tetrahydropyridine[4,3-c]pyrazol-3-yl]-3-fluoro-benzamide 1H-NMR (DMSO-d6) d ppm 2.8 (m), 2.9 (s), 3.45 (m), 4.2 (s), 7.35-7.9 (m).

N-[5-(benzylsulfonyl)-4,5,6,7-tetrahydropyridine[4,3-c]pyrazol-3-yl]-3-fluorobenzamide 1H-NMR (DMSO-d6) d ppm 2.6 (m), 3.4 (m), 4.2 (s), 4.4 (s), 7.3-7.9 (m).

N-[5-phenylacetyl-4,5,6,7-tetrahydropyridine[4,3-c]pyrazol-3-yl]-3-fluorobenzamide 1H-NMR (DMSO-d6) d ppm 2.5-2.65 (2m), 3.75-3.85 (2m), 4.35-4.6 (2s), 7.15-7.95 (m).

N-(5-acetyl-4,5,6,7-tetrahydro-1H-pyrazolo[4,3-c]pyridin-3-yl)-3-fluorobenzamide 1H-NMR (DMSO-d6) d ppm 2.0-2.1 (2s), 2.6-2.8 (2m), 3.6-3.8 (2m), 4.3-4.4 (2s), 7.4-7.9 (m).

N-(5-benzoyl-4,5,6,7-tetrahydropyridine[4,3-c]pyrazol-3-yl)-3fluorobenzamide 1H-NMR (DMSO-d6) d ppm 2.75 (bs), 3.5-3.9 (2bs), 4.3-4.6 (2bs), 7.3-7.9 (m).

N-{5-benzensulfonyl-4,5,6,7-tetrahydropyridine[4,3-c]pyrazol-3-yl}-3-fluorobenzamide 1H-NMR (DMSO-d6) d ppm 2.65 (m), 3.4 (m), 4.1 (s), 7.4-7.9 (m).

"N-isopropyl-N'-{3-(3-fluorobenzamido)-4,5,6,7-tetrahydropyridine[4,3-c]pyrazol-5-yl}urea;
1H-NMR (DMSO-d6) d ppm 1.0 (d), 2.6 (m), 3.6 (m), 3.7 (m), 4.2 (s), 6.2 (d), 7.4-7.9 (m)."

N-{5-benzensulfonyl-4,5,6,7-tetrahydropyridine[4,3-c]pyrazol-3-yl}-3-phenoxybenzamide 1H-NMR (DMSO-d6) d ppm 2.6 (m); 3.4 (m); 4.0 (s); 7.0-7.8 (m)

N-(5-benzoyl-4,5,6,7-tetrahydropyridine[4,3-c]pyrazol-3-yl)-3-phenoxy-benzamide 1H-NMR (DMSO-d6) d ppm 2.7 (bs); 3.5 (bs); 4.15-4.25 (2bs); 7.0-7.9 (m)

N-{5-benzylsulfonyl-4,5,6,7-tetrahydropyridine[4,3-c]pyrazol-3-yl}-3-phenoxybenzamide 1H-NMR (DMSO-d6) d ppm 2.6 (m); 3.4 (m); 4.1 (s); 4.4 (s); 7.0-7.8 (m)

N-(5-(1-naphthalenecarbonyl)-4,5,6,7-tetrahydropyridine[4,3-c]pyrazol-3-yl)-3-tphenoxy-benzamide 1H-NMR (DMSO-d6) d ppm 2.5-2.9 (2bs); 4.0-4.2 (2bs); 4.5-4.9 (2bs); 6.9-8.0 (m)

N-[5-phenylacetyl-4,5,6,7-tetrahydropyridine[4,3-c]pyrazol-3-yl]-3-phenoxybenzamide 1H-NMR (DMSO-d6) d ppm 2.4-2.7 (2m); 3.6-3.8 (2m); 4.3-4.5 (2s); 7.0-7.8 (m)

N-{5-(2-thienyl)acetyl-4,5,6,7-tetrahydropyridine[4,3-c]
pyrazol-3-yl}-3-phenoxybenzamide; 1H-NMR (DMSO-
d6) d ppm 2.6 (m); 3.75 (m); 3.9-4.1(2s); 4.3-4.5 (2s);
6.8-7.8 (m)

N-{5-(quinoxaline-2-carbonyl)-4,5,6,7-tetrahydropyridine
[4,3-c]pyrazol-3-yl-4-tertbutyl-benzamide; 1H-NMR
(DMSO-d6) d ppm 1.3 (s); 2.85 (m); 3.85 (m); 4.5-4.7 (2s);
7.3-8.2 (m)

N-{5-(quinoxaline-2-carbonyl)-4,5,6,7-tetrahydropyridine
[4,3-c]pyrazol-3-yl}-3-phenoxybenzamide; 1H-NMR
(DMSO-d6) d ppm 2.8 (m); 3.7-4.05 (2m); 4.5-4.7 (2s);
6.9-8.2 (m)

N-phenyl-N'-{3-(3-phenoxy-benzamido)-4,5,6,7-tetrahy-
dropyridine[4,3-c]pyrazol-5-yl}urea;
1H-NMR (DMSO-d6) d ppm 2.7 (m); 3.7 (m); 4.35 (s);
6.8-7.8 (m)"

N-(5-benzoyl-4,5,6,7-tetrahydropyridine[4,3-c]pyrazol-3-
yl)-phenylacetamide 2.70 (t, 2H), 3.58 (s, 2H), 3.60 (t, 2H),
4.20 (s, 2H), 7.20-7.50 (m, 10H).

N-(5-phenylacetyl-4,5,6,7-tetrahydropyridine[4,3-c]pyra-
zol-3-yl)-phenylacetamide 2.60 (t, 2H), 3.60 (s, 2H), 3.70
(t, 2H), 3.80 (s, 2H), 4.30 (s, 2H), 7.08-7.40 (m, 10H).

N-(5-aminocarbonyl-4,5,6,7-tetrahydropyridine[4,3-c]pyra-
zol-3-yl)-phenylacetamide 2.58 (t, 2H), 3.50 (t, 2H), 3.60
(s, 2H), 4.15 (s, 2H), 5.90 (s, 2H), 7.15-7.35 (m, 5H), 10.15
(bs, 1H), 12.10 (bs, 1H).

N-butyl-N'-{3-phenylacetamido-4,5,6,7-tetrahydropyridine
[4,3-c]pyrazol-5-yl}urea;
0.80 (t, 3H), 1.18-1.28 (m, 2H), 1.30-1.40 (m, 2H), 2.55 (t,
2H), 3.00 (t, 2H), 3.50 (t, 2H), 3.60 (s, 2H), 4.15 (s, 2H),
6.45 (bs, 1H), 7.20-7.45 (m, 5H), 10.22 (bs, 1H)."

N-ethyl-N'-(3-phenylacetamido-4,5,6,7-tetrahydropyridine
[4,3-c]pyrazol-5-yl)urea;
1H-NMR (DMSO-d6) d ppm 1 (d) 1.00 (t, 3H), 2.80 (t, 2H),
2.95-3.05 (m, 2H), 3.50 (t, 2H), 3.60 (s, 2H), 4.20 (s, 2H),
6.50 (bs, 1H), 7.20-7.35 (m, 5H), 10.35 (s, 1H)."

N-phenyl-N'-{3-phenylacetamido-4,5,6,7-tetrahydropyri-
dine[4,3-c]pyrazol-5-yl}urea;
2.65 (t, 2H), 3.60 (s, 2H), 3.65 (t, 2H), 4.35 (s, 2H), 6.90 (t,
1H), 7.15-7.40 (m, 9H), 8.60 (s, 1H), 10.25 (s, 1H). "

N-benzyl-N'-{3-phenylacetamido-4,5,6,7-tetrahydropyri-
dine[4,3-c]pyrazol-5-yl}urea;
1H-NMR (DMSO-d6) d ppm 1 (d) 2.60 (t, 2H), 3.60 (t, 2H),
3.70 (s, 2H), 4.18-4.22 (m, 4H), 7.10 (bs, 1H), 7.15-7.25
(m, 10H), 10.20 (bs, 1H)."

N-ethyl-N'-{3-(2-naphthalene)acetamido-4,5,6,7-tetrahy-
dropyridine[4,3-c]pyrazol-5-yl}urea;
0.95 (t, 3H), 2.65 (t, 2H), 2.95-3.05 (m, 2H), 3.50 (t, 2H), 3.80
(s, 2H), 4.15 (s, 2H), 6.45 (t, 1H), 7.40-7.50 (m, 3H),
7.80-7.90 (m, 4H)."

N-(5-(2-methoxybenzoyl)-4,5,6,7-tetrahydropyridine[4,3-c]
pyrazol-3-yl)-(2-naphthalene)acetamide 2.55-2.65 (m, 2H),
3.40 (t, 2H), 3.50-3.60 (m, 2H), 3.75 (s, 2H), 4.00-4.45 (m,
2H), 6.80-7.20 (m, 3H), 7.25-7.55 (m, 4H), 7.65-7.90 (m,
4H).

N-phenyl-N'-{3-(2-naphthalene)acetamido-4,5,6,7-tetrahy-
dropyridine[4,3-c]pyrazol-5-yl}urea;
1H-NMR (DMSO-d6) d ppm 1 (d) 2.68 (t, 2H), 3.65 (t, 2H),
3.80 (s, 2H), 4.35 (s, 2H), 6.90 (t, 1H), 7.25-7.32 (m, 2H),
7.35-7.50 (m, 5H), 7.80 (s, 1H), 7.85-7.90 (m, 4H), 8.60 (s,
1H)."

N-[5-benzoyl-4,5,6,7-tetrahydropyridine[4,3-c]pyrazol-3-
yl]-(2-naphthalene)acetamide 2.65 (t, 2H), 3.65 (bs, 2H),
3.75 (bs, 2H), 7.30-7.50 (m, 8H), 7.70-7.90 (m, 4H).

N-(5-phenylacetyl-4,5,6,7-tetrahydropyridine[4,3-c]pyra-
zol-3-yl)-(2-naphthalene)acetamide 2.58 (t, 2H), 3.65 (t,
2H), 3.70-3.80 (m, 4H), 4.30-4.40 (m, 2H), 7.02-7.30 (m,
5H), 7.40-7.52 (m, 3H), 7.80-7.90 (m, 4H).

N-(5-acetyl-4,5,6,7-tetrahydropyridine[4,3-c]pyrazol-3-yl)-
(2-naphtalene)acetamide 2.05 (s, 3H), 2.55-2.70 (m, 2H),
3.60-3.70 (m, 2H), 3.80 (s, 2H), 4.25-4.35 (m, 2H), 7.40-
7.50 (m, 3H), 7.80-7.90 (m, 4H).

N-butyl-N'-{3-(2-naphthalene)acetamido-4,5,6,7-tetrahy-
dropyridine[4,3-c]pyrazol-5-yl}urea;
1H-NMR (DMSO-d6) d ppm 1 (d) 0.83 (t, 3H), 1.18-1.28
(m, 2H), 1.30-1.40 (m, 2H), 2.55 (t, 2H), 2.90-3.00 (m,
2H), 3.50 (t, 2H), 3.78 (s, 2H), 4.15 (s, 2H), 6.40 (t, 1H),
7.40-7.50 (m, 3H), 7.80-7.90 (m, 4H)."

N-benzyl-N'-{3-(2-naphthalene)acetamido-4,5,6,7-tetrahy-
dropyridine[4,3-c]pyrazol-5-yl}urea;
1H-NMR (DMSO-d6) d ppm 1 (d) 2.60 (t, 2H), 3.55 (t, 2H),
3.75 (s, 2H), 4.15-4.25 (m, 4H), 7.08 (t, 1H), 7.12-7.28 (m,
5H), 7.40-7.50 (m, 3H), 7.80-7.90 (m, 4H). "

N-(5-(2-furoyl)-4,5,6,7-tetrahydropyridine[4,3-c]pyrazol-3-
yl)-(2-naphtalene)acetamide 2.75 (bs, 2H), 3.75 (bs, 2H),
3.80 (bs, 2H), 4.50 (bs, 2H), 6.55 (bs, 1H), 6.95 (bs, 1H),
7.40-7.55 (m, 3H), 7.70 (bs, 1H), 7.80-7.90 (m, 4H).

N-(5-acetyl-4,5,6,7-tetrahydropyridine[4,3-c]pyrazol-3-yl)-
3-methylbutanamide 0.88 (s, 3H), 0.90 (s, 3H), 2.00-2.10
(m, 4H), 2.15 (d, 2H), 2.60-2.70 (m, 2H), 3.60-3.70 (m,
2H), 4.25-4.35 (m, 2H).

N-(5-benzoyl-4,5,6,7-tetrahydropyridine[4,3-c]pyrazol-3-
yl)-3-ethylbutanamide 0.90-0.95 (m, 6H), 2.00-2.20 (m,
3H), 2.70 (bs, 2H), 3.50-3.90 (m, 2H), 4.20-4.50 (m, 2H),
7.30-7.50 (m, 5H).

N-(5-phenylacetyl-4,5,6,7-tetrahydropyridine[4,3-c]pyra-
zol-3-yl)-3-methylbutanamide 0.85-0.95 (m, 6H),
1.95-2.10 (m, 1H), 2.15 (d, 2H), 2.55 (t, 2H), 3.70 (t, 2H),
3.80 (s, 2H), 4.35 (s, 2H), 7.15-7.30 (m, 5H).

N-(5-(2-furoyl)-4,5,6,7-tetrahydropyridine[4,3-c]pyrazol-3-
yl)-3-methylbutanamide 0.85-0.95 (m, 6H), 1.95-2.05 (m,
1H), 2.15 (d, 2H), 2.75 (bs, 2H), 3.80 (t, 2H), 4.50 (bs, 2H),
6.58-6.62 (m, 1H), 6.98 (bs, 1H), 7.80 (bs, 1H).

N-isopropyl-N'-{3-(3-methyl-butanamido)-4,5,6,7-tetrahy-
dropyridine[4,3-c]pyrazol-5-yl}urea;
1H-NMR (DMSO-d6) d ppm 1 (d) 0.90 (s, 3H), 0.95 (s, 3H),
1.02 (s, 3H), 1.04 (s, 3H), 2.00-2.10 (m, 1H), 2.15 (d, 2H),
2.65 (t, 2H), 3.60 (t, 2H), 3.65-3.75 (m, 1H), 4.15 (s, 2H),
6.15 (d, 1H)."

N-benzyl-N'-{3-(3-methyl-butanamido)-4,5,6,7-tetrahydro-
pyridine[4,3-c]pyrazol-5-yl}urea;
1H-NMR (DMSO-d6) d ppm 1 (d) 0.88 (s, 3H), 0.90 (s), 3H),
1.95-2.10 (m, 1H), 2.15 (d, 2H), 2.60 (t, 2H), 3.60 (t, 2H),
4.20-4.28 (m, 4H), 7.10 (t, 1H), 7.15-7.30 (m, 5H)."

N-butyl-N'-{3-(3-methyl-butanamido)-4,5,6,7-tetrahydro-
pyridine[4,3-c]pyrazol-5-yl}urea;
0.85 (t, 3H), 0.88 (s, 3H), 0.90 (s, 3H), 1.20-1.30 (m, 2H),
1.32-1.40 (m, 2H), 1.95-2.10 (m, 1H), 2.15 (d, 2H), 2.55 (t,
2H), 2.95-3.02 (m, 2H), 3.55 (t, 2H), 4.15 (s, 2H), 6.45 (t,
1H)."

N-phenyl-N'-{3-(3-methyl-butanamido)-4,5,6,7-tetrahydro-
pyridine[4,3-c]pyrazol-5-yl}urea;
0.90-0.95 (m, 6H), 2.00-2.10 (m, 1H), 2.15 (d, 2H), 2.65 (t,
2H), 3.65 (t, 2H), 4.25 (s, 2H), 6.85 (t, 1H), 7.15-7.22 (m,
2H), 7.28-7.32 (m, 2H), 8.60 (s, 1H)."

N-ethyl-N'-{3-(3-methyl-butanamido)-4,5,6,7-tetrahydro-
pyridine[4,3-c]pyrazol-5-yl}urea;
0.88-0.90 (m, 6H), 1.00 (t, 3H), 1.95-2.10 (m, 1H), 2.15 (d,
2H), 2.58 (t, 2H), 2.95-3.08 (m, 2H), 3.55 (t, 2H), 4.15 (s,
2H), 6.45 (t, 1H)."

N-ethyl-N'-{3-(4-phenyl)phenylacetamido-4,5,6,7-tetrahy-
dropyridine[4,3-c]pyrazol-5-yl}urea;

0.95 (t, 3H), 2.58 (t, 2H), 2.95-3.05 (m, 2H), 3.50 (t, 2H), 3.65 (s, 2H), 4.15 (s, 2H), 6.45 (t, 1H), 7.30-7.50 (m, 4H), 7.55-7.65 (m, 3H)."

N-isopropyl-N'-{3-(4-phenyl)phenylacetamido-4,5,6,7-tetrahydropyridine[4,3-c]pyrazol-5-yl}urea;

1.00-1.05 (m, 6H), 2.55 (t, 2H), 3.40 (t, 2H), 3.65 (s, 2H), 3.70-3.80 (m, 1H), 4.15 (s, 2H), 6.15 (d, 1H), 7.30-7.45 (m, 5H), 7.55-7.65 (m, 4H)."

N-(5-benzoyl-4,5,6,7-tetrahydropyridine[4,3-c]pyrazol-3-yl)-(4-phenyl)phenylacetamide 2.70 (t, 2H), 3.60-3.70 (m, 4H), 4.40 (bs, 2H), 7.30-7.62 (m, 14H).

N-(5-(2-furoyl)-4,5,6,7-tetrahydropyridine[4,3-c]pyrazol-3-yl)-(4-phenyl)phenylacetamide 2.75 (bs, 2H), 3.65 (bs, 2H), 3.80 (bs, 2H), 4.50 (bs, 2H), 6.60 (bs, 1H), 6.95 (bs, 1H), 7.30-7.50 (m, 5H), 7.55-7.65 (m, 4H), 7.80 (bs, 1H).

N-propyl-N'-{3-(4-phenyl)phenylacetamido-4,5,6,7-tetrahydropyridine[4,3-c]pyrazol-5-yl}urea;

0.85 (t, 3H), 1.20-1.30 (m, 2H), 1.35-1.40 (m, 2H), 2.55 (t, 2H), 2.95-3.00 (m, 2H), 3.50 (t, 2H), 3.62 (s, 2H), 4.15 (s, 2H), 6.42 (t, 1H), 7.30-7.50 (m, 5H), 7.55-7.65 (m, 4H)."

N-(5-(2-methoxyphenyl)-4,5,6,7-tetrahydropyridine[4,3-c]pyrazol-3-yl)-(4-phenyl)phenylacetamide 2.50-2.65 (m, 2H), 3.40-3.70 (m, 2H), 3.75 (s, 3H), 4.00-4.45 (m, 2H), 6.85-7.25 (m, 4H), 7.30-7.55 (m, 5H), 7.57-7.64 (m, 4H).

N-benzyl-N'-{3-(4-phenyl)phenylacetamido-4,5,6,7-tetrahydropyridine[4,3-c]pyrazol-5-yl}urea;

2.60 (t, 2H), 3.55 (t, 2H), 3.62 (s, 2H), 4.20-4.30 (m, 4H), 7.10 (t, 1H), 7.15-7.65 (m, 14H)."

N-phenyl-N'-{3-(4-phenyl)phenylacetamido-4,5,6,7-tetrahydropyridine[4,3-c]pyrazol-5-yl}urea;

2.65 (t, 2H), 3.60-3.70 (m, 4H), 4.35 (s, 2H), 6.90 (t, 1H), 7.15-7.20 (m, 2H), 7.30-7.50 (m, 8H), 7.55-7.65 (m, 3H), 8.60 (s, 1H)."

N-isopropyl-N'-{3-[4-(1-pirrolidin-2-on)]phenylacetamido-4,5,6,7-tetrahydropyridine[4,3-c]pyrazol-5-yl}urea;

1.02-1.07 (m, 6H), 2.00-2.10 (m, 2H), 2.45 (t, 2H), 2.55 (t, 2H), 3.50 (t, 2H), 3.55 (s, 2H), 3.62-3.75 (m, 1H), 3.80 (t, 2H), 4.15 (s, 2H), 6.15 (d, 1H), 7.25-7.35 (m, 2H), 7.55-7.60 (m, 2H)."

N-ethyl-N'-{3-(2-(2-naphthalene)propionamido)-4,5,6,7-tetrahydropyridine[4,3-c]pyrazol-5-yl}urea;

0.98 (t, 3H), 1.48 (d, 3H), 2.55 (t, 2H), 2.95-3.05 (m, 2H), 3.55 (t, 2H), 4.00 (m, 1H), 4.10-4.22 (m, 2H), 6.42 (t, 1H), 7.40-7.58 (m, 3H), 7.80-7.90 (m, 4H)."

N-isopropyl-N'-{3-(2-(2-naphthalene)propionamido)-4,5,6,7-tetrahydropyridine[4,3-c]pyrazol-5-yl}urea;

1.00-1.05 (m, 6H), 1.50 (d, 3H), 2.55 (t, 2H), 3.45-3.55 (m, 2H), 3.62-3.75 (m, 1H), 4.00 (m, 1H), 4.10-4.25 (m, 2H), 6.15 (d, 1H), 7.40-7.55 (m, 3H), 7.80-7.90 (m, 4H)."

N-butyl-N'-{3-(2-(2-naphthalene)propionamido)-4,5,6,7-tetrahydropyridine[4,3-c]pyrazol-5-yl}urea;

0.80 (t, 3H), 1.18-1.27 (m, 2H), 1.30-1.40 (m, 2H), 1.48 (d, 3H), 2.55 (t, 2H), 2.95-3.02 (m, 2H), 3.40-3.60 (m, 2H), 4.00 (m, 1H), 4.08-4.22 (m, 2H), 6.40 (t, 1H), 7.40-7.55 (m, 3H), 7.80-7.90 (m, 4H)."

"N-benzyl-N'-{3-(2-(2-naphthalene)propionamido)-4,5,6,7-tetrahydropyridine[4,3-c]pyrazol-5-yl}urea;

1.45 (d, 3H), 2.60 (t, 2H), 3.50-3.62 (m, 2H), 4.00 (m, 1H), 4.20 (s, 2H), 4.25 (d, 2H), 7.08 (t, 1H), 7.15-7.30 (m, 5H), 7.40-7.55 (m, 4H), 7.80-7.90 (m, 3H), 10.10 (s, 1H), 12.10 (s, 1H)."

N-(5-(2-furoyl)-4,5,6,7-tetrahydropyridine[4,3-c]pyrazol-3-yl)-)propanamide 1.50 (d, 3H), 2.70 (bs, 2H), 3.80 (bs, 2H), 4.00 (bs, 2H), 4.30-4.55 (m, 2H), 6.50 (bs, 1H), 6.90 (bs, 1H), 7.40-7.58 (m, 4H), 7.70 (bs, 1H), 7.80-7.90 (m, 3H), 10.18 (s, 1H), 12.18 (s, 1H).

N-(5-(2-methoxy-benzoyl)-4,5,6,7-tetrahydropyridine[4,3-c]pyrazol-3-yl)-[4-(1-pirrolidin-2-on)]phenylacetamide 2.00-2.10 (m, 2H), 2.45 (t, 2H), 2.55-2.65 (m, 2H), 3.30-3.45 (m, 2H), 3.60 (s, 2H), 3.80 (t, 2H), 4.00-4.45 (m, 2H), 6.90-7.15 (m, 4H), 7.30-7.40 (m, 2H), 7.50-7.60 (m, 2H).

N-ethyl-N'-{3-[2-(4-phenyl-3-fluoro-phenyl)propionamido]-4,5,6,7-tetrahydropyridine[4,3-c]pyrazol-5-yl}urea;

0.95 (t, 3H), 1.42 (d, 3H), 2.55 (t, 2H), 2.95-3.05 (m, 2H), 3.40-3.60 (m, 2H), 3.95 (m, 1H), 4.10-4.22 (m, 2H), 6.45 (t, 1H), 7.25-7.55 (m, 8H)."

N-isopropyl-N'-{3-[2-(4-phenyl-3-fluoro-phenyl)propionamido]-4,5,6,7-tetrahydropyridine[4,3-c]pyrazol-5-yl}urea;

1.00-1.05 (m, 6H), 1.42 (d, 3H), 2.55 (t, 2H), 3.40-3.60 (m, 2H), 3.70 (m, 1H), 4.08-4.22 (m, 2H), 6.15 (d, 1H), 7.22-7.57 (m, 8H)."

N-butyl-N'-{3-[2-(4-phenyl-3-fluoro-phenyl)propionamido]-4,5,6,7-tetrahydropyridine[4,3-c]pyrazol-5-yl}urea;

0.82 (t, 3H), 1.18-1.28 (m, 2H), 1.30-1.38 (m, 2H), 1.42 (d, 3H), 2.55 (t, 2H), 2.95-3.02 (m, 2H), 3.40-3.60 (m, 2H), 3.90 (m, 1H), 4.10-4.20 (m, 2H), 6.42 (t, 1H), 7.25-7.58 (m, 8H)."

N-(5-(2-furoyl)-4,5,6,7-tetrahydropyridine[4,3-c]pyrazol-3-yl)-2-(3-fluoro-4-phenyl-phenyl)propanamide 1.40 (d, 3H), 2.75 (bs, 2H), 3.80 (bs, 2H), 3.90 (m, 1H), 4.40-4.60 (m, 2H), 6.60 (bs, 1H), 6.95 (bs, 1H), 7.25-7.55 (m, 8H), 7.80 (bs, 1H).

N-isopropyl-N'-{3-(1-methyl-indol-3-yl)acetamido-4,5,6,7-tetrahydropyridine[4,3-c]pyrazol-5-yl}urea;

1.00-1.05 (m, 6H), 2.55 (t, 2H), 3.50 (t, 2H), 3.65-3.75 (m, 6H), 4.15 (s, 2H), 6.12 (d, 1H), 7.00 (t, 1H), 7.12 (t, 1H), 7.20 (s, 1H), 7.35 (d, 1H), 7.60 (d, 1H)."

N,N-isopropyl-N'-{3-(benzo[1,3]dioxol-5-yl)acetamido-4,5,6,7-tetrahydropyridine[4,3-c]pyrazol-5-yl}urea;

1.00-1.05 (m, 6H), 2.55 (t, 2H), 3.45-3.55 (m, 4H), 3.65-3.75 (m, 1H), 4.15 (s, 2H), 5.95 (s, 2H), 6.15 (d, 1H), 6.75 (d, 1H), 6.80-6.88 (m, 3H)."

N,N-dimethyl-N'-{3-(benzo[1,3]dioxol-5-yl)acetamido-4,5,6,7-tetrahydropyridine[4,3-c]pyrazol-5-yl}urea;

2.65 (t, 2H), 2.70 (s, 6H), 3.48 (s, 2H), 4.00 (s, 2H), 5.95 (s, 2H), 6.75 (d, 1H), 6.80-6.88 (m, 3H)."

N-ethyl-N'-{3-(2-(6-methoxy-2-naphthalene)propionamido)-4,5,6,7-tetrahydropyridine[4,3-c]pyrazol-5-yl}urea;

0.95 (t, 3H), 1.42 (d, 3H), 2.55 (t, 2H), 2.95-3.05 (m, 2H), 3.40-3.60 (m, 2H), 3.82 (s, 3H), 3.95 (m, 1H), 4.10-4.22 (m, 2H), 6.42 (t, 1H), 7.10 (d, 1H), 7.25 (s, 1H), 7.45 (d, 1H), 7.65-7.82 (m, 3H)

N-isopropyl-N'-{3-(2-(6-methoxy-2-naphthalene)propionamido)-4,5,6,7-tetrahydropyridine[4,3-c]pyrazol-5-yl}urea;

1.00-1.05 (m, 6H), 1.45 (d, 3H), 2.53 (t, 2H), 3.40-3.60 (m, 2H), 3.65-3.75 (m, 1H), 3.85 (s, 3H), 3.95 (m, 1H), 4.05-4.22 (m, 2H), 6.15 (d, 1H), 7.12 (d, 1H), 7.25 (s, 1H), 7.45 (d, 1H), 7.70-7.81 (m, 3H)-"

N-butyl-N'-{3-(2-(6-methoxy-2-naphthalene)propionamido)-4,5,6,7-tetrahydropyridine[4,3-c]pyrazol-5-yl}urea;

0.82 (t, 3H), 1.18-1.28 (m, 2H), 1.30-1.40 (m, 2H), 1.45 (d, 3H), 2.55 (t, 2H), 2.90-3.00 (m, 2H), 3.40-3.60 (m, 2H), 3.85 (s, 3H), 3.95 (m, 1H), 4.08-4.22 (m, 2H), 6.41 (t, 1H), 7.12 (d, 1H), 7.25 (m, 4H), 7.45 (d, 1H), 7.70-7.80 (m, 3H)."

N-benzyl-N'-{3-(2-(6-methoxy-2-naphthalene)propionamido)-4,5,6,7-tetrahydropyridine[4,3-c]pyrazol-5-yl}urea;

1.42 (d, 3H), 2.58 (t, 2H), 3.45-3.65 (m, 2H), 3.82 (s, 3H), 3.95 (m, 1H), 4.10-4.30 (m, 2H), 7.10 (t, 1H), 7.15-7.30 (m, 7H), 7.45 (d, 1H), 7.70-7.80 (m, 3H)."

N-phenyl-N'-{3-(3-fluorobenzamido)-4,5,6,7-tetrahydropyridine[4,3-c]pyrazol-5-yl}urea;
1H-NMR (DMSO-d6) d ppm 2.7 (m), 3.7 (m), 4.4 (s), 6.9-8.6 (m)."

N-{5-benzensulfonyl-4,5,6,7-tetrahydropyridine[4,3-c]pyrazol-3-yl}-cyclopropanecarboxamide 1H-NMR (DMSO-d6) d ppm 0.7 (m), 1.8 (m), 2.6 (m), 3.4 (m), 4.0 (s), 7.5-7.8 (m).

N-{5-(quinoline-8-sulfonyl)-4,5,6,7-tetrahydropyridine[4,3-c]pyrazol-3-yl}-3-fluorobenzamide 1H-NMR (DMSO-d6) d ppm 2.6 (m), 3.75 (m), 4.35 (s), 7.35-9.0 (m).

N-[5-(benzylsulfonyl)-4,5,6,7-tetrahydropyridine[4,3-c]pyrazol-3-yl]benzamide 1H-NMR (DMSO-d6) d ppm 2.6 (m), 3.4(m), 4.2 (s), 4.4 (s), 7.3-8.0 (m).

N-{5-benzensulfonyl-4,5,6,7-tetrahydropyridine[4,3-c]pyrazol-3-yl}-3-bromobenzamide 1H-NMR (DMSO-d6) d ppm 2.65 (m), 4.05 (s), 7.4-8.0 (m).

N-[5-(benzylsulfonyl)-4,5,6,7-tetrahydropyridine[4,3-c]pyrazol-3-yl]-3-bromobenzamide 1H-NMR (DMSO-d6) d ppm 2.6 (m), 4.15 (s), 4.4 (s), 7.3-8.0 (m).

N-{5-(4-fluorobenzene)sulfonyl-4,5,6,7-tetrahydropyridine[4,3-c]pyrazol-3-yl}-3-bromobenzamide 1H-NMR (DMSO-d6) d ppm 2.7 (m); 3.4 (m); 4.1 (s); 7.4-8.2 (m)

N-{5-(3-trifluoromethylbenzene)sulfonyl-4,5,6,7-tetrahydropyridine[4,3-c]pyrazol-3-yl}-3-bromo-benzamide 1H-NMR (DMSO-d6) d ppm 2.6 (m); 3.5 (m); 4.2 (s); 7.4-8.2 (m)

N-{5-(4-toluensulfonyl)-4,5,6,7-tetrahydropyridine[4,3-c]pyrazol-3-yl}-3-bromobenzamide 1H-NMR (DMSO-d6) d ppm 2.4 (s); 2.7 (m); 3.3 (m); 4.0 (s); 7.4-8.2 (m)

N-{5-(4-methoxybenzene)sulfonyl-4,5,6,7-tetrahydropyridine[4,3-c]pyrazol-3-yl}-3-bromobenzamide 1H-NMR (DMSO-d6) d ppm 2.7 (m); 3.3 (m); 3.8 (s); 4.0 (s); 7.1-8.2 (m)

N-{5-(4-tertbutylbenzene)sulfonyl-4,5,6,7-tetrahydropyridine[4,3-c]pyrazol-3-yl}-3-bromobenzamide 1H-NMR (DMSO-d6) d ppm 1.3 (s); 2.7 (m); 3.3 (m); 4.1 (s); 7.4-8.2 (m)

N-{5-(4-chlorobenzene)sulfonyl-4,5,6,7-tetrahydropyridine[4,3-c]pyrazol-3-yl}-3-bromobenzamide 1H-NMR (DMSO-d6) d ppm 2.7 (m); 3.4 (m); 4.1 (s); 7.4-8.2 (m)

N-{5-(2-naphthalene)sulfonyl-4,5,6,7-tetrahydropyridine[4,3-c]pyrazol-3-yl}-3-bromobenzamide 1H-NMR (DMSO-d6) d ppm 2.7 (m); 3.6 (m); 4.3 (s); 7.4-8.6 (m)

N-{5-(2-thienyl)acetyl-4,5,6,7-tetrahydropyridine[4,3-c]pyrazol-3-yl}-4-fluorobenzamide; 1H-NMR (DMSO-d6) d ppm 2.6 (m); 3.75 (m); 3.9-4.1 (2s); 4.35-4.5 (2s); 6.8-8.1 (m)

N-{5-(2-thienyl)acetyl-4,5,6,7-tetrahydropyridine[4,3-c]pyrazol-3-yl}-3-methoxybenzamide; 1H-NMR (DMSO-d6) d ppm 2.6 (m); 3.75 (m); 3.8 (s); 3.9-4.1 (2s); 4.3-4.5 (2s); 6.8-7.6 (m)

N-[5-(1,3-benzodioxol-5-ylcarbonyl)-4,5,6,7-tetrahydropyridine[4,3-c]pyrazol-3-yl]-4-tertbutyl-benzamide 1H-NMR (DMSO-d6) d ppm 1.3 (s); 2.75 (m); 4.4 (s); 6.0 (s); 6.9-7.6 (m)

N-[5-(1,3-benzodioxol-5-ylcarbonyl)-4,5,6,7-tetrahydropyridine[4,3-c]pyrazol-3-yl]-3-methoxybenzamide 1H-NMR (DMSO-d6) d ppm 2.75 (m); 3.6 (m); 3.8 (s); 4.4 (s); 6.0 (s); 6.9-7.6 (m)

N-[5-(1,3-benzodioxol-5-ylcarbonyl)-4,5,6,7-tetrahydropyridine[4,3-c]pyrazol-3-yl]-3-phenoxybenzamide 1H-NMR (DMSO-d6) d ppm 2.7 (m); 4.4 (s); 6.0 (s); 6.9-7.8 (m)

N-[5-(1,3-benzodioxol-5-ylcarbonyl)-4,5,6,7-tetrahydropyridine[4,3-c]pyrazol-3-yl]-3-phenoxybenzamide 1H-NMR (DMSO-d6) d ppm 1.95-2.05 (2s); 2.55-2.65 (2m); 3.55-3.75 (2m); 4.3-4.4 (2s); 7.0-7.8 (m)

N-[5-phenylacetyl-4,5,6,7-tetrahydropyridine[4,3-c]pyrazol-3-yl]-3-methoxybenzamide 1H-NMR (DMSO-d6) d ppm 2.5-2.65 (2m); 3.5-3.7 (2m); 3.8 (s); 4.35-4.5 (2s); 7.1-7.6 (m)

N-benzyl-N'-{3-(3-methoxy-benzamido)-4,5,6,7-tetrahydropyridine[4,3-c]pyrazol-5-yl}urea;
1H-NMR (DMSO-d6) d ppm 2.65 (m); 3.65 (m); 3.8 (s); 4.15-4.3 (m); 7.1-7.6 (m)"

N-{5-benzylsulfonyl-4,5,6,7-tetrahydropyridine[4,3-c]pyrazol-3-yl}-3-methoxybenzamide 1H-NMR (DMSO-d6) d ppm 2.6 (m); 3.4 (m); 3.8 (s); 4.2 (s); 4.4 (s); 7.1-7.6 (m)

N-isopropyl-N'-{3-(3-methoxy-benzamido)-4,5,6,7-tetrahydropyridine[4,3-c]pyrazol-5-yl})urea;
1H-NMR (DMSO-d6) d ppm 1.0 (d); 2.6 (m); 3.55 (m); 4.2 (s); 7.1-7.6 (m)"

N,N-dimethyl-N'-{3-(2-phenyl-thiazol-4-yl)acetamido-4,5,6,7-tetrahydropyridine[4,3-c]pyrazol-5-yl}urea;
2.60-2.75 (m, 6H), 3.30 (t, 2H), 3.82 (s, 2H), 4.10 (s, 2H), 7.40-7.55 (m, 4H), 7.85-7.95 (m, 2H).

N-isopropyl-N'-{3-(2-phenyl-1,3-thiazol-4-yl)acetamido-4,5,6,7-tetrahydropyridine[4,3-c]pyrazol-5-yl}urea;
1.02 (s, 3H), 1.04 (s, 3H), 2.55 (t, 2H), 3.55 (t, 2H), 3.65-3.88 (m, 1H), 3.95 (s, 2H), 4.20 (s, 2H), 6.15 (d, 1H), 7.40-7.55 (m, 4H), 7.88-7.98 (m, 2H).

N-ethyl-N'-{3-(4-fluorobenzamido)-4,5,6,7-tetrahydropyridine[4,3-c]pyrazol-5-yl}urea;
1H-NMR (DMSO-d6) d ppm: 8.08-7.34 (m, 4H), 4.17 (s, 2H), 3.58-2.7 (6H), 1.00 (m, 3H).

EXAMPLE 17

Preparation of N-{3-phenylacetamido-5-(carbo-tbutoxy)-6,6-dimethyl-4,6-dihydropyrrolo[3,4-c]pyrazol-1-yl}, N'-methylpolystyrene urea A solution of phenylacetyl chloride (24.08 mmol, 3.18 ml) in 10 ml of anhydrous dichlorometane was added dropwise to N-{3-amino-5-(carbo-tbutoxy)-6,6-dimethyl-4,6-dihydropyrrolo[3,4-c]pyrazol-1-yl},N'-methylpolystyrene urea (3.01 mmol, 3.5 g) previously swelled in 90 ml of anhydrous dichlorometane and 16.5 ml of DIEA (96.32 mmol). The resulting suspension was gently stirred at 22° C. for 18 hours. The resin was then filtered, washed with dichloromethane, methanol and dried under vacuum.

Analogously, the following compounds can be prepared by using the appropriate acyl chloride:

N-{3-(2-naphthalene)acetamido-5-(carbo-tbutoxy)-6,6-diethyl-4,6-dihydropyrrolo[3,4-c]pyrazol-1-yl},N'-methylpolystyrene urea N-{3-(3-bromo)benzamido-5-(carbo-tbutoxy)-6,6-dimethyl-4,6-dihydropyrrolo[3,4-c]pyrazol-1-yl},N'-methylpolystyrene urea N-{3-cyclopropanecarboxamido-5-(carbo-tbutoxy)-6,6-dimethyl-4,6-dihydropyrrolo[3,4-c]pyrazol-1-yl},N'-methylpolystyrene urea N-{3-(4-fluoro)benzamido-5-(carbo-tbutoxy)-6,6-dimethyl-4,6-dihydropyrrolo[3,4-c]pyrazol-1-yl},N'-methylpolystyrene urea N-{3-(4-tertbutyl)benzamido-5-(carbo-tbutoxy)-6,6-dimethyl-4,6-dihydropyrrolo[3,4-c]pyrazol-1-yl},N'-methylpolystyrene urea

EXAMPLE 18

Preparation of N-{3-substituted-6,6-dimethyl-4,6-dihydropyrrolo[3,4-c]pyrazol-1-yl},N'-methylpolystyrene ureas By treating compounds of example 16 with trifluoroacetic acid as described in example 7, the following compounds can be obtained:

N-{3-phenylacetyl-6,6-dimethyl-4,6-dihydropyrrolo[3,4-c]pyrazol-1-yl},N'-methylpolystyrene urea
N-{3-(2-naphthalene)acetamido-6,6-dimethyl-4,6-dihydropyrrolo[3,4-c]pyrazol-1-yl},N'-methylpolystyrene urea
N-{3-(3-bromo)benzamido-6,6-dimethyl-4,6-dihydropyrrolo[3,4-c]pyrazol-1-yl},N'-methylpolystyrene urea
N-{3-cyclopropanecarboxamido-5-(carbo-tbutoxy)-6,6-ethyl-4,6-dihydropyrrolo[3,4-c]pyrazol-1-yl},N'-methylpolystyrene urea
N-{3-(4-fluoro)benzamido-6,6-dimethyl-4,6-dihydropyrrolo[3,4-c]pyrazol-1-yl},N'-methylpolystyrene urea
N-{3-(4-tertbutyl)benzamido-6,6-dimethyl-4,6-dihydropyrrolo[3,4-c]pyrazol-1-yl},N'-methylpolystyrene urea

EXAMPLE 19

Preparation of N-{3,5-substituted-6,6-dimethyl-4,6-dihydropyrrolo[3,4-c]pyrazol-1-yl},N'-methylpolystyrene ureas By treating compounds of example 17 with the appropriate carboxylic acid, isocyanate, or sulfonyl chloride according to the procedures described in examples 8,9,10, the following compounds can be obtained:

N-{3-phenylacetyl-5-acetyl-6,6-dimethyl-4,6-dihydropyrrolo[3,4-c]pyrazol-1-yl},N'-methylpolystyrene urea
N-{3-(2-naphthalene)acetamido-5-acetyl-6,6-dimethyl-4,6-dihydropyrrolo[3,4-c]pyrazol-1-yl},N'-methylpolystyrene urea
N-{3-(3-bromo)benzamido-5-acetyl-6,6-dimethyl-4,6-dihydropyrrolo[3,4-c]pyrazol-1-yl},N'-methylpolystyrene urea
N-{3-cyclopropanecarboxamido-5-(carbo-tbutoxy)-5-acetyl-6,6-dimethyl-4,6-dihydropyrrolo[3,4-c]pyrazol-1-yl},N'-methylpolystyrene urea
N-{3-(4-fluoro)benzamido-5-acetyl-6,6-dimethyl-4,6-dihydropyrrolo[3,4-c]pyrazol-1-yl},N'-methylpolystyrene urea
N-{3-(4-tertbutyl)benzamido-5-acetyl-6,6-dimethyl-4,6-dihydropyrrolo[3,4-c]pyrazol-1-yl},N'-methylpolystyrene urea
N-{3-phenylacetyl-5-(2-thienyl-acetyl)-6,6-dimethyl-4,6-dihydropyrrolo[3,4-c]pyrazol-1-yl},N'-methylpolystyrene urea
N-{3-(2-naphthalene)acetamido-5-(2-thienyl-acetyl)-6,6-dimethyl-4,6-dihydropyrrolo[3,4-c]pyrazol-1-yl},N'-methylpolystyrene urea
N-{3-(3-bromo)benzamido-5-(2-thienyl-acetyl)-6,6-dimethyl-4,6-dihydropyrrolo[3,4-c]pyrazol-1-yl},N'-methylpolystyrene urea
N-{3-cyclopropanecarboxamido-5-(carbo-tbutoxy)-5-(2-thienyl-acetyl)-6,6-dimethyl-4,6-dihydropyrrolo[3,4-c]pyrazol-1-yl},N'-methylpolystyrene urea
N-{3-(4-fluoro)benzamido-5-(2-thienyl-acetyl)-6,6-dimethyl-4,6-dihydropyrrolo[3,4-c]pyrazol-1-yl},N'-methylpolystyrene urea
N-{3-(4-tertbutyl)benzamido-5-(2-thienyl-acetyl)-6,6-dimethyl-4,6-dihydropyrrolo[3,4-c]pyrazol-1-yl},N'-methylpolystyrene urea
N-{3-phenylacetyl-5-ethylaminocarbonyl-6,6-dimethyl-4,6-dihydropyrrolo[3,4-c]pyrazol-1-yl},N'-methylpolystyrene urea
N-{3-(2-naphthalene)acetamido-5-ethylaminocarbonyl-6,6-dimethyl-4,6-dihydropyrrolo[3,4-c]pyrazol-1-yl},N'-methylpolystyrene urea
N-{3-(3-bromo)benzamido-5-ethylaminocarbonyl-6,6-dimethyl-4,6-dihydropyrrolo[3,4-c]pyrazol-1-yl},N'-methylpolystyrene urea
N-{3-cyclopropanecarboxamido-5-(carbo-tbutoxy)-5-ethylaminocarbonyl-6,6-dimethyl-4,6-dihydropyrrolo[3,4-c]pyrazol-1-yl},N'-methylpolystyrene urea
N-{3-(4-fluoro)benzamido-5-ethylaminocarbonyl-6,6-dimethyl-4,6-dihydropyrrolo[3,4-c]pyrazol-1-yl},N'-methylpolystyrene urea
N-{3-(4-tertbutyl)benzamido-5-ethylaminocarbonyl-6,6-dimethyl-4,6-dihydropyrrolo[3,4-c]pyrazol-1-yl},N'-methylpolystyrene urea
N-{3-phenylacetyl-5-ethylaminocarbonyl-6,6-dimethyl-4,6-dihydropyrrolo[3,4-c]pyrazol-1-yl},N'-methylpolystyrene urea
N-{3-(2-naphthalene)acetamido-5-ethylaminocarbonyl-6,6-dimethyl-4,6-dihydropyrrolo[3,4-c]pyrazol-1-yl},N'-methylpolystyrene urea
N-{3-(3-bromo)benzamido-5-ethylaminocarbonyl-6,6-dimethyl-4,6-dihydropyrrolo[3,4-c]pyrazol-1-yl},N'-methylpolystyrene urea
N-{3-cyclopropanecarboxamido-5-(carbo-tbutoxy)-5-ethylaminocarbonyl-6,6-dimethyl-4,6-dihydropyrrolo[3,4-c]pyrazol-1-yl},N'-methylpolystyrene urea
N-{3-(4-fluoro)benzamido-5-ethylaminocarbonyl-6,6-dimethyl-4,6-dihydropyrrolo[3,4-c]pyrazol-1-yl},N'-methylpolystyrene urea
N-{3-(4-tertbutyl)benzamido-5-ethylaminocarbonyl-6,6-dimethyl-4,6-dihydropyrrolo[3,4-c]pyrazol-1-yl},N'-methylpolystyrene urea
N-{3-phenylacetyl-5-butylaminocarbonyl-6,6-dimethyl-4,6-dihydropyrrolo[3,4-c]pyrazol-1-yl},N'-methylpolystyrene urea
N-{3-(2-naphthalene)acetamido-5-butylaminocarbonyl-6,6-dimethyl-4,6-dihydropyrrolo[3,4-c]pyrazol-1-yl},N'-methylpolystyrene urea
N-{3-(3-bromo)benzamido-5-butylaminocarbonyl-6,6-dimethyl-4,6-dihydropyrrolo[3,4-c]pyrazol-1-yl},N'-methylpolystyrene urea N-{3-cyclopropanecarboxamido-5-(carbo-tbutoxy)-5-butylaminocarbonyl-6,6-dimethyl-4,6-dihydropyrrolo[3,4-c]pyrazol-1-yl},N'-methylpolystyrene urea N-{3-(4-fluoro)benzamido-5-butyl aminocarbonyl-6,6-dimethyl-4,6-dihydropyrrolo[3,4-c]pyrazol-1-yl},N'-methylpolystyrene urea N-{3-(4-tertbutyl)benzamido-5-butylaminocarbonyl-6,6-dimethyl-4,6-dihydropyrrolo[3,4-c]pyrazol-1-yl},N'-methylpolystyrene urea

EXAMPLE 20

Preparation of 6,6-dimethyl-4,6-dihydropyrrolo[3,4-c]pyrazol derivatives

By alkaline hydrolisis of compounds of example 18 according to the procedure described in example 11, the following compounds can be obtained:

N-{5-phenylacetyl-6,6-dimethyl-4,6-dihydropyrrolo[3,4-c]pyrazol-3-yl}-(2-naphthalene)acetamide N-{5-phenylacetyl-6,6-dimethyl-4,6-dihydropyrrolo[3,4-c]pyrazol-3-yl}-(3-bromo)benzamide N-{5-phenylacetyl-6,6-dimethyl-4,6-dihydropyrrolo[3,4-c]pyrazol-3-yl}cyclopropanecarboxamide N-{5-phenylacetyl-6,6-dimethyl-4,6-dihydropyrrolo[3,4-c]pyrazol-3-yl}-(4-fluoro)benzamide N-{5-phenylacetyl-6,6-dimethyl-4,6-dihydropyrrolo[3,4-c]pyrazol-3-yl}-(4-tertbutyl)benzamide N-{5-acetyl-6,6-dimethyl-4,6-dihydropyrrolo[3,4-c]pyrazol-3-yl}phenylacetamide N-{5-acetyl-6,64-dimethyl-4,6-dihydropyrrolo[3,4-c]pyrazol-3-yl}-(2-naphthalene)acetamide N-{5-acetyl-6,6-dimethyl-4,6-dihydropyrrolo[3,4-c]pyrazol-3-yl}-(3-bromo)benzamide 1H-NMR (DMSO-d6) d ppm: 8.2 (t), 7.7-8.0 (m), 4.6 (s), 2.0 (s), 1.6 (s).

N-{5-acetyl-6,6-dimethyl-4,6-dihydropyrrolo[3,4-c]pyrazol-3-yl}cyclopropanecarboxamide N-{5-acetyl-6,6-dimethyl-4,6-dihydropyrrolo[3,4-c]pyrazol-3-yl}-(4-fluoro)benzamide N-{5-acetyl-6,6-dimethyl-4,6-dihydropyrrolo[3,4-c]pyrazol-3-yl}-(4-tertbutyl)benzamide N-{5-(2-thienyl-acetyl)-6,6-dimethyl-4,6-dihydropyrrolo[3,4-c]pyrazol-3-yl}phenylacetamide N-{5-(2-thienyl-acetyl)-6,6-dimethyl-4,6-dihydropyrrolo[3,4-c]pyrazol-3-yl}-(2-naphthalene)acetamide 1H-NMR (DMSO-d6) d ppm: 7.8-8 (m), 7.4-7.6 (m), 7.2-7.3 (m), 4.6 (s), 1.6 (s).

N-{5-(2-thienyl-acetyl)-6,6-dimethyl-4,6-dihydropyrrolo[3,4-c]pyrazol-1-yl}-(3-bromo)benzamide N-{5-(2-thienyl-acetyl)-6,6-dimethyl-4,6-dihydropyrrolo[3,4-c]pyrazol-3-yl}cyclopropanecarboxamide 1H-NMR (DMSO-d6) d ppm: 7.4-7.6 (m), 6.8-7.0 (m), 4.6 (s), 3.9 (s), 0.8 (m).

N-{5-(2-thienyl-acetyl)-6,6-dimethyl-4,6-dihydropyrrolo[3,4-c]pyrazol-3-yl}-(4-fluoro)benzamide N-{5-(2-thienyl-acetyl)-6,6-dimethyl-4,6-dihydropyrrolo[3,4-c]pyrazol-3-yl}-(4-tertbutyl)benzamide N-{5-(4-fluorobenzoyl)-6,6-dimethyl-4,6-dihydropyrrolo[3,4-c]pyrazol-3-yl}phenylacetamide N-{5-(4-fluorobenzoyl)-6,6-dimethyl-4,6-dihydropyrrolo[3,4-c]pyrazol-3-yl}-(2-naphthalene)acetamide N-{5-(4-fluorobenzoyl)-6,6-dimethyl-4,6-dihydropyrrolo[3,4-c]pyrazol-1-yl}-(3-bromo)benzamide N-{5-(4-fluorobenzoyl)-6,6-dimethyl-4,6-dihydropyrrolo[3,4-c]pyrazol-3-yl}cyclopropanecarboxamide N-{5-(4-fluorobenzoyl)-6,6-dimethyl-4,6-dihydropyrrolo[3,4-c]pyrazol-1-yl}-(4-fluoro)benzamide N-{5-(4-fluorobenzoyl)-6,6-dimethyl-4,6-dihydropyrrolo[3,4-c]pyrazol-3-yl}-(4-tertbutyl)benzamide N-ethyl-N'-{3-phenylacetamido-6,6-dimethyl-4,6-dihydropyrrolo[3,4-c]pyrazol-5-yl}urea N-ethyl-N'-{3-(2-naphthalene)acetamido-6,6-dimethyl-4,6-dihydropyrrolo[3,4-c]pyrazol-1-yl}urea 1H-NMR (DMSO-d6) d ppm: 7.8-8 (m), 7.4-7.6 (m), 4.3 (s), 1.6 (s), 1.0 (t).

N-ethyl-N'-{3-(3-bromo)benzamido-6,6-dimethyl-4,6-dihydropyrrolo[3,4-c]pyrazol-1-yl}urea N-ethyl-N'-{3-cyclopropanecarboxamido-6,6-dimethyl-4,6-dihydropyrrolo[3,4-c]pyrazol-1-yl}urea 1H-NMR (DMSO-d6) d ppm: 4.6 (s), 1.75-1.85 (m), 1.6 (s), 1.0 (t).

N-ethyl-N'-{3-(4-fluoro)benzamido-6,6-dimethyl-4,6-dihydropyrrolo[3,4-c]pyrazol-1-yl}urea 1H-NMR (DMSO-d6) d ppm: 8.0-8.2 (m), 7.2-7.4 (m), 4.5 (s), 3.0-3.2 (m), 1.6 (s), 1.1 (t).

N-ethyl-N'-{3-(4-tertbutyl)benzamido-6,6-dimethyl-4,6-dihydropyrrolo[3,4-c]pyrazol-1-yl}urea 1H-NMR (DMSO-d6) d ppm: 8.0 (d), 7.8 (d), 4.6 (s), 3.0-3.2 (m), 1.6 (s), 0.9 (t).

N-butyl-N'-{3-phenylacetamido-6,6-dimethyl-4,6-dihydropyrrolo[3,4-c]pyrazol-5-yl}urea N-butyl-N'-{3-(2-naphthalene)acetamido-6,6-dimethyl-4,6-dihydropyrrolo[3,4-c]pyrazol-1-yl}urea 1H-NMR (DMSO-d6) d ppm: 7.8-8 (m), 7.4-7.6 (m), 4.3 (s), 1.6 (s), 0.9 (t).

N-butyl-N'-{3-(3-bromo)benzamido-6,6-dimethyl-4,6-dihydropyrrolo[3,4-c]pyrazol-1-yl}urea N-butyl-N'-{3-cyclopropanecarboxamido-6,6-dimethyl-4,6-dihydropyrrolo[3,4-c]pyrazol-1-yl}urea 1H-NMR (DMSO-d6) d ppm: 4,6 (s), 3.0 (t), 1.6 (s), 0.9 (t).

N-butyl-N'-{3-(4-fluoro)benzamido-6,6-dimethyl-4,6-dihydropyrrolo[3,4-c]pyrazol-1-yl}urea 1H-NMR (DMSO-d6) d ppm: 8.0-8.2 (m), 7.2-7.4 (m), 4.5 (s), 3.0-3.2 (m), 1.6 (s), 1.2-1.3 (m), 0.9 (t).

N-butyl-N'-{3-(4-tertbutyl)benzamido-6,6-dimethyl-4,6-dihydropyrrolo[3,4-c]pyrazol-1-yl}urea 1H-NMR (DMSO-d6) d ppm: 8.0 (d), 7.8 (d), 4.5 (s), 3.0-3.2 (m), 1.6 (s), 0.9 (t).

EXAMPLE 21

Preparation of N-{3-(tertbutyl-benzetamido)-6-(carbo-tbutoxy)-4,5,6,7-tetrahydropyridine[3,4-c]pyrazol-1-yl},N'-methylpolystyrene urea A solution of tertbutyl chloride (24.08 mmol, 4.5 ml) in 10 ml of anhydrous dichlorometane was added dropwise to N-{3-amino-6-(carbo-tbutoxy)-4,5,6,7-tetrahydropyridine[3,4-c]pyrazol-1-yl},N'-methylpolystyrene urea (3.01 mmol, 3.5 g) previously swelled in 90 ml of anhydrous dichlorometane and 16.5 ml of DIEA (96.32 mmol). The resulting suspension was gently stirred at 22° C. for 18 hours. The resin was then filtered, washed with dichloromethane, methanol and dried under vacuum.

EXAMPLE 22

Preparation of N-{3-(tertbutyl-benzetamido)-4,5,6,7-tetrahydropyridine[3,4-c]pyrazol-1-yl},N'-methylpolystyrene urea By treating N-{3-(tertbutyl-benzetamido)-6-(carbo-tbutoxy)-4,5,6,7-tetrahydropyridine[3,4-c]pyrazol-1-yl},N'-methylpolystyrene urea with trifluoroacetic acid as described in example 7, N-{3-(tertbutyl-benzetamido)-4,5,6,7-tetrahydropyridine[3,4-c]pyrazol-1-yl},N'-methylpolystyrene urea was obtained.

EXAMPLE 23

Preparation of N-{3-(terbutyl-benzamido)-6-substituted-4,5,6,7-tetrahydropyridine[3,4-c]pyrazol-1-yl}, N'-methylpolystyrene ureas By treating N-{3-(tertbutyl-benzetamido)-4,5,6,7-tetrahydropyridine[3,4-c]pyrazol-1-yl},N'-methylpolystyrene urea with the appropriate carboxylic acid, isocyanate, or sulfonyl chloride according to the procedures described in examples 8,9,10, the following compounds can be obtained:

N-{3-(4-tertbutyl-benzamido)-6-isopropylaminocarbonyl-4,5,6,7-tetrahydropyridine[3,4-c]pyrazol-6-yl},N'-methylpolystyrene urea N-{3-(4-tertbutyl-benzamido)-6-(2-thienyl)acetyl-4,5,6,7-tetrahydropyridine[3,4-c]pyrazol-3-yl},N'-methylpolystyrene urea N-{3-(4-tertbutyl-benzamido)-6-acetyl-4,5,6,7-tetrahydropyridine[3,4-c]pyrazol-3-yl},N'-methylpolystyrene urea N-{3-(4-tertbutyl-benzamido)-6-methansulfonyl-4,5,6,7-tetrahydropyridine[3,4-c]pyrazol-3-yl},N'-methylpolystyrene urea N-{3-(4-tertbutyl-benzamido)-6-ethylaminocarbonyl-4,5,6,7-tetrahydropyridine[3,4-c]pyrazol-6-yl}urea,N'-methylpolystyrene urea N-{3-(4-tertbutyl-benzamido)-6-(3-methyl)butyryl-4,5,6,7-tetrahydropyridine[3,4-c]pyrazol-3-yl},N'-methylpolystyrene urea N-{3-(4-tertbutyl-benzamido)-6-(2-furoyl)-4,5,6,7-tetrahydropyridine[3,4-c]pyrazol-3-yl},N'-methylpolystyrene urea N-{3-(4-tertbutyl-benzamido)-6-phenylacetyl-4,5,6,7-tetrahydropyridine[3,4-c]pyrazol-3-yl},N'-methylpolystyrene urea N-{3-(4-tertbutyl-benzamido)-6-phenylsulfonyl-4,5,6,7-tetrahydropyridine[3,4-c]pyrazol-3-yl},N'-methylpolystyrene urea N-{3-(4-tertbutyl-benzamido)-4,5,6,7-tetrahydropyridine[3,4-c]pyrazol-3-yl}-4-tertbutyl-benzamide,N'-methylpolystyrene urea

EXAMPLE 24

Preparation of 3-(tertbutyl-benzamido)-4,5,6,7-tetrahydropyridine[3,4-c]pyrazol-6-yl derivatives By alkaline hydrolisis of compounds of example 22 according to the procedure described in example 11, the following compounds were obtained:

N-isopropyl-N'-{3-(4-tertbutyl-benzamido)-4,5,6,7-tetrahydropyridine[3,4-c]pyrazol-6-yl}urea, 1H-NMR (DMSO-d6) d ppm: 7.90-7.47 (m, 4H), 4.41 (s, 2H), 3.75 (m, 1H), 3.47 (m, 2H), 2.39 (m, 2H), 1.3 (s, 9H) 1.04 (6H).

N-{6-(2-thienyl)acetyl-4,5,6,7-tetrahydropyridine[3,4-c]pyrazol-3-yl}-4-tertbutyl-benzamide; 1H-NMR (DMSO-d6) d ppm: 7.9-7.47 (m, 4H), 4.58 (m, 2H), 4.04 (s, 2H), 3.71 (m, 2H), 2.44 (m, 2H), 1.3 (s, 9H).

N-{6-acetyl-4,5,6,7-tetrahydropyridine[3,4-c]pyrazol-3-yl}-4-tertbutyl-benzamide;

N-{6-methansulfonyl-4,5,6,7-tetrahydropyridine[3,4-c]pyrazol-3-yl}-4-tertbutyl-benzamide; 1H-NMR (DMSO-d6) d ppm: 7.9-7.47 (m, 4H), 4.3 (s, 2H), 3.40 (m, 2H), 2.94 (s, 3H), 2.52 (m, 2H), 1.30 (s, 9H).

N-ethyl-N'-{3-(4-tertbutyl-benzamido)-4,5,6,7-tetrahydropyridine[3,4-c]pyrazol-6-yl}urea; 1H-NMR (DMSO-d6) d ppm: 7.90-7.47 (4H), 4.41 (s, 2H), 3.49-3.04 (m, 4H), 2.38 (m, 2H), 1.30 (s, 9H), 1.01 (t, 3H).

N-{6-(3-methyl)butyryl-4,5,6,7-tetrahydropyridine[3,4-c]pyrazol-3-yl}-4-tertbutyl-benzamide; 1H-NMR (DMSO-d6) d ppm: 7.91-7.47 (m, 4H), 4.56 (s, 2H), 3.62-2.27 (m, 6H), 1.30 (s, 9H), 0.88 (m, 6H).

N-{6-(2-furoyl)-4,5,6,7-tetrahydropyridine[3,4-c]pyrazol-3-yl}-4-tertbutyl-benzamide; 1H-NMR (DMSO-d6) d ppm: 7.91-6.62 (m, 7H), 3.82 (m, 2H), 2.56 (m, 2H), 1.30 (s, 9H).

N-{6-phenylacetyl-4,5,6,7-tetrahydropyridine[3,4-c]pyrazol-3-yl)}-4-tertbutyl-benzamide; 1H-NMR (DMSO-d6) d ppm: 7.90-7.29 (m, 9H), 4.6 (2H), 3.8 (s, 2H), 3.68 (m, 2H), 2.4 (m, 2H), 1.30 (s, 9H).

N-{6-phenylsulfonyl-4,5,6,7-tetrahydropyridine[3,4-c]pyrazol-3-yl}-4-tertbutyl-benzamide;

N-{6-(quinoline-8-sulfonyl)-4,5,6,7-tetrahydropyridine[3,4-c]pyrazol-3-yl}-4-tertbutyl-benzamide; 1H-NMR (DMSO-d6) d ppm: 8.9-7.47 (m, 10H), 4.6 (2H), 3.56(m, 2H), 2.26 (m, 2H), 1.30 (s, 9H).

EXAMPLE 25

Preparation of N-{3-(4-tbutyl)benzamido-5-(3-methylbut)-4,6-dihydropyrrolo[3,4-c]pyrazol-1-yl},N'-methylpolystyrene urea N-{3-(4-tbutyl)benzaamido-4,6-dihydropyrrolo[3,4-c]pyrazol-1-yl},N'-methylpolystyrene urea (0.086 mmol, 100 mg) was swollen in 4 mL of anhydrous DMF/EtOH (3:1) and treated with isovaleraldehyde (0.86 mmol, 74.1 mg) and borane-pyridine complex (BAP) (0.86 mmol, 79.9 mg). The mixture was gently shaken in argon atmosphere for 4 days at 22° C. Then the resin was filtered, washed with DMF/EtOH, DCM and MeOH and dried under vacuum.

Analogously, the following compounds can be prepared:

N-{3-(4-tbutyl)benzamido-5-(2-phenylethyl)-4,6-dihydropyrrolo[3,4-c]pyrazol-1-yl},N'-methylpolystyrene urea N-{3-(4-tbutyl)benzamido-5-[2-(2-thienyl)ethyl]-4,6-dihydropyrrolo[3,4-c]pyrazol-1-yl},N'-methylpolystyrene urea

EXAMPLE 26

Preparation of 3-(tertbutyl-benzamido)-4,6-dihydropyrrolo[3,4-c]pyrazol-5-alkyl derivatives By alkaline hydrolisis of compounds of example 22 according to the procedure described in example 11, the following compounds were obtained:

N-{5-isopentyl-4,6-dihydropyrrolo[3,4-c]pyrazol-3-yl}-4-tertbutylbenzamide

1H-NMR (DMSO-d6) d ppm: 7.9-7.8 (m); 7.5-7.4 (m); 4.0-3.8 (m); 1.7-1.6 (m); 1.5-1.4 (m); 1.30 (s); 0.90 (d).

N-{5-phenylethyl-4,6-dihydropyrrolo[3,4-c]pyrazol-3-yl}-4-tertbutylbenzamide

1H-NMR (DMSO-d6) d ppm: 7.9-7.8 (m); 7.5-7.4 (m); 7.3-7.1 (m); 4.0-3.8 (m); 3.1-2.8 (m); 1.30 (s).

N-[5-(2-thien-2-ylethyl)-4,6-dihydropyrrolo[3,4-c]pyrazol-3-yl]-4-tertbutyl-benzamide; 1H-NMR (DMSO-d6) d ppm: 7.92-6.92 (m, 7H), 3.2 (m, 4H), 1.3 (9H).

EXAMPLE 27

Preparation of 3-Amino-4,6-dihydro-pyrrolo[3,4-c]pyrazole-1,5-dicarboxylic acid 5-tert-butyl ester 1-ethyl ester A solution of ethyl chlorocarbonate (8.9 ml, 93 mmol) in THF (250 ml) was added slowly to a mixture of 3-amino-4,6-dihydro-1H-pyrrolo[3,4-c]pyrazole-5-carboxylic acid tert-butyl ester (20 g, 89 mmol) and DIEA (92 ml, 528 mmol) in THF (500 ml) at 0-5° C. The reaction was kept at the same temperature for two hours then allowed to reach r.t. and stirred overnight. The obtained mixture was evaporated to dryness under vacuum. The resulting residue was extracted with AcOEt and water. The organic phase was separated, dried over sodium sulfate and evaporated to dryness. The mixture was purified by flash-chromatography (eluent: ethyl acetate/cyclohexane 4/6 to 7/3) to give 19 g (72% yield) of the title compound as a white solid.

EXAMPLE 28

Preparation of 3-(2-Naphthalen-2-yl-propionylamino)-4,6-dihydro-pyrrolo[3,4-c]pyrazole-1,5-dicarboxylic acid 5-tert-butyl ester 1-ethyl ester To a solution of 2-naphthalen-2-yl-propionic acid (1.48 g, 7.4 mmol) in DCM (40 ml) and DMF cat., (COCl)2 (0.83 ml, 9.65 mmol) in DCM (10 ml) was added dropwise. The mixture was stirred at r.t. for 30 min. The reaction mixture was concentrated under vacuum, reconstituted twice with toluene and concentrated. A solution of the obtained acyl-chloride in THF (40 ml) was added slowly to a mixture of 3-amino-4,6-dihydro-pyrrolo[3,4-c]pyrazole-1,5-dicarboxylic acid 5-tert-butyl ester 1-ethyl ester (2.0 g, 6.75 mmol) and DIEA (5.8 ml, 33.3 mmol) in THF (40 ml) at 0-5° C. The reaction was allowed to reach r.t. and stirred overnight. The mixture was filtered and the solution evaporated to dryness under vacuum. The resulting residue was dissolved in DCM and the obtained solution washed with brine, dried over sodium sulfate, filtered and evaporated to dryness. The crude product was purified by flash-chromatography (eluent:ethyl acetate/cyclohexane 3/7 then 4/6) to give 3.0 g (93% yield) of the title compound as a white solid.

EXAMPLE 29

Preparation of 3-(2-Naphthalen-2-yl-propionylamino)-5,6-dihydro-4H-pyrrolo[3,4-c]pyrazole-1-carboxylic acid ethyl ester 2.5 g (5.2 mmol) of 3-(2-naphthalen-2-yl-propionylamino)-4,6-dihydro-pyrrolo[3,4-c]pyrazole-1,5-dicarboxylic acid 5-tert-butyl ester 1-ethyl ester in 15 ml DCM was treated with 16 ml of (1:1) TFA/DCM. The reaction mixture was stirred for 30 min. and evaporated to dryness. The resulting residue was dissolved in DCM and the solution washed with brine and then treated with NaHCO3 aq. The obtained precipitate was filtered, washed with water and DCM, and then dried under vacuum to give 2.0 g (quantitative yield) of the title compound.

EXAMPLE 30

N-{5-(piperidin-1-yl)carbamoyl)-4,6-dihydropyrrolo[3,4-c]pyrazol-3-yl}-3-(2-naphthalen-2-yl)-propionamide A solution of 4-nitrophenylchloroformate (0.213 g, 1.06 mmol) in dry THF (10 ml) was added dropwise to a solution of 3-(2-Naphthalen-2-yl-propionylamino)-5,6-dihydro-4H-pyrrolo[3,4-c]pyrazole-1-carboxylic acid ethyl ester (0.4 g, 1.06 mmol) and DIEA (0.184 ml, 1.06 mmol) in dry THF (10 ml). The resulting suspension was stirred at room temperature for about 4 hours. After evaporation of the solvents the reaction mixture was dissolved in DCM, washed with water, dried over sodium sulfate and evaporated to a yellow solid (0.55 g, quantitative). The solid was dissolved in acetonitrile (15 ml), treated with 4-DMAP (130 mg, 1.06 mmol) and piperidine (2.75 mmol, 0.27 ml). The reaction mixture was refluxed for about 24 hours, evaporated, dissolved in DCM, washed with 1N NaOH, brine, 0.1N HCl, brine, dried over sodium sulfate, filtered and evaporated. The title compound was obtained after chromatographic purification on silica gel using DCM/MeOH 95:5 as eluent (0.115 g, 26% yield).

1H-NMR (DMSO-d6) d ppm: 7.8-7.5 (m); 4.4(m); 4.0(m); 3.1(m); 1.5(m).

Analogously the following derivatives can be prepared starting from the appropriate amine:

N,N-dimethyl-N'-{3-(2-naphthalen-2-yl-propionamido)-4,6-dihydropyrrolo[3,4-c]pyrazol-5-yl}urea 1H-NMR (DMSO-d6) d ppm: 7.8-7.5 (m); 4.4(m); 4.0(m); 2.8(s); 1.5(d).

N,N-dimethyl-N'-{3-(2-phenyl-thiazol-4-yl)acetamido-4,5,6,7-tetrahydropyridine[4,3-c]pyrazol-5-yl}urea;

1H-NMR (DMSO-d6) d ppm: 2.60-2.75 (m, 6H), 3.30 (t, 2H), 3.82 (s, 2H), 4.10 (s, 2H), 7.40-7.55 (m, 4H), 7.85-7.95 (m, 2H).

FORMULATION EXAMPLES

Example 1

Dry Capsules 5000 capsules, each of which contain 0.25 g of one of the compounds of the formula (I) mentioned in the preceding Examples as active ingredient, are prepared as follows:

Composition Active ingredient 1250 g

Talc 180 g

Wheat starch 120 g

Magnesium stearate 80 g

Lactose 20 g

Preparation process: The powdered substances mentioned are pressed through a sieve of mesh width 0.6 mm. Portions of 0.33 g of the mixture are transferred to gelatine capsules with the aid of a capsule-filling machine.

Example 2

Soft Capsules 5000 soft gelatine capsules, each of which contain 0.05 g of one of the compounds of the formula (I) mentioned in the preceding Examples as active ingredient, are prepared as follows:

Composition Active ingredient 250 g
Lauroglycol 2 litres

Preparation process: The powdered active ingredient is suspended in Lauroglykole (propylene glycol laurate, Gattefoss S.A., Saint Priest, France) and ground in a wet-pulveriser to a particle size of about 1 to 3 gm. Portions of in each case 0.419 g of the mixture are then transferred to soft gelatine capsules by means of a capsule-filling machine.

Example 3

Soft Capsules 5000 soft gelatine capsules, each of which contain 0.05 g of one of the compounds of the formula (I) mentioned in the preceding or following Examples as active ingredient, are prepared as follows:

Composition Active ingredient 250 g
PEG 400 1 litre
Tween 80 1 litre

Preparation process: The powdered active ingredient is suspended in PEG 400 (polyethylene glycol of Mr between 380 and about 420, Sigma, Fluka, Aldrich, USA) and Tween' 80 (polyoxyethylene sorbitan monolaurate, Atlas Chem. Inc., USA, supplied by Sigma, Fluka, Aldrich) and ground in a wet-pulveriser to a particle size of about 1 to 3 mm. Portions of in each case 0.43 g of the mixture are then transferred to soft gelatine capsules by means of a capsule-filling machine.

We claim:

1. A method for treating a mammal, including humans, suffering from a disease caused by and/or associated with an altered protein kinase activity, by administering to said mammal in need thereof a therapeutically effective amount of a bicyclo-pyrazole compound of formula (I):

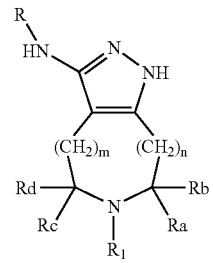

wherein
R is an optionally further substituted group selected from the group consisting of —COR', —COOR', —CONHR', —CONR'R", —NH—C(=NH)NHR', —C(=NH)NHR', —$SO_2$R', —$SO_2$NHR' and —$SO_2$NR'R";

$R_1$ is a hydrogen atom or an optionally further substituted group selected from the group consisting of R', —COR', —COOR', —CONHR', —CONR'R", —NH—C(=NH)NHR', —C(=NH)NHR', —$SO_2$R', —$SO_2$NHR' and —$SO_2$NR'R"; wherein R' and R" are the same or different and are independently hydrogen, straight or branched $C_1$-$C_6$ alkyl, aryl, $C_3$-$C_6$ cycloalkyl or aryl $C_1$-$C_6$ alkyl or R' and R" taken together form a $C_4$-$C_6$ alkylene chain;

Ra, Rb, Rc and Rd, being the same or different, are independently selected among hydrogen, optionally further substituted straight or branched $C_1$-$C_6$ alkyl, aryl, aryl $C_1$-$C_6$ alkyl or —$CH_2$OR' groups, wherein R' is as above defined, or Ra and Rb and/or Rc and Rd, taken together with the carbon atom to which they are bonded, form an optionally substituted $C_3$-$C_6$ cycloalkyl group;

m and n, each independently, represents 0 or an integer from 1 to 2, provided that m+n is lower than, or equal to, 2 (m+n≦2);

or a pharmaceutically acceptable salt thereof, and wherein said disease caused by and/or associated with an altered protein kinase activity is selected from the group consisting of cancer and cell proliferative disorders wherein the cancer is selected from the group consisting of leukemia, ovary, colon, breast, lung, and pancreas.

* * * * *